US010815222B2

(12) United States Patent
Biancofiore et al.

(10) Patent No.: US 10,815,222 B2
(45) Date of Patent: Oct. 27, 2020

(54) COMPOUNDS FOR USE IN THE TREATMENT OF KINETOPLASTID INFECTION

(71) Applicant: C.N.C.C.S. S.c.a.r.l. COLLEZIONE NAZIONALE DEI COMPOSTI CHIMICI E CENTRO SCREENING, Pomezia (RM) (IT)

(72) Inventors: Ilaria Biancofiore, Pomezia (IT); Alina Ciammaichella, Pomezia (IT); Federica Ferrigno, Pomezia (IT); Steven Harper, Pomezia (IT); Savina Malancona, Pomezia (IT); Jesus Maria Ontoria Ontoria, Pomezia (IT); Giacomo Paonessa, Pomezia (IT); Simona Ponzi, Pomezia (IT); Vincenzo Summa, Pomezia (IT)

(73) Assignee: C.N.C.C.S. S.C.A.R.L. COLLEZIONE NAZIONALE DEI COMPOSTI CHIMICI E CENTRO SCREENING, Pomezia (RM) (IT)

( * ) Notice: Subject to any disclaimer, the term of this patent is extended or adjusted under 35 U.S.C. 154(b) by 0 days.

(21) Appl. No.: 16/471,841

(22) PCT Filed: Dec. 21, 2017

(86) PCT No.: PCT/EP2017/084076
§ 371 (c)(1),
(2) Date: Jun. 20, 2019

(87) PCT Pub. No.: WO2018/115275
PCT Pub. Date: Jun. 28, 2018

(65) Prior Publication Data
US 2020/0095232 A1 Mar. 26, 2020

(30) Foreign Application Priority Data
Dec. 23, 2016 (EP) ..................... 16206601

(51) Int. Cl.
*A61K 45/06* (2006.01)
*A61K 31/551* (2006.01)
*A61K 31/496* (2006.01)
*C07D 417/14* (2006.01)
*C07D 403/04* (2006.01)
*C07D 403/14* (2006.01)
*C07D 405/14* (2006.01)
*C07D 401/14* (2006.01)
*C07D 413/14* (2006.01)
*A61K 31/4709* (2006.01)

(52) U.S. Cl.
CPC ........ *C07D 403/14* (2013.01); *A61K 31/4709* (2013.01); *A61K 31/496* (2013.01); *A61K 31/551* (2013.01); *A61K 45/06* (2013.01); *C07D 401/14* (2013.01); *C07D 403/04* (2013.01); *C07D 405/14* (2013.01); *C07D 413/14* (2013.01); *C07D 417/14* (2013.01)

(58) Field of Classification Search
CPC .... A61K 45/06; A61K 31/551; A61K 31/496; C07D 417/14; C07D 403/04; C07D 403/14; C07D 405/14; C07D 401/14; C07D 413/14
See application file for complete search history.

(56) References Cited

U.S. PATENT DOCUMENTS

2003/0134846 A1    7/2003    Windsor

FOREIGN PATENT DOCUMENTS

WO    2009026858 A1    3/2009
WO    2016004297 A1    1/2016

OTHER PUBLICATIONS

International Search Report and Written Opinion for Corresponding International Application No. PCT/EP2017/084076 (9 Pages) (dated Feb. 26, 2018).

*Primary Examiner* — Sun Jae Yoo
(74) *Attorney, Agent, or Firm* — Lucas & Mercanti, LLP

(57) ABSTRACT

The present invention relates to a class of novel heterocyclic compounds, to pharmaceutical compositions containing the compounds and their use in the treatment of kinetoplastid infections.

14 Claims, No Drawings

COMPOUNDS FOR USE IN THE TREATMENT OF KINETOPLASTID INFECTION

CROSS-REFERENCE TO RELATED APPLICATIONS

This application is a 371 of PCT/EP2017/084076, filed Dec. 21, 2017, which claims the benefit of European Patent Application No. 16206601.3, filed Dec. 23, 2016.

FIELD OF THE INVENTION

The present invention relates to a class of novel heterocyclic compounds, to pharmaceutical compositions comprising the compounds and their use in the treatment or prevention of a kinetoplastid infection, in particular a *Trypanosoma* or *Leishmania* infection.

BACKGROUND OF THE INVENTION

Human African trypanosomiasis (HAT or Sleeping Sickness), Nagana, Chagas disease and Leishmaniasis are serious infections caused by protozoa of the order Kinetoplastidae. They were described over a century ago by seminal work of different physician-researchers and, despite the initial discoveries, few drugs have been made available for the treatment of these infections. A growing interest in the development of effective drugs for the specific therapy of protozoan parasitic infections such as Chagas' disease, sleeping sickness and leishmaniasis has produced a vast amount of data and generated potential new targets for chemotherapy. Recently, a variety of novel approaches using drugs already established for other illnesses has emerged based on an increasing understanding of the parasite's biochemical, physiological and metabolic aspects. Several of those advances were results of the genomic revolution caused by the data emerging from the genome efforts on *Trypanosoma* and *Leishmania* (M. T. A. da Silva et al. *Experimental Parasitology*, Vol 166, 2016, pp. 189-193).

The organisms that cause such diseases are classified together as trypanosomatids and share many distinctive and unique characteristics, for example the kinetoplast, glycosomes, the enzyme trypanothione reductase, and an extensive microtubular skeleton, although the phylogenetic trees based upon molecular parameters show a divergence in this group of organisms.

Trypanosomes are unicellular parasitic protozoa belonging to the *Trypanosoma* genus of the Trypanosomatidae class. A large number of species and subspecies of Trypanosomes have been described. Different species of trypanosomes infect a variety of different vertebrates, including animals and humans. Most species are transmitted by insects, in particular by the tse-tse flies (*Glossina* genus).

*Leishmania* is a genus of trypanosomes that are responsible for the disease leishmaniasis. *Leishmania* parasites are transmitted through the bites of infected female phlebotomine sandflies. The epidemiology of leishmaniasis depends on the characteristics of the parasite species, the local ecological characteristics of the transmission sites, current and past exposure of the human population to the parasite, and human behaviour. Some 70 animal species, including humans, have been found as natural reservoir hosts of *Leishmania* parasites.

Human African trypanosomiasis (HAT), is a vector-transmitted disease caused by two subspecies of the digenetic protozoan parasite *Trypanosoma brucei*, namely, *T. brucei gambiense*, which is found in West Africa and responsible for more than 95% of the cases of the disease, and *T. brucei rhodesiense* in East Africa, which is responsible for the other 5% of the cases. A third subspecies, *T. brucei brucei*, is unable to infect primates, although it is genotypically very similar to the two pathogenic subspecies, making it a good experimental model. *T. brucei* is also the causative agent of the Animal African Trypanosomiasis (AAT). In animals, tsetse-vectored trypanosomiases include nagana, souma, and surra according to the animal infected and the trypanosome species involved (*T. brucei brucei, T. congolensis, T. vivax, T. evansis*).

HAT is endemic in 36 sub-Saharan Africa countries where the vector, the parasite, and the animal reservoir coexist. It has a fatal outcome if left untreated. Although the number of reported cases dropped from 37,385 in 1998 to 9689 in 2009, many remain unreported—and therefore untreated—due to the lack of specificity of the clinical diagnostic and the limited access to the infected populations.

Because there are no vaccines available, drugs remain the main control strategy for HAT. There are several approved drugs for chemotherapy. Suramin, pentamidine, and melarsoprol are the most widely used and were developed before 1950. Eflornithine was approved in 1990, and since then advances in HAT treatment have been slow. Furthermore, current treatments possess several limitations, such as limited efficacy and severe side effects due to toxicity, including mortality due to treatment. Nifurtimox, a drug used for the treatment of Chagas disease, was introduced in 2009 in the World Health Organization's (WHO) List of Essential Medicines to be used as part of the nifurtimoxeflornithine combination therapy (NECT), providing a treatment less favourable toward the development of drug resistance and simpler to administer than the eflornithine monotherapy.

Many of the compounds which are approved for treatment of sleeping sickness also have significant side effects as the compounds do not differentiate between human and *Trypanosoma brucei* targets. Thus, there is still a need to identify alternative, improved and/or more selective drugs for the treatment of kinetoplastid infection, in particular sleeping sickness.

WO2016/004297 describes compounds which can be used to treat human African trypanosomiasis, including a 4-amino-2-piperidone and a tetracyclic tetrahydro-beta-carboline. Such compounds are selective inhibitors of the methionyl t-RNA synthetase of *Trypanosoma brucei*.

US2003134846 discloses a method of treating and or preventing infections of *Trypanosoma brucei* by administering to a patient, in need of such treatment, an effective amount of a Farnesyl Protein Transferase Inhibitor alone or in combination with an additional anti-*Trypanosoma brucei* agent and/or an anti-*Trypanosoma brucei* resistance reversing agent.

WO2009026858 relates to the synthesis and evaluation of acridinone derivatives as anti-parasitic, anti-fungal and anti-viral agents. Said derivatives have an activity against *Plasmodium falciparum, Trypanosoma brucei* and *Trypanosoma cruzi* protozoans, as well as *Microsporum canis* and strains of the Junin virus and Dengue.

In view of the known deficiencies of the established therapeutic approaches and of the state of the art in the search of novel series of kinetoplastid infection inhibitors, the technical problem underlying the present invention can be seen as the provision of alternative or improved means and methods of treating or preventing kinetoplastid infection, in particular Human African Trypanosomiasis, Animal African Trypanosomiasis and *Leishmania*.

SUMMARY OF THE INVENTION

In this invention it is shown that a series of compounds are able to specifically inhibit the growth of kinetoplastid parasites. In particular, the compounds of the invention are very potent inhibitors of the growth of *Trypanosoma brucei* parasites without displaying significant toxicity against human cell lines. Further, the compounds possess a good pharmacokinetic profile, blood brain barrier permeability and are several fold selectively toxic to parasites with respect to host cells.

Although there are differences in the biochemistry of trypanosomes and leishmanias, different compounds are known to be active for the treatment of both HAT and leishmaniasis, such as pentamidine (Croft S L, Brun R, Drugs against parasitic diseases: R&D methodologies and issues, 2003, pp. 165-175), auranofine (M. T. A. da Silva et al. *Experimental Parasitology*, Vol 166, 2016, pp. 189-193) or azasterols derivatives (Lorente S O et al. *antimicrob. Agents Chemother,* 2004, 48(8), pp. 2937-50). Moreover various experimental inhibitors of trypanothione reductase (TryR) also have lethal activity against trypanosomes and *leishmania* in vitro (Werbovetz, K. A. (2000) Target-based drug discovery for malaria, leishmaniasis, and trypanosomiasis. Current Medicinal Chemistry, 7: 835-860).

It is therefore an object of the invention a compound of general formula (I):

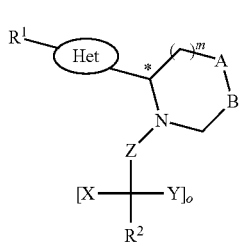

(I)

wherein:
* indicates a stereogenic center;
A is absent, or is N—$(CH_2)_p R^3$, O, S, $SO_2$, CH—$N(R^4)$ $(CH_2)_p R^5$ or CH—$OR^6$;
B is absent, or is $(CH_2)_n$ or CO;
Z is absent, or is CO, $SO_2$, $CONR^a$ or COO;
X and Y are each independently selected from H, $C_{1-6}$alkyl, halo-$C_{1-6}$alkyl, $C_{1-6}$alkoxy or X and Y are linked together forming a ring selected from cyclopropyl, cyclobutyl, cyclopentyl or cyclo hexyl;
m and n are selected from 1 or 2, with the proviso that at least one of m and n must be equal to 1;
o and p are independently selected from 0, 1 or 2;
Het is a 5 membered heterocycle selected from 1H-imidazole, 4H-1,2,4-triazole, 1,3,4-oxadiazole, 1,2,4-oxadiazole or oxazole;
$R^1$ is a substituent selected from naphthalen-2-yl, 2-methoxyquinolin-3-yl, pyrimidin-5-yl, 1-methyl-1H-pyrazol-4-yl, 1-methyl-1H-indazol-5-yl, oxazol-4-yl, quinoxalin-6-yl, 1H-pyrazol-1-yl, quinolin-6-yl, isoquinolin-7-yl, quinolin-5-yl, 2-methoxy-6-phenylpyridin-3-yl, 4-(1H-pyrazol-1-yl)phenyl, 1H-pyrrolo[2,3-b]pyridin-5-yl, 3H-imidazo[4,5-b]pyridin-6-yl, benzo[d]thiazol-6-yl, 1H-indol-2-yl, 1H-pyrrolo[2,3-b]pyridin-3-yl, 1-benzyl-1H-pyrazol-4-yl, 2-cyclopropylpyrimidin-5-yl, pyridin-2-yl-ethynyl, 2-methoxy-5-phenylpyridin-3-yl, isoquinolin-3-yl, quinolin-3-yl, 1H-benzo[d]imidazol-5-yl, 2-methoxypyridin-3-yl, 6-(1H-pyrazol-1-yl)pyridin-3-yl, 4-pyridin-2-yl-phenyl, 4-pyridin-3-yl-phenyl, 4-pyridin-4-yl-phenyl, quinolin-2-yl, pyrazin-2-yl-ethynyl, pyridin-4-yl-ethynyl, pyridazin-3-yl-ethynyl, 5-methylpyridin-2-yl, styryl; any of which being optionally further substituted with one or more groups independently chosen from cyano, halogen, hydroxy, $C_{1-6}$alkyl, $C_{3-10}$cycloalkyl, $C_{1-6}$alkoxy, halo$C_{1-6}$alkoxy, $N(R^a)_2$, $C_{1-6}$alkyl-$N(R^a)_2$, $SO_2N(R^a)_2$;

each $R^a$ is independently selected from hydrogen, $C_{1-6}$ alkyl, $C_{6-10}$aryl, or $N(R^a)_2$ is a cyclic amine selected from pyrrolidine, pyperidine, pyperazine, N-methylpiperazine, morpholine, thiomorpholine, azetidine;

$R^2$ is selected from H, $C_{6-10}$aryl, $C_{6-10}$aryl-$SO_2$, $C_{3-15}$ heterocyclyl, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, 8-13 membered unsaturated or partially saturated heterocycle containing heteroatoms independently selected from O, N and S wherein each of said ring is optionally substituted by one or more groups independently chosen from $C_{1-6}$ alkyl, $C_{1-6}$ alkoxy, halogen, cyano, hydroxyl, halo-$C_{1-6}$alkyl, $CONH_2$, $SO_2C_{1-6}$alkyl, $C_{3-10}$cycloalkyl, benzyl, tetrahydrofuranyl, 2-oxoimidazolidinyl, phenyl or 6 membered unsaturated heterocycle containing 1, 2 or 3 nitrogen atoms wherein said phenyl and 6 membered unsaturated heterocycle are optionally substituted with one or more methyl or methoxy groups;

$R^3$ is selected from H, $C_{1-6}$alkyl, $C_{1-6}$alkylsulphonyl, N,N-dimethylsulphamoyl, 4-oxohexanoyl, 4-oxohexyl, 4-hydroxyhexyl, 4-methoxy-4-oxobutyl, 4-amino-4-oxobutyl, 4-methylamino4oxobutyl, 3-carboxypropyl, oxetan-3-yl, tetrahydrofuran-3-yl, tetrahydro-2H-pyran-4-yl, tetrahydro-2H-thiopyran-4-yl, 1,1-dioxidotetrahydro-2H-pyran-4-yl, piperidin-4-yl, $C_{3-10}$ cycloalkyl, phenyl, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, tetrahydrofuran-3-carbonyl, piperidine-4-carbonyl, 1H-pyrazole-4-carbonyl, any of which substituent being optionally substituted with one or more groups selected from halogen, $C_{1-6}$ alkyl, $C_{1-6}$ alkoxy;

$R^4$ is H or $C_{1-6}$ alkyl;

$R^5$ is selected from H, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, oxetan-3-yl, tetrahydrofuran-3-yl, tetrahydro-2H-pyran-4-yl, $C_{3-10}$ cycloalkyl, any of said rings being optionally substituted with one or more substitutent selected from halogen, hydroxyl, $C_{1-6}$ alkyl, $C_{1-6}$ alkoxy;

or $R^4$ and $R^5$ are linked together forming a cyclic amine ring selected from aziridine, azetidine, pyrrolidine, piperidine, morpholine, thiomorpholine or piperazine;

$R^6$ is selected from linear or branched $C_{1-6}$ alkyl, $C_{3-10}$ cycloalkyl, phenyl-$C_{1-3}$alkyl, heteroaryl-$C_{1-3}$alkyl;

and pharmaceutically acceptable salts, tautomers, stereoisomers thereof.

Still preferably, the compound as described above has general formula (II):

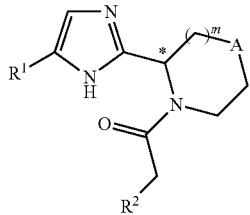

wherein A is as defined above;
m is selected from 1 or 2;
$R^1$ is a substituent selected from naphthalen-2-yl, 2-methoxyquinolin-3-yl, 1-methyl-1H-indazol-5-yl, quinoxalin-6-yl, quinolin-6-yl, isoquinolin-7-yl, quinolin-5-yl, 2-methoxy-6-phenylpyridin-3-yl, 4-(1H-pyrazol-1-yl)phenyl, 1H-pyrrolo[2,3-b]pyridin-5-yl, 3H-imidazo[4,5-b]pyridin-6-yl, benzo[d]thiazol-6-yl, 1H-indol-2-yl, 1H-pyrrolo[2,3-b]pyridin-3-yl, 2-methoxy-5-phenylpyridin-3-yl, isoquinolin-3-yl, quinolin-3-yl, 1H-benzo[d]imidazol-5-yl, 6-(1H-pyrazol-1-yl)pyridin-3-yl; any of which being optionally further substituted with one or more groups independently chosen from cyano, halogen, hydroxy, $C_{1-6}$alkyl, $C_{3-10}$cycloalkyl, $C_{1-6}$alkoxy, halo$C_{1-6}$alkoxy, $N(R^a)_2$, $C_{1-6}$alkyl-$N(R^a)_2$, $SO_2N(R^a)_2$;
$R^2$ is 8-13 membered unsaturated or partially saturated heterocycle containing heteroatoms independently selected from O, N and S, optionally substituted by one or more groups independently chosen from $C_{1-6}$alkyl, $C_{1-6}$alkoxy, halogen, cyano, hydroxyl, halo-$C_{1-6}$alkyl, $CONH_2$, $SO_2C_{1-6}$ alkyl, $C_{3-10}$cycloalkyl; and pharmaceutically acceptable salts, tautomers, stereoisomers thereof. In a preferred embodiment A is N—$CH_2$—$R^3$, and $R^3$ is selected from H, cyclopropyl, difluoromethyl, trifluoromethyl, cyclobutyl, tetrahydrofuran-3-yl, oxetan-3-yl, phenyl, 2-fluorophenyl, thiazol-2-yl, furan-3-yl, pyridin-3-yl, pyridin-2-yl, 1-methyl-1H-pyrazol-3-yl, 1-methyl-1H-pyrazol-4-yl, 2-methoxypyrimidin5-yl, pyrazyn-2-yl, 1-methyl-1H-1,2,3-triazol-4-yl, oxazol-4-yl, isoxazol-3-yl, thiazol-4-yl, 5-methyl-1,2,4-oxadiazol-3-yl, oxazol-2-yl, pyrimidin-5-yl, 5-fluoropyridin-3-yl, pyrazine-2-yl; (pyridin-2-yl)methyl; (1H-pyrazol-1-yl)methyl; (4H-1,2,4-triazol-4-yl)methyl; (2-methylthiazol-4-yl)methyl; (1-methyl-1H-pyrazol-5-yl)methyl; (isoxazol-4-yl)methyl; 5-methyl-1,2,4-oxadiazol-3-yl; oxazol-2-yl; isoxazol-3-yl and pharmaceutically acceptable salts, tautomers, stereoisomers thereof.

In a further preferred embodiment $R^2$ is selected from 5-methoxy-2-methyl-1H-indol-3-yl, 1H-indol-3-yl, 1-methyl-1H-indol-3-yl, 1H-pyrrolo[2,3-b]pyridin-3-yl, 5-fluoro-2-methyl-1H-indol-3-yl, 3-methylbenzo[b]thiophen-2-yl, 5-methoxy-1-H-indol-3-yl, 2-methyl-1H-benzo[d]imidazol-1-yl, 5,6-difluoro-2-methyl-1H-benzo[d]imidazol-1-yl, 2-trifluoromethyl-1H-benzo[d]imidazol-1-yl, 2-cyclopropyl-1H-benzo[d]imidazol-1-yl, 5-methoxybenzo[d]isoxazol-3-yl, (6-methoxy-2-methyl-1H-benzo[d]imidazol-1-yl, (6-methoxy-2-methyl-1H-indol-1-yl) and (6-methoxy-2-(trifluoromethyl)-1H-benzo[d]imidazol-1-yl) and pharmaceutically acceptable salts, tautomers, stereoisomers thereof.

Preferably, in the compound of the invention the stereogenic center marked by * is in the S-configuration in enantiomerically resolved state; still preferably the stereogenic center marked by * is in the R-configuration in enantiomerically resolved state.

It is a further object of the invention a compound selected from the following list:
6-(4-(2-(5-methoxy-2-methyl-1H-indol-3-yl)acetyl)-3-(5-(naphthalen-2-yl)-1H-imidazol-2-yl)piperazin-1-yl)hexan-3-one;
1-(4-hexyl-2-(5-(naphthalen-2-yl)-1H-imidazol-2-yl)piperazin-1-yl)-2-(5-methoxy-2-methyl-1H-indol-3-yl)ethan-1-one;
2-(5-methoxy-2-methyl-1H-indol-3-yl)-1-(4-methyl-2-(5-(naphthalen-2-yl)-1H-imidazol-2-yl)piperazin-1-yl)ethan-1-one;
1-(4-(4-hydroxyhexyl)-2-(5-(naphthalen-2-yl)-1H-imidazol-2-yl)piperazin-1-yl)-2-(5-methoxy-2-methyl-1H-indol-3-yl)ethan-1-one;
6-(4-(2-(5-methoxy-2-methyl-1H-indol-3-yl)acetyl)-3-(5-(2-methoxyquinolin-3-yl)-1H-imidazol-2-yl)piperazin-1-yl)hexan-3-one;
1-(4-(cyclopropylmethyl)-2-(5-(naphthalen-2-yl)-1H-imidazol-2-yl)piperazin-1-yl)-2-(5-methoxy-2-methyl-1H-indol-3-yl)ethan-1-one;
2-(5-methoxy-2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one;
2-(2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one;
2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one;
2-(5-methoxy-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one;
2-(5-fluoro-2-methyl-1H-indol-3-yl)-1-(2-(5-(2-methoxyquinolin-3-yl)-1H-imidazol-2-yl)-4-(thiazol-2-ylmethyl)piperazin-1-yl)ethan-1-one;
1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one;
2-(5-fluoro-2-methyl-1H-indol-3-yl)-1-(2-(5-(2-methoxyquinolin-3-yl)-1H-imidazol-2-yl)-4-(pyrazin-2-ylmethyl)piperazin-1-yl)ethan-1-one;
1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one;
1-((S)-2-(5-(2-methoxyquinolin-3-yl)-1H-imidazol-2-yl)-4-(((S)-tetrahydrofuran-3-yl)methyl)piperazin-1-yl)-2-(2-(trifluoromethyl)-1H-benzo[d]imidazol-1-yl)ethan-1-one;
1-((S)-2-(5-(2-methoxyquinolin-3-yl)-1H-imidazol-2-yl)-4-(((R)-tetrahydrofuran-3-yl)methyl)piperazin-1-yl)-2-(2-(trifluoromethyl)-1H-benzo[d]imidazol-1-yl)ethan-1-one;
(S)-1-(2-(5-(2-methoxyquinolin-3-yl)-1H-imidazol-2-yl)-4-((1-methyl-1H-pyrazol-3-yl)methyl)piperazin-1-yl)-2-(2-(trifluoromethyl)-1H-benzo[d]imidazol-1-yl)ethan-1-one;
(S)-1-(4-(isoxazol-3-ylmethyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
(S)-1-(2-(5-(2-methoxyquinolin-3-yl)-1H-imidazol-2-yl)-4-(thiazol-4-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(thiazol-2-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(pyridin-3-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(pyridin-2-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(oxetan-3-yl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(tetrahydro-2H-pyran-4-yl)piperazin-1-yl)-2-(2-(trifluoromethyl)-1H-benzo[d]imidazol-1-yl)ethan-1-one;

(S)-1-(4-benzyl-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;

(S)-1-(4-(1-acetylpiperidin-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;

(S)-1-(4-(4,4-difluorocyclohexyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-((5-methyl-1,2,4-oxadiazol-3-yl)methyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(oxazol-2-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(oxazol-4-ylmethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(2,2,2-trifluoroethyl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(pyrimidin-5-ylmethyl)piperazin-1-yl)-2-(2-(trifluoromethyl)-1H-benzo[d]imidazol-1-yl)ethan-1-one;

(S)-1-(4-((5-fluoropyridin-3-yl)methyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(oxetan-3-ylmethyl)piperazin-1-yl)-2-(2-(trifluoromethyl)-1H-benzo[d]imidazol-1-yl)ethan-1-one;

(S)-1-(4-(1,1-dioxidotetrahydro-2H-thiopyran-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;

(S)-1-(2-(5-(2-methoxyquinolin-3-yl)-1H-imidazol-2-yl)-4-(pyrazin-2-ylmethyl)piperazin-1-yl)-2-(2-(trifluoromethyl)-1H-benzo[d]imidazol-1-yl)ethan-1-one;

2-(5-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-methyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(5,6-dimethoxy-2-(trifluoromethyl)-1H-benzo[d]imidazol-1-yl)-1-((2 S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(2-(tert-butyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

1-((2S)-2-(5-(2-methoxyquinolin-3-yl)-1H-imidazol-2-yl)-4-((tetrahydrofuran-3-ylmethyl)piperazin-1-yl)-2-(2-methyl-6-(trifluoromethyl)-1H-benzo[d]imidazol-1-yl)ethan-1-one;

2-(6-methoxy-2-methyl-1H-indol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-(trifluoromethyl)-1H-benzo[d]imidazol-1-yl)-1-(2-(5-(2-methoxyquinolin-3-yl)-1H-imidazol-2-yl)piperidin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-((tetrahydrofuran-3-yl)methyl)-1,4-diazepan-1-yl)ethan-1-one;

2-(6-methoxy-2-methyl-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one;

1-(4-(2-(1H-pyrazol 11-yl)ethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol 11-yl)ethan-1-one;

(S)-2-(6-methoxy-2-(trifluoromethyl)-1H-benzo[d]imidazol-1-yl)-1-(2-(5-(2-methoxyquinolin-3-yl)-4H-1,2,4-triazol-3-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(pyridin-2-ylmethyl)-1,4-diazepan-1-yl)ethan-1-one (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(pyridin-2-yl)ethyl)piperazin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(2-methylthiazol-4-yl)ethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(2-(1-methyl-1H-pyrazol-5-yl)ethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one;

(S)-1-(4-(2-(isoxazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

1-((2S,4S)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one;

2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(thiazol-2-ylmethyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((thiazol-2-ylmethyl)amino)piperidin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-4-ylmethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-4-ylmethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-2-ylmethyl)-1,4-diazepan-1-yl)ethan-1-one;

1-(4-(isoxazol-3-ylmethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazo-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((tetrahydrofuran-3-yl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(tetrahydrofuran-3-yl)amino)piperidin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-4-ylmethyl)piperazin-1-yl)ethan-1-one;

(S)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyrazin-2-ylmethyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-pyrazol-3-yl)methyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one;

(S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

1-(4-(1,1-dioxidotetrahydro-2H-thiopyran-4-yl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazo-1-yl)ethan-1-one;

1-((2S,4S)-4-((isoxazol-3-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((tetrahydrofuran-3-yl)methyl)amino)piperidin-1-yl)ethan-1-one;

1-((2 S,4S)-4-((2-(1H-pyrazol-1-yl)ethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(oxetan-3-ylamino)piperidin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-1,2,4-triazol-5-yl)methyl)piperazin-1-yl)ethan-1-one;

1-((2S,4S)-4-(isopropylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyridazin-4-ylmethyl)piperazin-1-yl)ethan-1-one;

1-((2S,4S)-4-(isobutylamino)-2-(5-(2-methoxyquinolin-3-yl)-1H-imidazol-2-yl)piperidin-1-yl)-2-(6-methoxy-2-(trifluoromethyl)-1H-benzo[d]imidazo-1-yl)ethan-1-one;

1-((2S,4S)-4-(cyclobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(R)-2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

1-((2S,4S)-4-(isopropyl((1-methyl-1H-pyrazol-3-yl)methyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((S)-tetrahydrofuran-3-yl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((R)-tetrahydrofuran-3-yl)amino)piperidin-1-yl)ethan-1-one;

1-((2S,4S)-4-((2-hydroxyethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyridin-2-ylmethyl)amino)piperidin-1-yl)ethan-1-one;

2-(6-methoxy-2-(trifluoromethyl)-1H-benzo[d]imidazol-1-yl)-1-((2S)-2-(5-(2-methoxyquinolin-3-yl)-1H-imidazol-2-yl)-4-(methyl(pyrazin-2-ylmethyl)amino)piperidin-1-yl)ethan-1-one;

2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((1-methyl-1H-pyrazol-3-yl)methyl)amino)piperidin-1-yl)ethan-1-one;

1-((2S,4S)-4-methoxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

1-((2S,4S)-4-methoxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one;

1-((2S)-4-hydroxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-imidazol-5-yl)methyl)amino)piperidin-1-yl)ethan-1-one;

1-((2S,4S)-4-(ethyl(tetrahydrofuran-3-yl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one;

2-(6-methoxy-2-(trifluoromethyl)-1H-benzo[d]imidazol-1-yl)-1-((2S,4S)-4-((3-methoxycyclobutyl)amino)-2-(5-(2-methoxyquinolin-3-yl)-1H-imidazol-2-yl)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((oxetan-3-ylmethyl)amino)piperidin-1-yl)ethan-1-one;

2-(5-methoxy-2-methyl-1H-indol-3-yl)-1-(2-(5-(2-methoxyquinolin-3-yl)-1H-imidazol-2-yl)-4-methylpiperazin-1-yl)ethan-1-one;

1-(2-(5-(2-methoxyquinolin-3-yl)-1H-imidazol-2-yl)-4-((tetrahydrofuran-3-yl)methyl)piperazin-1-yl)-2-(2-methyl-1H-benzo[d]imidazo-1-yl)ethan-1-one;

2-(5-fluoro-2-methyl-1H-indol-3-yl)-1-(2-(5-(2-methoxyquinolin-3-yl)-1H-imidazol-2-yl)-4-((1-methyl-1H-pyrazol-4-yl)methyl)piperazin-1-yl)ethan-1-one;

2-(5-fluoro-2-methyl-1H-indol-3-yl)-1-(2-(5-(2-methoxyquinolin-3-yl)-1H-imidazol-2-yl)-4-(tetrahydro-2H-pyran-4-yl)piperazin-1-yl)ethan-1-one;

2-(5-fluoro-2-methyl-1H-indol-3-yl)-1-(2-(5-(2-methoxyquinolin-3-yl)-1H-imidazol-2-yl)-4-methylpiperazin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(pyrrolidin-1-yl)piperidin-1-yl)ethan-1-one;

1-((2S,4S)-4-((isoxazol-4-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,5R)-2-(5-(2-methoxyquinolin-3-yl)-1H-imidazol-2-yl)-5-((tetrahydrofuran-3-yl)amino)piperidin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(oxetan-3-ylmethyl)piperazin-1-yl)ethan-1-one;

2-(6-methoxy-2-methyl-1H-indol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(5-methoxy-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(5-fluoro-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

1-(7-(5-(2-methoxyquinolin-3-yl)-1H-imidazol-2-yl)-4-((1-methyl-1H-pyrazol-3-yl)methyl)-1,4-diazepan-1-yl)-2-(2-(trifluoromethyl)-1H-benzo[d]imidazol-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydrofuran-3-yl)-1,4-diazepan-1-yl)ethan-1-one;

1-(4-cyclobutyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one 1-((2S)-4-((1-acetylpyrrolidin-3-yl)methyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydro-2H-pyran-4-yl)-1,4-diazepan-1-yl)ethan-1-one and pharmaceutically acceptable salts, tautomers, stereoisomers thereof.

It is an object of the invention the compound as defined above for medical use. Preferably, the compounds of the invention are for use in the treatment or prevention of a kinetoplastid infection.

In a preferred embodiment the kinetoplastid infection is a *Trypanosoma* infection or a *Leishmania* infection, still preferably the *Trypanosoma* infection is a *Trypanosoma brucei* infection.

It is a further object of the invention a pharmaceutical composition comprising an effective amount of one or more compounds according to anyone of the previous claims, either alone or in combination with at least one further active compound, and at least one pharmaceutically acceptable excipient.

Preferably said pharmaceutical composition is for use in the treatment or prevention of a kinetoplastid infection, preferably a *Trypanosoma* infection or a *Leishmania* infection.

In a preferred embodiment, said pharmaceutical composition comprises at least one further active compound selected from the group consisting of: agents useful for treating or preventing parasitic diseases, including malaria, toxoplasmosis, trypanosomiasis, Chagas disease, leishmaniasis, schistosomiasis, amebiasis, giardiasis, clonorchiasis, fasciolopsiasis, lymphatic filariasis, onchocerciasis, thricomoniasis and cestodiasis, anti-inflammatory agents, anti-pain agents and antipyretic agents.

Preferably the further active compound is selected from the group consisting of: cloroquine, proguanil, mefloquine, quinine, pyrimethamine-sulphadoxine, doxocycline, berberine, halofantrine, primaquine, atovaquone, pyrimethamine-dapsone, artemisinin, meglumine antimonite, sodium stibogluconate, amphotericin B, praziquantel, oxamniquine, Suramin, pentamidine, and melarsoprol, Eflornithine, Nifurtimox.

It is a further object of the invention a method for the synthesis of the compounds of general formula (I) or (II) as defined above.

In a preferred embodiment the technical effect of compounds of the invention is to exert a selective toxicity for parasites with respect to host cells, namely a selective killing and/or growth-inhibiting activity of said parasites in a mammal.

The skilled person shall select suitable dosages and regimens to have compounds of the invention exert their selective toxicity and/or killing and/or growth inhibiting activity on parasites.

The present invention includes within its scope prodrugs of the compounds of formula (I) or (II). In general, such prodrugs will be functional derivatives of the compounds of formula (I) or (II) which are readily convertible in vivo into the required compound of formula (I) or (II). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable occurs more than one time in any constituent, its definition on each occurrence is independent of every other occurrence. Also, combinations of substituents and variables are permissible only if such combinations result in stable compounds.

It is understood that substituents and substitution patterns on the compounds of the instant invention can be selected by one of ordinary skill in the art to provide compounds that are chemically stable and that can be readily synthesized from readily available starting materials by techniques known in the art, as well as those methods set forth below. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_{1-6}$ alkyl" is defined to include groups having 1, 2, 3, 4, 5 or 6 carbons in a linear or branched arrangement. For example, "$C_{1-6}$ alkyl" specifically includes methyl, ethyl, n-propyl, i-propyl, n-butyl, t-butyl, i-butyl, pentyl, hexyl, and so on. The term "cycloalkyl" means a monocyclic, bicyclic or polycyclic saturated aliphatic hydrocarbon group having the specified number of carbon atoms. For example, "$C_{3-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy.

The terms "haloC$_{1-6}$alkyl" and "haloC$_{1-6}$alkoxy" mean a C$_{1-6}$alkyl or C$_{1-6}$alkoxy group in which one or more (in particular, 1 to 3) hydrogen atoms have been replaced by halogen atoms, especially fluorine or chlorine atoms. Preferred are fluoroC$_{1-6}$alkyl and fluoroC$_{1-6}$alkoxy groups, in particular fluoroC$_{1-3}$alkyl and fluoroC$_{1-3}$alkoxy groups, for example, CF$_3$, CHF$_2$, CH$_2$F, CH$_2$CH$_2$F, CH$_2$CHF$_2$, CH$_2$CF$_3$, OCF$_3$, OCHF$_2$, OCH$_2$F, OCH$_2$CH$_2$F, OCH$_2$CHF$_2$ or OCH$_2$CF$_3$, and most especially CF$_3$, OCF$_3$ and OCHF$_2$.

The term "hydroxyC$_{1-6}$alkyl" means a C$_{1-6}$alkyl group in which one or more (in particular, 1 to 3) hydrogen atoms have been replaced by hydroxy groups. Preferred are CH$_2$OH, CH$_2$CHOH and CHOHCH$_3$.

As used herein, the term "C$_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "C$_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "C$_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

As used herein, "heteroaryl" is intended to mean any stable monocyclic or bicyclic ring containing 1, 2, 3 or 4 heteroatoms independently selected from N, O and S, wherein at least one ring is aromatic. In particular the term heteroaryl includes 5 membered aromatic heterocycles containing 1, 2, 3 or 4 heteroatoms independently selected from N, O and S, but not more than one of which is O or S; 6 membered aromatic heterocycles containing 1, 2 or 3 nitrogen atoms; or a 7-13 membered aromatic heterocycle containing heteroatoms independently selected from N, O or S of 5 to 10 atoms, wherein at least one ring is aromatic.

Examples of particular heteroaryl of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl, imidazolyl, imidazothiazolyl, indolinyl, indolyl, indolizinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, oxoquinazolinyl isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolyl, quinoxalinyl, quinolizinyl, tetrazolyl, tetrazolopyridyl, thiadiazolyl, thiazolidinyl, thiazolyl, thienyl, triazolyl, imidazopyridinyl, phthalazinyl, naphthyridinyl, quinazolinyl, pteridinyl and N-oxides thereof. Attachment of a heterocycles substituent can occur via a carbon atom or via a heteroatom.

The term "C$_{3-15}$heterocyclyl" refers to a non-aromatic 3- to 15-member ring radical, which consists of carbon atoms and at least one heteroatom of nitrogen, phosphorus, oxygen or sulfur. The heterocyclic ring may be a mono-, bi-, tri-, or tetracyclic ring system, which may include fused, bridged or spiro ring systems, and the nitrogen, phosphorus, carbon, oxygen, or sulfur atoms in the heterocyclic ring radical may be optionally oxidized to various oxidation states. In addition, the nitrogen atom may be optionally quaternized.

The term C$_{3-15}$heterocyclyl-C$_{1-3}$alkyl refers to a radical of the formula —R$_a$R$_c$ wherein R$_a$ is an alkylene chain having from 1 to 3 carbon atoms and R$_c$ is an heterocyclyl group as defined above.

The term heteroaryl-C$_{1-3}$alkyl refers to a radical of the formula —R$_a$R$_c$ wherein R$_a$ is an alkylene chain having from 1 to 3 carbon atoms and R$_c$ is an heteroaryl group as defined above.

Examples of particular heterocyclyl of the invention are tetrahydrofuranyl, tetrahydropyranyl, tetrahydrothiopyranyl, tetrahydroisoquinolinyl, azetidinyl, 1,4-dioxanyl, hexahydroazepinyl, piperazinyl, piperidyl, pyridin-2-onyl, pyrrolidinyl, imidazolinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, azabicycloheptanyl, chromenonyl, triazolopyrimidinyl, dihydrobenzoxazinyl, thiazolotriazolyl, azoniabicycloheptanyl, azoniabicyclooctanyl. Attachment of a heterocyclyl substituent can occur via a carbon atom or via a heteroatom.

A preferred 4 membered saturated heterocycle is azetidine.

A preferred 5 membered saturated heterocycle is tetrahydrofurane.

Preferred 6 membered saturated or partially saturated heterocycles are pyrrolidinyl, piperidyl, piperazinyl, morpholinyl, thiomorpholinyl and thiazolidinyl.

Preferred 5 membered heteroaryls are thienyl, thiazolyl, pyrazolyl, isoxazolyl, imidazolyl, thiadiazolyl, oxazolyl, triazolyl, tetrazolyl, furyl and oxadiazolyl.

Preferred 6 membered heteroaryls are pyridinyl and pyrymidinyl.

Preferred 8-10 membered heteroaryls are benzothienyl, indolyl, benzothiadiazolyl, benzoxadiazolyl, thiazolotriazolyl, dihydrobenzodioxinyl, dihydrothiazolopyrimidinyl, dihydrobenzoxazinyl, dihydrobenzofuranyl, benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl, triazolopyrimidinyl and tetrahydroquinolinyl.

As used herein, the term 'halogen' refers to fluorine, chlorine, bromine and iodine, of which fluorine, chlorine and bromine are preferred.

Included in the instant invention is the free base of compounds of formula (I), as well as the pharmaceutically acceptable salts and stereoisomers thereof. Some of the specific compounds exemplified herein are the protonated salts of amine compounds. Compounds of formula (I) containing one or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of formula (I). The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reaction of the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reaction of a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. Preferably, a pharmaceutically acceptable salt of this invention contains one equivalent of a compound of formula (I) and 1, 2 or 3 equivalent of an inorganic or organic acid. More particularly, pharmaceutically acceptable salts of this invention are the tartrate, trifluoroacetate or the chloride salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention find use in a variety of applications for human and animal health. As used herein, the term "kinetoplastid infection" refers to a pathological condition in a host organism caused by infection or infestation by a kinetoplastid parasite in said host organism. Analogous definitions apply for "*trypanosoma* infection", "*leishmania* infection" and any other parasite infection mentioned in the present application. For example, kinetoplastid infections include but are not limited to: Human African Trypanosomiasis (HAT or Sleeping Sickness), Nagana, Chagas disease, Leishmaniasis, Animal African Trypanosomiasis (AAT), souma, and surra.

Kinetoplastids are a group of flagellated protozoan parasites that are human pathogens with devastating health and economic effects. They include the *Trypanosoma* and *Leishmania* species. They are motile protozoans with a single flagellum that originates near their large single mitochondrion and emanates from a pocket in the cell membrane, where endocytosis also occurs; their peroxisomes are modified to perform glycolysis and are therefore known as "glycosomes;" their cell membrane is underlain with a sheet of microtubules and is highly decorated with species-specific molecules that are critical for their survival; they typically grow asexually, and although sexual recombination has been shown for *T. brucei*, inferred for *T. cruzi*, and might occur in some species of *Leishmania*, it is not obligate in any; and they divide by binary fission during which their nucleus does not undergo membrane dissolution or chromosome condensation (K. Stuart et al., *J Clin Invest.*, 2008; 118(4): 1301-1310.).

The compounds of the invention are characterized in that they kill parasites and/or inhibit parasite growth and/or impair parasite reproduction in the host organism, thereby leading to prevention or treatment of parasite infection. In one embodiment, the compounds of the present invention control parasite infestation in the host organism.

The compounds of the invention are selective inhibitors of *Trypanosoma brucei* parasites and can be used in the treatment and/or prevention of *Trypanosoma brucei* infections.

Trypanosomes are unicellular parasitic protozoa belonging to the *Trypanosoma* genus of the Trypanosomatidae class. Trypanosomatids are a group of kinetoplastid protozoa distinguished by having only a single flagellum. All members are exclusively parasitic, found primarily in insects. A few genera have life-cycles involving a secondary host, which may be a vertebrate, invertebrate or plant. These includes several species that cause major diseases in humans. The three major human diseases caused by trypanosomatids are African trypanosomiasis (Sleeping Sickness, caused by *Trypanosoma brucei* and transmitted by Tsetse flies), South American trypanosomiasis (Chagas Disease, caused by *Trypanosoma cruzi* and transmitted by triatomine bugs) and leishmaniasis (a set of trypanosomal diseases caused by various specied of *Leishmania* transmitted by sandflies.

The present invention concerns the use of compounds of general formula (I) for the treatment and/or the prevention of a kinetoplastid infection, including a *Trypanosoma* infection and *Leishmania* infection, in an animal, preferably a mammal, and more preferably a human.

In a more specific embodiment of the invention, said kinetoplastid infection is an infection with a *Trypanosoma* parasite. In other specific embodiments of the invention, said kinetoplastid infection is an infection with a *Leishmania* parasite. In even more particular embodiments of the invention, said kinetoplastid infection is an infection with *Trypanosoma brucei* or *Leishmania donovani*.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution may be then introduced into a water and glycerol mixture and processed to form a microemulstion. The injectable solutions or microemulsions may be introduced into a patient's blood stream by local bolus injection.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the invention are employed. The compounds of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage regimen will normally be determined by the prescribing physician with the dosage generally varying according to the age, weight, sex and response of the individual patient, as well as the severity of the patient's symptoms.

The instant compounds are also useful in combination with known therapeutic agents for simultaneous, separate or sequential administration.

In an embodiment, the compounds of the present invention may be used in combination with known agents useful for treating or preventing parasitic diseases, including malaria, toxoplasmosis, trypanosomiasis, Chagas disease, leishmaniasis, schistosomiasis, amebiasis, giardiasis, clonorchiasis, fasciolopsiasis, lymphatic filariasis, onchocerciasis, thricomoniasis and cestodiasis. Combinations of the presently disclosed compounds with other agents useful for treating or preventing parasitic disease are within the scope of the invention. A person of ordinary skill in the art would be able to discern which combinations of agents would be useful based on the particular characteristics of the drugs and the disease involved.

In particular, existing therapies for malaria include, but are not limited to cloroquine, proguanil, mefloquine, quinine, pyrimethamine-sulphadoxine, doxocycline, berberine, halofantrine, primaquine, atovaquone, pyrimethamine-dapsone, artemisinin and quinhaosu.

Existing therapies for leishmaniasis include, but are not limited to meglumine antimonite, sodium stibogluconate and amphotericin B.

Existing therapies for schistosomiasis include, but are not limited to praziquantel and oxamniquine.

Anti-inflammatory agents include nonsteroidal anti-inflammatory drugs or NSAIDs and indicate a drug class that groups together drugs that provide analgesic (pain-killing) and antipyretic (fever-reducing) effects, and, in higher doses, anti-inflammatory effects.

The term "administration" and variants thereof (e.g., "administering" a compound) in reference to a compound of the invention means introducing the compound or a prodrug of the compound into the system of the subject in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

When a compound of the present invention is administered into a human subject, the daily dosage regimen will normally be determined by the prescribing physician, with the dosage generally varying according to the age, weight, and response of the individual patient, as well as the severity of the patient's symptoms. In one exemplary application, oral dosages of the present invention will range between about 0.01 mg per kg of body weight per day (mg/kg/day) to about 100 mg/kg/day, preferably 0.01 to 10 mg/kg/day, and most preferably 0.1 to 5.0 mg/kg/day.

These and other aspects of the invention will be apparent from the teachings contained herein.

Materials and Methods

A. Chemistry

As used herein, the following abbreviations have the following meanings. If an abbreviation is not defined, it has its generally accepted meaning.

Abbreviations

AcOH: Acetic acid; DCE: 1,2-Dichloroethane; DCM: Dichloromethane; DIPEA: N,N-Diisopropylethylamine; DMAP: 4-(Dimethylamino)pyridine; DME: 1,2-Dimethoxyethane; DMF: Dimethylformamide; DMP: Dess-Martin periodinane; DMSO: Dimethylsulfoxide; EDC.HCl: N-(3-Dimethylaminopropyl)-N'-ethylcarbodiimide hydrochloride; eq: equivalent; ES$^+$: Electrospray Positive Ionisation; EtOAc: Ethyl acetate; EtOH: Ethanol; Et$_2$O: Diethyl ether; h: hour; HATU: 1-[Bis(dimethylamino)methylene]-1H-1,2,3-triazolo[4,5-b]pyridinium 3-oxid hexafluorophosphate; HOBt: 1-Hydroxybenzotriazole hydrate; HBTU: N,N,N',N'-Tetramethyl-O-(1H-benzotriazol-1-yl)uronium hexafluorophosphate; TBAF: Tetrabutylammonium fluoride hydrate; NIS: N-Iodosuccinimide; BOC-ON: 2-(Boc-oxyimino)-2-phenylacetonitrile; HPLC: High Performance Liquid Chromatography; LCMS: Liquid Chromatography Mass Spectrometry; MeCN: Acetonitrile; MeOH: Methanol; NMP: 1-Methyl-2-pyrrolidone; min: minute; DBU: 1,8-Diazabicyclo[5.4.0]undec-7-ene; MP-(OAc)$_3$BH: Macroporous Polystyrene—Sodium triacetoxyborohydride; PS-TBD: 3,4,6,7,8,9-hexahydro-2H-pyrimido[1,2-a]pyrimidine Polimer Supported; PS-BEMP: N-phenyl-tris(di-methylamino)iminophosphorane Polymer Supported; PS-TsNHNH$_2$: Tosyl Hydrazine Polymer Supported; RP: Reverse Phase; SFC: Supercritical fluid chromatography; TBTU: O-(Benzotriazol-1-yl)-N,N,N,N'-tetramethyluronium tetrafluoroborate; TEA: Triethylamine; TFA: Trifluoroacetic acid; THF: Tetrahydrofurane; TsCl: Tosyl chloride; PdCl$_2$(dppf)DCM: 1,1'-Bis(diphenylphosphino)ferrocene] dichloropalladium(II), complex with dichloromethane; (PPh$_3$)$_4$Pd: Tetrakis(triphenylphosphine)palladium(0); UPLC: Ultra High Performance Liquid Chromatography.

Solvents and reagents were obtained from commercial suppliers and were used without further purification. Flash chromatography purifications were performed on prepacked cartridges on a Biotage system. Purity of final compounds were determined using MS and UPLC. UPLC-MS analyses were performed on a Waters Acquity UPLC™, equipped with a diode array and a ZQ mass spectrometer, using an X-Terra C18 column (5 μm, 4.6×50 mm) or a BEH C18 column (1.7 mm, 2.1×50 mm). Mobile phase comprised a linear gradient of binary mixtures of H$_2$O containing 0.1% formic acid (A), and MeCN containing 0.1% formic acid (B). The linear gradient used is: (A): 90% (0.1 min), 90%-0% (2.6 min), 0% (0.3 min), 0%-90% (0.1 min) with a 0.5 mL/min flow. Separation of epimers was obtained by chiral SFC on a Berger SFC™ MiniGram-Mettler Toledo AG using two different methods: Method 1 using a Chiralpak® IA (2×25 cm) as column (flow: 10 ml/min, T$_{col}$ 35° C., Pd: 100 bar, modifier: 30% isopropanol using CO$_2$ as supercritic eluent); Method 2 using Chiralcel® OJ (2×25 cm) as column (flow: 10 ml/min, Td 35° C., P$_{col}$: 100 bar, modifier: 20% MeOH for 13 mins than 30% using CO$_2$ as supercritic eluent).

Purity of final compounds were >95%. All $^1$H spectra were recorded on Bruker AV400 spectrometer at 400 except where indicated. Chemical shift (δ) are reported in parts per million relative to TMS using CDCl$_3$, CD$_3$CN or DMSO-d$_6$ as solvent. Coupling costants (J) are reported in Hertz (Hz). Multiplicities are reported as singlet (s), broad (br), doublet (d), doublet of doublets (dd), doublet of doublets of doublets (ddd), triplet (t), doublet of triplet (dt) or multiplet (m). Unless indicated, spectra were acquired at 300 K. Temperatures are expressed in degrees Celsius (° C.) and are uncorrected.

Where the synthesis of intermediates and starting materials is not described, these compounds are commercially available or can be made from commercially available compounds by standard methods or by extension of the Examples herein. During any of the synthetic sequences described herein it may be necessary and/or desirable to protect sensitive or reactive groups on any of the molecules concerned. This may be achieved by means of conventional protecting groups, such as those described in Protecting Groups in Organic Synthesis (3$^{rd}$ Edition, Greene, T. W. and Wuts, P. G. M.; Wiley Interscience, 1999) and Protecting Groups (Kocienski, P. J.; Thieme, 1994). The protecting groups may be removed at a convenient subsequent stage using methods known from the art. For example, when the Boc protecting group is present, it may be removed by the addition of solvents such as TFA and DCM. The compound may also be hydrogenated using standard methods, such as treating with a catalyst such as Pd/C, in a solvent such as methanol in a hydrogen atmosphere.

The compounds, or pharmaceutically acceptable salts thereof, compositions, and methods described herein are further illustrated by the following non-limiting examples.

DETAILED DESCRIPTION OF THE INVENTION

Example 1

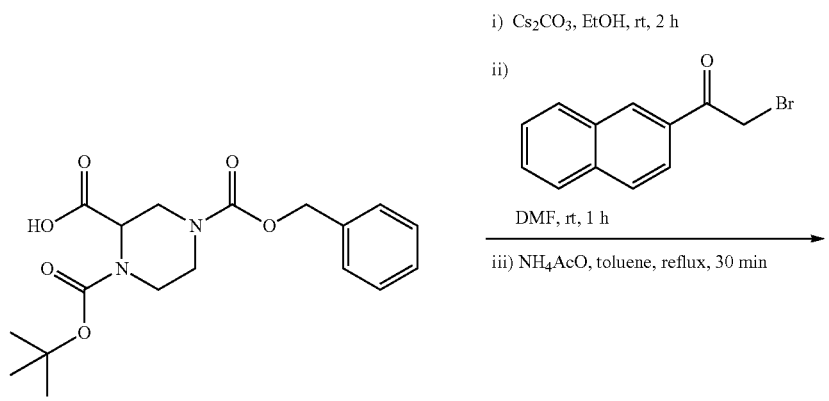

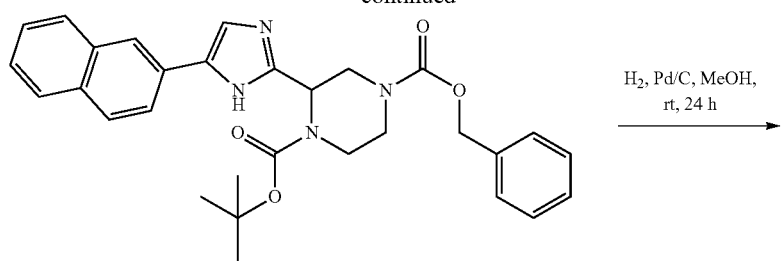
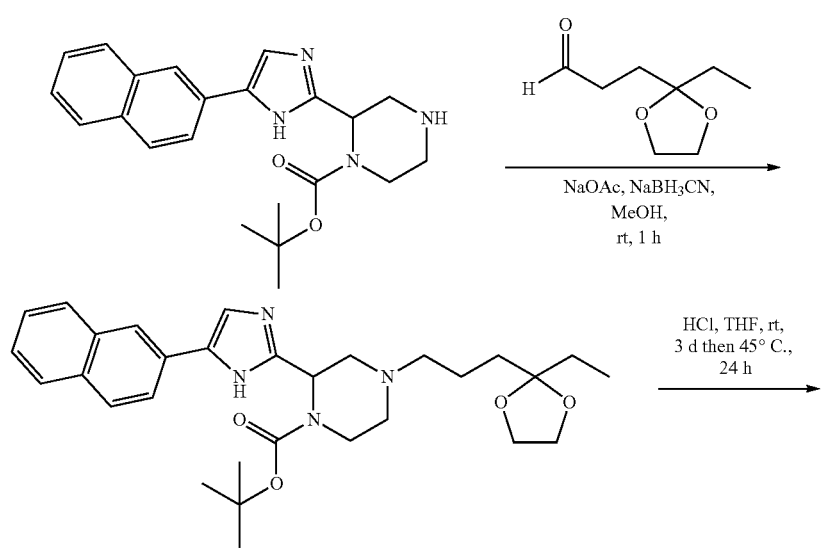
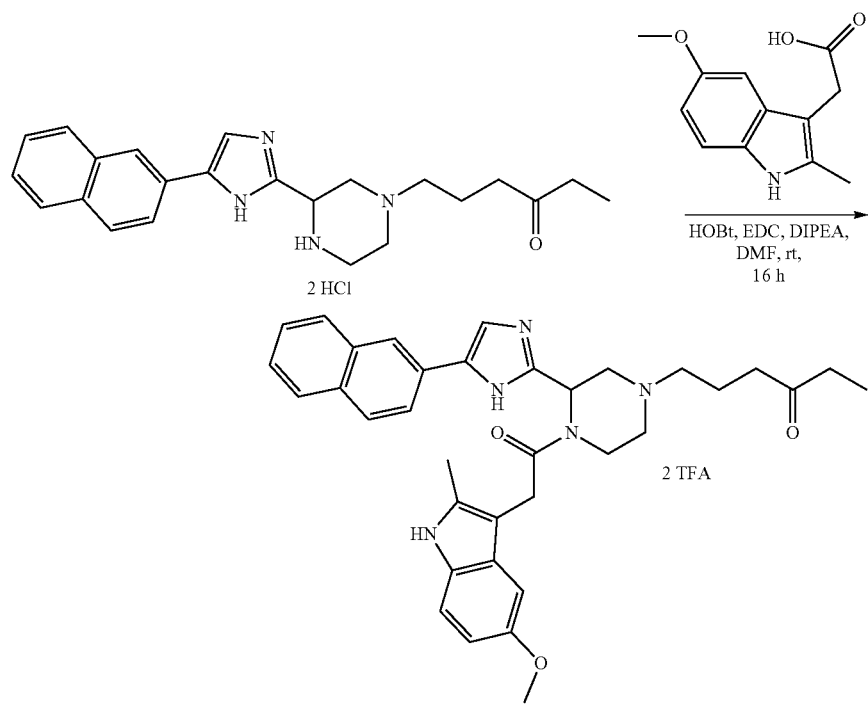

Example 1: 6-(4-(2-(5-methoxy-2-methyl-1H-indol-3-yl)acetyl)-3-(5-(naphthalen-2-yl)-1H-imidazol-2-yl)piperazin-1-yl)hexan-3-one (Trifluoroacetate Salt) (A5)

Step 1: 4-benzyl 1-(tert-butyl) 2-(5-(naphthalen-2-yl)-1H-imidazol-2-yl)piperazine-1,4-dicarboxylate (A1)

$Cs_2CO_3$ (0.5 eq) was added to a stirred solution of 4-((benzyloxy)carbonyl)-1-(tert-butoxycarbonyl)piperazine-2-carboxylic acid (1.0 eq) in EtOH (0.54 M). Stirring was continued at 20° C. for 2 h then solvent was evaporated and cesium 4-((benzyloxy)carbonyl)-1-(tert-butoxycarbonyl)-1,4-diazepane-5-carboxylate was dried at high vacuum pump for 1 h, then it was dissolved with DMF (0.54 M) and 2-bromo-1-(naphthalen-2-yl)ethan-1-one (1.0 eq) was added. The mixture was stirred at 20° C. for 1 h, then DMF was removed under reduced pressure co-evaporating with toluene. The residue was diluted with EtOAc and filtered off. Filtrate was evaporated to give 4-benzyl 1-(tert-butyl) 2-(2-(naphthalen-2-yl)-2-oxoethyl) piperazine-1,2,4-tricarboxylate. The latter was dissolved with toluene (0.13 M) and $NH_4OAc$ (20 eq) was added. The mixture was stirred at reflux using a Dean Stark apparatus for 30 min. Toluene was removed under reduced pressure, the residue was diluted with EtOAc, washed with sat. aq. $NaHCO_3$, brine, dried and concentrated to give an orange oily residue. This material was purified by flash chromatography (petroleum ether/EtOAc from 95:5 to 20:80) to give the title compound (86%) as an orange solid. MS (ES$^+$) m/z 513 (M+H)$^+$.

Step 2: tert-butyl 2-(5-(naphthalen-2-yl)-1H-imidazol-2-yl)piperazine-1-carboxylate (A2)

A1 (1 eq) was dissolved in MeOH (0.1 M) and treated with Pd/C wet (10% wt) 1:1 in weight. The mixture was purged with $N_2$ and stirred on $H_2$ atmosphere at 20° C. for 24 h. Then, the mixture was filtered through a pad of Solka Floc and filtrate was concentrated under vacuum to give the title compound (99%) which was directly used in the next step. MS (ES$^+$) m/z 379 (M+H)$^+$.

Step 3: tert-butyl 4-(3-(2-ethyl-1,3-dioxolan-2-yl)propyl)-2-(5-(naphthalen-2-yl)-1H-imidazol-2-yl)piperazine-1-carboxylate (A3)

3-(2-ethyl-1,3-dioxolan-2-yl)propanal (1.5 eq) and AcONa (1.5 eq) were sequentially added to a stirred solution of A2 in MeOH (0.1 M). Upon dissolution of substrates, $NaBH_3CN$ (1.5 eq) was added and the mixture was stirred at 20° C. for 16 h. Reaction state was monitored by UPLC and addition of $NaBH_3CN$ (6 eq) was needed to drive the reaction to completion. Then EtOAc was added and the organic phase was washed with sat. aq. $NaHCO_3$, brine, dried and concentrated. This material was purified by flash chromatography (petroleum ether/EtOAc from 90:10 to 0:100) to give the title compound (55%) as an oil. MS (ES$^+$) m/z 521 (M+H)$^+$.

Step 4: 6-(3-(5-(naphthalen-2-yl)-1H-imidazol-2-yl)piperazin-1-yl)hexan-3-one (chlorhydrate salt) (A4)

To a stirred solution of A3 (1.0 eq) in THF (0.12 M) cooled to 0° C. was slowly added aqueous HCl (1 N, 4.0 eq). The mixture warmed to 20° C. and stirred for 72 h, then heated at 45° C. for 24 h. THF was removed under reduced pressure. The resulting aqueous residue was diluted with MeCN (MeCN/$H_2O$=1:1 solution) and lyophilized to give the title compound (76%) which was directly used in the next step. MS (ES$^+$) m/z 377 (M+H)$^+$.

Step 5: 6-(4-(2-(5-methoxy-2-methyl-1H-indol-3-yl)acetyl)-3-(5-(naphthalen-2-yl)-1H-imidazol-2-yl)piperazin-1-yl)hexan-3-one (Trifluoroacetate Salt) (A5)

A solution of 2-(5-methoxy-2-methyl-1H-indol-3-yl)acetic acid (1.0 eq), HOBt (1.0 eq), EDC.HCl (1.0 eq) in DMF (0.22 M) was stirred for 15 min at 20° C., then a solution of A4 (0.77 eq) and DIPEA (3.0 eq) in DMF (0.34 M) was added and stirring was continued at 20° C. overnight. The mixture was filtered and purified by RP-HPLC to give after lyophilization the title compound (57%) as a solid. $^1$H-NMR (400 MHz, 300 K, DMSO-d$_6$) δ (7:3* mixture of rotamers) 10.66 (br s, 1H), 8.34 (s, 1H), 8.03-7.87 (m, 5H), 7.57-7.45 (m, 2H), 7.13 (d, 1H, J=8.4 Hz), 6.98-6.91 (m, 1H), 6.63 (dd, 1H, J=8.4, 2.4 Hz), 6.11 and 5.97*(br s, 1H), 4.65-4.55 and 4.35-4.10* (m, 2H), 4.05-3.85 (m, 1H), 3.85-3.65 (m, 1H), 3.72 (s, 2H), 3.70 (s, 1H), 3.50-3.35 (m, 2H), 3.35-3.20 (m, 1H), 3.15-3.05 (m, 2H), 3.00-2.85 (m, 1H), 2.65-2.55 (m, 2H), 2.45-2.35 (m, 2H), 2.31 (s, 3H), 2.05-1.80 (m, 2H), 0.88 (t, 3H, J=7.4 Hz). MS (ES$^+$) m/z 578 (M+H)$^+$.

Example 2

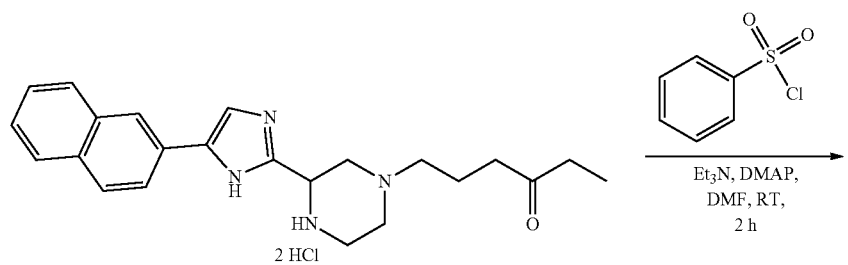

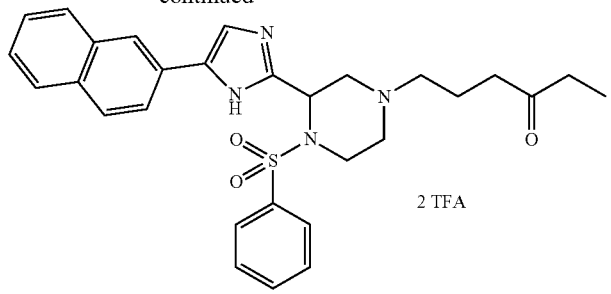

2 TFA

Example 2: 6-(3-(5-(naphthalen H-imidazol-2-yl)-4-(phenylsulfonyl)piperazin-1-yl)hexan-3-one (Trifluoroacetate Salt) (B1)

Benzenesulfonyl chloride (2.0 eq), Et$_3$N (2.0 eq) and DMAP (0.1.0 eq) were sequentially added to a stirred solution of A4 (1.0 eq) and Et$_3$N (3.0 eq) in DMF (0.1 M). The mixture was stirred at 20° C. for 2 h, then diluted with water, filtered and purified by RP-HPLC to give after lyophilization the title compound (33%) as a solid. $^1$H-NMR (400 MHz, 300 K, DMSO-d$_6$) δ 8.24 (s, 1H), 7.95-7.85 (m, 6H), 7.77 (s, 1H), 7.67-7.60 (m, 1H), 7.60-7.45 (m, 4H), 5.50 (br s, 1H), 4.00-3.80 (m, 2H), 3.55-3.35 (m, 2H), 3.25-3.05 (m, 1H), 3.05-2.75 (m, 3H), 2.55-2.45 (m overlapped with DMSO, 2H), 2.36-2.26 (m, 2H), 1.93-1.73 (m, 2H), 0.83 (t, 3H, J=7.2 Hz). MS (ES$^+$) m/z 517 (M+H)$^+$.

Example 3

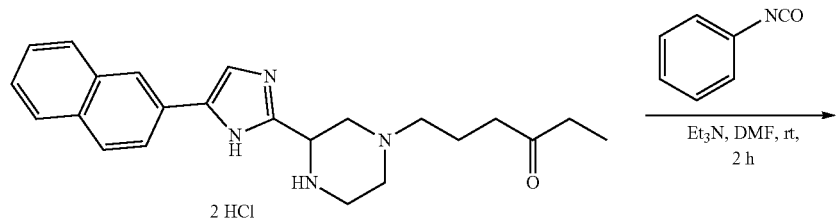

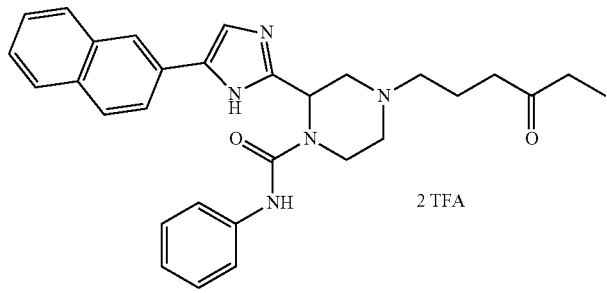

2 TFA

Example 3: 2-(5-(naphthalen-2-yl)-1H-imidazol-2-yl)-4-(4-oxohexyl)-N-phenylpiperazine-1-carboxamide (Trifluoroacetate Salt) (C1)

Isocyanatobenzene (2.0 eq) and Et$_3$N (2.0 eq) were sequentially added to a stirred solution of A4 (1.0 eq) and Et$_3$N (3.0 eq) in DMF (0.1 M). The mixture was stirred at 20° C. for 2 h, then diluted with water, filtered and purified by RP-HPLC to give after lyophilization the title compound (47%) as a solid. $^1$H-NMR (400 MHz, 300 K, DMSO-d$_6$) δ 8.96 (s, 1H), 8.36 (s, 1H), 8.04-7.88 (m, 5H), 7.58-7.44 (m, 4H), 7.34-7.26 (m, 2H), 7.04-6.98 (m, 1H), 5.90 (br s, 1H), 4.40-4.20 (m, 2H), 3.50-3.36 (m, 2H), 3.28-3.06 (m, 4H), 2.70-2.60 (m, 2H), 2.42 (q, 2H, J=7.4 Hz), 2.10-1.90 (m, 2H), 0.91 (t, 3H, J=7.4 Hz). MS (ES$^+$) m/z 496 (M+H)$^+$.

Example 4

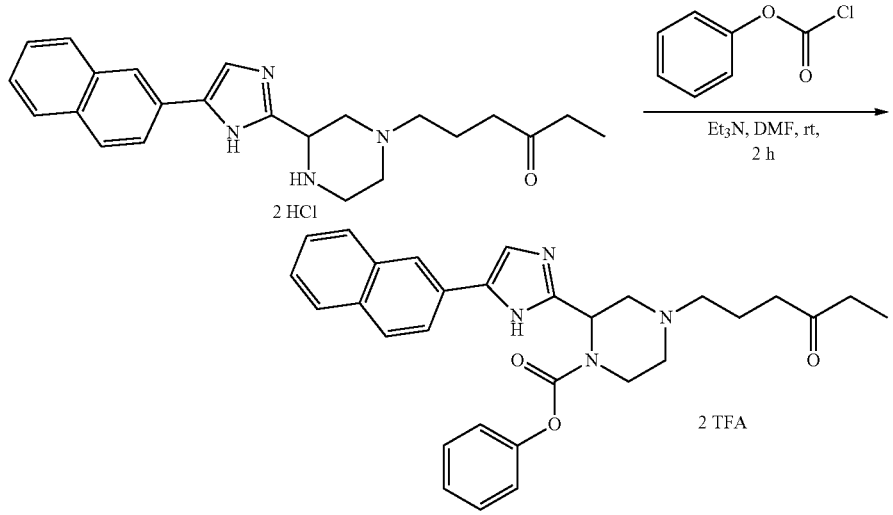

Example 4: phenyl 2-(5-(naphthalen-2-yl)-1H-imidazol-2-yl)-4-(4-oxohexyl)piperazine-1-carboxylate (Trifluoroacetate Salt) (D1)

Phenyl carbonochloridate (2.0 eq) and Et$_3$N (2.0 eq) were added to a stirred solution of A4 (1.0 eq) and Et$_3$N (3.0 eq) in DMF (0.1 M). The mixture was stirred at 20° C. for 2 h, then diluted with water, filtered and purified by RP-HPLC to give after lyophilization the title compound (37%) as a solid.

$^1$H-NMR (400 MHz, 300 K, DMSO-d$_6$) δ (7:3* mixture of rotamers) 8.36 (s, 1H), 8.05-7.87 (m, 5H), 7.57-7.40 (m, 4H), 7.33-7.22 (m, 3H), 5.98 and 5.78* (br s, 1H), 4.46-4.18 (m, 2H), 3.62-3.04 (m, 6H), 2.71-2.60 (m, 2H), 2.42 (q, 2H, J=7.1 Hz), 2.12-1.88 (m, 2H), 0.91 (t, 3H, J=7.4 Hz). MS (ES$^+$) m/z 497 (M+H)$^+$.

Example 5

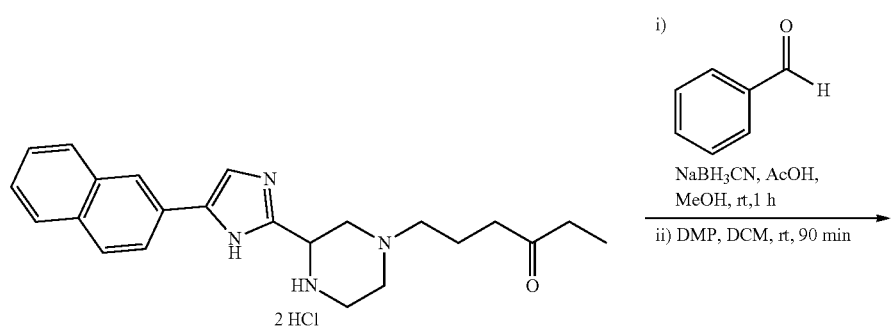

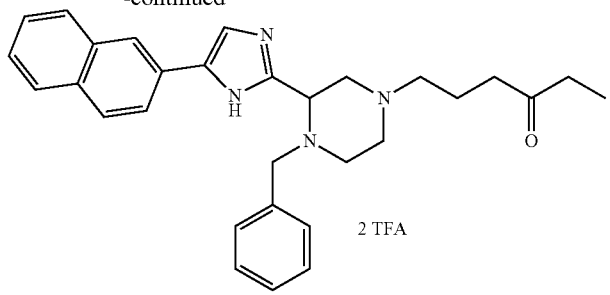

2 TFA

Example 5: 6-(4-benzyl-3-(5-(naphthalen-2-yl)-1H-imidazol-2-yl)piperazin-1-yl)hexan-3-one (Trifluoroacetate Salt) (E1)

Benzaldehyde (1.5 eq), NaBH₃CN (1.5 eq) and AcOH (until pH=6) were added to a stirred solution of A4 (1.0 eq) in MeOH (0.12 M). The mixture was stirred at 20° C. for 1 h, then quenched by HCl 1 N. Volatiles were removed under reduced pressure. The residue was portioned between DCM and sat. aq. NaHCO₃. Organic phase was separated, dried and concentrated to give 6-(4-benzyl-3-(5-(naphthalen-2-yl)-1H-imidazol-2-yl)piperazin-1-yl)hexan-3-ol as yellow oily residue. The latter (1.0 eq) was dissolved with DCM (0.12 M) and DMP (1.5 eq) was added. The mixture was stirred at 20° C. for 90 min then quenched by addition of sat. aq. NaHCO₃ and aq. sol. Na₂S₂O₃ and extracted with DCM. Organic phases were dried and concentrated to give a residue which was purified by RP-HPLC to give after lyophilization the title compound (40%) as a solid. ¹H-NMR (400 MHz, 300 K, DMSO-d₆) δ 9.8 (br s, 1H), 8.33 (s, 1H), 8.02-7.86 (m, 5H), 7.56-7.44 (m, 2H), 7.40-7.20 (m, 5H), 4.52-4.32 (m, 1H), 4.16-3.92 (m, 2H), 3.84-2.80 (m, 8H), 2.70-2.47 (m overlapped with DMSO, 2H), 2.47-2.35 (m, 2H), 2.12-1.88 (m, 2H), 0.91 (t, 3H, J=6.8 Hz). MS (ES⁺) m/z 467 (M+H)⁺.

Example 6

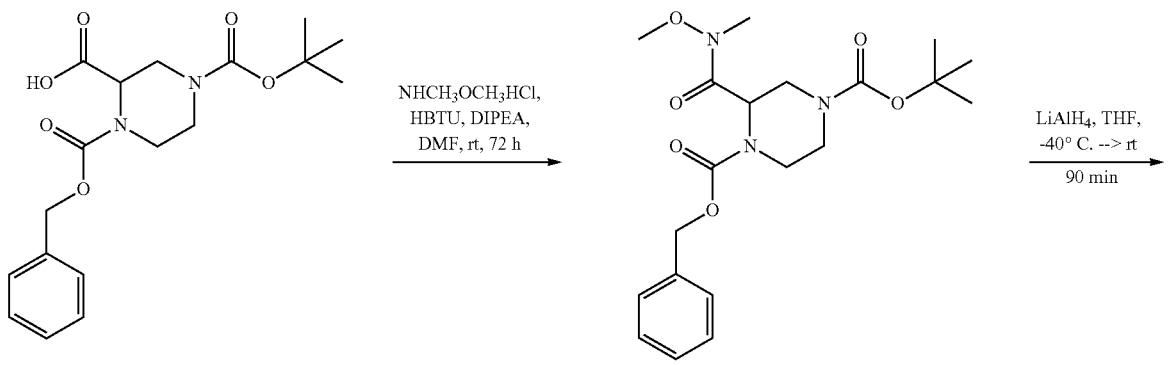

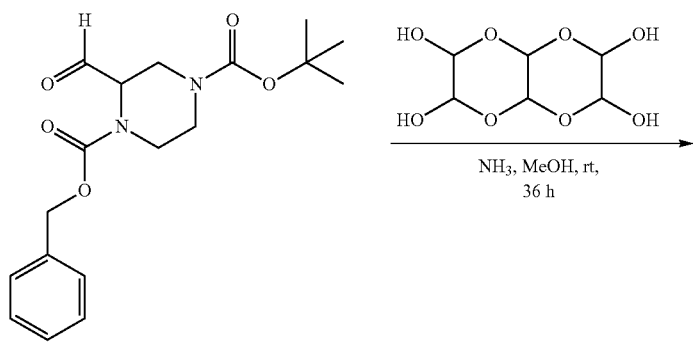

35
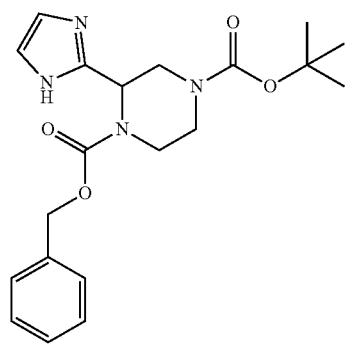
NIS, CH₃CN,
0° C. --> rt, 2 h
-continued
36
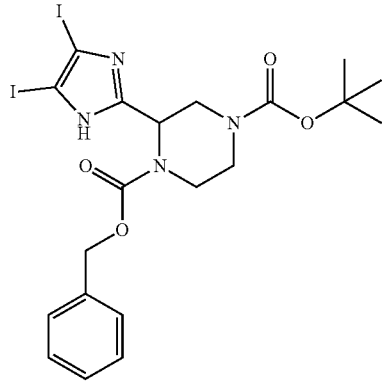
Na₂SO₃,
(Bu₄N)HSO₄
dioxane/H₂O,
reflux,
16 h
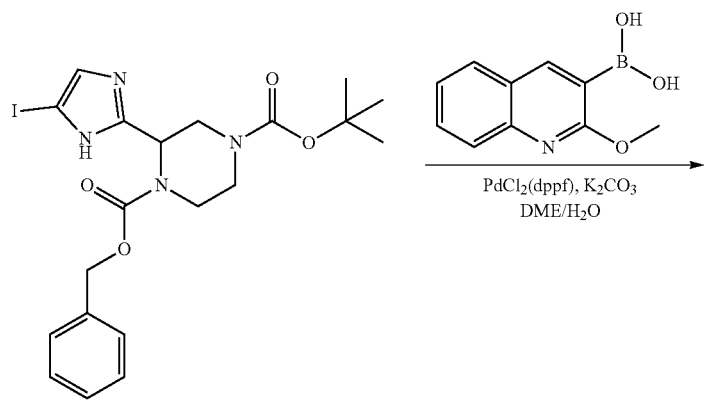
PdCl₂(dppf), K₂CO₃
DME/H₂O
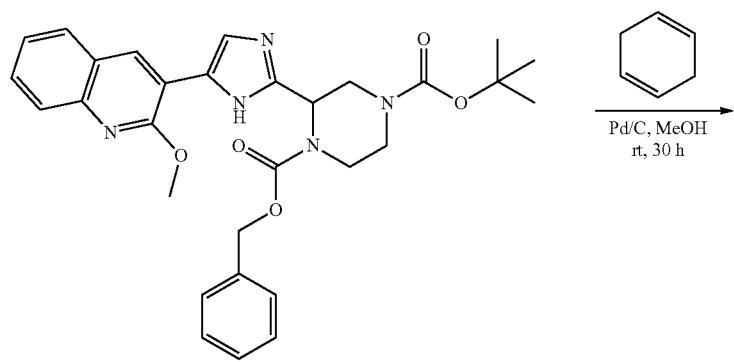
Pd/C, MeOH
rt, 30 h
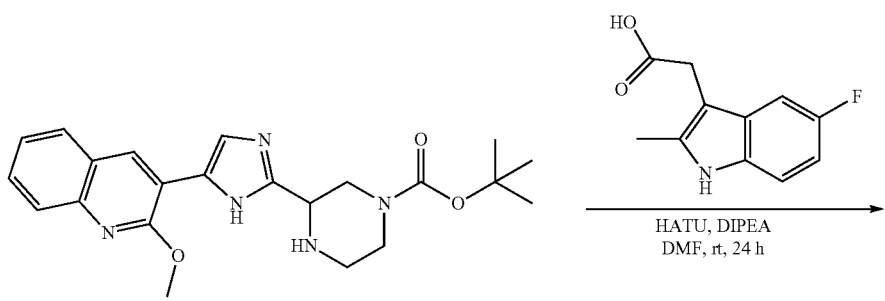
HATU, DIPEA
DMF, rt, 24 h

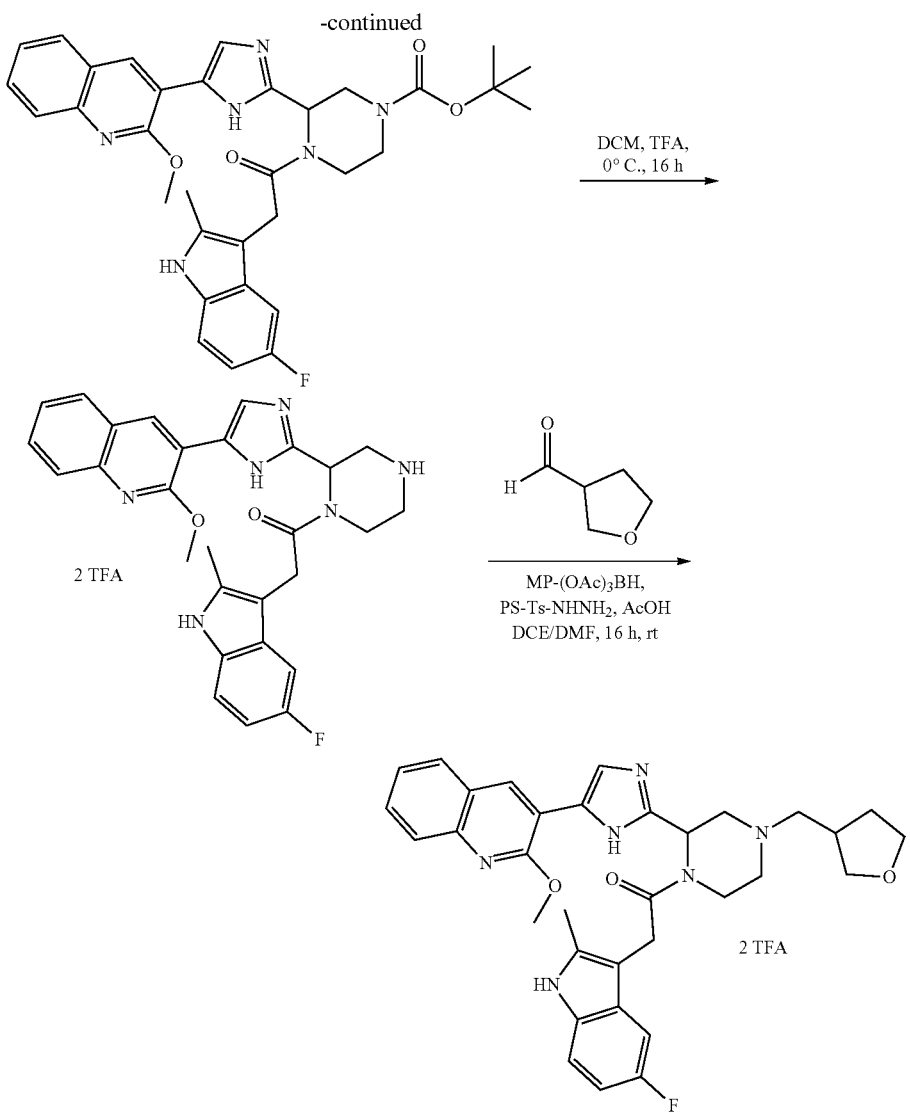

Example 6: 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl) ethan-1-one (Trifluoroacetate Salt) (F10)

Step 1: 1-benzyl 4-(tert-butyl) 2-(methoxy (methyl) carbamoyl) piperazine-1,4-dicarboxylate (F1)

A solution of 1-((benzyloxy)carbonyl)-4-(tert-butoxycarbonyl)piperazine-2-carboxylic acid (1.0 eq) and HBTU (1.4 eq) in DMF (0.6 M) was stirred for 15 min at 20° C. then N,O-dimethylhydroxylamine hydrochloride (1.4 eq) and DIPEA (4.0 eq) were sequentially added. After stirring at 20° C. for 72 h, the mixture was diluted with DCM, washed two times with HCl 1 N, aq. sol. NaHCO$_3$, brine then dried and concentrated to give an oily crude which was purified by flash chromatography (petroleum ether/EtOAc from 100:0 to 30:70) to give the title compound (50%) as a pale yellow oil. $^1$H-NMR (400 MHz, 300 K, CDCl$_3$) δ 7.36-7.31 (m, 5H), 5.20-5.14 (m, 2H), 4.92 (m, 1H), 4.43-4.26 (m, 1H), 4.16-3.86 (m, 1H), 3.81 (s, 3H), 3.40 (br s, 3H), 3.25-3.11 (m, 3H), 3.02-2.82 (m, 1H), 1.42 (s, 9H). MS (ES$^+$) m/z 408 (M+H)$^+$.

Step 2: 1-benzyl 4-(tert-butyl) 2-formylpiperazine-1,4-dicarboxylate (F2)

LiAlH$_4$ (1.25 eq, 1 M in THF) was added to a stirred solution of F1 in THF (0.15 M) cooled to −40° C. The mixture was stirred at −40° C. for 60 min then cooling bath was removed and EtOAc and HCl 0.1 N were added. The resulting white solid was filtered off and washed with EtOAc. The organic phase was separated and the aqueous phase extracted into EtOAc. The combined organic extracts were washed with H$_2$O, brine, dried over Na$_2$SO$_4$ and concentrated under reduced pressure to give the title compound as an orange oil which was used in the next step without further purification. MS (ES$^+$) m/z 371 (M+Na)$^+$.

Step 3: 1-benzyl 4-(tert-butyl) 2-(1H-imidazol-2-yl) piperazine-1,4-dicarboxylate (F3)

Glyoxal trimer dihydrated (1.0 eq) was added to a stirred solution of F2 (1.0 eq) in MeOH (0.5 M) at 20° C. followed by slowly addition of ammonia (5.0 eq, 7.0 M in MeOH). The mixture was stirred in a sealed tube at 20° C. for 72 h performing three subsequent additions of both glyoxal trimer dihydrated and ammonia until no more progress of the reaction was observed. The mixture was filtered off and organic solvent was concentrated under reduced pressure to give a crude that was purified by flash chromatography (petroleum ether/EtOAc from 90:10 to 0:100) to give the title compound (10%) as a yellow solid. MS (ES$^+$) m/z 387 (M+H)$^+$.

Step 4: 1-benzyl 4-(tert-butyl) 2-(4,5-diiodo-1H-imidazol-2-yl) piperazine-1,4-dicarboxylate (F4)

NIS (2.2 eq) was added portionwise to a stirred solution of F3 (1.0 eq) in CH$_3$CN (0.07 M) cooled to 0° C. The mixture was left warming to 20° C. and stirred for 2 h. Acetonitrile was removed under reduced pressure then dissolved in EtOAc and washed with aq. sol. NaHCO$_3$, brine, dried and concentrated. The residue was purified by flash chromatography (petroleum ether/EtOAc from 100:0 to 0:100) to give the title compound (80%) as pale orange solid. MS (ES$^+$) m/z 639 (M+H)$^+$.

Step 5: 1-benzyl 4-(tert-butyl) 2-(5-iodo-1H-imidazol-2-yl)piperazine-1,4-dicarboxylate (F5)

(Bu$_4$N)HSO$_4$ (2.0 eq) and Na$_2$SO$_3$ (10 eq) were added to a stirred solution of F4 (1.0 eq) in dioxane/water (4:1, 0.1 M) and the mixture was stirred at reflux in a sealed tube for 16 h. The mixture was diluted with EtOAc, filtered off, washed with sat. aq.NaHCO$_3$, brine, dried and concentrated to give the title compound (70%) as a white solid. $^1$H-NMR (400 MHz, 300 K, DMSO-d$_6$) δ 7.37-7.24 (m, 5H), 5.18-5.07 (m, 3H), 4.28 (d, 1H, J=13.6 Hz), 3.88-3.83 (m, 2H), 3.47 (m, 1H), 3.3 (m, 1H), 3.04 (m, 1H), 1.29 (s, 9H). MS (ES$^+$) m/z 513 (M+H)$^+$.

Step 6: 1-benzyl 4-(tert-butyl) 2-(5-(2-methoxyquinolin-3-yl)-1H-imidazol-2-yl)piperazine-1,4-dicarboxylate (F6)

Compound F6 was prepared according to the procedure reported in the Example 12, Step 5 to give the title compound (70%) as a solid. $^1$H-NMR (400 MHz, 300 K, DMSO-d$_6$) δ (7:3* mixture of rotamers) 12.17 (s, 1H), 8.73 and 8.46* (s, 1H), 7.87 (d, 1H, J=8.0 Hz), 7.77 (d, 1H, J=8.0 Hz), 7.67 (br s, 1H), 7.60 (t, 1H, J=8.0 Hz), 7.46-7.22 (m, 6H), 5.29 (br s, 1H), 5.19-5.14 (m, 2H), 4.60-4.32 (m, 1H), 4.14 (s, 3H), 4.10-3.90 (m, 2H), 3.72-3.58 (m, 1H), 3.41-3.34 (m, 1H), 2.93-2.88 (m, 1H), 1.23 (s, 9H). MS (ES$^+$) m/z 544 (M+H)$^+$.

Step 7: tert-butyl 3-(5-(2-methoxyquinolin-3-yl)-1H-imidazol-2-yl)piperazine-1-carboxylate (F7)

Pd/C (10% wt) (1/1 in weight) was added to a solution of F6 (1.0 eq) in EtOAc (0.05 M). Mixture was purged with N$_2$ and stirred on H$_2$ atmosphere at 20° C. for 20 h. The resulting suspension was filtered and concentrated under reduced pressure to give the title compound (99%) as a pale yellow foam. $^1$H-NMR (400 MHz, 300 K, CDCl$_3$) δ 8.67 (br s, 1H), 7.86 (d, 1H, J=8.4 Hz), 7.83 (d, 1H, J=7.8 Hz), 7.67 (s, 1H), 7.60 (t, 1H, J=7.3 Hz), 7.40 (t, 1H, J=7.3 Hz), 4.14 (s, 3H), 4.16-3.87 (m, 3H), 3.08-2.9 (m, 4H), 1.7 (s, 9H). MS (ES$^+$) m/z 410 (M+H)$^+$.

Step 8: tert-butyl 4-(2-(5-fluoro-2-methyl-1H-indol-3-yl)acetyl)-3-(5-(2-methoxyquinolin-3-yl)-1H-imidazol-2-yl)piperazine-1-carboxylate (F8)

HATU (1.5 eq, 0.3 M in DMF), F7 (1.0 eq, 0.1 M in DMF) and DIPEA (2.0 eq, 0.75 M in DMF) were sequentially added to a stirred solution of 2-(5-fluoro-2-methyl-1H-indol-3-yl)acetic acid (1.5 eq, 1 M in DMSO). Mixture was stirred for 24 h at 20° C. then was filtered on a SiCO$_3$ cartridge (2 g) eluting with MeOH. The solvent was evaporated and obtained a crude that was directly used in the next step. MS (ES$^+$) m/z 599 (M+H)$^+$.

Step 9: 2-(5-fluoro-2-methyl-1H-indol-3-yl)-1-(2-(5-(2-methoxyquinolin-3-yl)-1H-imidazol-2-yl)piperazin-1-yl)ethan-1-one (Trifluoroacetate Salt) (F9)

TFA (16 eq) was slowly added to a stirred solution of F7 (1.0 eq) in DCM (0.04 M) cooled at 0° C. The mixture was left at 0° C. for 16 h then 1 mL of toluene was added and solvents evaporated under reduced pressure to give the title compound (99%) as TFA salt.

Step 10: 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one (Trifluoroacetate Salt)(F10)

F9 (1.0 eq) and tetrahydrofuran-3-carbaldehyde (1.5 eq) were stirred in DCE/DMF (1:1, 0.04 M) and acetic acid (1.0 eq). After 1 h, MP-(OAc)$_3$BH (10 eq, loading 2.3 mmol/g) was added and the mixture was stirred for 16 h. PS-TsNHNH$_2$ (7.5 eq, loading 2.96 mmol/g) was added and the suspension was stirred for 4 h at 20° C. Resins were filtered washing with DMF (3 mL) and solvents were evaporated under pressure. The reaction crude was purified by RP-HPLC to give after lyophilization the title compound as a white powder. MS (ES$^+$) m/z 583 (M+H)$^+$.

Example 7

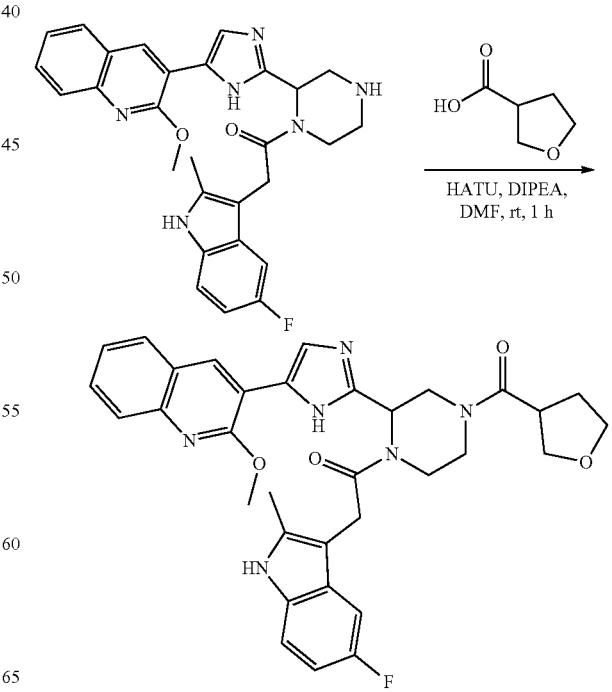

Example 7: 2-(5-fluoro-2-methyl-1H-indol-3-yl)-1-(2-(5-(2-methoxyquinolin-3-yl)-1H-imidazol-2-yl)-4-(tetrahydrofuran-3-carbonyl)piperazin-1-yl)ethan-1-one (Trifluoroacetate Salt) (G1)

Tetrahydrofuran-3-carboxylic acid (1.5 eq), HATU (1.5 eq) and DIPEA (3.0 eq) were sequentially added to a stirred solution of F9 (1.0 eq) in DMF (0.06 M). Mixture was stirred at 20° C. for 1 h then filtered on a SiCO₃ cartridge (2.0 g) eluting with MeOH. The solvent was evaporated and obtained the reaction crude which was purified by RP-HPLC to give after lyophilisation the title compound (29%) as white powder. MS (ES⁺) m/z 597 (M+H)⁺.

Example 8

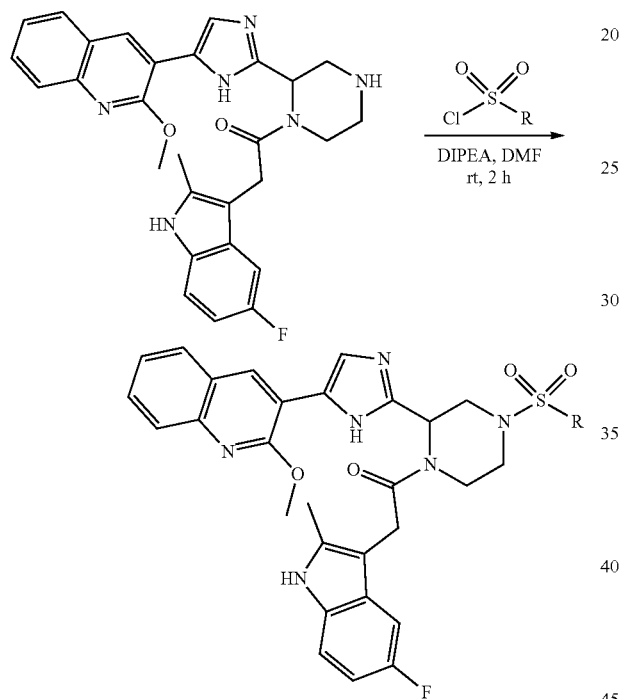

Example 8A: 2-(5-fluoro-2-methyl-1H-indol-3-yl)-1-(4-(isopropylsulfinyl)-2-(5-(2-methoxyquinolin-3-yl)-1H-imidazol-2-yl)piperazin-1-yl)ethan-1-one (Trifluoroacetate Salt) (H1)

Propane-2-sulfonyl chloride (1.5 eq) and DIPEA (3.0 eq) were added to a solution F9 in DMF (0.06 M). Resulting solution was left stirring at 20° C. for 2 h. The crude material was purified by RP-HPLC to give after lyophilization the title compound (8%) as a colorless foam. MS (ES⁺) m/z 605 (M+H)⁺.

Example 8B: 4-(2-(5-fluoro-2-methyl-1H-indol-3-yl)acetyl)-3-(5-(2-methoxyquinolin-3-yl)-1H-imidazol-2-yl)-N,N-dimethylpiperazine-1-sulfonamide (Trifluoroacetate Salt) (H2)

N,N-dimethylsulfamoyl chloride (1.5 eq) and DIPEA (3.0 eq) were added to a solution of F9 in DMF (0.06 M). Resulting solution was left stirring at 20° C. for 2 h. The crude material was then purified by RP-HPLC to give after lyophilization the title compound (6%) as a colorless foam. MS (ES⁺) m/z 606 (M+H)⁺.

Example 8

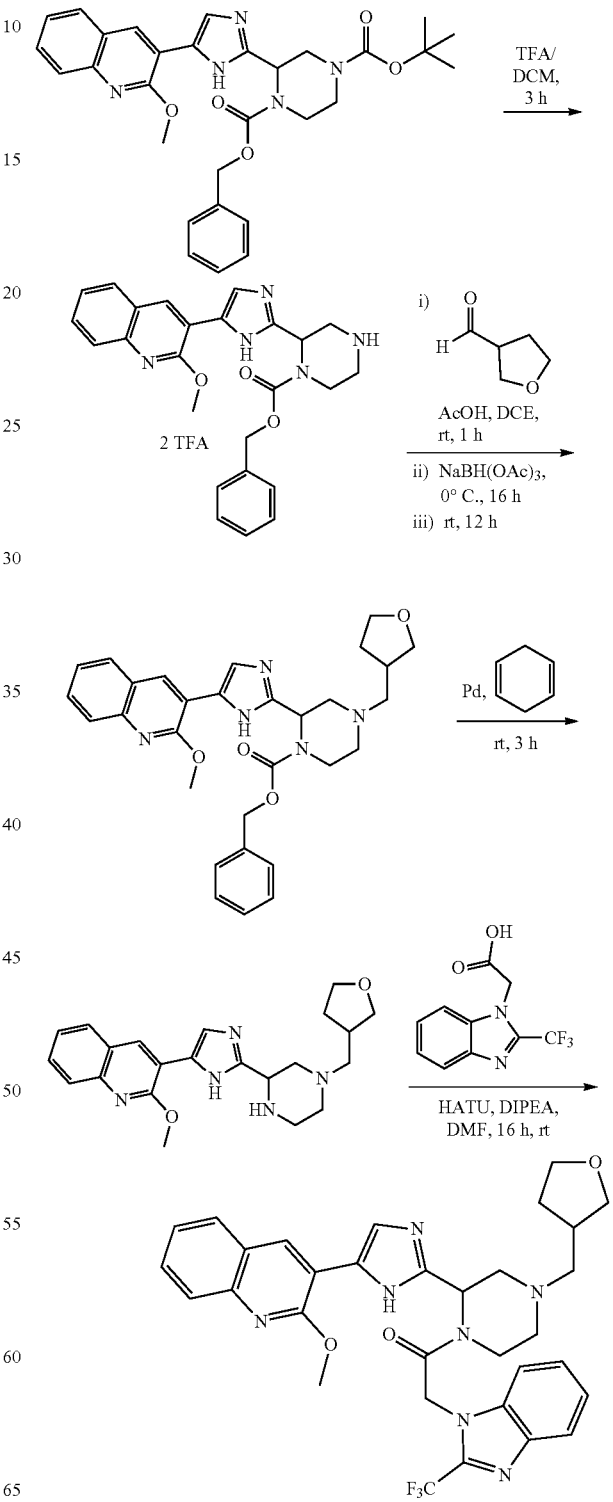

Example 9: 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one (L-tartaric Acid Salt) (14)

Step 1: benzyl 2-(5-(2-methoxyquinolin-3-yl)-1H-imidazol-2-yl)piperazine-1-carboxylate (Trifluoroacetate Salt) (I1)

A solution of F6 (1.0 eq) in DCM (0.07 M) was cooled to 0° C. and TFA (21.0 eq) was added dropwise. The mixture was stirred 3 h at 0° C. then it was allowed to reach 20° C. over 8 h. Volatiles were removed under reduced pressure, the resulting oily residue was co-evaporated with toluene first and then with $Et_2O$ to give the title compound (99%) as pale yellow oil which was directly used in the next step. MS ($ES^+$) m/z 444 (M+H)$^+$.

Step 2: benzyl 2-(5-(2-methoxyquinolin-3-yl)-1H-imidazol-2-yl)-4-((tetrahydrofuran-3-yl)methyl)piperazine-1-carboxylate (I2)

Tetrahydrofuran-3-carbaldehyde (1.5 eq) and AcOH (1.5 eq) were added to a solution of I1 (1.0 eq) in DCE (0.55 M) at 0° C. The mixture was allowed to reach 20° C. and stirring was continued for 1 h. After this time, sodium triacetoxyborohydride (5.0 eq) was added at 0° C. and the mixture was left stirring for 16 h at 20° C. The mixture was diluted with EtOAc: organic phase was washed with sat. aq. $NaHCO_3$, brine, dried and concentrated to give a crude which was purified by flash chromatography (petroleum ether/EtOAc from 80:20 to 0:100) to give the title compound (80%) as a yellow solid. MS ($ES^+$) m/z 528 (M+H)$^+$.

Step 3: 2-methoxy-3-(2-(4-((tetrahydrofuran-3-yl)methyl)piperazin-2-yl)-1H-imidazol-5-yl)quinoline (I3)

I2 (1.0 eq) was dissolved in MeOH (0.04 M) and cyclohexa-1,4-diene (10 eq) was added and stirred for 5 min at 20° C. After this time Pd/C 10% wet (5 eq) was added and mixture stirred at 20° C. for 3 h. The mixture was filtered through a pad of Solka-Floc and filtrate was concentrated under reduced pressure to give the title compound (99%) as a yellow solid which without further purification in the next reaction step. MS ($ES^+$) m/z 394 (M+H)$^+$.

Step 4: 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one (L-tartaric Acid Salt) (I4)

2-(2-(trifluoromethyl)-1H-benzo[d]imidazol-1-yl)acetic acid (2.0 eq) and HATU (2.0 eq) in DMF (0.4 M) were added to a solution of I3 (1.0 eq) in DMF (0.4 M) at 20° C. followed by dropwise addition of DIPEA (3.0 eq). Mixture was stirred for 16 h then it was diluted with DCM and washed with $NaHCO_3$ and brine. Organic layer was dried and filtered, concentrated and purified by RP-HPLC (MeCN/$H_2O$+0.01% TFA). After lyophilisation the product (71%) was obtained as pale creamy powder TFA salt. This material was partitioned between DCM and sat. aq. $NaHCO_3$. The organic phase was dried over $Na_2SO_4$, filtered and concentrated under reduced pressure to obtain the free base. The resulting solid was dissolved in acetonitrile/$H_2O$ (1:1) and treated with L-tartaric acid (1.0 eq). The resulting solution was lyophilized obtaining a 1:1 mixture of diastereomers (a 1:1** mixture of rotamers as seen for one isomer) of the title compound as tartrate salt. $^1$H-NMR (400 MHz, 300 K, $CD_3CN$) δ 8.90 and 8.86*, 8.85** (s, 1H), 7.87* and 7.75 (d, 1H, J=7.7 Hz), 7.83* and 7.80 (d, 1H, J=7.6 Hz), 7.82 and 7.74* (s, 1H), 7.79 (d, 1H, J=7.7 Hz), 7.75-7.59 (m, 2H), 7.48 and 7.40 (t, 1H, J=7.3 Hz), 7.40 and 7.09 (m, 1H), 7.40 and 7.27* (m, 1H), 6.15-6.10 and 5.45-5.41* (m, 1H), 5.93-5.91 and 5.37* (m and br s, 1H), 5.62-5.59 and 5.26-5.22* (m, 1H), 4.38 (s, 1H), 4.18 and 4.14* (s, 3H), 4.18-4.17 and 3.98-3.95* and 3.70-3.66* and 2.90-2.95 (m, 2H), 3.91-3.86* and 3.05-2.97 and 3.58-3.53* and 2.74-2.71 (m, 2H), 3.83-3.80 and 3.49-3.46 (m, 2H), 3.78-3.82 and 2.61-2.56 (m, 2H), 3.14-3.12* and 3.09-3.06 and 2.27-2.20 (m, 2H), 3.04-2.98* and 2.61-2.56 (m, 2H), 2.59-2.52 (m, 1H), 2.18-2.11 and 2.08-2.02 and 1.68-1.58 (m, 2H).

MS ($ES^+$) m/z 620 (M+H)$^+$.

Example 10

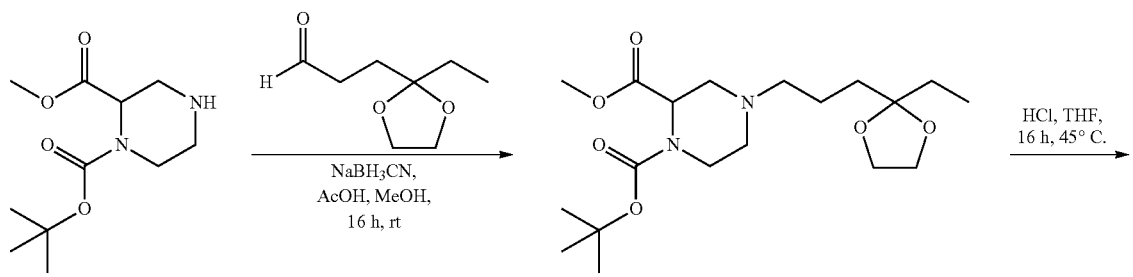

-continued
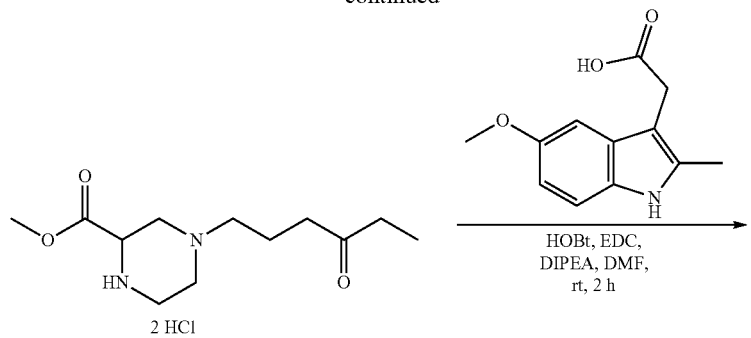
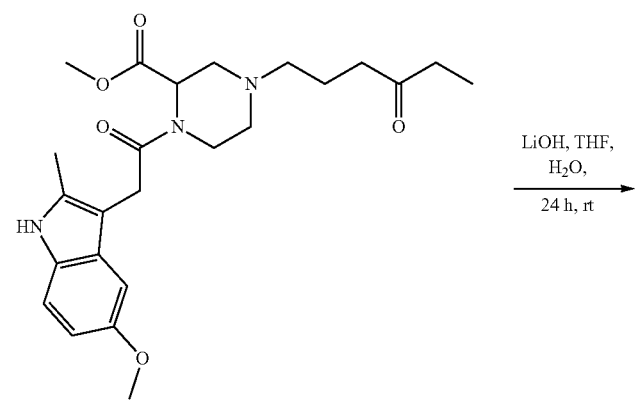
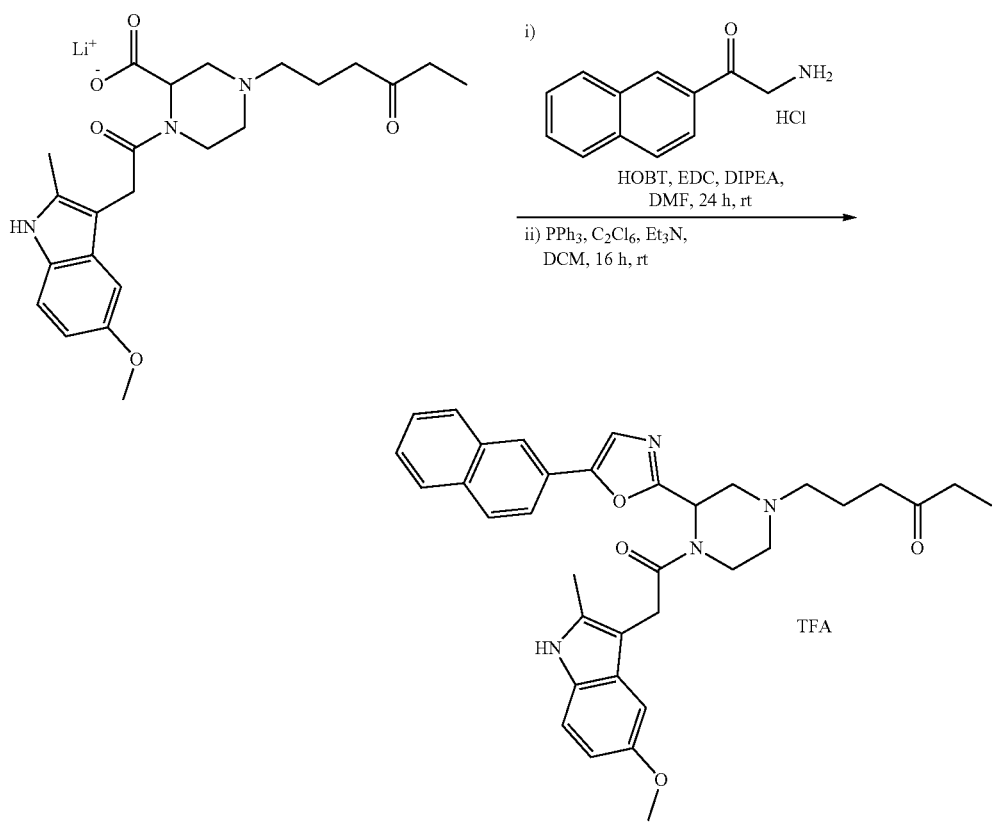

Example 10: 6-(4-(2-(5-methoxy-2-methyl-1H-indol-3-yl)acetyl)-3-(5-(naphthalen-2-yl)oxazol-2-yl)piperazin-1-yl)hexan-3-one (Trifluoroacetate Salt) (J5)

Step 1: 1-(tert-butyl) 2-methyl 4-(3-(2-ethyl-, 3-dioxolan-2-yl)propyl)piperazine-1,2-dicarboxylate (J1)

3-(2-ethyl-1,3-dioxolan-2-yl)propanal (1.5 eq) (prepared as described by Kuehne, M. E. et al *J. Org. Chem.* 1981, 46, 3443) was added to a stirred solution of 1-(tert-butyl) 2-methyl piperazine-1,2-dicarboxylate (1.0 eq) in MeOH (0.1 M), followed by AcOH (until pH=6) and stirred for 1 h. Then NaBH$_3$CN (1.5 eq) was added and the mixture was stirred at 20° C. for 16 h. Two subsequent additions of 3-(2-ethyl-1,3-dioxolan-2-yl)propanal (0.5 eq+0.5 eq) and NaBH$_3$CN (1.0 eq+1.0 eq) after 1 h and 2 h were done. MeOH was removed under reduced pressure. The residue was dissolved with DCM, washed with aq. sol. NaHCO$_3$, brine, dried and concentrated to give the title compound as yellow oil which was used in the next step without further purification. MS (ES$^+$) m/z 387 (M+H)$^+$.

Step 4: methyl 4-(4-oxohexyl)piperazine-2-carboxylate (chlorhydrate salt) (J2)

HCl 1 N (4.0 eq) was slowly added to a stirred solution of J1 (1.0 eq) in THF (0.12 M). The mixture was heated at 45° C. for 16 h. THF was removed under reduced pressure and the resulting aqueous residue was diluted with MeCN (MeCN/H$_2$O=1:1 solution) and lyophilized to give the title compound which was directly used in the next step. MS (ES$^+$) m/z 243 (M+H)$^+$.

Step 5: methyl 1-(2-(5-methoxy-2-methyl-1H-indol-3-yl)acetyl)-4-(4-oxohexyl)piperazine-2-carboxylate (J3)

A solution of 2-(5-methoxy-2-methyl-1H-indol-3-yl)acetic acid (1.0 eq), HOBt (1.0 eq), EDC.HCl (1.0 eq) and DIPEA (1.0 eq) in DMF (0.9 M) was stirred for 15 min at 20° C. then a solution of J2 (0.67 eq) and DIPEA (1.67 eq) in DMF (0.4 M) was added and stirring was continued at 20° C. for 1 h. The mixture was diluted with EtOAc, washed with sat. aq.NaHCO$_3$ sol., brine, dried and concentrated. The residue was purified by flash chromatography (petroleum ether/EtOAc from 90:10 to 0:100) to give the title compound (21% over three steps) as an orange solid. MS (ES$^+$) m/z 444 (M+H)$^+$.

Step 6: lithium 1-(2-(5-methoxy-2-methyl-1H-indol-3-yl)acetyl)-4-(4-oxohexyl)piperazine-2-carboxylate (J4)

A solution of LiOH.H$_2$O (1.5 eq) in H$_2$O (THF/H$_2$O=4:1, 0.06 M) was added to a stirred solution of J3 (1.0 eq) in THF. The mixture was stirred at 20° C. for 24 h. THF was removed under reduced pressure, the aqueous phase was washed with Et$_2$O then diluted with an equal volume of MeCN and lyophilized to give the title compound (99%) as a yellow solid (99%) which was used in the next step without further purification. MS (ES$^+$) m/z 430 (M+H)$^+$.

Step 7: 6-(4-(2-(5-methoxy-2-methyl-1H-indol-3-yl)acetyl)-3-(5-(naphthalen-2-yl)oxazol-2-yl)piperazin-1-yl)hexan-3-one (trifluoroacetate Salt) (J5)

A solution of M4 (1.0 eq), HOBt (1.5 eq), EDC.HCl (1.5 eq) in DMF (0.3 M) was stirred for 15 min at 20° C. then 2-amino-1-(naphthalen-2-yl)ethan-1-one hydrochloride (2.0 eq) and DIPEA (3.5 eq) were added and stirring was continued at 20° C. for 16 h. The mixture was diluted with EtOAc, washed with sat. aq.NaHCO$_3$, brine, dried and concentrated to give 1-(2-(5-methoxy-2-methyl-1H-indol-3-yl)acetyl)-N-(2-(naphthalen-2-yl)-2-oxoethyl)-4-(4-oxohexyl)piperazine-2-carboxamide which was purified by flash chromatography (eluents: petroleum ether/EtOAc from 9:1 to 0:10 then EtOAc/MeOH from 10:0 to 9:1). This intermediate (1.0 eq) was dissolved with DCM (0.06 M) and added to a pre-stirred solution of PPh$_3$ (2.0 eq), C$_2$Cl$_6$ (2.0 eq) and Et$_3$N (4.0 eq) in DCM (0.1 M). The mixture was stirred at 20° C. overnight. The mixture was diluted with DCM, washed with sat. aq.NaHCO$_3$, brine, dried and concentrated. The residue was purified by RP-HPLC to give after lyophilization the title compound (0.6%) as a solid. MS (ES$^+$) m/z 579 (M+H)$^+$.

Example 11

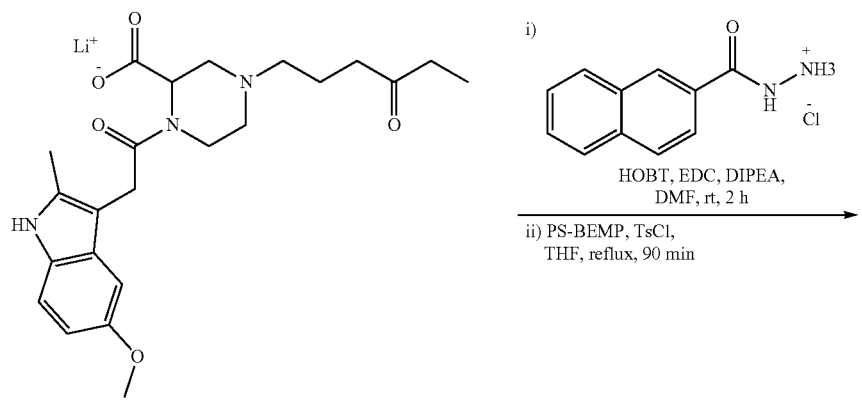

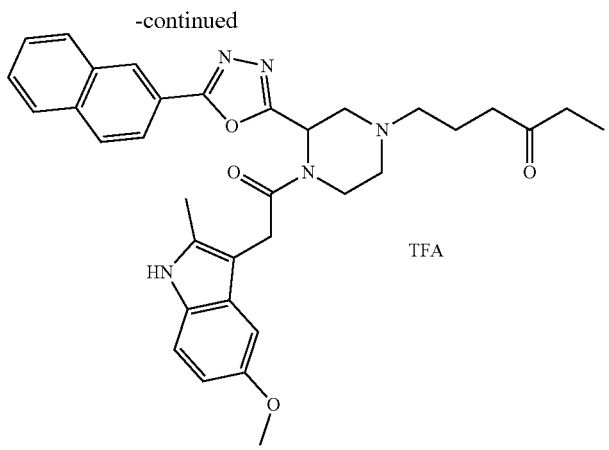

Example 11: 6-(4-(2-(5-methoxy-2-methyl-1H-indol-3-yl)actyl)-3-(5-(naphthalen-2-yl)-1,3,4-oxadiazol-2-yl)piperazin-1-yl)hexan-3-one (Trifluoroacetate Salt) (K1)

A solution of J4 (1.0 eq), HOBt (1.4 eq), EDC.HCl (1.4 eq) and DIPEA (2.0 eq) in DMF (0.3 M) was stirred for 15 min at 20° C. then 2-naphthohydrazide hydrochloride (2.0 eq) was added and stirring was continued at 20° C. for 2 h. The mixture was diluted with EtOAc, washed with sat. aq.NaHCO$_3$, brine, dried and concentrated to give N'-(2-naphthoyl)-1-(2-(5-methoxy-2-methyl-1H-indol-3-yl)acetyl)-4-(4-oxohexyl)piperazine-2-carbohydrazide. This intermediate (1.0 eq) was dissolved with THF (0.03 M), then PS-BEMP (5.0 eq) and TsCl (1.2 eq) were added and stirring was continued at reflux for 90 min. The mixture was filtered through a pad of Solka Floc eluting with THF and MeOH. The filtrate was concentrated and the residue was purified by RP-HPLC to give after lyophilization the title compound (10%) as a solid. $^1$H-NMR (400 MHz, 300 K, DMSO-d$_6$) δ (6:4* mixture of rotamers) 10.70 and 10.57* (br s, 1H), 8.56 and 8.41* (s, 1H), 8.20-8.00 (m, 3H), 8.00-7.90 (m, 1H), 7.75-7.62 (m, 2H), 7.20-7.10 and 7.02-6.92* (m, 2H), 6.67-6.65 and 6.48-6.46* (m, 1H), 6.34 and 6.16* (br s, 1H), 4.6 and 4.35* (br s, 2H), 4.25-3.75 (m, 1H), 3.70 and 3.69* (s, 3H), 3.65-3.20 (m overlapped with H$_2$O, 7H), 3.16-3.01 (br s, 2H), 2.60-2.40 (m overlapped with DMSO, 2H), 2.33 (s, 3H), 1.90-1.70 (br s, 2H), 1.00-0.70 (br s, 3H). MS (ES$^+$) m/z 580 (M+H)$^+$.

Example 12

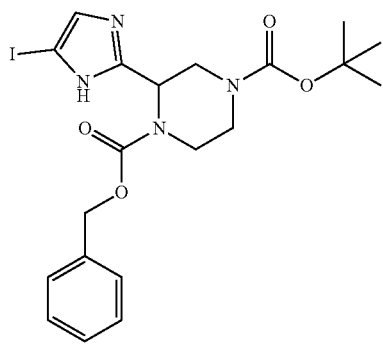

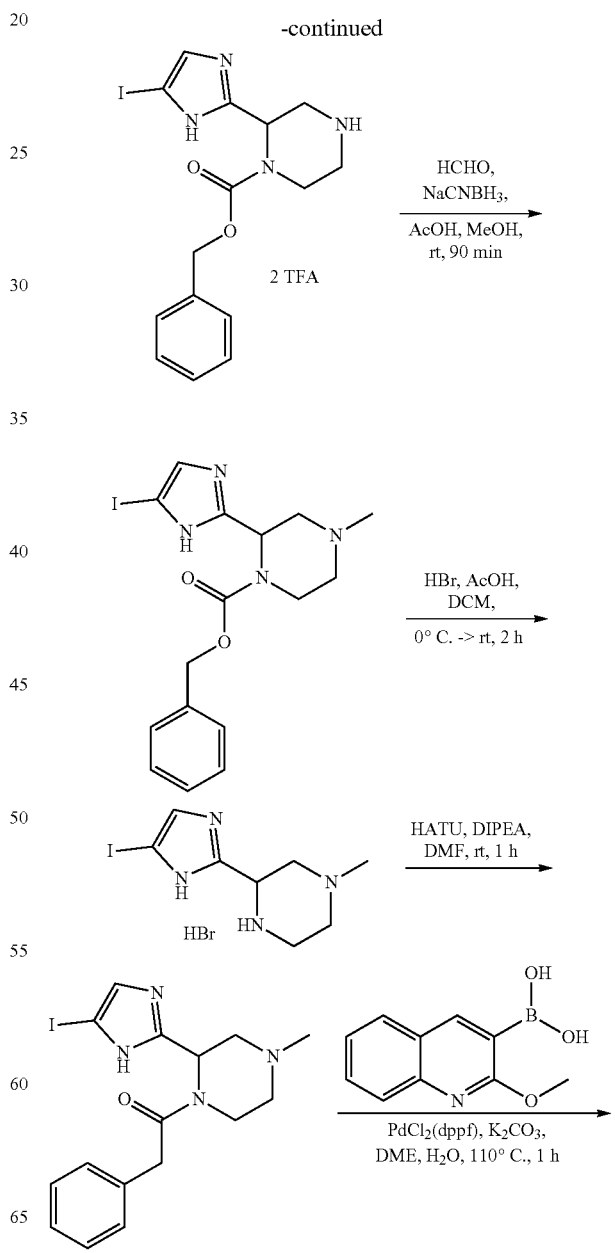

-continued

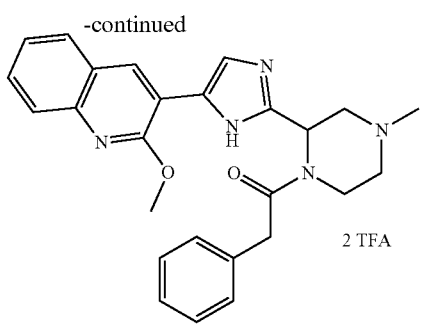

2 TFA

Example 12: 1-(2-(5-(2-methoxyquinolin-3-yl)-1H-imidazol-2-yl)-4-methylpiperazin-1-yl)-2-phenylethan-1-one (Trifluoroacetate Salt) (L5)

Step 1: benzyl 2-(5-iodo-1H-imidazol-2-yl)-4-methylpiperazine-1-carboxylate (trifluoroacetate salt) (L1)

TFA (DCM/TFA=4:1 sol., 0.1 M) was slowly added to a solution of F5 in DCM cooled to 0° C. The mixture was left warming to 20° C. and stirred for 1 h, then concentrated under reduced pressure. The resulting oily residue was co-evaporated with $Et_2O$, then dissolved in MeCN/$H_2O$=1:1 solution and lyophilized to give the title compound which was directly used in the next step. MS ($ES^+$) m/z 413 $(M+H)^+$.

Step 2: benzyl 2-(5-iodo-1H-imidazol-2-yl)-4-methylpiperazine-1-carboxylate (L2)

HCHO (1.5 eq) was added to a stirred solution of L1 (1.0 eq) in MeOH (0.1 M) and stirring was continued for 1 h. Then $NaBH_3CN$ (1.5 eq) was added and the mixture was stirred at 20° C. for 30 min and diluted with EtOAc. The organic phase was washed with sat. aq.$NaHCO_3$, brine, dried and concentrated. The residue was purified by flash chromatography (petroleum ether/EtOAc from 9:1 to 0:10) to give the title compound (99%) as a solid. MS ($ES^+$) m/z 427 $(M+H)^+$.

Step 3: 3-(5-iodo-1H-imidazol-2-yl)-1-methylpiperazine (hydrobromide salt) (L3)

HBr in AcOH (0.016 M) was added to a stirred solution of L2 in DCM (0.033 M) cooled to 0° C. The mixture was stirred at 0° C. for 10 min and 20° C. for 2 h, then it was concentrated under reduced pressure. The oily residue was co-evaporated with toluene and resulting solid was triturated with $Et_2O$ and filtered off. The precipitate was dissolved in MeCN/$H_2O$ (2:3) solution and lyophilized to give the title compound (99%) which was directly used in the next step. MS ($ES^+$) m/z 293 $(M+H)^+$.

Step 4: 1-(2-(5-iodo-1H-imidazol-2-yl)-4-methylpiperazin-1-yl)-2-phenylethan-1-one (L4)

A solution of 2-hydroxy-1-phenylethan-1-one (1.0 eq), HATU (1.0 eq) and DIPEA (3.8 eq) in DMF (0.3 M) was stirred for 15 min at 20° C. then added to a solution of L3 (0.77 eq) in DMF (2.6 M) and stirring was continued at 20° C. for 1 h. The mixture was diluted with EtOAc, washed with sat. aq. $NaHCO_3$ sol, brine, dried and concentrated. The residue was purified by flash chromatography (petroleum ether/EtOAc from 9:1 to 0:10 then EtOAc/MeOH from 10:0 to 9:1) to give the title compound (66%) as a solid. MS ($ES^+$) m/z 411 $(M+H)^+$.

Step 5: 1-(2-(5-(2-methoxyquinolin-3-yl)-1H-imidazol-2-yl)-4-methylpiperazin-1-yl)-2-phenylethan-1-one (Trifluoroacetate Salt) (L5)

A degassed microwave vial was charged with L4 (1.0 eq), (2-methoxyquinolin-3-yl)boronic acid (2.0 eq), $PdCl_2$(dppf) (0.2 eq) and $K_2CO_3$ (3.0 eq). A degassed solution of DME/$H_2O$=1:1 (0.05 M) was added and the suspension was degassed for further 2 min then heated at 110° C. for 1 h. After cooling, the mixture was diluted with MeCN and filtered through a pad of Solka Floc. Volatiles were removed under reduced pressure. The residue was dissolved with DMF, filtered and purified by RP-HPLC to give after lyophilization the title compound (44%) as a solid. $^1$H-NMR (400 MHz, 300 K, DMSO-$d_6$) δ (7:3* mixture of rotamers) 8.83 (s, 1H), 7.93-7.88 (m, 1H), 7.82-7.76 (m, 1H), 7.73 (s, 1H), 7.67-7.60 (m, 1H), 7.50-7.43 (m, 1H), 7.38-7.20 (m, 5H), 6.13-6.08* and 5.94-5.88 (m, 1H), 4.66-4.56 (m, 1H), 4.28-4.19 (m, 1H), 4.15 (s, 3H), 3.91 (br s, 2H), 3.50-3.35 (m, 3H), 3.16-3.00 (m, 1H), 2.94 (s, 3H). MS ($ES^+$) m/z 442 $(M+H)^+$.

Example 13

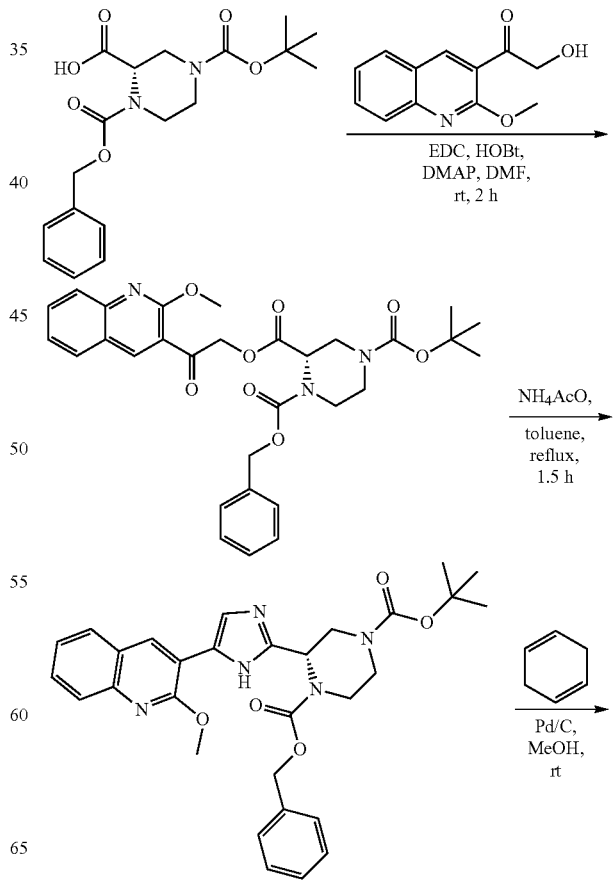

-continued

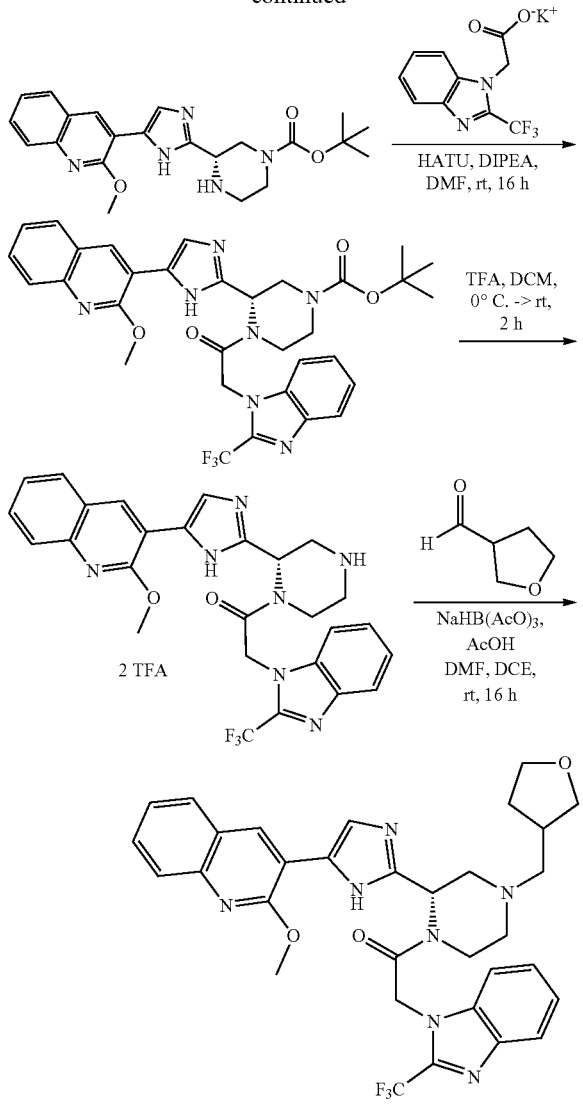

Example 13: 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one (L-Tartaric Acid Salt) (M6)

Step 1: 1-benzyl 4-(tert-butyl) 2-(2-(2-methoxyquinolin-3-yl)-2-oxoethyl) (S)-piperazine-1,2,4-tricarboxylate (M1)

EDC.HCl (1.5 eq) and HOBt (1.5 eq) were added to a solution of (S)-1-((benzyloxy)carbonyl)-4-(tert-butoxycarbonyl)piperazine-2-carboxylic acid (1.0 eq) in DMF (0.3 M) and the resulting mixture was stirred at 20° C. for 15 min, then 2-hydroxy-1-(2-methoxyquinolin-3-yl)ethan-1-one (1.0 eq) and DMAP (0.3 eq) were added. After 2 h the solvent was removed and the residue was dissolved in EtOAc, washed with H$_2$O, brine, dried and concentrated. The residue was purified by flash chromatography (petroleum ether/EtOAc, from 100:0 to 20:80) to give the title compound (35%). MS (ES$^+$) m/z 564 (M+H)$^+$.

Step 2: 1-benzyl 4-(tert-butyl) (S)-2-(5-(2-methoxyquinolin-3-yl)-1H-imidazol-2-yl)piperazine-1,4-dicarboxylate (M2)

M1 (1.0 eq) was dissolved in toluene (0.1 M), NH$_4$AcO (10 eq) was added and the mixture heated to reflux using a Dean Stark apparatus for 12 h. The mixture was concentrate and diluted with EtOAc, washed with H$_2$O and brine then dried and concentrated. The residue was purified by flash chromatography (petroleum ether/EtOAc, from 80:20 to 0:100) to give the title compound (80%) as a solid. MS (ES$^+$) m/z 544 (M+H)$^+$.

Step 3: tert-butyl (S)-3-(5-(2-methoxyquinolin-3-yl)-1H-imidazol-2-yl)piperazine-1-carboxylate (M3)

Pd/C (10% wt) (1/1 in weight) and cyclohexa-1,4-diene (10 eq) were sequentially added to a solution of M2 (0.04 M) under nitrogen and the suspension was left stirring at 20° C. overnight. The mixture was filtered on a pad of Solka Floc, washed with EtOAc and evaporated in vacuo to give the title compound (99%) as a pale yellow foam. MS (ES$^+$) m/z 410 (M+H)$^+$.

Step 4: tert-butyl (S)-3-(5-(2-methoxyquinolin-3-yl)-1H-imidazol-2-yl)-4-(2-(2-(trifluoromethyl)-1H-benzo[d]imidazol-1-yl)acetyl)piperazine-1-carboxylate (M4)

Potassium 2-[2-(trifluoromethyl)benzimidazol-1-yl]ethanoate (1.3 eq), HATU (1.5 eq) and DIPEA (1.3 eq) were sequentially added to a solution of M3 in DMF (0.14 M) and the resulting orange solution was stirred at 20° C. for 16 h. The solution was diluted with EtOAc and washed with aq. sol. NaHCO$_3$, brine, dried and evaporated in vacuo to give a crude which was purified by flash chromatography to give the title compound (99%) as a foam MS (ES$^+$) m/z 636 (M+H)$^+$.

Step 5: (S)-1-(2-(5-(2-methoxyquinolin-3-yl)-1H-imidazol-2-yl)piperazin-1-yl)-2-(2-(trifluoromethyl)-1H-benzo[d]imidazol-1-yl)ethan-1-one (Trifluoroacetate Salt) (M5)

TFA (0.07 M) was added dropwise to a solution of M4 in DCM (0.07 M) cooled to 0° C. and the suspension was left warming to 20° C. and stirred for 2 h. Solvent was then removed in vacuo to give the title compound (99%) which was directly used in the next step. MS (ES$^+$) m/z 536 (M+H)$^+$.

Step 6: 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one (L-tartaric Acid Salt) (M6)

Tetrahydrofuran-3-carbaldehyde (1.5 eq) and AcOH (1.5 eq) were sequentially added to a solution of M5 (1.0 eq) in DMF/DCE (1:1, 0.124 M) and the solution was stirred at 20° C. for 1 h. Sodium triacetoxyborohydride (5 eq) was added at 0° C. and the suspension left warming to 20° C. and stirred for 16 h. Mixture was diluted with EtOAc and washed with aq. sol. NaHCO$_3$, brine, dried and concentrated to give a residue which was purified by RP-HPLC to give after lyophilization the title compound as TFA salt. The obtained powder was dissolved in DCM and washed with aq. sol. NaHCO$_3$. The organic phase was dried over Na$_2$SO$_4$ and evaporated in vacuo to give the free base which was dissolved in water/AcCN (1:1) and treated with L-tartaric acid (1.0 eq). After lyophilization the title compound (37%) was obtained as a white powder tartrate salt. MS (ES+) m/z 620 (M+H)+.

Step 7: 1-((S)-2-(5-(2-methoxyquinolin-3-yl)-1H-imidazol-2-yl)-4-(((R)-tetrahydrofuran-3-yl)methyl)piperazin-1-yl)-2-(2-fluoromethyl)-1H-benzo[d]imidazol-1-yl)ethan-1-one and 1-((S)-2-(5-(2-methoxyquinolin-3-yl)-1H-imidazol-2-yl)-4-(((S)-tetrahydrofuran-3-yl)methyl)piperazin-1-yl)-2-(2-(trifluoromethyl)-1H-benzo[d]imidazol-1-yl)ethan-1-one (M7 and M8)

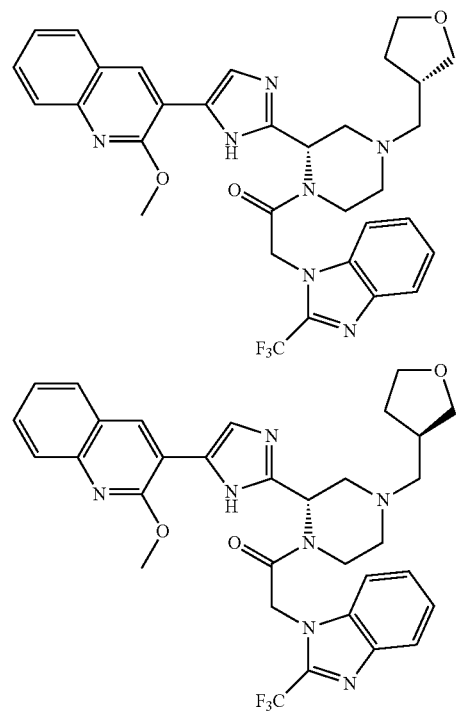

The title compounds with unknown absolute configuration at THF ring were obtained by SFC chiral separation of L6 following the Method 1: the first eluted (35%, 100% ee) retention time equal to 20.4 mins, and the second eluted (31%, 99% ee) retention time equal to 24.7 mins.

Example 14

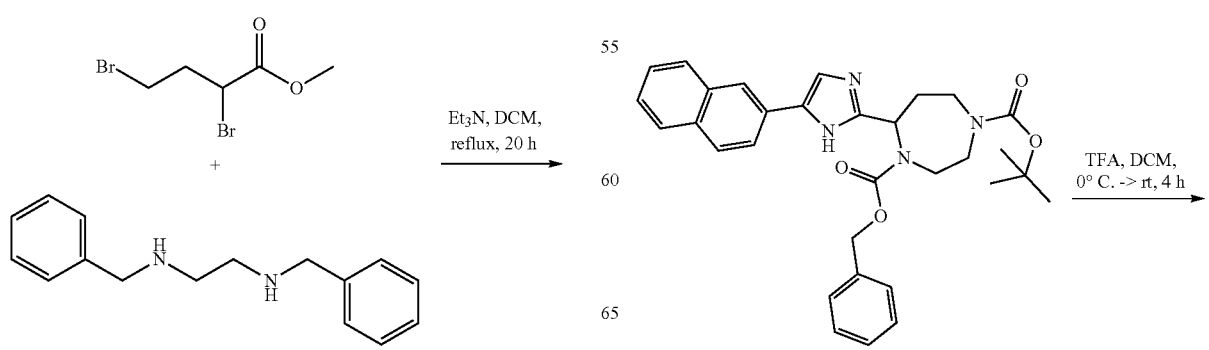

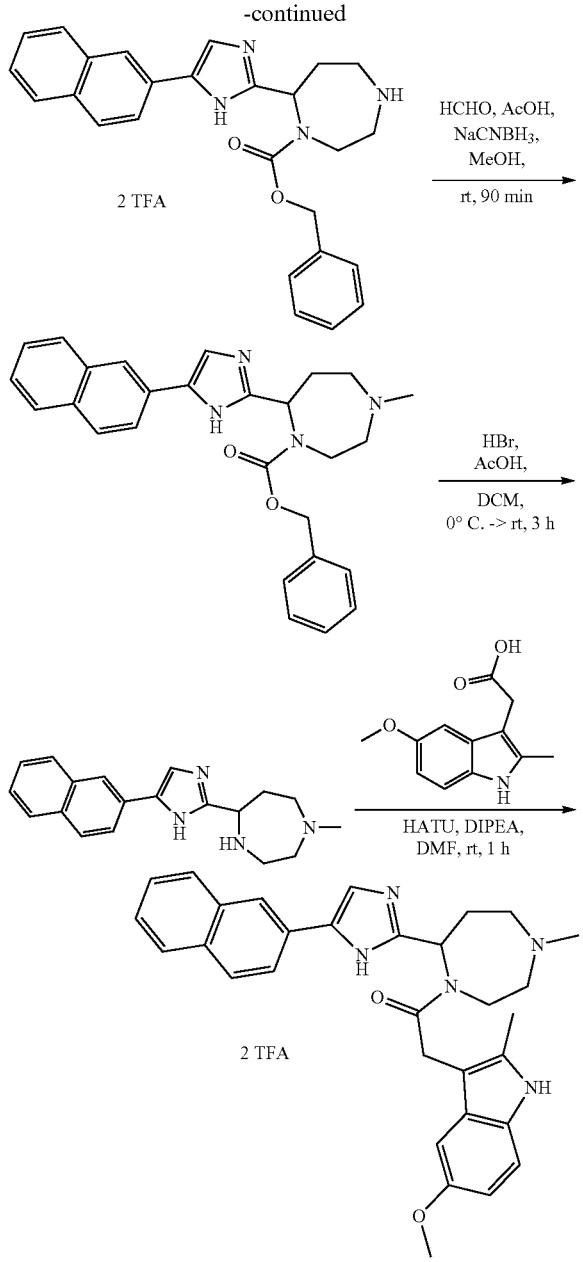

Example 14: 2-(5-methoxy-2-methyl-1H-indol-3-yl)-1-(4-methyl-7-(5-(naphthalen-2-yl)-1H-imidazol-2-yl)-1,4-diazepan-1-yl)ethan-1-one (trifluoroacetate Salt) (N9)

Step 1: methyl 1,4-dibenzyl-1,4-diazepane-5-carboxylate (N1)

A solution of N$_1$,N$_2$-dibenzylethane-1,2-diamine (1.0 eq), methyl 2,4-dibromobutanoate (1.1.0 eq) and Et$_3$N (3.0 eq) in DCM (0.77 M) was stirred in a sealed tube at 60° C. of 16 h. The mixture was diluted with DCM, washed with sat. aq. NaHCO$_3$, brine, dried and concentrated. The residue was purified by flash chromatography (petroleum ether/EtOAc from 90:10 to 0:100) to give the title compound (57%) as an oil. MS (ES$^+$) m/z 339 (M+H)$^+$.

Step 2: methyl 1,4-diazepane-5-carboxylate (N2)

N1 (1 eq) was dissolved in EtOH (0.05 M) and treated with wet Pd(OH)$_2$ (20% wt) (1:1 in weight). The mixture was purged with N$_2$ and stirred on H$_2$ atmosphere at 20° C. overnight. Then, the mixture was filtered through a pad of Solka Floc and the filtrate was concentrated under vacuum to give the title compound (91%) which was directly used in the next step. $^1$H-NMR (400 MHz, 300 K, DMSO-d$_6$) δ 3.61 (s, 3H), 3.52-3.47 (m, 1H), 2.90-2.83 (m, 1H), 2.77 (t, 1H, J=5.9 Hz), 2.74-2.68 (m, 1H), 2.66-2.63 (m, 1H), 2.60-2.59 (m, 1H), 2.58-2.52 (m, 1H), 2.04-1.94 (m, 1H), 1.71-1.60 (m, 1H).

Step 3: 4-benzyl 1-(tert-butyl) 5-methyl 1,4-diazepane-1,4,5-tricarboxylate (N3)

A solution of N2 (1.0 eq) in a 1,4-dioxane/water=1:1 solution (0.24 M) was made basic (pH 11) with aq. 50% (wt/wt) NaOH solution. A solution of BOC-ON (1.1.0 eq) in 1,4-dioxane (1 M) was then added and the resulting solution was stirred at 20° C. overnight. The mixture was extracted with Et$_2$O and acidified with conc. HCl (pH=2). The aqueous layer was extracted with EtOAc and basified (until pH=10) with aq. 50% (wt/wt) NaOH solution. A solution of Cbz-succinimide (1.1.0 eq) in 1,4-dioxane (1 M) was added dropwise at 0° C. and the mixture was stirred at 20° C. for 3 days (2×1.0 eq of Cbz-succinimide were added after 2 h and 3 h before leaving the mixture stirring for 3 days). 1,4-dioxane was evaporated under reduced pressure and the basic solution was extracted with Et$_2$O and after being acidified with conc. HCl (pH 2) was extracted with EtOAc. The combined organic layers were dried and evaporated to give 4-((benzyloxy)carbonyl)-1-(tert-butoxycarbonyl)-1,4-diazepane-5-carboxylic acid. This product was dissolved in MeOH (1.3 M) and the solution was cooled to 0° C., then SOCl$_2$ (4.2 eq) was slowly added. The mixture was stirred at 20° C. for overnight, then concentrated under reduced pressure. The residue was purified by SCX Isolute cartridge eluting first with MeOH then with 7 N NH$_3$/MeOH solution which was concentrated under reduced pressure to give 1-benzyl 7-methyl 1,4-diazepane-1,7-dicarboxylate. The latter was dissolved with DCM (0.25 M) and Et$_3$N (2.1.0 eq) was added, then the resulting solution was cooled to 0° C. and Boc$_2$O (2.2 eq) was added. The mixture was stirred at 20° C. for 1 h, then diluted with DCM, washed with HCl 0.5 N, sat. aq. NaHCO$_3$, brine, dried and concentrated to give the title compound (99%) as an oil which was used in the next step without further purification. MS (ES$^+$) m/z 415 (M+Na)$^+$.

Step 4: 4-((benzyloxy)carbonyl)-1-(tert-butoxycarbonyl)-1,4-diazepane-5-carboxylic acid (N4)

LiOH.H$_2$O (2.0 eq) in H$_2$O (THF/H$_2$O=4:1 sol., 0.055 M) was added to a stirred solution of N3 (1.0 eq) in THF. The mixture was stirred at 20° C. for 3 h (2.0 eq of LiOH.H$_2$O were added after 1 h) then the THF was removed under reduced pressure and the aqueous phase was washed with Et$_2$O. Aqueous phase was acidified with HCl 1 N (pH=4) and the product was extracted with DCM. The combined organic phases were washed with brine, dried and concentrated to give the title compound (71%) as an oil which was used in the next step without further purification. MS (ES$^+$) m/z 401 (M+Na)$^+$.

Step 5: 4-benzyl 1-(tert-butyl) 5-(5-(naphthalen-2-yl)-1H-imidazol-2-yl)-1,4-diazepane-1,4-dicarboxylate (N5)

Cs₂CO₃ (0.5 eq) was added to a stirred solution of N4 (1.0 eq) in EtOH (0.6 M). The mixture was stirred at 20° C. for 2 h then the solvent was evaporated and cesium 4-((benzyloxy)carbonyl)-1-(tert-butoxycarbonyl)-1,4-diazepane-5-carboxylate was dried at high vacuum pump for 16 h, then it was dissolved with DMF (0.6 M) and 2-bromo-1-(naphthalen-2-yl)ethan-1-one (1.1.0 eq) was added. The mixture was stirred at 20° C. for 1 h, then DMF was removed under reduced pressure co-evaporating with toluene. The residue was diluted with EtOAc and filtered off. Filtrate was evaporated to give 4-benzyl 1-(tert-butyl) 5-(2-(naphthalen-2-yl)-2-oxoethyl)-1,4-diazepane-1,4,5-tricarboxylate. The latter was dissolved with toluene (0.06 M) and NH₄OAc (20 eq) was added. The mixture was stirred at reflux using a Dean Stark apparatus for 2 h, then it was diluted with EtOAc, washed with sat. aq.NaHCO₃, brine, dried and concentrated to give an orange oily residue. The residue was purified by flash chromatography (petroleum ether/EtOAc from 90:10 to 0:100) to give the title compound (44%) as an orange solid. MS (ES⁺) m/z 527 (M+H)⁺.

Step 6: benzyl 7-(5-(naphthalen-2-yl)-1H-imidazol-2-yl)-1,4-diazepane-1-carboxylate (Trifluoroacetate Salt) (N6)

TFA (DCM/TFA=9:1 sol., 0.05 M) was slowly added to a solution of N5 (1.0 eq) in DCM cooled to 0° C. The mixture was left warming to 20° C. and stirred for 4 h, then concentrated under reduced pressure. The resulting oily residue was co-evaporated with Et₂O, then dissolved in MeCN/H₂O=1:1 solution and lyophilized to give the title compound (99%) which was directly used in the next step. MS (ES⁺) m/z 427 (M+H)⁺.

Step 7: benzyl 4-methyl-7-(5-(naphthalen-2-yl)-1H-imidazol-2-yl)-1,4-diazepane-1-carboxylate (N7)

HCHO (3.0 eq) was added to a stirred solution of N6 (1.0 eq) in MeOH (0.05 M) and stirring was continued for 1 h. Then NaBH₃CN (1.5 eq) was added and the mixture was stirred at 20° C. for 30 min and diluted with EtOAc. The organic phase was washed with sat. aq. NaHCO₃ sol., brine, dried and concentrated. The residue was purified by flash chromatography (petroleum ether/EtOAc from 90:10 to 0:100, then EtOAc/MeOH from 100:0 to 80:20) to give the title compound (80%) as a solid. MS (ES⁺) m/z 441 (M+H)⁺.

Step 8: 1-methyl-5-(5-(naphthalen-2-yl)-1H-imidazol-2-yl)-1,4-diazepane (N8)

A solution of HBr in AcOH (HBr in AcOH/DCM=1:2 sol., 0.05 M) was added to a stirred solution of N7 in DCM cooled to 0° C. The mixture was stirred at this temperature for 1 h and at 20° C. for 2 h, then it was concentrated under reduced pressure. The resulting oily residue was co-evaporated with toluene. The residue was purified by SCX Isolute cartridge eluting first with MeOH then with 7 N NH₃/MeOH solution which was concentrated under reduced pressure. The residue was dissolved in MeCN/H₂O=1:1 solution and lyophilized to give the title compound (99%) which was directly used in the next step. MS (ES⁺) m/z 307 (M+H)⁺.

Step 9: 2-(5-methoxy-2-methyl-1H-indol-3-yl)-1-(4-methyl-7-(5-(naphthalen-2-yl)-1H-imidazol-2-yl)-1,4-diazepan-1-yl)ethan-1-one (Trifluoroacetate Salt) (N9)

A solution of 2-(5-methoxy-2-methyl-1H-indol-3-yl)acetic acid (1.0 eq), HATU (1.0 eq) and DIPEA (2.3 eq) in DMF (0.16 M) was stirred for 15 min at 20° C. then added to a solution of N8 (0.77 eq) in DMF (0.5 M) and stirring was continued at 20° C. for 1 h. The mixture was filtered and purified by RP-HPLC to give after lyophilization the title compound (31%) as a solid. ¹H-NMR (400 MHz, 300 K, DMSO-d₆) δ (6:4* mixture of rotamers) 10.66 and 10.64* (s, 1H), 8.25 and 8.22* (s, 1H), 8.05-7.77 (m, 5H), 7.60-7.45 (m, 2H), 7.12 and 7.06* (d, 1H, J=8.7 Hz), 6.90-6.80 (m, 1H), 6.62-6.55 (m, 1H), 5.60-5.53 and 5.50-5.45* (m, 1H), 4.35-4.17 (m, 1H), 4.00-3.82 (m, 2H), 3.82-3.67 (m, 1H), 3.64 and 3.62* (s, 3H), 3.60-3.47 (m, 1H), 3.45-3.22 (m, 2H), 3.20-3.02 (m, 1H), 2.97-2.85 (m, 1H), 2.83 and 2.75* (s, 3H), 2.70-2.52 (m, 1H), 2.28*-2.25 (s, 3H). MS (ES⁺) m/z 508 (M+H)⁺.

Example 15

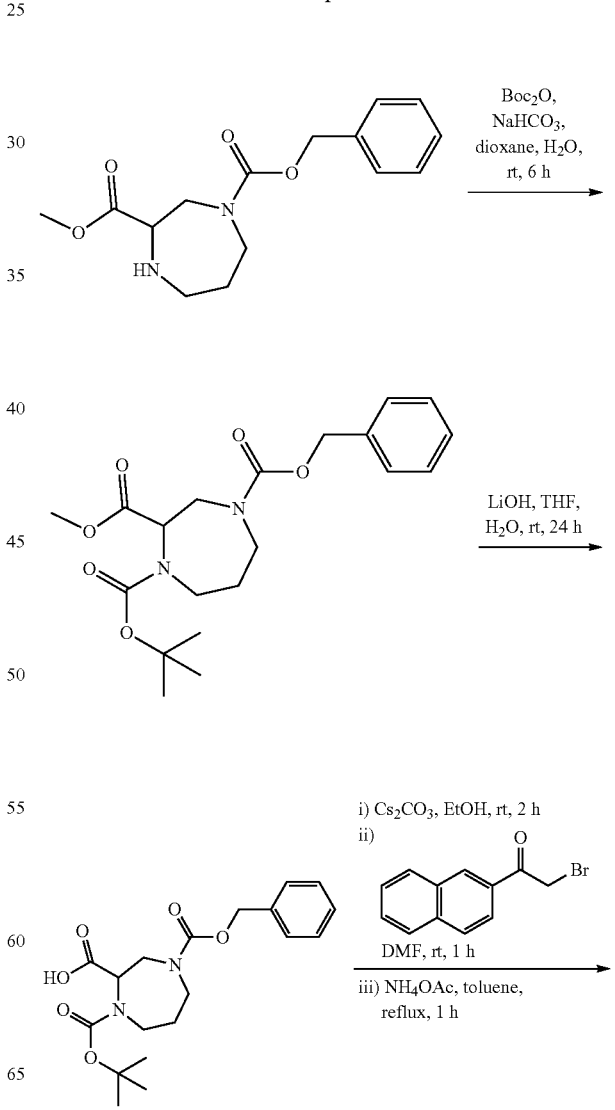

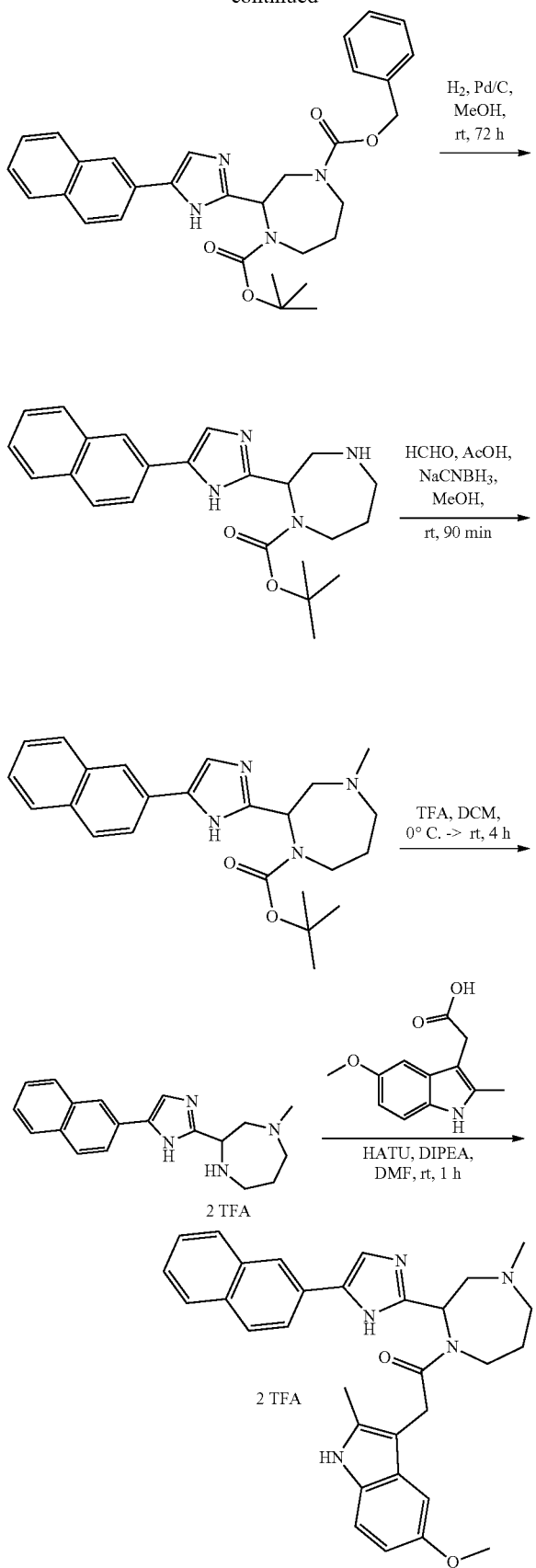

Example 15: 2-(5-methoxy-2-methyl-1H-indol-3-yl)-1-(4-methyl-2-(5-(naphthalen-2-yl)-1H-imidazol-2-yl)-1,4-diazepan-1-yl)ethan-1-one (O7)

Step 1: 4-benzyl 1-(tert-butyl) 2-methyl 1,4-diazepane-1,2,4-tricarboxylate (O1)

A solution of $NaHCO_3$ (4.0 eq) in $H_2O$ (1,4-dioxane/$H_2O$=1:1, 0.09 M) was added to a stirred solution of 1-benzyl 3-methyl 1,4-diazepane-1,3-dicarboxylate (1.0 eq) in 1,4-dioxane. The mixture was cooled to 0° C. then $Boc_2O$ (2.0 eq) was added and stirring was continued at 20° C. for 6 h, until the conversion was complete. Resulting solution was diluted with EtOAc and water phase was separated. Organic phase was washed with brine, dried, filtered and concentrated. The aqueous phase was acidified then extracted with DCM, dried and concentrated. The residues were combined to give a yellow oily residue which was used in the next step without further purification. MS ($ES^+$) m/z 415 $(M+Na)^+$.

Step 2: 4-((benzyloxy)carbonyl)-1-(tert-butoxycarbonyl)-1,4-diazepane-2-carboxylic acid (O2)

A solution of $LiOH.H_2O$ (2.0 eq) in $H_2O$ (THF/$H_2O$=4:1 sol., 0.06 M) in THF was added to a stirred solution of O1 (1.0 eq). The mixture was stirred at 20° C. for 24 h then the THF was removed under reduced pressure. The aqueous phase was washed with $Et_2O$ then acidified with HCl 1 N (pH=4) and the product was extracted with EtOAc. The recombined organic phases were washed with brine, dried and concentrated to give the title compound (89%) as an oil which was used in the next step without further purification. MS ($ES^+$) m/z 379 $(M+H)^+$.

Step 3: 4-benzyl 1-(tert-butyl) 2-(5-(naphthalen-2-yl)-1H-imidazol-2-yl)-1,4-diazepane-1,4-dicarboxylate (O3)

$Cs_2CO_3$ (0.5 eq) was added to a stirred solution of 02 (1.0 eq) in EtOH (0.6 M). The mixture was stirred at 20° C. for 2 h then solvent was evaporated and cesium 4-((benzyloxy)carbonyl)-1-(tert-butoxycarbonyl)-1,4-diazepane-2-carboxylate was dried at high vacuum pump for 16 h, then was dissolved with DMF (0.6 M) and 2-bromo-1-(naphthalen-2-yl)ethan-1-one (1.1.0 eq) was added. The mixture was stirred at 20° C. for 1 h, then DMF was removed under reduced pressure co-evaporating with toluene. The residue was diluted with EtOAc and filtered off. Filtrate was evaporated to give 4-benzyl 1-(tert-butyl) 2-(2-(naphthalen-2-yl)-2-oxoethyl) 1,4-diazepane-1,2,4-tricarboxylate. The latter was dissolved with toluene (0.06 M) and $NH_4OAc$ (20 eq) was added. The mixture was stirred at reflux using a Dean Stark apparatus for 1 h, then it was diluted with EtOAc, washed with sat. aq. $NaHCO_3$, brine, dried and concentrated to give an orange oily residue. The residue was purified by flash chromatography (petroleum ether/EtOAc from 90:10 to 0:100) to give the title compound (60%) as an orange solid. MS ($ES^+$) m/z 527 $(M+H)^+$.

Step 4: tert-butyl 2-(5-(naphthalen-2-yl)-1H-imidazol-2-yl)-1,4-diazepane-1-carboxylate (O4)

O3 (1.0 eq) was dissolved in MeOH (0.04 M) and treated with wet Pd/C (10% wt) (1:1 in weight). The mixture was purged with $N_2$ and stirred on $H_2$ atmosphere at 20° C. for 72 h. The suspension was filtered through a pad of Solka Floc and filtrate was concentrated under vacuum to give the title compound (99%) which was directly used in the next step. MS (ES+) m/z 393 (M+H)+.

Step 5: tert-butyl 4-methyl-2-(5-(naphthalen-2-yl)-1H-imidazol-2-yl)-1,4-diazepane-1-carboxylate (O5)

HCHO (1.5 eq) and AcOH (1.0 eq) (pH=4-5) were sequentially added to a stirred solution of 04 (1.0 eq) in MeOH (0.05 M) and stirring was continued for 1 h. Then NaBH$_3$CN (1.5 eq) was added and the mixture was stirred at 20° C. for 30 min then it was diluted with EtOAc. The organic phase was washed with sat. aq.NaHCO$_3$, brine, dried and concentrated. The residue was purified by flash chromatography (petroleum ether/EtOAc from 9:1 to 0:10, then EtOAc/MeOH from 100:0 to 80:20) to give the title compound (80%) as a solid. MS (ES+) m/z 407 (M+H)+.

Step 6: 1-methyl-3-(5-(naphthalen-2-yl)-1H-imidazol-2-yl)-1,4-diazepane (Trifluoroacetate Salt) (O6)

TFA (DCM/TFA=4:1 sol., 0.05 M) was slowly added to a solution of 05 (1.0 eq) in DCM cooled to 0° C. The mixture was left warming to 20° C. and stirred for 4 h, then concentrated under reduced pressure. The resulting oily residue was co-evaporated with Et$_2$O, then dissolved in MeCN/H$_2$O=1:1 solution and lyophilized to give the title compound (99%) which was directly used in the next step. MS (ES+) m/z 307 (M+H)+.

Step 7: 2-(5-methoxy-2-methyl-1H-indol-3-yl)-1-(4-methyl-2-(5-(naphthalen-2-yl)-1H-imidazol-2-yl)-1,4-diazepan-1-yl)ethan-1-one (Trifluoroacetate Salt) (O7)

A solution of 2-(5-methoxy-2-methyl-1H-indol-3-yl)acetic acid (1.0 eq), HATU (1.0 eq) and DIPEA (2.3 eq) in DMF (0.16 M) was stirred for 15 min at 20° C. then added to a solution of 06 (0.77 eq) in DMF (0.5 M) and stirring was continued at 20° C. for 1 h. The mixture was filtered and purified by RP-HPLC to give after lyophilization the title compound (27%) as a solid. $^1$H-NMR (400 MHz, 300 K, DMSO-d$_6$) δ (7:3* mixture of rotamers) 10.55 (s, 1H), 9.98 (br s, 1H), 8.25 (s, 1H), 7.98-7.82 (m, 4H), 7.82-7.64 (m, 1H), 7.56-7.42 (m, 2H), 7.12 (d, 1H, J=8.4 Hz), 6.95 (s, 1H), 6.63 (d, 1H, J=8.4 Hz), 6.00-5.70 (m, 1H), 4.40-4.25* and 4.20-3.97 (m, 3H), 3.95-3.72 (m, 2H), 3.70 (s, 3H), 3.67-3.52 (m, 1H), 3.50-3.20 (m, 2H), 3.15-2.75 (m, 3H), 2.29 (s, 3H), 2.15-1.70 (m, 3H). MS (ES+) m/z 508 (M+H)+.

Example 16

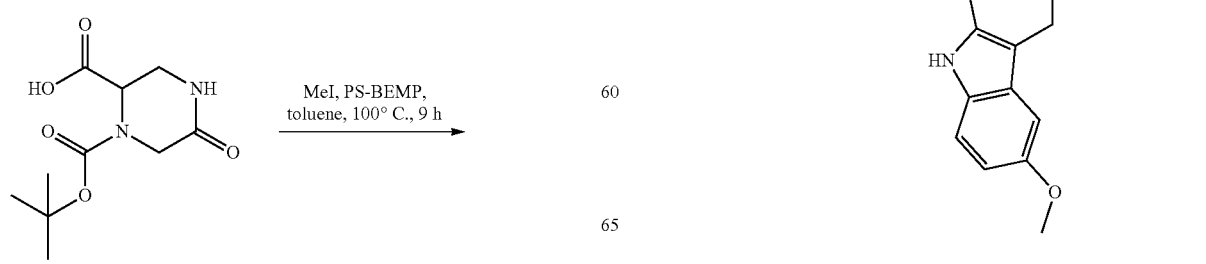

Example 16: 4-(2-(5-methoxy-2-methyl-1H-indol-3-yl)acetyl)-1-methyl-5-(5-(naphthalen-2-yl)-1H-imidazol-2-yl)piperazin-2-one (Trifluoroacetate Salt) (P5)

Step 1: 1-(tert-Butyl) 2-methyl 4-methyl-5-oxopiperazine-1,2-dicarboxylate (P1)

PS-BEMP (0.5 eq) and iodomethane (6 eq) were added to a stirred solution of 1-(tert-butoxycarbonyl)-5-oxopiperazine-2-carboxylic acid (1.0 eq) in toluene (0.066 M) at 20° C. The mixture was heated in a sealed tube to 100° C. for 9 h. After cooling to 20° C., the mixture was diluted with EtOAc (100 mL) and filtered. The organic layer was washed with sat. aq.NaHCO$_3$, dried and concentrated to give the title compound as a colourless oil, which was used in the next step without further purification. $^1$H-NMR (400 MHz, 300 K, CDCl$_3$) δ 5.01 (br s, 1H), 4.24 (d, 1H, J$_{AB}$=18.4 Hz), 4.02 (d, 1H, J$_{AB}$=18.4 Hz), 3.80 (s, 3H), 3.57-3.54 (m, 2H), 3.01 (s, 3H), 1.51 (s, 9H). MS (ES$^+$) m/z 295 (M+Na)$^+$.

Step 2: 1-(tert-Butoxycarbonyl)-4-methyl-5-oxopiperazine-2-carboxylic acid (P2)

LiOH.H$_2$O (2 eq) was added to a stirred solution of P1 (1.0 eq) in THF/H$_2$O (4:1, 0.1 M) at 20° C. The mixture was stirred at 20° C. for 1 h. After dilution with water, the aqueous solution was acidified until pH 2-3 and extracted with EtOAc. The combined organic layers were dried and concentrated to give the title compound as a pale brown syrup which was used in the next step without further purification. MS (ES$^+$) m/z 259 (M+H)$^+$.

Step 3: tert-Butyl 4-methyl-2-(5-(naphthalen-2-yl)-1H-imidazol-2-yl)-5-oxopiperazine-1-carboxylate (P3)

Cs$_2$CO$_3$ (0.5 eq) was added to a stirred solution of P2 (1.0 eq) in EtOH (0.5 M) at 20° C. The mixture was stirred for 1 h then the solvent was evaporated under reduced pressure giving a residue which was dissolved in DMF (0.5 M) and 2-bromo-1-(naphthalen-2-yl)ethan-1-one (1.0 eq) was added. The mixture was stirred at 20° C. for 4 h, then diluted with toluene and concentrated under reduced pressure. The resulting residue was dissolved in toluene (0.12 M) and NH$_4$OAc (20 eq) was added. The mixture was heated to reflux under Dean-Stark conditions for 1 h. After cooling to 20° C. solvent was evaporated under reduced pressure to give a residue which was diluted with EtOAc. The organic layer was washed with sat. aq.NaHCO$_3$, brine, dried and concentrated. The crude was purified by flash chromatography (petroleum ether/EtOAc from 90:10 to 30:70) to give the title compound (5% over 3 steps) as a colorless foam. $^1$H-NMR (400 MHz, 300 K, CDCl$_3$) δ 8.14 (br s, 1H), 7.87-7.77 (m, 5H), 7.52-7.42 (m, 2H), 5.43 (dd, 1H, J=4.4, 2.8 Hz), 4.30-4.24 (m, 1H), 4.27 (d, 1H, J=17.6 Hz), 3.98-3.85 (m, 1H), 3.90 (dd, 1H, J=4.8, 13.2 Hz), 3.20 (br s, 3H), 1.54 (s, 9H). MS (ES$^+$) m/z 407 (M+H)$^+$.

Step 4: 1-methyl-5-(5-(naphthalen-2-yl)-1H-imidazol-2-yl)piperazin-2-one (Trifluoroacetate Salt) (P4)

TFA was slowly added to a stirred solution of P3 (1.0 eq) in DCM (0.1 M) cooled to 0° C. The mixture was stirred at 20° C. for 2 h then the solvent was evaporated under reduced pressure to give the title compound (99%) as a pale brown oil which was used in the next step without further purification. MS (ES$^+$) m/z 307 (M+H)$^+$.

Step 5: 4-(2-(5-methoxy-2-methyl-1H-indol-3-yl)acetyl)-1-methyl-5-(5-(naphthalen-2-yl)-1H-imidazol-2-yl)piperazin-2-one (Trifluoroacetate Salt) (P5)

HOBt (1.5 eq) and EDC.HCl (1.5 eq) were added to a stirred solution of P4 (1.0 eq), 2-(5-methoxy-2-methyl-1H-indol-3-yl)acetic acid (1.5 eq) and DIPEA (5.0 eq) in DMF (0.05 M) at 20° C. The mixture was stirred for 2 h then purified by RP-HPLC to give the title compound (23%) as white powder. $^1$H-NMR (400 MHz, 300 K, DMSO-d$_6$) δ 10.66 (s, 1H), 8.25 (s, 1H), 8.08-7.87 (m, 4H), 7.60-7.48 (m, 2H), 7.12 (d, 1H, J=8.8 Hz), 6.94 (brs, 2H), 6.63-6.58 (m, 1H), 5.74 (brs, 1H), 4.39 (br s, 2H), 4.00-3.72 (m, 2H), 3.68 (s, 3H), 2.82 (s, 3H). MS (ES$^+$) m/z 508 (M+H)$^+$.

Example 17

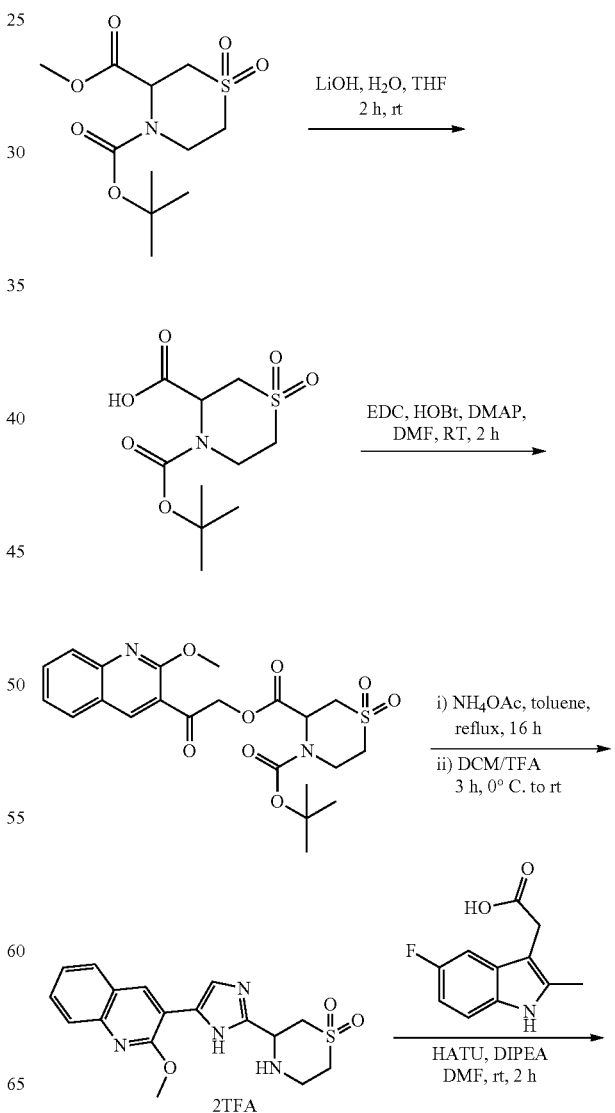

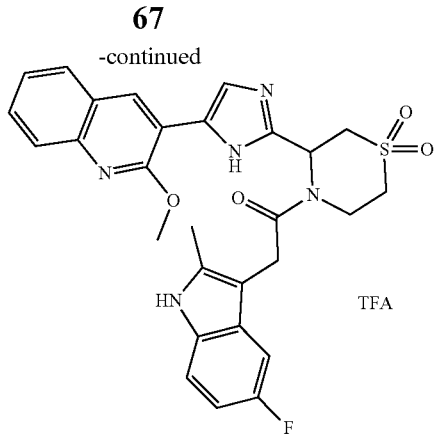

Example 17: 2-(5-fluoro-2-methyl-1H-indol-3-yl)-1-(3-(5-(2-methoxyquinolin-3-yl)-1H-imidazol-2-yl)-1,1-dioxidothiomorpholino)ethan-1-one (Trifluoroacetate Salt) (Q4)

Step 1: 4-(tert-butoxycarbonyl)thiomorpholine-3-carboxylic acid 1,1-dioxide (Q1)

4-(tert-butyl) 3-methyl thiomorpholine-3,4-dicarboxylate 1,1-dioxide (1.0 eq) was dissolved in THF (0.1 M) and LiOH (2.2 eq in H$_2$O, 0.1 M) was added. The mixture was stirred for 2 h at 20° C. then concentrated under reduced pressure. HCl 1 N was added until pH=2-3 and the aqueous phase extracted with EtOAc. The organic layer was washed with brine, dried and concentrated under reduced pressure to give the title compound (96%) as a white solid. MS (ES$^+$) m/z 280 (M+H)$^+$.

Step 2: 4-(tert-butyl) 3-(2-(2-methoxyquinolin-3-yl)-2-oxoethyl) thiomorpholine-3,4-dicarboxylate 1,1-dioxide (Q2)

EDC.HCl (1.5 eq) and HOBt (1.5 eq) were added to a stirred solution of Q1 (1.0 eq) in DMF (0.3 M) and the resulting mixture was stirred at 20° C. for 15 min, then 2-hydroxy-1-(2-methoxyquinolin-3-yl)ethan-1-one (1.0 eq) and DMAP (0.3 eq) were added and stirring was continued for 2 h. Solvent was removed under reduced pressure, the residue was dissolved in EtOAc, washed with H$_2$O, brine, dried, filtered and concentrated. The residue was purified by flash chromatography (petroleum ether/EtOAc, from 80:20 to 20 80) to give the title compound (32%). $^1$H NMR (400 MHz, 300 K, CD$_3$CN) δ 8.75 (s, 1H), 8.00 (d, 1H, J=8.0 Hz), 7.90-7.80 (m, 2H), 7.54-7.51 (m, 1H), 5.67-5.56 (m, 2H), 5.38-5.33 (m, 1H), 4.57-4.44 (m, 1H), 4.18 and 4.17 (s, 3H), 3.74-3.55 (m, 2H), 3.48-3.43 (m, 1H), 3.19-3.13 (m, 1H), 3.01-2.93 (m, 1H), 1.53 and 1.50 (s, 9H). MS (ES$^+$) m/z 479 (M+H)$^+$.

Step 3: tert-butyl 3-(5-(2-methoxyquinolin-3-yl)-1H-imidazol-2-yl)thiomorpholine-4-carboxylate 1,1-dioxide (Q3)

NH$_4$AcO (10 eq) was added to a solution of Q2 (1.0 eq) in toluene (0.1 M) and the mixture stirred at reflux using a Dean Stark apparatus for 12 h. The mixture was concentrate under reduced pressure, diluted with EtOAc, washed with H$_2$O, brine, dried and purified by flash chromatography (pethroleum ether/EtOAc, from 80:20 to 0:100) to give the title compound (68%) as a white powder. $^1$H NMR (400 MHz, 300 K, CD$_3$CN) δ (9:1* mixture of rotamers) 10.95* and 10.45 (s, 1H), 8.81 and 8.41* (s, 1H), 7.90 and 7.86* (d, 1H, J=7.9 Hz), 7.80 (d, 1H, J=8.3 Hz), 7.74 (br s, 1H), 7.68-7.54 (m, 1H), 7.51-7.42 (m, 1H), 6.06-5.98 (m, 1H), 4.56-4.54 (m, 1H), 4.20 (s, 3H), 4.02-3.86 (m, 1H), 3.77-3.66 (m, 1H), 3.59 (dd, 1H, J=14.6, 5.9 Hz), 3.22 (m, 1H), 3.04-2.98 (m, 1H), 1.52 (s, 9H). MS (ES$^+$) m/z 459 (M+H)$^+$.

Step 4: 3-(5-(2-methoxyquinolin-3-yl)-1H-imidazol-2-yl)thiomorpholine 1,1-dioxide (Trifluoracetate Salt) (Q4)

To a stirred solution of Q3 (1.0 eq) in DCM (0.01 M) cooled to 0° C. TFA (95 eq) was slowly added. The mixture was stirred at 0° C. for 9 h. Then solvent was evaporated under reduced pressure to afford an oily residue that was co-evaporated first with toluene then with Et$_2$O to give the title compound (99%) as a yellow powder. MS (ES$^+$) m/z 359 (M+H)$^+$.

Step 5: 2-(5-fluoro-2-methyl-1H-indol-3-yl)-1-(3-(5-(2-methoxyquinolin-3-yl)-1H-imidazol-2-yl)-1,1-dioxidothiomorpholino)ethan-1-one (Trifluoroacetate Salt) (Q5)

2-(5-fluoro-2-methyl-1H-indol-3-yl)acetic acid (1.5 eq), and HATU (2.0 eq) were added to a stirred solution Q4 (1.0 eq) in DMF (0.03 M) then DIPEA (2.0 eq) was added and the solution was left stirring at 20° C. for 2 h. The mixture was filtered on Si—CO$_3$ cartridge (2 g), eluting with MeOH, then organic solvent was evaporated under reduced pressure and the reaction crude was purified by RP-HPLC to give the title compound (5%) as a white powder. $^1$H NMR (400 MHz, 300 K, CD$_3$CN) δ 9.20 (s, 1H), 8.67 (s, 1H), 7.95-7.82 (m, 3H), 7.74 (t, 1H, J=7.5 Hz), 7.51 (t, 1H, J=7.5 Hz), 7.27 (br s, 1H), 7.19 (dd, 1H, J=10.2, 2.6 Hz), 6.84 (t, 1H, J=9.3 Hz), 6.71 (br s, 1H), 4.52 (br s, 1H), 4.20 (s, 3H), 4.12-4.02 (m, 2H), 4.02-3.93 (m, 2H), 3.97 (d, 2H, J=8.0 Hz), 3.63 (dd, 2H, J=15.1, 5.9 Hz), 2.38 (s, 3H). MS (ES$^+$) m/z 548 (M+H)$^+$.

Step 6: (S)-2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one and (R)-2-(6-methoxy-2-(trifluoromethyl)-1H-benzo[d]imidazol-1-yl)-1-(3-(5-(2-methoxyquinolin-3-yl)-1H-imidazol-2-yl)-1,4-dioxidothiomorpholino)ethan-1-one (Q6 and Q7)

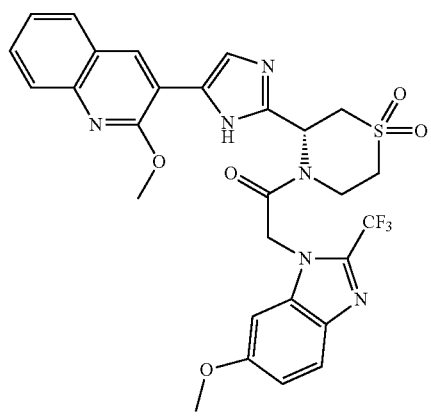

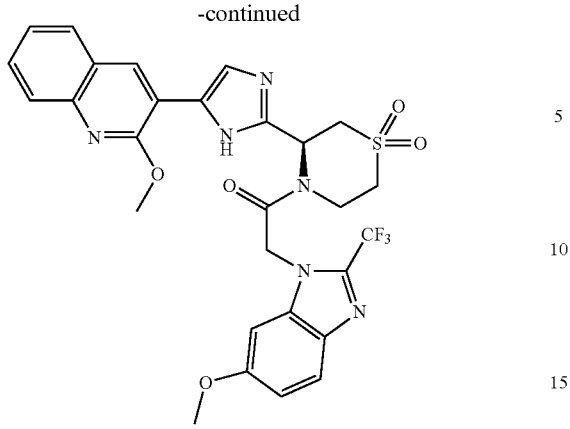
The title compounds with unknown absolute configuration at thiomorpholine ring were obtained by SFC chiral separation of Q5 following the Method 1: the first eluted (6%, 100% ee) retention time equal to 13.22 mins, and the second eluted (7%, 100% ee) retention time equal to 19.0 mins.
Example 18
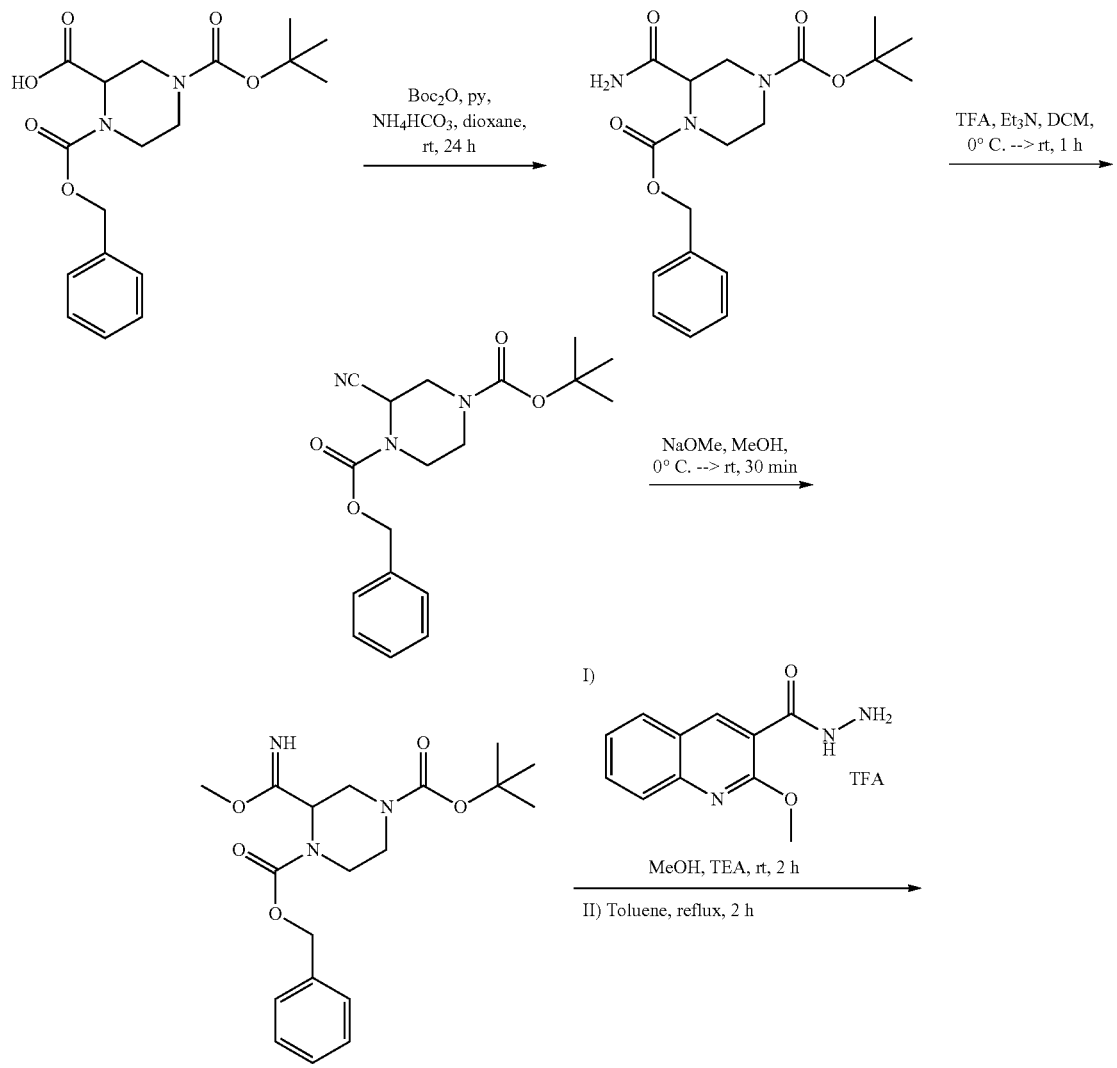

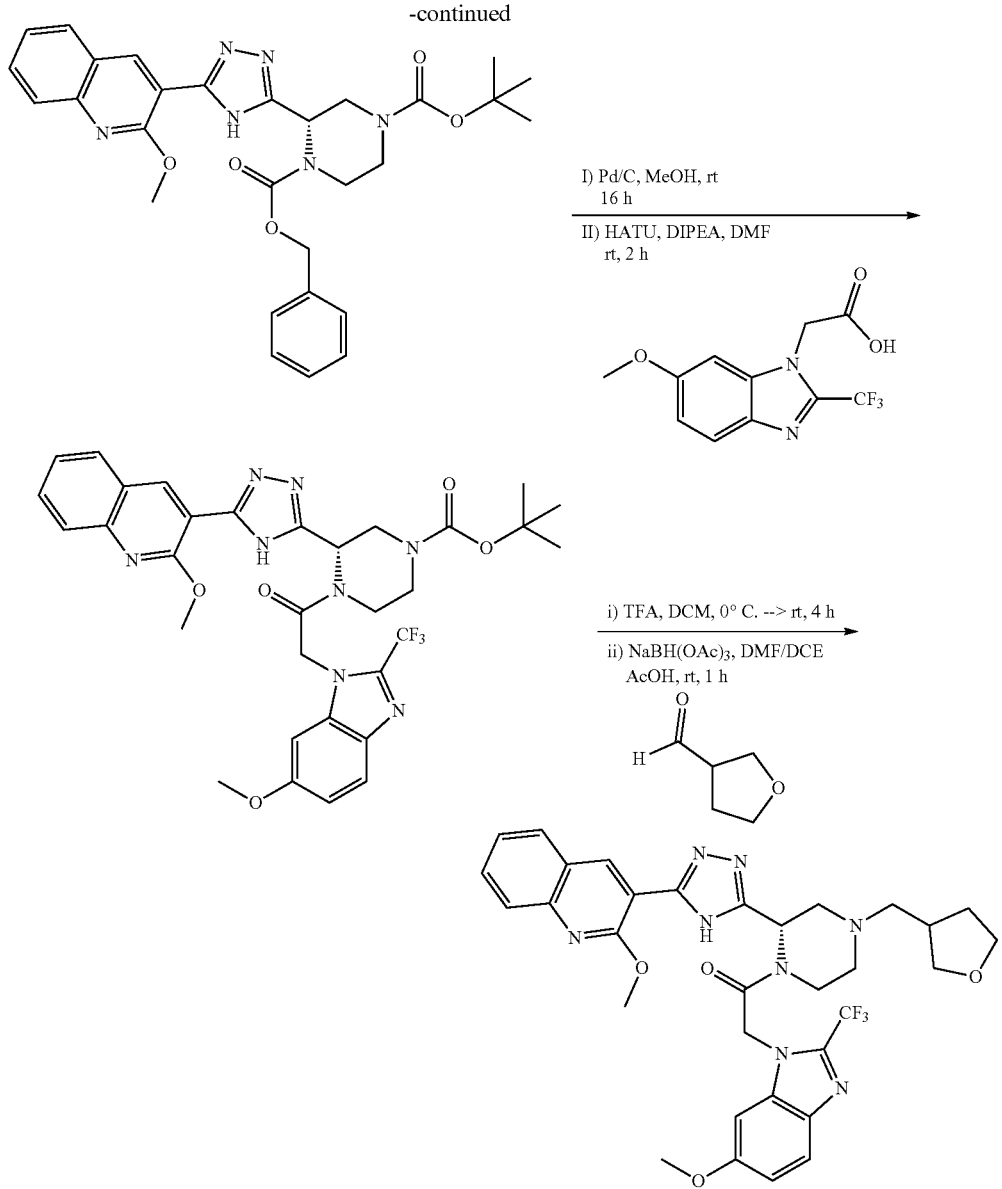

Example 18: 2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one (R8)

Step 1: 1-benzyl 4-(tert-butyl) 2-carbamoylpiperazine-1,4-dicarboxylate (R1)

Pyridine (1.0 eq), tert-butoxycarbonyl tert-butyl carbonate (1.3 eq) and ammonium bicarbonate (2.6 eq) were added to a stirred solution of (2S)-1-[(benzyloxy)carbonyl]-4-(tert-butoxycarbonyl)piperazine-2-carboxylic acid (1.0 eq) in 1,4-dioxane (0.3 M). Mixture was stirred at 20° C. for 24 h then concentrate under reduced pressure. The residue was diluted with EtOAc, washed with H₂O, 1 N aq. HCl sol., brine, dried and concentrated under pressure to give the title compound (100%) as a white solid. MS (ES⁺) m/z 364 (M)⁺.

Step 2: 1-benzyl 4-(tert-butyl) 2-cyanopiperazine-1,4-dicarboxylate (R2)

Trifluoroacetic anhydride (2.0 eq) was added to a solution of R1 (1.0 eq) and TEA (2.2 eq) in DCM (0.3 M) cooled to 0° C. Mixture was left warming to 20° C. and stirred for 1 h then DCM was added and washed with aq. sat. NaHCO₃ sol., H₂O, brine. Organic solution was dried, concentrated and purified by flash chromatography (petroleum ether/EtOAc from 80:20 to 0:100) to give the title compound (32%) as yellow solid. MS (ES⁺) m/z 346 (M+H)⁺.

Step 3: 1-benzyl 4-(tert-butyl) 2-(imino(methoxy)methyl)piperazine-1,4-dicarboxylate (R3)

Sodium methanolate (1.0 eq) was added to a stirred solution of R2 (1.0 eq) in methanol (0.1 M) cooled to 0° C. The resulting suspension was stirred at 20° C. for 30 min then quenched by addition of acetic acid until pH 7 and used in the next reaction step without further purification. MS (ES$^+$) m/z 378 (M)$^+$.

Step 4: 1-benzyl 4-(tert-butyl) (S)-2-(5-(2-methoxy-quinolin-3-yl)-4H-1,2,4-triazol-3-yl)piperazine-1,4-dicarboxylate (R4)

2-methoxyquinoline-3-carbohydrazide (Trifluoroacetate Salt) (1.1.0 eq) was dissolved in MeOH (0.05 M) and treated with TEA (1.1.0 eq) until neutral pH. This solution was filtered off and added to previous mixture of R3 (1.0 eq). The reaction was stirred at 20° C. for 2 h then the organic solvent was evaporated and toluene (0.05 M) was added. Mixture was stirred at reflux for 2 h then EtOAc was added and organic solution was washed with sat. aq. sol. NaHCO$_3$, brine, dried, concentrated and purified by flash chromatography (petroleum ether/EtOAc from 80:20 to 0:100). The title compound (14%) was obtained as yellow solid. MS (ES$^+$) m/z 545 (M+H)$^+$.

Step 5: tert-butyl (S)-3-(5-(2-methoxyquinolin-3-yl)-4H-1,2,4-triazol-3-yl)piperazine-1-carboxylate (R5)

R4 (1.0 eq) was dissolved in MeOH (0.1 M) and treated with wet Pd/C (10% wt) (1:1 in weight). The mixture was purged with N$_2$ and stirred on H$_2$ atmosphere at 20° C. for 16 h. The suspention was filtered through a pad of Solka Floc and filtrate was concentrated under vacuum to give the title compound (99%) as grey solid. MS (ES$^+$) m/z 411 (M+H)$^+$.

Step 6: tert-butyl (S)-4-(2-(6-methoxy-2-(trifluoromethyl)-1H-benzo[d]imidazol-1-yl)acetyl)-3-(5-(2-methoxyquinolin-3-yl)-4H-1,2,4-triazol-3-yl)piperazine-1-carboxylate (R6)

A solution of HATU (1.1.0 eq) and 2-[6-methoxy-2-(trifluoromethyl)benzimidazol-1-yl]ethanoic acid (1.1.0 eq) in DMF (0.05M) was stirred for 5 min and added to a solution of R5 (1.0 eq) in DMF (0.05 M) at 20° C. then DIPEA (2 eq) was added and the solution was left stirring at 20° C. for 2 h. The solution was diluted with EtOAc and washed with aq. sat. aq.NaHCO$_3$, brine, dried, concentrated and purified by flash chromatography (DCM/MeOH from 100:0 to 90:10) to give the title compound (62%) as pale pink solid. MS (ES$^+$) m/z 667 (M+H)$^+$.

Step 7: (S)-2-(6-methoxy-2-(trifluoromethyl)-1H-benzo[d]imidazol-1-yl)-1-(2-(5-(2-methoxyquinolin-3-yl)-4H-1,2,4-triazol-3-yl)piperazin-1-yl)ethan-1-one (Trifluoroacetate Salt) (R7)

TFA (25 eq) was slowly added to a solution of R6 (1.0 eq) in DCM (0.05 M) cooled to 0° C. The mixture was stirred at 0° C. for 4 h then solvent was evaporated under reduced pressure to afford an oily residue that was co-evaporated with Et$_2$O to give the title compound (99%) as pale pink solid. MS (ES$^+$) m/z 567 (M+H)$^+$.

Step 8: 2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one (R8)

Tetrahydrofuran-3-carbaldehyde (1.5 eq) and AcOH (1.5 eq) were sequentially added to a solution of R7 (1.0 eq) in DMF/DCE (2:8, 0.08 M) and the solution was stirred at 20° C. for 1 h. Sodium triacetoxyborohydride (5 eq) was added at 0° C. and the suspension left warming to 20° C. and stirred for 2 h. The suspension was diluted with DCM and washed with aq. sol. NaHCO$_3$, brine, dried and concentrated to give a residue which was purified by flash chromatography (petroleum ether/MeOH from 100:0 to 90:10) to give the title compound (69%) as white powder. $^1$H-NMR (400 MHz, 300 K, DMSO-d$_6$) δ (60:40*) 14.06 and 13.9* (s, 1H), 8.97-8.95 (m, 1H), 8.02 (d, 1H, J=7.6 Hz), 7.88-7.85 (m, 1H), 7.80-7.75 (m, 1H), 7.70 (d, 1H, J=8.2 Hz), 7.54 (t, 1H, J=7.4 Hz), 7.28* and 7.08 (s, 1H), 6.99 (dd, 1H, J=2.2, 8.9 Hz), 5.78-5.72 (m, 1H), 5.78-5.72 (m, 1H), 5.54-5.49 (m, 1H), 5.44-5.40* and 5.27-5.22 (m, 1H), 4.20 and 4.18* (s, 3H), 4.06-4.0 (m, 1H), 3.86-3.53 (m, 4H), 3.77* and 3.7 (s, 3H), 3.28-3.24 and 3.21-3.18* (m, 1H), 3.06-2.78 (m, 2H), 2.38-2.28 (m, 3H), 2.15-2.09 (m, 1H), 1.96-1.88 (m, 1H), 1.50-1.40 (m, 1H). MS (ES$^+$) m/z 651 (M+H)$^+$.

Example 19

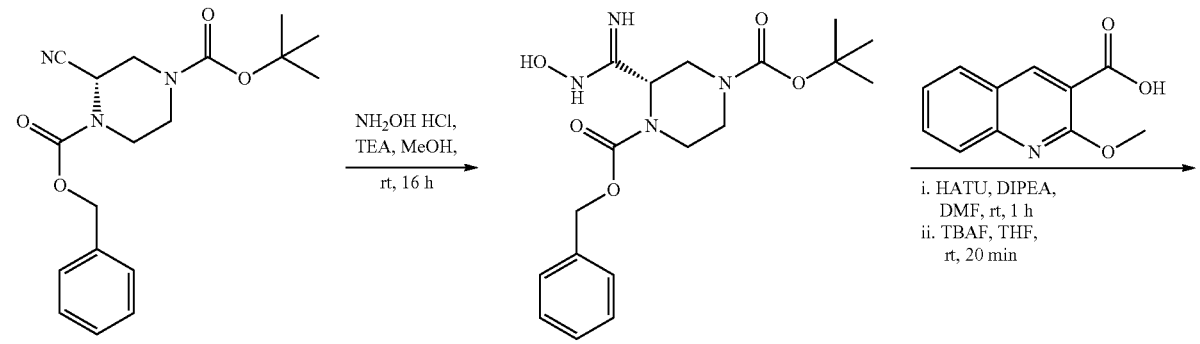

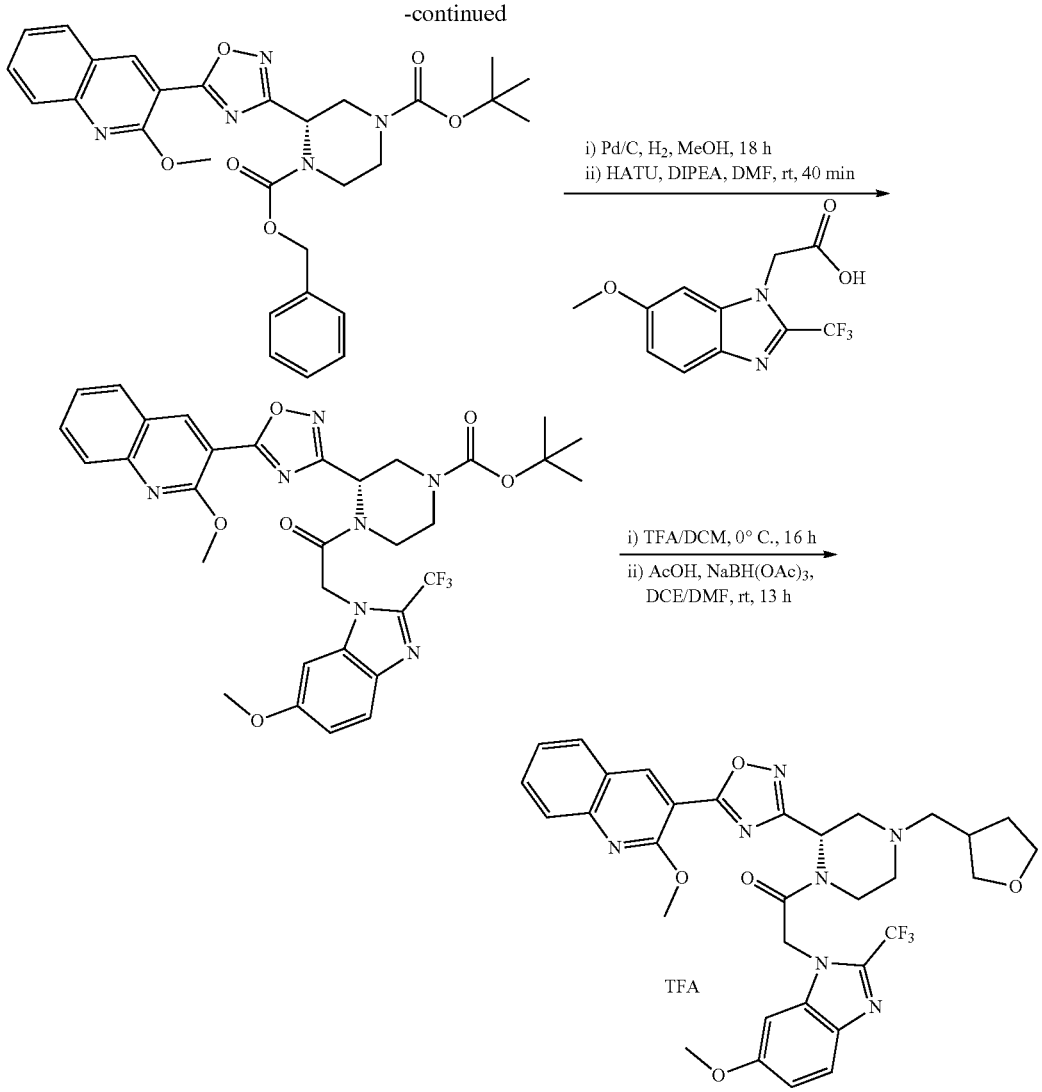

Example 19: 2-(6-methoxy-2-(trifluoromethyl)-1H-benzo[d]imidazol-1-yl)-1-((2S)-2-(5-(2-methoxyquinolin-3-yl)-1,2,4-oxadiazol-3-yl)-4-((tetrahydrofuran-3-yl)methyl)piperazin-1-yl)ethan-1-one (Trifluoroacetate Salt) (S7)

Step 1: 1-benzyl 4-(tert-butyl) (S)-2-(N-hydroxycarbamimidoyl)piperazine-1,4-dicarboxylate (S1)

TEA (1.3 eq) and hydroxylamine hydrochloride (1.5 eq) were added to a stirred solution of 1-benzyl 4-(tert-butyl) (S)-2-cyanopiperazine-1,4-dicarboxylate (1.0 eq) in MeOH (0.1 M). The solution was stirred at 20° C. for 20 h then concentrated, diluted with EtOAc and washed with water. Organic phase was dried, concentrated and used in the next step without further purification. MS (ES+) m/z 379 (M+H)+.

Step 2: 1-benzyl 4-(tert-butyl) (S)-2-(5-(2-methoxyquinolin-3-yl)-1,2,4-oxadiazol-3-yl)piperazine-1,4-dicarboxylate (S2)

S1 (1.0 eq) and DIPEA (3.0 eq) were added to a solution of 2-methoxyquinoline-3-carboxylic acid (1.5 eq) and HATU (1.5 eq) in THF (0.7 M). The mixture was stirred at 20° C. for 1 h then diluted with EtOAc and washed with H₂O. Organic phase was dried, concentrated and purified by flash chromatography (petroleum ether/EtOAc from 100:0 to 50:50). The obtained product was dissolved in THF (0.35 M), treated with tetra-n-butylammonium fluoride (1.0 eq) and stirred for 20 min at 20° C. The solution was diluted with EtOAc and washed with water, dried and concentrated. The residue was purified by flash chromatography (petroleum ether/EtOAc from 100:0 to 20:80) to give the title compound (27%) as pale yellow powder. MS (ES+) m/z 546 (M+H)+.

Step 3: tert-butyl (S)-3-(5-(2-methoxyquinolin-3-yl)-1,2,4-oxadiazol-3-yl)piperazine-1-carboxylate (S3)

S2 (1.0 eq) was dissolved in MeOH (0.04 M) and treated with wet Pd/C (10% wt) (1: in weight).

The mixture was purged with N₂ and stirred on H₂ atmosphere at 20° C. for 18 h. The suspension was filtered through a pad of Solka Floc and filtrate was concentrated under vacuum to give the title compound (83%) as white solid. MS (ES⁺) m/z 412 (M+H)⁺.

Step 4: tert-butyl (S)-4-(2-(6-methoxy-2-(trifluoromethyl)-1H-benzo[d]imidazol-1-yl)acetyl)-3-(5-(2-methoxyquinolin-3-yl)-1,2,4-oxadiazol-3-yl)piperazine-1-carboxylate (S4)

DIPEA (2.0 eq) was added to a stirred solution of S3 (1.0 eq), 2-[6-methoxy-2-(trifluoromethyl)benzimidazol-1-yl]ethanoic acid (1.1.0 eq) and HATU (1.1.0 eq) in DMF (0.2 M) at 20° C. Mixture was stirred for 40 min then diluted with EtOAc and washed with aq. sat. aq.NaHCO₃, brine, dried and concentrated. The dark residue was purified by flash chromatography (petroleum ether/EtOAC from 100:0 to 0:100) to give the title compound (9.5%) as pale yellow solid. MS (ES⁺) m/z 668 (M+H)⁺.

Step 5: (S)-2-(6-methoxy-2-(trifluoromethyl)-1H-benzo[d]imidazol-1-yl)-1-(2-(5-(2-methoxyquinolin-3-yl)-1,2,4-oxadiazol-3-yl)piperazin-1-yl)ethan-1-one (Trifluoroacetate Salt) (S5)

TFA (25 eq) was slowly added to a stirred solution of S4 (1.0 eq) in DCM (0.04 M) cooled to 0° C. The mixture was stirred at 0° C. for 16 h then solvent was evaporated under reduced pressure to afford an oily residue that was co-evaporated with Et₂O to give the title compound (99%) as pale yellow solid. MS (ES⁺) m/z 568 (M+H)⁺.

Step 6: 2-(6-methoxy-2-(trifluoromethyl)-1H-benzo[d]imidazol-1-yl)-1-((2S)-2-(5-(2-methoxyquinolin-3-yl)-1,2,4-oxadiazol-3-yl)-4-((tetrahydrofuran-3-yl)methyl)piperazin-1-yl)ethan-1-one (Trifluoroacetate Salt) (S6)

Tetrahydrofuran-3-carbaldehyde (1.5 eq) and AcOH (1.5 eq) were sequentially added to a solution of S7 (1.0 eq) in DMF/DCE (2:8, 0.06 M) and stirred at 20° C. for 2 h. Sodium triacetoxyborohydride (5 eq) was added at 0° C. and the suspension was left warming to 20° C. and stirred for 1 h. The mixture was diluted with DCM and washed with aq. sat. aq.NaHCO₃, brine, dried, concentrated and purified by flash chromatography (petroleum ether/MeOH from 100:0 to 90:10) to give the title compound (20%) as white powder. ¹H-NMR (400 MHz, 300 K, DMSO) δ (45:55 mixture of rotamers) 9.11** and 9.08 (s, 1H), 8.08 (t, 1H, J=6.7 Hz), 7.92-7.83 (m, 2H), 7.71 (dd, 1H, J=3.2, 8.8 Hz), 7.58 (m, 1H), 7.24 and 7.16* (brs, 1H), 7.02 and 6.99* (brs, 1H), 6.20 (brs, 1H), 5.83 (d, 1H, J=18.0 Hz), 5.58 (dd, 1H, J=6.6, 18.0 Hz), 4.54-4.32 (m, 2H), 4.16* and 4.15 (s, 3H), 3.92-3.84 (m, 1H), 3.81-3.74 (m, 2H), 3.80 and 3.75* (brs, 3H), 3.72-3.67 (m, 2H), 3.51-3.37 (m, 3H), 3.33-3.24 and 3.19-3.13**(m, 2H), 2.82-2.67 (m, 1H), 2.18-2.11 (m, 1H), 1.75-1.58 (m, 1H). MS (ES⁺) m/z 652 (M+H)⁺.

Example 20

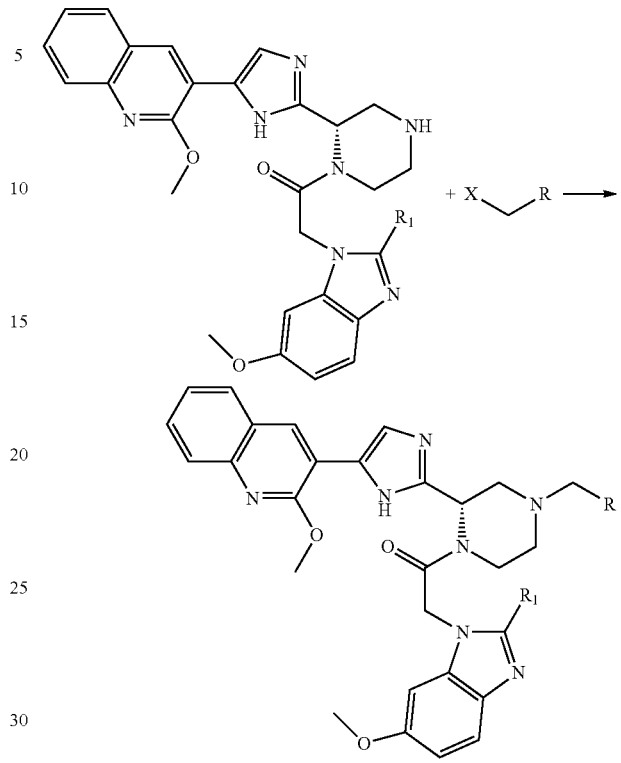

Example 20A: (S)-2-(6-methoxy-2-(trifluoromthyl)-1H-benzo[d]imidazol-1-yl)-1-(2-(5-(2-methoxyquinolin-3-yl)-1H-imidazol-2-yl)-4-(2-(2-methylthiazol-4-yl)ethyl)piperazin-1-yl)ethan-1-one (trifluoroacetate Salt) (T1)

A solution of 4-(2-chloroethyl)-2-methyl-1,3-thiazole hydrochloride (5.0 eq) and TEA (5.0 eq) in NMP (0.1 M) was treated with (S)-2-(6-methoxy-2-(trifluoromethyl)-1H-benzo[d]imidazol-1-yl)-1-(2-(5-(2-methoxyquinolin-3-yl)-1H-imidazol-2-yl)piperazin-1-yl)ethan-1-one (prepared according to example 13, step 5) (1.0 eq) and PS-TBD (1.5 eq). Mixture was stirred at microwave (140° C.) for 25 min then purified by RP-HPLC to give after lyophilization the title compound (17%) as a pale yellow solid. ¹H-NMR (400 MHz, 300 K, DMSO-d₆) δ (86:14* mixture of rotamers) 8.83 and 8.7* (s, 1H), 7.95 (brs, 1H), 7.86-7.82 (m, 2H), 7.71 (brs, 2H), 7.51 (brs, 2H), 7.34 (s, 1H), 7.0 (d, 1H, J=8.2 Hz), 6.22 and 6.13* (brs, 1H), 5.75 (m, 2H), 4.64-4.56 (m, 1H), 4.47-4.38 (m, 2H), 4.15 (s, 3H), 3.95-3.89 (m, 1H), 3.82 (s, 3H), 3.78-3.66 (m, 1H), 3.58 (m, 2H), 3.38-3.32 (m, 1H), 3.23-3.19 (m, 2H), 2.58 (s, 3H). MS (ES⁺) m/z 691 (M+H)⁺.

Example 20B: (S)-2-(6-methoxy-2-(trifluoromthyl)-1H-benzo[d]imidazol-yl)-1-(2-(5-(2-methoxyquinolin-3-yl)-1H-imidazol-2-yl)-4-(2-(2-methylthiazol-4-yl)ethyl)piperazin-1-yl)ethan-1-one (Trifluoroacetate Salt) (T2)

(S)-2-(6-methoxy-2-methyl-1H-benzo[d]imidazol-1-yl)-1-(2-(5-(2-methoxyquinolin-3-yl)-1H-imidazol-2-yl)piperazin-1-yl)ethan-1-one (1.0 eq) (prepared according to example 13, step 5) was dissolved in DMF (0.05 M) and 3-(Chloromethyl)-4-methyl-4H-1,2,4-triazole (1.1.0 eq) and DBU (2.2 eq) were sequentially added. Mixture was stirred for 12 h at 20° C. then concentrated and purified by RP-HPLC to give after lyophilization the title compound (53%) as a white solid. $^1$H-NMR (400 MHz, 300 K, CD$_3$CN) δ (75:25* mixture of rotamers) 9.21 and 9.13* (s, 1H), 8.34 (s, 1H), 8.07 and 7.97* (d, 1H, J=8.1 Hz), 7.98 (s, 1H), 7.83 and 7.77*(d, 1H, J=8.5 Hz), 7.76-7.60 and 7.67-7.63* (m, 2H), 7.46 (dd, 1H, J=7.3, 7.3 Hz), 7.37* and 7.26 (brs, 1H), 7.16-7.13 (m, 1H), 6.14* and 5.53*and 5.36 (m, 2H), 5.97 (s, 1H), 4.38-4.34* and 3.86 and 3.49-3.41* (m, 2H), 4.19* and 4.1 (s, 3H), 4.07-4.03, 3.97-3.92 and 3.90-3.96* (m, 2H), 3.90, 3.83 and 2.77-2.72*(m, 2H), 3.87 (s, 3H), 3.61 (s, 3H), 3.11-3.08 and 2.95-2.99* (m, 2H), 2.85* and 2.82 (s, 3H). MS (ES$^+$) m/z 607 (M+H)$^+$.

Example 20C: 1-((2S)-4-((1,1-dioxidotetrahydrothiophen-3-yl)methyl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one (Trifluoroacetate Salt) (T3)

(S)-2-(6-methoxy-2-methyl-1H-benzo[d]imidazol-1-yl)-1-(2-(5-(2-methoxyquinolin-3-yl)-1H-imidazol-2-yl)piperazin-1-yl)ethan-1-one (1.0 eq) (prepared according to example 13, step 5) was dissolved in THF (0.012 M) and K$_2$CO$_3$ (3.0 eq) and 3-(Chloromethyl)tetrahydrothiophene 1,1-dioxide (5.0 eq) were sequentially added. Mixture was stirred for 9 h at reflux then filtered, concentrated and purified by RP-HPLC (MeCN, H$_2$O+0.1% TFA) to give the title compound (4%) as a white solid. NMR (400 MHz, 300 K, CD$_3$CN) δ (50:50* mixture of rotamers) 9.46 and 9.23* (s, 1H), 8.17-8.02 (m, 2H), 7.95-7.92 (m, 1H), 7.79-7.73 (m, 2H), 7.62-7.60 (m, 1H), 7.14-7.10 (m, 2H), 6.06 and 6.02-5.97* (brs and m*, 1H), 5.36-5.25 and 5.17-5.03* (m, 2H), 1.19 and 1.25* (s, 3H), 4.13-3.98 (m, 3H), 3.80 (s, 3H), 3.76-3.65 (m, 3H), 3.50-3.37 (m, 4H), 3.18-3.08 (m, 1H), 3.06-2.96 (m, 3H), 2.92-2.87 (m, 1H), 2.65 and 2.63* (s, 3H). MS (ES$^+$) m/z 644 (M+H)$^+$ Example 21

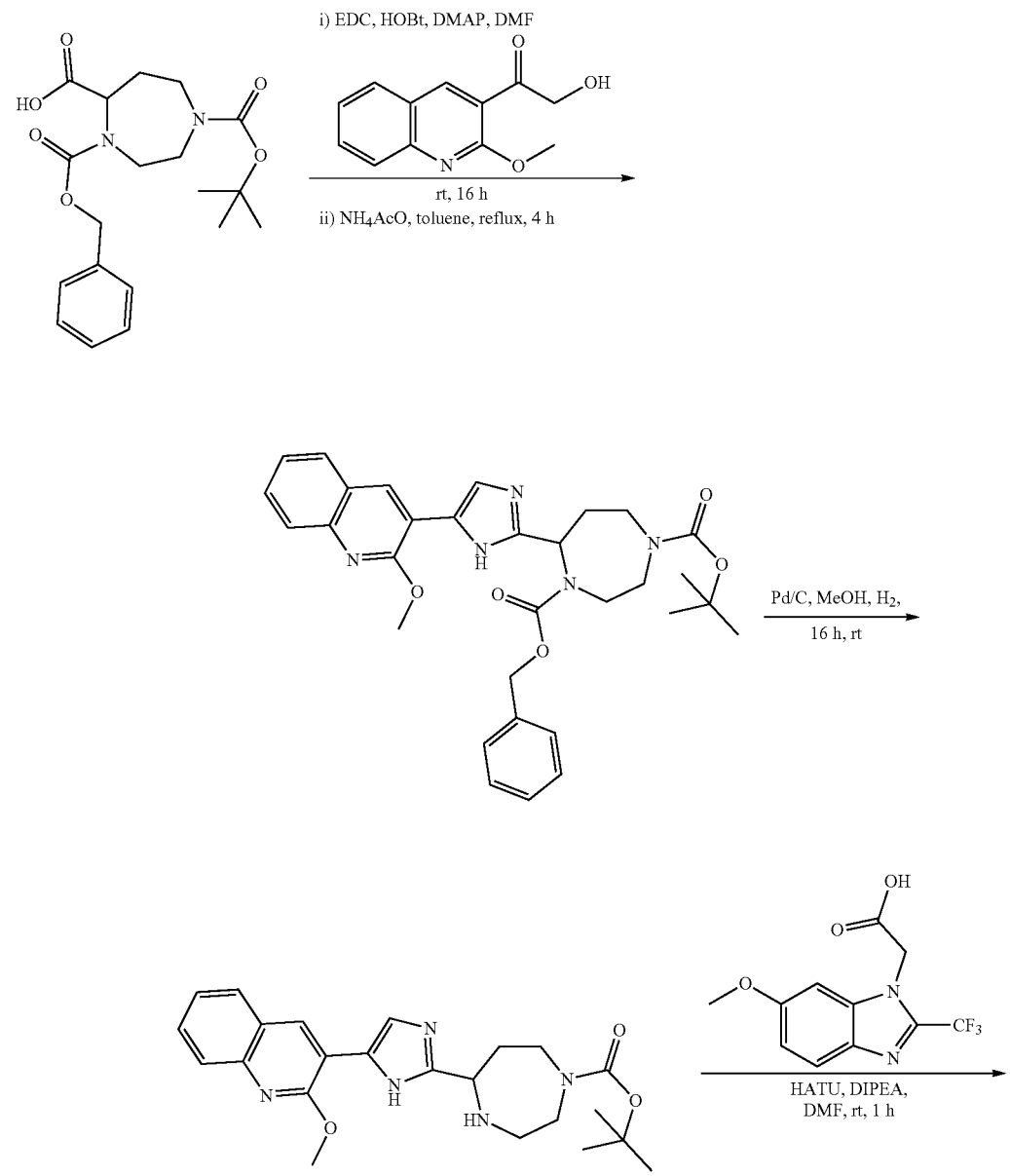

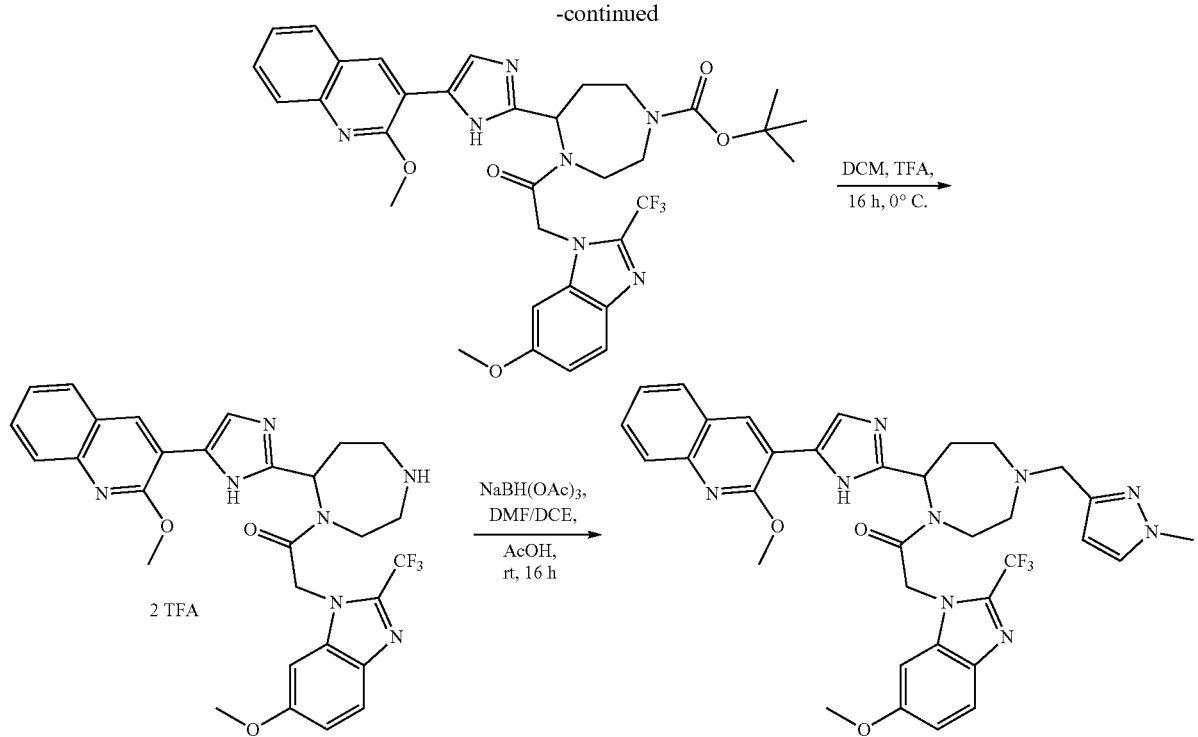

Example 21: 2-(6-methoxy-2-(trifluoromthyl)-1H-benzo[d]imidazol-1-yl)-1-(7-(2-methoxyquinolin-3-yl)-1H-imidazol-2-yl)-4-((1-methyl-1H-pyrazol-3-yl)methyl)-1,4-diazepan-1-yl)ethan-1-one (U6)

Step 1: 4-benzyl 1-(tert-butyl) 5-(5-(2-methoxyquinolin-3-yl)-1H-imidazol-2-yl)-1,4-diazepane-1,4-dicarboxylate (U1)

EDC.HCl (1.5 eq) and HOBt (1.5 eq) were added to a solution of 04 (1.0 eq) in DMF (0.26 M) and the resulting mixture was stirred at 20° C. for 15 min, then 2-hydroxy-1-(2-methoxyquinolin-3-yl)ethan-1-one (1.0 eq) and DMAP (0.3 eq) were added. After 2 h the solvent was removed under reduced pressure and the residue was dissolved in EtOAc, washed with H$_2$O, brine, dried and concentrated. The residue was purified by flash chromatography (petroleum ether/EtOAc, from 100:0 to 20:80) to give the title compound (27%) as yellow oil. MS (ES$^+$) m/z 578 (M+H)$^+$.

Step 2: 4-benzyl 1-(tert-butyl) 5-(5-(2-methoxyquinolin-3-yl)-1H-imidazol-2-yl)-1,4-diazepane-1,4-dicarboxylate (U2)

U1 (1.0 eq) was dissolved in toluene (0.1 M) then NH$_4$OAc (10 eq) was added and the solution heated to reflux using a Dean Stark apparatus for 12 h. The mixture was concentrated under reduced pressure, diluted with EtOAc, washed with H$_2$O, brine, dried and concentrated. The residue was purified by flash chromatography (petroleum ether/EtOAc, from 100:0 to 40:60) to give the title compound (77%) as a solid. MS (ES$^+$) m/z 558 (M+H)$^+$.

Step 3: tert-butyl 5-(5-(2-methoxyquinolin-3-yl)-1H-imidazol-2-yl)-1,4-diazepane-1-carboxylate (U3)

U2 was dissolved in MeOH (0.08 M) and treated with wet Pd/C (10% wt) (1:1 in weight). The mixture was purged with N$_2$ and stirred on H$_2$ atmosphere at 20° C. for 16 h. The suspension was filtered through a pad of Solka Floc and filtrate was concentrated under vacuum to give the title compound (99%) which was directly used in the next step. MS (ES$^+$) m/z 424 (M+H)$^+$.

Step 4: tert-butyl 4-(2-(6-methoxy-2-(trifluoromethyl)-1H-benzo[d]imidazol-1-yl)acetyl)-5-(5-(2-methoxyquinolin-3-yl)-1H-imidazol-2-yl)-4-diazepane-1-carboxylate (U4)

A solution of HATU (1.5 eq) and 2-[6-methoxy-2-(trifluoromethyl)benzimidazol-1-yl]ethanoic acid (1.0 eq) in DMF (0.5 M) was stirred for 15 min then DIPEA (2 eq) and U3 (1.0 eq) were sequentially added. Mixture was stirred for 1 h at 20° C. then EtOAc was added and organic phase was washed with aq. sat. NaHCO$_3$ sol. and brine. Organic layers were combined, dried, concentrated under reduced pressure and purified by flash chromatography (petroleum ether/EtOAc from 100:0 to 0:100) to give the title compound (53%) as a yellow powder. MS (ES$^+$) m/z 680 (M+H)$^+$.

Step 5: 2-(6-methoxy-2-(trifluoromethyl)-1H-benzo[d]imidazol-1-yl)-1-(7-(5-(2-methoxyquinolin-3-yl)-1H-imidazol-2-yl)-1,4-diazepan-1-yl)ethan-1-one (Trifluoroacetate Salt) (U5)

TFA (DCM/TFA=9:1 sol., 0.05 M) was slowly added to a solution of U4 (1.0 eq) in DCM cooled to 0° C. The mixture was stirred at 0° C. for 16 h, then concentrated under reduced pressure. The resulting oily residue was co-evaporated with Et₂O to give the title compound (99%) as yellow solid which was directly used in the next step. MS (ES⁺) m/z 580 (M+H)⁺.

Step 6: 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one (U6)

1-methylpyrazole-3-carbaldehyde (1.5 eq) and AcOH (1.5 eq) were added to a solution of U5 (1.0 eq) in DCE/DMF (0.065 M, 5:1) at 20° C. The mixture was stirred for 1 h then sodium triacetoxyborohydride (5 eq) was added and obtained suspension was left stirring overnight at 20° C. EtOAc was added and organic phase was washed with sat. aq. NaHCO₃ sol., brine, dried, concentrated and purified by flash chromatography (DCM/MeOH from 100:0 to 90:10) to give the title compound (70%) as a white solid. ¹H-NMR (400 MHz, 300 K, DMSO-d₆) δ (50:50* mixture of rotamers) 12.51 and 11.88* (s, 1H), 8.78 (d, 1H, J=13.8 Hz), 7.97 and 7.85* (d, 1H, J=7.6 Hz), 7.78 (d, 1H, J=8.2 Hz), 7.74 (t, 1H, J=2.1 Hz), 7.70 and 7.68* (d, 1H, J=3.5 Hz), 7.64 and 7.53* (d, 1H, J=2.4 Hz), 7.63-7.57 (m, 1H), 7.43-7.39 (m, 1H), 7.23 and 6.92* (d, 1H, J=2.3 Hz), 6.98-6.95 (m, 1H), 6.17 (dd, 1H, J=2.1 Hz), 5.91-5.75 and 5.44-5.35 (m, 2H), 5.64 and 5.27 (d, 1H, J=18.0 Hz), 4.16 and 4.12* (s, 3H), 4.04-3.92 and 3.75-3.71* (m, 2H), 3.81 and 3.79* (s, 3H), 3.79 and 3.77* (s, 3H), 3.62* and 3.59 (brs, 2H), 3.57-3.56 (m, 1H), 3.16-3.0 and 2.90-2.87* (m, 2H), 2.47-2.32 (m, 2H), 2.22-2.11 (m, 1H). MS (ES⁺) m/z 674 (M+H)⁺.

Step 7: (R)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one and (S)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one (U7 and U8)

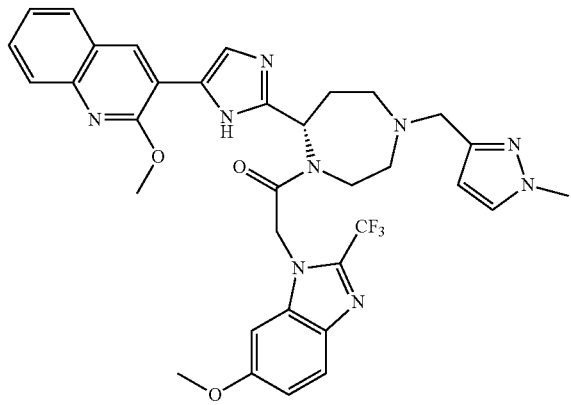

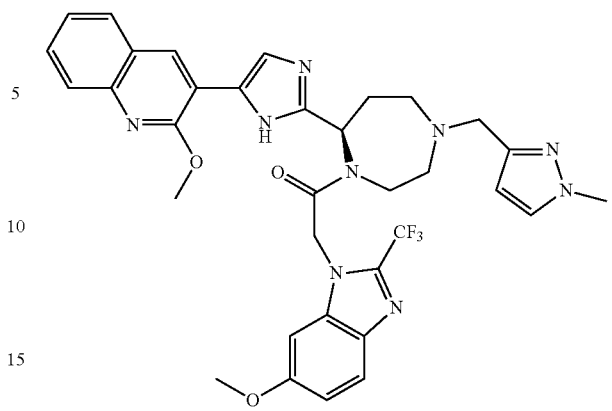

Title compounds with unknown absolute configuration at homopiperazine ring were obtained by SFC chiral separation of T6 following the Method 2: the first eluted (28%, 100% ee), retention time equal to 21.7 min and the second eluted (29%, 100% ee), retention time equal to 25.3 min.

Example 22

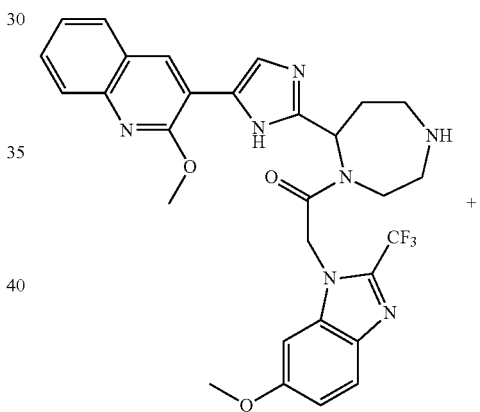

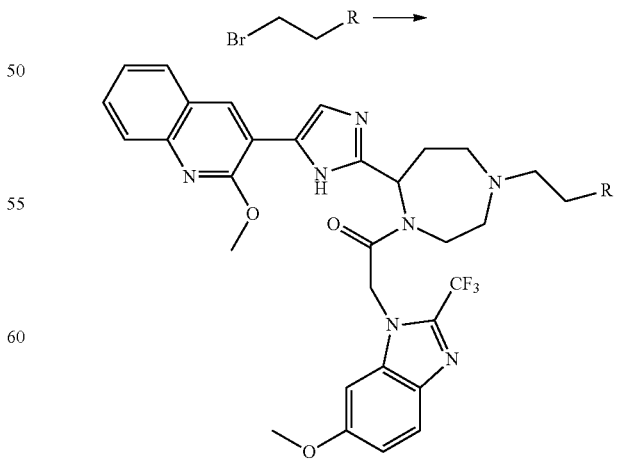

Example 22A: 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(pyridin-2-yl)ethyl)-1,4-diazepan-1-yl)-ethan-1-one (V1)

A solution of U5 (1.0 eq) in DMF (0.08 M) was treated with 2-(2-Bromoethyl)pyridine hydrobromide (1.1.0 eq) and DBU (2.2 eq) ans stirred for 16 h at 90° C. Mixture was diluted with DCM and washed with aq. sat. NaHCO$_3$ sol., brine, dried, concentrated and purified by flash chromatography (DCM/MeOH from 100:0 to 90:10) to give the title compound (11%) as white solid. $^1$H-NMR (400 MHz, 300 K, DMSO-d$_6$) δ (50:50* mixture of rotamers) 12.51 and 11.90* (s, 1H), 8.80 and 8.76* (s, 1H), 8.51-8.48 (m, 1H), 7.96 and 7.86* (d, 1H, J=7.8 Hz), 7.78 (d, 1H, J=7.6 Hz), 7.75-7.68 (m, 2H), 7.62-7.57 (m, 1H), 7.54 and 7.25* (d, 1H, J=2.4 Hz), 7.43-7.39 (m, 1H), 7.33 (dd, 1H, J=8.7, 9.6 Hz), 7.24-7.19 (m, 2H), 6.99-6.94 (m, 1H), 5.93-5.80 (m, 1H), 5.68 and 5.32* (d, 1H, J=17.3 Hz), 5.46-5.38 (m, 1H), 4.16 and 4.12* (s, 1H), 4.06-3.93 (m, 2H), 3.77 and 3.58* (s, 3H), 3.18-3.08 (m, 2H), 3.01, 2.83 (m, 4H), 2.33-2.17 (m, 4H), 1.65-1.50 (m, 2H). MS (ES$^+$) m/z 685 (M+H)$^+$.

Example 22B: 2-(6-methoxy-2-trifluoromthyl)-1H-benzo[d]imidazol-1-yl)-1-(7-(5-(2-methoxyquinolin-3-yl)-1H-imidazol-2-yl)-4-(2-(1-methyl-1H-pyrazol-5-yl)ethyl)-1,4-diazepan-1-yl)ethan-1-one (Trifluoroacetate Salt) (V2)

A solution of US (1.0 eq) in DMF (0.086 M) was treated with PS-TBD (3.0 eq), 5-(2-bromoethyl)-1-methyl-1H-pyrazole (10 eq) and TEA (10 eq) and stirred under microwave irradiation for 30 min at 120° C. Mixture was purified by RP-HPLC to give the title compound (8%) as white powder. $^1$H-NMR (400 MHz, 300 K, DMSO) δ (15:85* mixture of rotamers) 8.73* and 8.63 (s, 1H), 8.14* and 8.04 (s, 1H), 7.92* and 7.88 (d, 1H, J=8.3 Hz), 7.83 (d, 1H, J=8.4 Hz), 7.74-7.70 (m, 1H), 7.65 (d, 1H), 7.52-7.48 (m, 1H), 7.46 and 7.44* (brs, 1H), 7.21 (brs, 1H), 7.11* and 7.09 (s, 1H), 6.98-6.94 (m, 1H), 6.25 and 6.22* (s, 1H), 5.58 (brs, 2H), 4.42-4.33 (m, 2H), 4.24-4.19 (m, 1H), 4.16* and 4.12 (s, 3H), 3.97-3.90 (m, 2H), 3.84 and 3.81* (s, 3H), 3.77* and 3.72 (s, 3H), 3.61-3.48 (m, 3H), 3.20-3.16 (m, 2H), 2.68 (brs, 2H). MS (ES$^+$) m/z 686 (M+H)$^+$.

Example 23

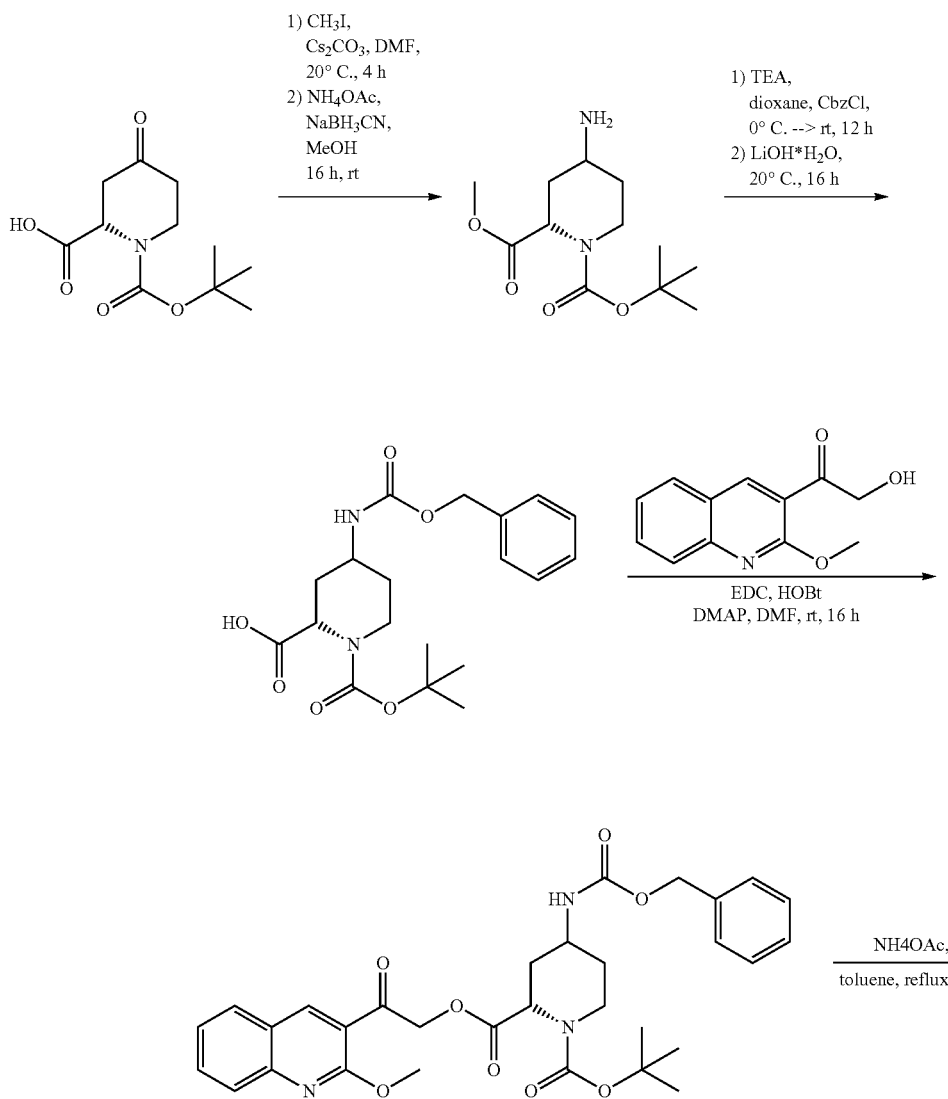

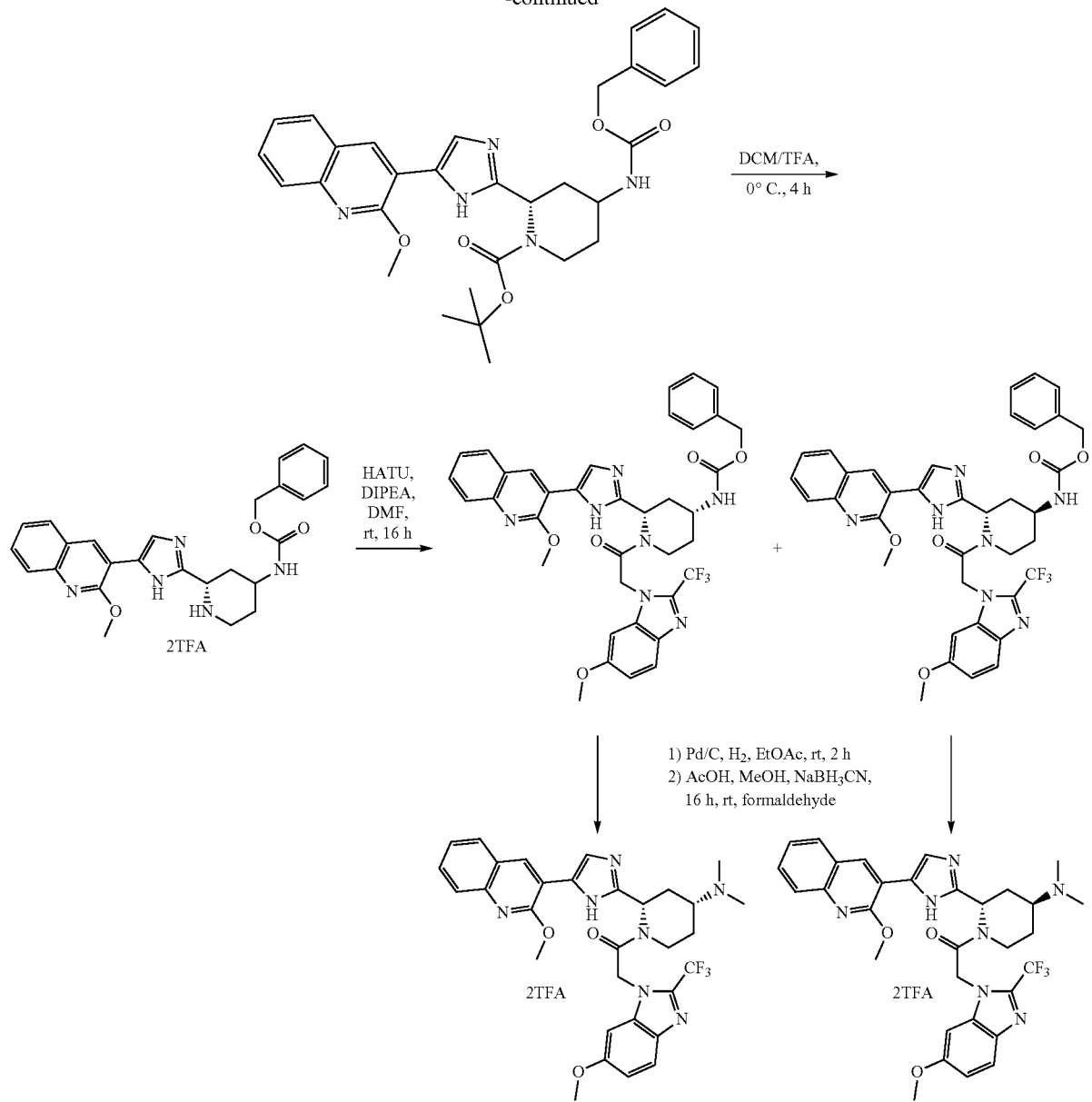

Example 23: 1-((2S,4S)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one (Trifluoroacetate Salt) (W9)

Step 1: 1-(tert-butyl) 2-methyl (S)-4-oxopiperidine-1,2-dicarboxylate (W1)

(2S)—N—(Boc)-4-oxopipecolic acid (1.0 eq) was dissolved in DMF (0.2 M) and treated with dicesium carbonate (0.5 eq) and iodomethane (1.1.0 eq). The mixture was stirred at 20° C. for 4 h, then diluted with EtOAc and washed with aq. sat.NaHCO₃ sol., aq. citric acid (10% w/w) sol., brine, dried and concentrated to give the title compound (99%) as yellow oil. ¹H-NMR (400 MHz, 300 K, DMSO-d₆) δ (40*:60 mixture of rotamers) 4.92* and 4.76 (brs, 1H), 3.41-3.87 (m, 1H), 3.66 (s, 3H), 3.59-3.50 (m, 1H), 2.95-2.90 (m, 1H), 2.60-2.56 (m, 1H), 2.47-2.43 (m, 1H), 2.41-2.32 (m, 1H), 1.43* and 1.38 (s, 9H).

Step 2: 1-(tert-butyl) 2-methyl (2S)-4-aminopiperidine-1,2-dicarboxylate (W2)

NH₄AcO (11.0 eq) and NaBH₃CN (1.0 eq) were added to a solution of W1 (1.0 eq) in MeOH (0.3 M) in the presence of molecular sieves (3 Å) and stirred at room temperature for 16 h. The mixture was filtered and concentrated under reduced pressure to give the title compound which was used in the next step without further purification. MS (ES⁺) m/z 259 (M+H)⁺.

Step 3: 1-(tert-butyl) 2-methyl (2S)-4-(((benzyloxy)carbonyl)amino)piperidine-1,2-dicarboxylate (W3)

Benzyl carbonochloridate (1.3 eq) was added dropwise to a solution of W2 (1.0 eq) and TEA (1.3 eq) in DCM (0.15

M) cooled to 0° C. The mixture was stirred at 20° C. for 12 h then the solvent was concentrated and obtained crude purified by flash chromatography (petroleum ether: EtOAc from 100:0 to 40:60) to give the title compound (31%) as pale yellow oil. MS (ES$^+$) m/z 393 (M+H)$^+$.

Step 4: (2S)-4-(((benzyloxy)carbonyl)amino)-1-(tert-butoxycarbonyl)piperidine-2-carboxylic acid (W4)

LiOH.H$_2$O (2 eq) was dissolved in H$_2$O (0.22 M) and added dropwise to a stirred solution of W3 (1.0 eq) in THF (0.1 M). The obtained mixture was stirred at 20° C. for 16 h then concentrated to eliminate the THF and diluted with EtOAc. The water phase was acidified with aq. HCl 1N sol. until pH 2÷3 and extracted with EtOAc then the organic layers were combined and concentrated to give the title compound (99%) as a pale yellow oil. MS (ES$^+$) m/z 379 (M+H)$^+$.

Step 5: 1-(tert-butyl) 2-(2-(2-methoxyquinolin-3-yl)-2-oxoethyl) (2S)-4-(((benzyloxy)carbonyl)amino)piperidine-1,2-dicarboxylate (W5)

W4 (1.0 eq) was dissolved in DMF and HOBt (1.5 eq) and EDC.HCl (1.5 eq) were sequentially added and the resulting mixture was stirred at 20° C. for 15 min, then 2-hydroxy-1-(2-methoxyquinolin-3-yl)ethanone (1.0 eq) and DMAP (0.3 eq) were added. Stirring was continued at 20° C. for 2 h then the solvent was removed under reduced pressure and the residue was dissolved in EtOAc, washed with H$_2$O, brine, dried and concentrated. The obtained crude was purified by flash chromatography (petroleum ether/EtOAc from 100:0 to 50:50) to give the title compound (77%) as a yellow solid. MS (ES$^+$) m/z 578 (M+H)$^+$.

Step 6: tert-butyl (2S)-4-(((benzyloxy)carbonyl)amino)-2-(5-(2-methoxyquinolin-3-yl)-1H-imidazol-2-yl)piperidine-1-carboxylate (W6)

W5 (1.0 eq) was dissolved in toluene (0.05 M) then NH$_4$OAc (25 eq) was added and the solution heated to reflux using a Dean Stark apparatus for 4 h. The mixture was concentrated under reduced pressure, diluted with EtOAc, washed with H$_2$O, brine, dried and concentrated. The residue was purified by flash chromatography (petroleum ether/EtOAc, from 100:0 to 40:60) to give the title compound (62%) as yellow solid. MS (ES$^+$) m/z 558 (M+H)$^+$.

Step 7: benzyl ((2S)-2-(5-(2-methoxyquinolin-3-yl)-1H-imidazol-2-yl)piperidin-4-yl)carbamate (Trifluoroacetate Salt) (W7)

TFA (DCM/TFA=9:1 sol., 0.05 M) was slowly added to a solution of W6 (1.0 eq) in DCM cooled to 0° C. The mixture was stirred at 0° C. for 4 h, then concentrated under reduced pressure. The resulting oily residue was co-evaporated with Et$_2$O to give the title compound (99%) as brown solid which was directly used in the next step without purification. MS (ES$^+$) m/z 458 (M+H)$^+$.

Step 8: benzyl ((2S,4S)-1-(2-(6-methoxy-2-(trifluoromethyl)-1H-benzo[d]imidazol-1-yl)acetyl)-2-(5-(2-methoxyquinolin-3-yl)-1H-imidazol-2-yl)piperidin-4-yl)carbamate (W8)

A solution of HATU (1.1.0 eq) and 2-[6-methoxy-2-(trifluoromethyl)benzimidazol-1-yl]ethanoic acid (1.1.0 eq) in DMF (0.1 M) was stirred for 15 min then DIPEA (2.0 eq) and W7 (1.0 eq) were sequentially added. Mixture was stirred for 16 h at 20° C. then EtOAc was added and organic phase was washed with aq. sat. NaHCO$_3$ sol. and brine. Organic layers were combined, dried, concentrated under reduced pressure and purified by flash chromatography (petroleum ether/EtOAc from 100:0 to 40:60) to give the title compound (60%) as first eluted diastereomer and as a pale yellow solids (second eluted diastereomer 12%). MS (ES$^+$) m/z 714 (M+H)$^+$ (first eluted diastereomer); MS (ES$^+$) m/z 714 (M+H)$^+$ (second eluted diastereomer).

Step 9: 1-((2S,4S)-4-amino-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one (W9)

W8 was dissolved in MeOH (0.08 M) and treated with Pd/C (10% wt) (1:1 in weight). The mixture was purged with N$_2$ and stirred on H$_2$ atmosphere at 20° C. for 2 h. The suspension was filtered through a pad of Solka Floc and filtrate was concentrated under vacuum to give the title compound (99%) which was directly used in the next step. $^1$H-NMR (400 MHz, 300 K, CD$_3$CN) δ (13*:87 mixture of rotamers) 8.66 and 8.49* (s, 1H), 7.97-7.94 (m, 2H), 7.91-7.81 (m, 2H), 7.74 (d, 1H, J=8.6 Hz), 7.61 (dd, 1H, J=7.4, 7.4 Hz), 7.09-7.02 (m, 2H), 6.97 (brs, 3H), 5.43-5.41 and 5.31-5.27* (m, 1H), 5.37-5.35 (m, 2H), 4.23 (s, 3H), 4.23-4.17 (m, 1H), 4.01-3.96 (m, 1H), 3.83-3.72 (m, 2H), 3.79 (s, 3H), 2.59-2.54 (m, 1H); 2.48-2.41 (m, 1H), 2.37-2.27 (m, 1H). MS (ES$^+$) m/z 580 (M+H)$^+$.

Step 10: 1-((2S,4S)-4-amino-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one (Trifluoroacetate Salt) (W10)

Formaldehyde (2.0 eq) and AcOH (1.5 eq) were added to a solution of W9 in MeOH (0.1 M). The mixture was stirred at 20° C. for 1 h then NaBH$_3$CN (5.0 eq) was added and stirring was continued for additional 16 h. After this time, the mixture was diluted with EtOAc, washed with aq. sat. NaHCO$_3$ sol., brine, dried, concentrated and purified by RP-HPLC (MeCN, H$_2$O+0.1% TFA) to give the title compound (50%) as a white powder. $^1$H-NMR (400 MHz, 300 K, CD$_3$CN) δ (80:20* mixture of rotamers) 8.8 (brs, 1H), 8.67 (s, 1H), 8-7.96* and 7.90-7.84 (m, 3H), 7.76-7.72 (m, 2H), 7.53-7.59 (m, 1H), 7.08 and 6.98*(brs, 1H), 7.05 (dd, 1H, J=2.3, 8.7 Hz), 6.26 and 5.86*(dd, 1H, J=1.2, 4.6 Hz), 5.49-5.37 (m, 2H), 4.19-4.15 (m, 1H), 4.12*-4.08 (s, 3H), 3.80 (s, 3H), 3.65-3.58 (m, 1H), 3.37-3.29 (m, 1H), 2.82 (d, 3H, J=5.0 Hz), 2.74 (d, 3H, J=5.0 Hz), 2.33-2.24 (m, 1H), 2.14-2.10 (m, 1H), 2.03 (m overlapped with acetonitrile, 2H). MS (ES$^+$) m/z 608 (M+H)$^+$.

Example 24

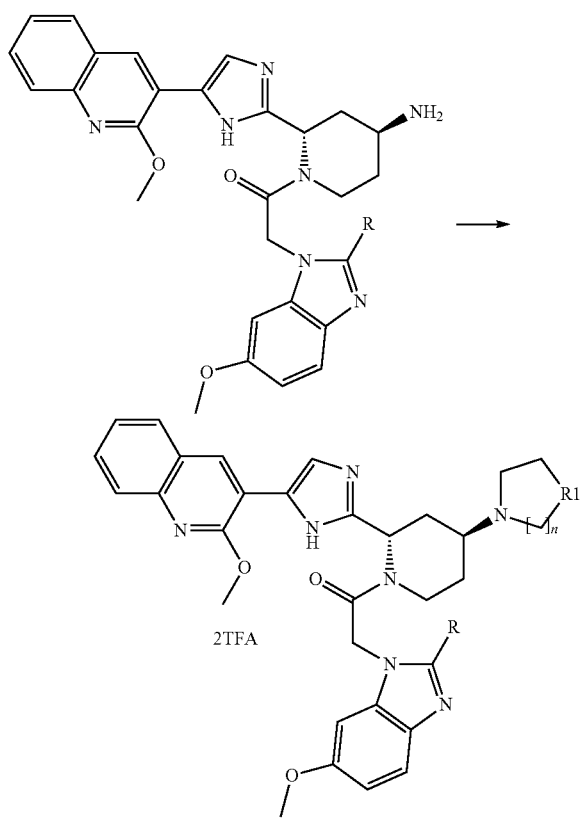

Example 24A: 2-(6-methoxy-2-(trifluoromthyl)-1H-benzo[d]imidazol-1-yl)-1-((2S,4S)-2-(5-(2-methoxy-quinolin-3-yl)-1H-imidazol-2-yl)-4-(pyrrolidin-1-yl)piperidin-1-yl)ethan-1-one (X1)

W9 (1.0 eq) was dissolved in MeCN (0.6 M) and 1,4-dibromobutane (1.5 eq) and K$_2$CO$_3$ (30.0 eq) were sequentially added. Mixture was stirred at microwave irradiation at 100° C. for 15 min then filtered and purified by RP-HPLC (MeCN, H$_2$O+0.1% TFA) to give the title compound (26%) as a white solid. $^1$H-NMR (400 MHz, 300 K, CD$_3$CN) (15*:85 mixture of rotamers) δ 8.90* and 8.86 (s, 1H), 8.08 (d, 1H, J=8.3 Hz), 8.02 (d, 1H, J=7.9 Hz), 7.94 (t, 1H, J=7.4 Hz), 7.90 (s, 1H), 7.79 (d, 1H, J=9.6 Hz), 7.71 (t, 1H, J=7.9 Hz), 7.19-7.16 and 7.06-7.04* (m, 2H), 6.24 and 5.83* (brs, 1H), 5.61-5.48 (m, 2H), 4.39* and 4.34 (s, 3H), 4.14-4.10 (m, 1H), 3.83 and 3.80* (s, 3H), 3.65-3.60 and 3.54-3.50* (m, 3H), 3.46-3.39 (m, 1H), 3.15-3.11 (m, 1H), 3.04-2.99 (m, 1H), 2.81-2.78 (m, 1H), 2.31-2.25 (m, 2H), 2.07-2.03 (m, 2H), 1.97-1.91 (m, 3H). MS (ES$^+$) m/z 634 (M+H)$^+$.

Example 24B: 2-(6-methoxy-2-methyl-1H-benzo[d]imidazol-yl)-1-((2S,4S)-2-(5-(2-methoxyquinolin-3-yl)-1H-imidazol-2-yl)-4-morpholinopiperidin-1-yl)ethan-1-one (X2)

W9 (1.0 eq) was dissolved in THF (0.05 M) and 1-bromo-2-(2-bromoethoxy)ethane (1.0 eq) and TEA (38.0 eq) were sequentially added. Mixture was stirred at 80° C. for 48 h then filtered and purified by RP-HPLC (MeCN, H$_2$O+0.1% TFA) to give the title compound (2.8%) as a white solid. MS (ES$^+$) m/z 596 (M+H)$^+$.

Example 25

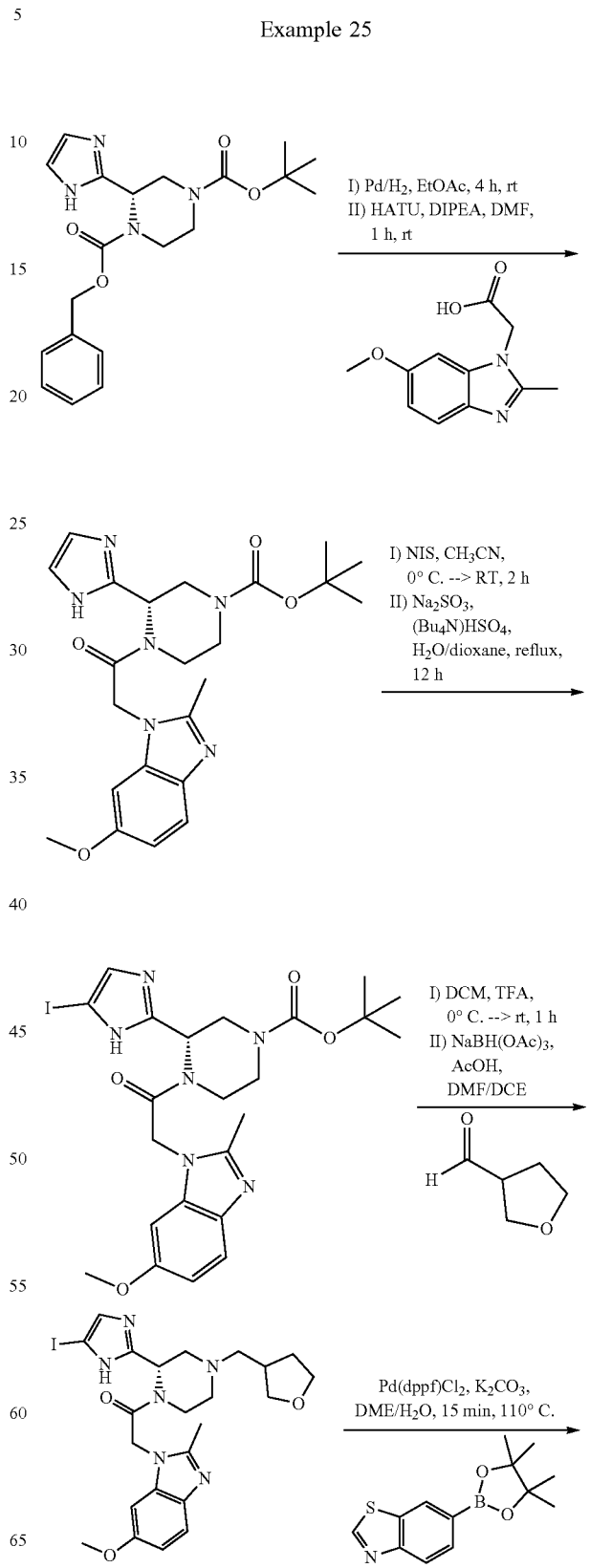

-continued

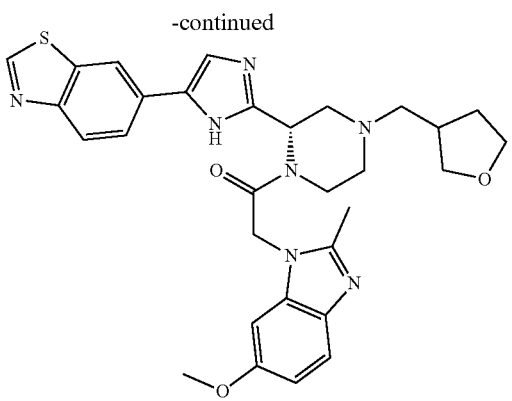

Example 25: 1-((2S)-2-(5-(benzo[d]thiazol-6-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one (Y8)

Step 1: 1-benzyl 4-(tert-butyl) (S)-2-(1H-imidazol-2-yl)piperazine-1,4-dicarboxylate (Y1)

1-benzyl 4-(tert-butyl) (S)-2-(1H-imidazol-2-yl)piperazine-1,4-dicarboxylate was prepared according to procedure reported in the Example 6 Step 3 starting from chiral (S)-1-((benzyloxy)carbonyl)-4-(tert-butoxycarbonyl)piperazine-2-carboxylic acid.

Step 2: tert-butyl (S)-3-(1H-imidazol-2-yl)piperazine-1-carboxylate (Y2)

Pd/C (10% wt) (1:1 in weight) was added to a solution of Y1 (1.0 eq) in EtOAc (0.23 M). The mixture was purged with $N_2$ and stirred under $H_2$ atmosphere at 20° C. for 4 h. The resulting suspension was filtered through a pad of Solka Floc washing with MeOH and concentrated under reduced pressure to give the title compound (98%) as a yellow powder. MS (ES$^+$) m/z 253 (M+H)$^+$.

Step 3: tert-butyl (S)-3-(1H-imidazol-2-yl)-4-(2-(6-methoxy-2-methyl-1H-benzo[d]imidazol-1-yl)acetyl)piperazine-1-carboxylate (Y3)

HATU (1.2 eq), 2-(6-methoxy-2-methyl-benzimidazol-1-yl)ethanoic acid hydrochloride (1.2 eq) and DIPEA (3.0 eq) were sequentially added to a stirred solution of Y2 (1.0 eq) in DMF (0.3 M). Mixture was stirred for 1 h at 20° C. then diluted with DCM and washed with aq. sat. NaHCO$_3$ sol, dried and concentrated. The obtained crude was purified by flash chromatography (DCM/MeOH from 100:0 to 90:10) to give the title compound (89%) as an orange powder. MS (ES$^+$) m/z 455 (M+H)$^+$.

Step 4: tert-butyl (S)-3-(4,5-diiodo-1H-imidazol-2-yl)-4-(2-(6-methoxy-2-methyl-1H-benzo[d]imidazol-1-yl)acetyl)piperazine-1-carboxylate (Y4)

NIS (2.2 eq) was added portionwise to a solution of Y3 (1.0 eq) in MeCN (0.06 M) cooled to 0° C. The mixture was left warming to 0° C. 20° C. and stirred for 1 h then organic solvent was evaporated under pressure and obtained mixture was purified by flash chromatography (DCM/MeOH from 100:0 to 90:10) to give the title compound (87%) as orange solid. MS (ES$^+$) m/z 707 (M+H)$^+$.

Step 5: tert-butyl (S)-3-(5-iodo-1H-imidazol-2-yl)-4-(2-(6-methoxy-2-methyl-1H-benzo[d]imidazol-1-yl)acetyl)piperazine-1-carboxylate (Y5)

(Bu$_4$N)HSO$_4$ (2.0 eq) and Na$_2$SO$_3$ (10.0 eq) were added to a stirred solution of Y4 (1.0 eq) in dioxane/water (4:1, 0.1 M) and obtained mixture was stirred at reflux for 16 h. The mixture was filtered, concentrated and purified by flash chromatography (DCM/MeOH from 100:0 to 90:10) to give title compound (91%) as a yellow oil. MS (ES$^+$) m/z 581 (M+H)$^+$.

Step 6: (S)-1-(2-(5-iodo-1H-imidazol-2-yl)piperazin-1-yl)-2-(6-methoxy-2-methyl-1H-benzo[d]imidazol-1-yl)ethan-1-one (Trifluoroacetate Salt) (Y6)

TFA (16.0 eq) was slowly added to a stirred solution of Y5 (1.0 eq) in DCM (0.08 M) cooled to 0° C. The mixture was left warming to 20° C. and stirred for 1 h then Et$_2$O was added and solvents evaporated to give the title compound (60%) as a pale yellow solid. MS (ES$^+$) m/z 481 (M+H)$^+$.

Step 7: 1-((2S)-2-(5-iodo-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one (Y7)

Y6 (1.0 eq) and tetrahydrofuran-3-carbaldehyde (2.0 eq) were stirred in DCE/DCM (1:1, 0.05 M) and acetic acid (1.0 eq). After 1 h, NaBH(OAc)$_3$ (2.0 eq) was added and stirring was continued for 9 h at 20° C. The mixture was diluted with DCM and organic phase was washed with aq. sat. NaHCO$_3$ sol., brine, dried and concentrated to give the title compound (72%) as a yellow powder which was directly used in the next step. MS (ES$^+$) m/z 565 (M+H)$^+$.

Step 8: 1-((2S)-2-(5-(benzo[d]thiazol-6-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one (Y8)

Y7 (1.0 eq) and 6-(4,4,5,5-tetramethyl-1,3,2-dioxaborolan-2-yl)-1,3-benzothiazole (1.2 eq) were dissolved in DME (0.03 M) and obtained solution was then degassed and K$_2$CO$_3$ (3 eq) in H$_2$O (0.03 M) was added followed by PdCl$_2$(dppf)DCM (0.5 eq). The mixture was heated at 110° C. and stirred for 1 h then filtered, concentrated and purified by RP-HPLC (MeCN, H$_2$O+0.1% TFA) to give the title compound (36%) as a white solid. $^1$H-NMR (400 MHz, 300 K, CD$_3$CN) 6 (80:20* mixture of rotamers) 9.14* and 9.12 (s, 1H), 8.60*-8.55 (d, 1H, J=4.4 Hz), 8.12 (d, 1H, J=8.4 Hz), 7.96-7.93 (m, 1H), 7.7 (d, 1H, J=8.9 Hz), 7.60 (s, 1H), 7.25 (s, 1H), 7.11 (dd, 1H, J=2.5, 8.9 Hz), 6.08 and 5.81* (brs, 1H), 5.56-5.51*, 5.41-5.28 (m, 2H), 4.14-3.59 (m, overlapped with H$_2$O+TFA, 7H), 3.85 (s, 3H), 3.52-3.48 (m, 1H), 3.34-3.13 (m, 4H), 2.74 (s, 3H), 2.24-2.10 (m, 1H), 1.89-1.81 (m, 1H), 1.73-1.64 (m, 1H). MS (ES$^+$) m/z 572 (M+H)$^+$.

Example 26

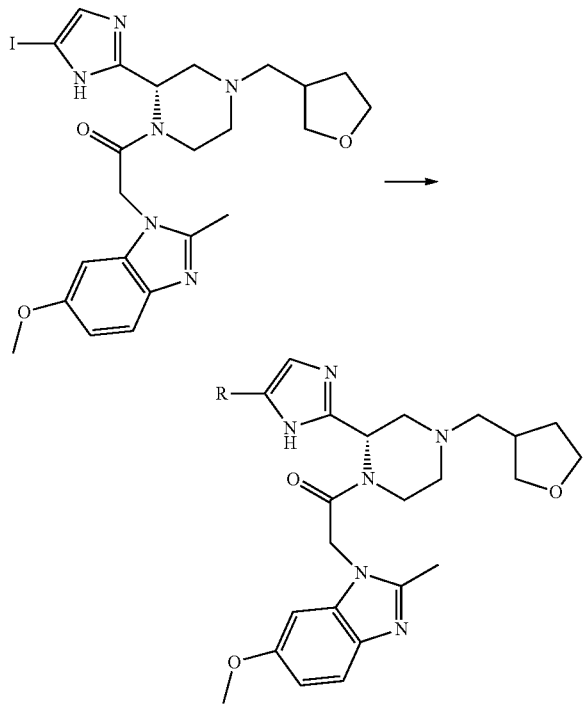

Example 26A: 2-(6-methoxy-2-methyl-1H-benzo[d]imidazol-1-yl)-1-((2S)-2-(5-(pyridin-2-ylethynyl)-1H-imidazol-2-yl)-4-((tetrahydrofuran-3-yl)methyl)piperazin-1-yl)ethan-1-one (Trifluoroacetate Salt) (Z1)

Y7 (1.0 eq), CuI (0.1 eq), TEA (4.0 eq) and 2-ethynylpyridine (1.5 eq) were dissolved in DMF (0.04 M) and obtained solution was purged with $N_2$ then $(PPh_3)_4Pd$ (0.05 eq) was added and heated at 80° C. for 4 h. After this time, the resulting solution was cooled to 0° C. 20° C., filtered, concentrated and purified by RP-HPLC (MeCN, $H_2O$+0.1% TFA) to give the title compound (6%) as an orange solid. $^1$H-NMR (400 MHz, 300 K, $CD_3CN$) δ (70:30* mixture of rotamers) 8.6 (s, 1H), 7.84-7.80 (m, 1H), 7.72 (d, 1H, J=8.7 Hz), 7.56 (d, 1H, J=7.56 Hz), 7.49 (s, 1H), 7.38 (t, 1H, J=6.6 Hz), 7.19 (brs, 1H), 7.12 (d, 1H, J=8.3 Hz), 5.95 and 5.61* (brs, 1H), 5.48* and 5.35 (d, 1H, J=17.7 Hz), 5.17 (d, 1H, J=17.7 Hz), 3.97-3.01 (m overlapped with $H_2O$+TFA, 14H) 3.87 (s, 3H), 2.74 (s, 3H), 1.71-1.63 (m, 1H). MS (ES$^+$) m/z 540 (M+H)$^+$.

Example 26B: 2-(6-methoxy-2-methyl-1H-benzo[d]imidazol-1-yl)-1-((2S)-2-(5-(5-methylpyridin-2-yl)-1H-imidazol-2-yl)-4-((tetrahydrofuran-3-yl)methyl)piperazin-1-yl)ethan-1-one (Trifluoroacetate Salt) (Z2)

3-bromoisoquinoline (1.0 eq) was added to a stirred solution of Zn (1.5 eq) in THF (2.4 M) and heated at reflux for 5 h. After cooling, the resulting mixture was added to a stirred solution of Y7 (1.0 eq) and $(PPh_3)_4Pd$ (0.05 eq) in THF (0.123 M) and stirred for 1 h at reflux. Obtained mixture was filtered, concentrated and purified by RP-HPLC (MeCN, $H_2O$+0.1% TFA) to give the title compound (1%) as a white powder. $^1$H-NMR (400 MHz, 300 K, $CD_3CN$) δ 9.67 (s, 1H), 8.67 (s, 1H), 8.47 (d, 1H, J=8.4 Hz), 8.20 (d, 2H, J=4 Hz), 8.0-7.96 (m, 2H), 7.69 (d, 1H, J=8.2 Hz), 7.21 (dd, 1H, J=2.4 and 8.8 Hz), 7.17 (brs, 1H), 6.07 (brs, 1H), 5.38 (d, 1H, J=17.8 Hz), 5.14 (d, 1H, J=17.8 Hz), 4.16-4.02 (m, 2H), 3.96-3.89 (m, 1H), 3.87 (s, 3H), 3.82-3.65 (m, 3H), 3.59-3.40 (m, 2H), 2.89-2.81 (m, 1H), 2.71 (s, 3H), 2.30-2.23 (m, 1H). MS (ES$^+$) m/z 566 (M+H)$^+$.

Example 26C: 2-(6-methoxy-2-methyl-1H-benzo[d]imidazol-1-yl)-1-((2S)-2-(5-((E)-styryl)-1H-imidazol-2-yl)-4-((tetrahydrofuran-3-yl)methyl)piperazin-1-yl)ethan-1-one (Trifluoroacetate Salt) (Z3)

Y7 (1.0 eq), styrene (2.0 eq), $PPh_3$ (0.05 eq), $K_2CO_3$ (2 eq) were dissolved in DMF (0.04 M) and obtained solution was purged with $N_2$ then $Pd(OAc)_2$ (0.004 eq) was added. The resulting mixture was heated at 100° C. for 4 h then was cooled to 20° C., filtered, concentrated and purified by RP-HPLC (MeCN, $H_2O$+0.1% TFA) to give the title compound (7%) as a grey powder. $^1$H-NMR (400 MHz, 300 K, $CD_3CN$) δ 7.69 (d, 1H, J=9.2 Hz), 7.59-7.57 (m, 3H), 7.46-7.38 (m, 3H), 7.35-7.22 (m, 3H), 7.1-7.06 (m, 1H), 5.54-5.41 (m, 3H), 4.32-4.26 (m, 1H), 4.11-3.99 (m, 3H), 3.91 (s, 3H), 3.89-3.87 (m, 1H), 3.80-3.75 (m, 2H), 3.79-3.66 (m, 2H), 3.47-3.36 (m, 3H), 2.86-2.82 (m, 1H), 2.78 (s, 3H), 2.33-2.28 (m, 2H). MS (ES$^+$) m/z 541 (M+H)$^+$.

Example 27

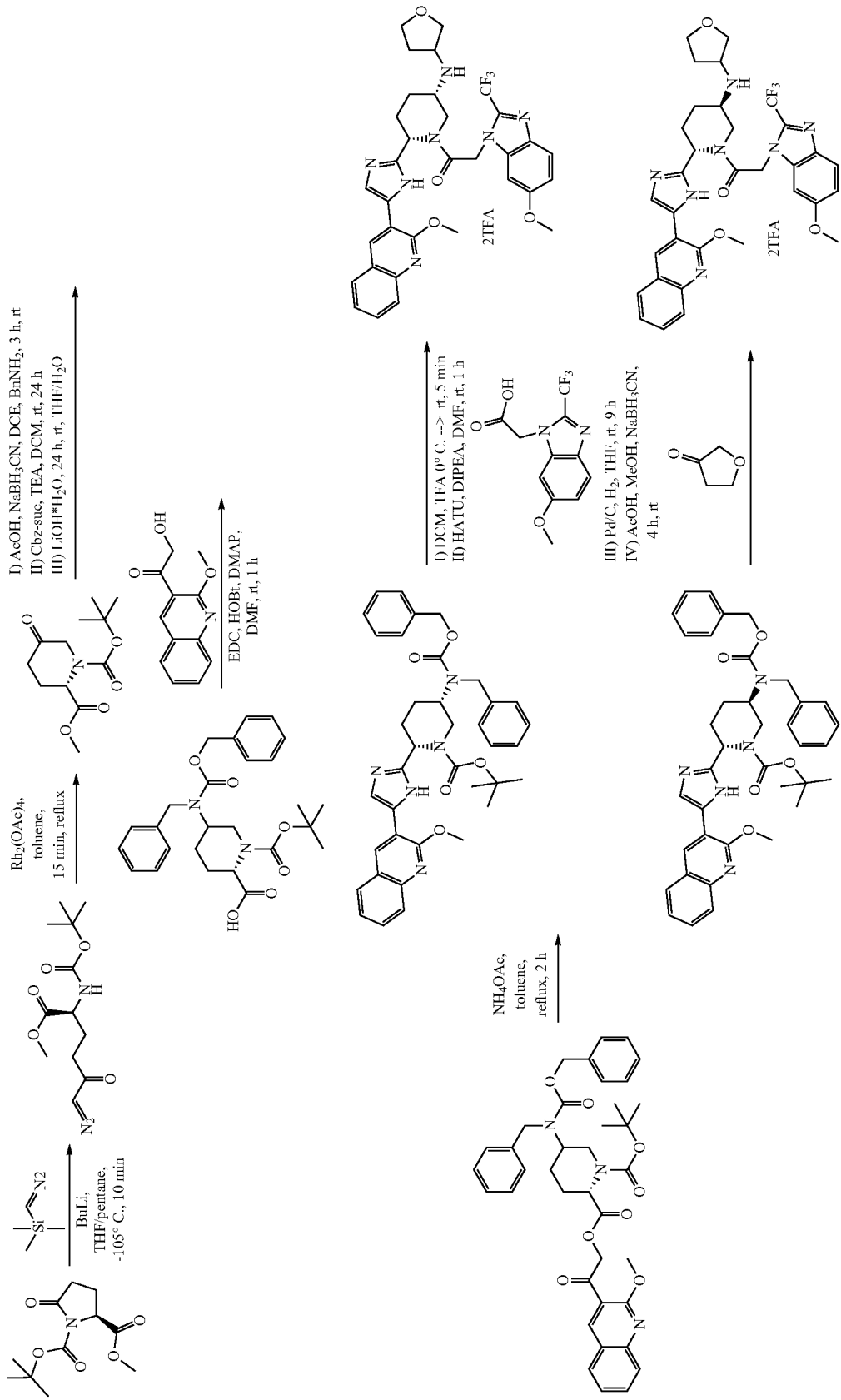

Example 27: 2-(6-methoxy-2-(trifluoromethyl)-1H-benzo[d]imidazol-1-yl)-1-((2S,5R)-2-(5-(2-methoxyquinolin-3-yl)-1H-imidazol-2-yl)-5-((tetrahydrofuran-3-yl)amino)piperidin-1-yl)ethan-1-one (Trifluoroacetate Salt) (AB11)

Step 1: methyl (S)-2-((tert-butoxycarbonyl)amino)-6-diazo-5-oxohexanoate (AB1)

nBuLi (1.3 eq) was slowly added to a solution of (diazomethyl)trimethylsilane (1.2 eq) in THF (0.05 M) previously cooled to −100° C. Mixture was stirred to this temperature for 30 min then added via a canula to a cooled solution (−100° C.) of 1-(tert-butyl) 2-methyl (S)-5-oxopyrrolidine-1,2-dicarboxylate (1.0 eq) (prepared as described by Anelli P. L. et al Org. Process Res. Dev., 2009, 13 (4), pp 739-746) in THF (0.05M). Stirring was continued for additional 10 min then a cold solution (0° C.) of sat. aq. $NH_4Cl$ was added. Mixture was diluted with DCM and organic phase was isolated, dried, concentrated and purified by flash chromatography (DCM/EtOAc from 80:20 to 20:80) to give the title compound (79%) as a yellow solid. MS (ES$^+$) m/z 286 (M+H)$^+$.

Step 2: 1-(tert-butyl) 2-methyl (S)-5-oxopiperidine-1,2-dicarboxylate (AB2)

AB1 (1.0 eq) was dissolved in toluene (0.05 M) and obtained mixture was added dropwise to a refluxing solution of $Rh_2(OAc)_4$ (0.01 eq) in toluene (0.05M). Stirring was continued for additional 15 min then the mixture was filtered, concentrated and purified by flash chromatography (petroleum ether/EtOAc from 90:10 to 20:80) to give the title compound (76%) as a white solid. MS (ES$^+$) m/z 258 (M+H)$^+$.

Step 3: 1-(tert-butyl) 2-methyl (2S)-5-(benzylamino)piperidine-1,2-dicarboxylate (AB3)

Phenylmethanamine (1.5 eq) and AcOH (11.0 eq) were added to a solution of AB2 (1.0 eq) in DCE (0.2 M) previously cooled to 0° C. and stirred to this temperature for 2 h. Then $NaBH_3CN$ (1.5 eq) was added and stirring was continued at 20° C. for additional 3 h. After this time, the mixture was diluted with DCM, washed with aq. sat. $NaHCO_3$ sol., brine, dried, concentrated and purified by flash chromatography (EtOAc/MeOH from 100:0 to 90:10) to give the title compound (85%) as a yellow oil. MS (ES$^+$) m/z 349 (M+H)$^+$.

Step 4: 1-(tert-butyl) 2-methyl (2S)-5-(benzyl((benzyloxy)carbonyl)amino)piperidine-1,2-dicarboxylate (AB4)

AB3 (1.0 eq) and TEA (1.3 eq) were dissolved in DCM (0.16 M) and obtained solution was cooled to 0° C. then benzyl (2,5-dioxopyrrolidin-1-yl) carbonate (1.3 eq) was added. Mixture was left warming to 20° C. and stirring was continued for additional 24 h. After this time, DCM was added and the organic phase was washed with aq. sat. $NaHCO_3$ sol., brine, dried, concentrated and purified by flash chromatography (petroleum ether/EtOAc from 100:0 to 40:60) to give the title compound (81%) as a colorless oil. MS (ES$^+$) m/z 483 (M+H)$^+$.

Step 5: (2S)-5-(benzyl((benzyloxy)carbonyl)amino)-1-(tert-butoxycarbonyl)piperidine-2-carboxylic acid (AB5)

AB4 (1.0 eq) was dissolved in THF (0.06 M) and a solution of LiOH (1.1 eq) in $H_2O$ (0.06 M) was added. Mixture was stirred at 20° C. for 24 h then the THF was evaporated under reduced pressure and EtOAc was added. Aqueous phase was acidified with aqueous HCl (6 N, until pH=5) and extracted with additional EtOAc. Combined organic phases were washed with brine, dried and concentrated to give the title compound as a white solid which was directly used in the next step without purification. MS (ES$^+$) m/z 469 (M+H)$^+$.

Step 6: 1-(tert-butyl) 2-(2-(2-methoxyquinolin-3-yl)-2-oxoethyl) (2S)-5-(benzyl((benzyloxy)carbonyl)amino)piperidine-1,2-dicarboxylate (AB6)

AB5 (1.0 eq) was dissolved in DMF (0.3 M) and HOBt (1.2 eq) and EDC.HCl (1.2 eq) were sequentially added. The resulting mixture was stirred at 20° C. for 15 min, then 2-hydroxy-1-(2-methoxyquinolin-3-yl)ethanone (1.0 eq) and DMAP (0.3 eq) were added. Stirring was continued at 20° C. for 2 h then the solvent was removed under reduced pressure and the residue was dissolved in EtOAc, washed with $H_2O$, brine, dried and concentrated. The obtained crude was purified by flash chromatography (petroleum ether/EtOAc from 100:0 to 0:100) to give the title compound (75%) as a yellow solid. MS (ES$^+$) m/z 668 (M+H)$^+$.

Step 7: tert-butyl (2S,5R)-5-(benzyl((benzyloxy)carbonyl)amino)-2-(5-(2-methoxyquinolin-3-yl)-1H-imidazol-2-yl)piperidine-1-carboxylate (AB7)

AB6 (1.0 eq) was dissolved in toluene (0.2 M) then $NH_4OAc$ (20.0 eq) was added and the solution heated to reflux using a Dean Stark apparatus for 2 h. The mixture was concentrated under reduced pressure, diluted with EtOAc, washed with $H_2O$, brine, dried and concentrated. The residue was purified by flash chromatography (petroleum ether/EtOAc, from 100:0 to 20:80) to give the title compound (27%) as second eluted orange solid diastereomer (first eluted diastereomer 40%). MS (ES$^+$) m/z 648 (M+H)$^+$ (first eluted diastereomer); MS (ES$^+$) m/z 648 (M+H)$^+$ (second eluted diastereomer).

Step 8: benzyl benzyl((3R,6S)-6-(5-(2-methoxyquinolin-3-yl)-1H-imidazol-2-yl)piperidin-3-yl)carbamate (Trifluoroacetate Salt) (AB8)

TFA (DCM/TFA=9:1 sol., 0.04 M) was slowly added to a solution of AB7 (1.0 eq) in DCM (0.04 M) cooled to 0° C. The mixture was stirred at 20° C. for 5 min, then concentrated under reduced pressure. The resulting oily residue was co-evaporated with $Et_2O$ to give the title compound (99%) as pale pink solid which was directly used in the next step without purification. MS (ES$^+$) m/z 548 (M+H)$^+$.

Step 9: benzyl benzyl((3R,6S)-1-(2-(6-methoxy-2-(trifluoromethyl)-1H-benzo[d]imidazol-1-yl)acetyl)-6-(5-(2-methoxyquinolin-3-yl)-1H-imidazol-2-yl)piperidin-3-yl)carbamate (AB9)

HATU (1.1 eq) and 2-[6-methoxy-2-(trifluoromethyl)benzimidazol-1-yl]ethanoic acid (1.1 eq) in DMF (0.2 M) were stirred for 15 min then DIPEA (8.0 eq) and AB8 (1.0 eq)

were sequentially added. Mixture was stirred for 1 h at 20° C. then EtOAc was added and organic phase was washed with aq. sat. NaHCO₃ sol. and brine. Organic layers were combined, dried, concentrated under reduced pressure and purified by flash chromatography (DCM/MeOH from 100:0 to 90:10) to give the title compound (80%) as an orange oil. MS (ES⁺) m/z 804 (M+H)⁺.

Step 10: 1-((2S,5R)-5-amino-2-(5-(2-methoxyquino-lin-3-yl)-1H-imidazol-2-yl)piperidin-1-yl)-2-(6-methoxy-2-(trifluoromethyl)-1H-benzo[d]imidazol-1-yl)ethan-1-one (AB10)

AB9 (1.0 eq) was dissolved in THF (0.02 M) and treated with Pd/C (10% wt) (1:1 in weight). The mixture was purged with N₂ and stirred on H₂ atmosphere at 20° C. for 9 h. The suspension was filtered through a pad of Solka Floc and filtrate was concentrated under vacuum to give the title compound (99%) as an orange solid which was directly used in the next step. MS (ES⁺) m/z 580 (M+H)⁺.

Step 11: 2-(6-methoxy-2-(trifluoromethyl)-1H-benzo[d]imidazol-1-yl)-1-((2S,5R)-2-(5-(2-methoxy-quinolin-3-yl)-1H-imidazol-2-yl)-S5-((tetrahydro-furan-3-yl)amino)piperidin-1-yl)ethan-1-one (Trifluoroacetate Salt) (AB11)

dihydrofuran-3(2H)-one (3.0 eq) and AcOH (1.5 eq) were added to a solution of AB10 (1.0 eq) in MeOH (0.05 M). The mixture was stirred at 20° C. for 1 h then NaBH₃CN (5.0 eq) was added and stirring was continued for additional 3 h. After this time, the mixture was diluted with EtOAc, washed with aq. sat. NaHCO₃ sol., brine, dried, concentrated and purified by RP-HPLC (MeCN, H₂O+0.1% TFA) to give the title compound (29%) as a white powder. ¹H-NMR (400 MHz, 300 K, CD₃CN) (20*:80 mixture of rotamers) δ 8.58* and 8.52 (s, 1H), 7.98-7.93* and 7.85-7.89 (m, 3H), 7.74-7.67 and 7.59-7.56* (m, 2H), 7.49 (t, 1H, J=7.4 Hz), 7.12-7.10* and 7.0-6.96 (dd* and m, 1H, J=2.2, 7.9 Hz), 7.0-6.96 (m, 1H), 5.75-5.70* and 5.43-5.30 and 4.78-4.71* (m, 3H), 4.19-4.10 (m, 4H), 4.03 (s, 3H), 3.98-3.80 (m, 5H), 3.81* and 3.67 (s, 3H), 2.42-2.31 (m, 3H), 2.19-2.06 (m, 2H). MS (ES⁺) m/z 650 (M+H)⁺.

Example 28

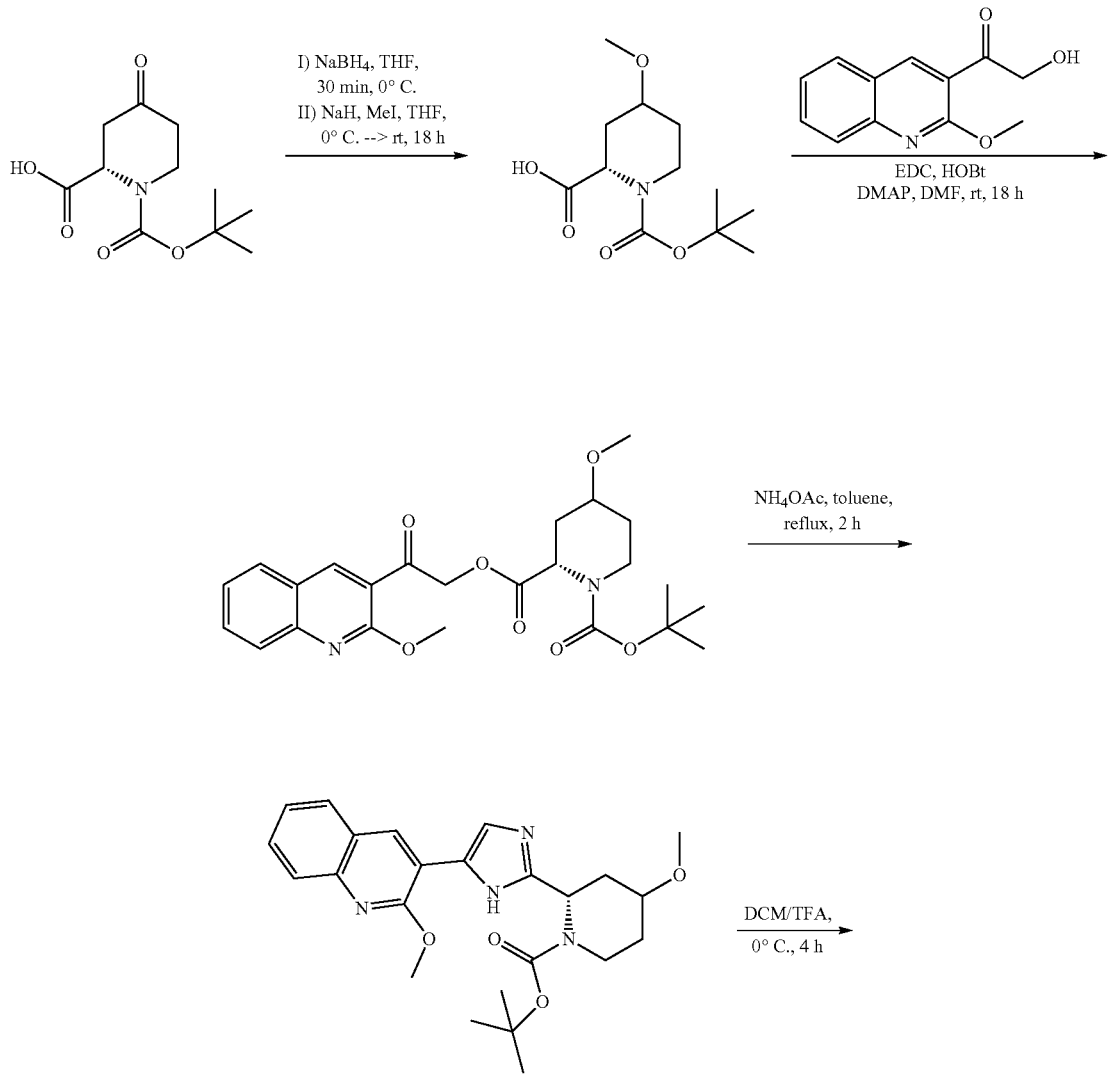

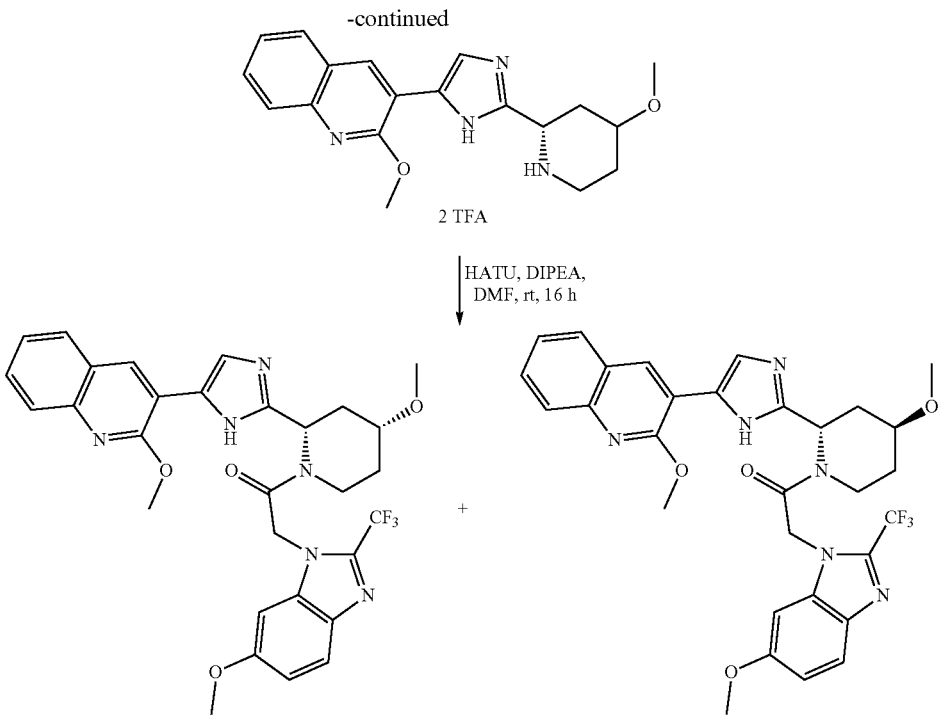

Example 28: 2-((2S. 4S)-4-methoxy-2-(5-(2-methoxyquinolin-3-yl)-1H-imidazol-2-ylpiperidin-1-yl)-2-(6-methoxy-2-(trifluoromethyl)-1H-benzo[d]imidazol-1-yl)ethan-1-one (Trifluoroacetate Salt) (AC6)

Step 1: (2S)-1-(tert-butoxycarbonyl)-4-hydroxypiperidine-2-carboxylic Acid (AC1)

NaBH$_4$ (1.1 eq) was added to a solution of (S)-1-(tert-butoxycarbonyl)-4-oxopiperidine-2-carboxylic acid (1.0 eq) in THF (0.2 M) previously cooled to 0° C. Mixture was stirred to this temperature for 30 min then quenched by addition of sat. aq. NH$_4$Cl. EtOAc and HCl 1N were added and organic phase was isolated, dried and concentrated to give the title compound as a white solid which was directly used in the next step without purification. MS (ES$^+$) m/z 246 (M+H)$^+$.

Step 2: (2S)-1-(tert-butoxycarbonyl)-4-methoxypiperidine-2-carboxylic Acid (AC2)

AC1 (1.0 eq) was dissolved in THF (0.08 M) and NaH (4.0 eq) was added at 0° C. The temperature was raised to 20° C. and the mixture was stirred for 40 min, then the solution was cooled back to 0° C. and iodomethane (10.0 eq) was added. After stirring for 18 h at 20° C., the reaction was quenched by addition of water, diluted with EtOAc and acidified with HCl 1N. Organic phase was isolated, dried and concentrated to give the title compound as a pale yellow solid which was directly used in the next step. MS (ES$^+$) m/z 260 (M+H)$^+$.

Step 3: 1-(tert-butyl) 2-(2-(2-methoxyquinolin-3-yl)-2-oxoethyl) (2S)-4-methoxypiperidine-1,2-dicarboxylate (AC3)

AC2 (1.0 eq) was dissolved in DMF (0.2 M) and HOBt (1.5 eq) and EDC.HCl (1.5 eq) were sequentially added. The resulting mixture was stirred at 20° C. for 15 min, then 2-hydroxy-1-(2-methoxyquinolin-3-yl)ethanone (1.0 eq) and DMAP (0.3 eq) were added. Stirring was continued at 20° C. for 18 h then the solvent was removed under reduced pressure and the residue was dissolved in EtOAc, washed with H$_2$O, brine, dried and concentrated. The obtained crude was purified by flash chromatography (petroleum ether/EtOAc from 100:0 to 50:50) to give the title compound (70%) as a yellow solid. MS (ES$^+$) m/z 459 (M+H)$^+$.

Step 4: tert-butyl (2S)-4-methoxy-2-(5-(2-methoxyquinolin-3-yl)-1H-imidazol-2-yl)piperidine-1-carboxylate (AC4)

AC3 (1.0 eq) was dissolved in toluene (0.2 M) then NH$_4$OAc (20.0 eq) was added and the solution heated to reflux using a Dean Stark apparatus for 2 h. The mixture was concentrated under reduced pressure, diluted with EtOAc, washed with H$_2$O, brine, dried and concentrated. The residue was purified by flash chromatography (petroleum ether/EtOAc, from 100:0 to 50:50) to give the title compound (51%) as pale orange solid. MS (ES$^+$) m/z 439 (M+H)$^+$.

Step 5: 2-methoxy-3-(2-((2S)-4-methoxypiperidin-2-yl)-1H-imidazol-5-yl)quinoline (AC5)

TFA (DCM/TFA=9:1 sol., 0.04 M) was slowly added to a solution of AC4 (1.0 eq) in DCM (0.04 M) cooled to 0° C. and stirred for 3 h to this temperature, then concentrated under reduced pressure. The resulting oily residue was co-evaporated with Et$_2$O to give the title compound (96%) as a pale yellow solid which was directly used in the next step without purification. MS (ES$^+$) m/z 453 (M+H)$^+$.

Step 6: 1-((2S,4S)-4-methoxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one (AC6)

A solution of HATU (1.0 eq) and 2-[6-methoxy-2-(trifluoromethyl)benzimidazol-1-yl]ethanoic acid (1.0 eq) in DMF (0.2 M) was stirred for 15 min then DIPEA (8.0 eq) and AC5 (1.0 eq) were sequentially added. Mixture was stirred for 18 h at 20° C. then EtOAc was added. Organic phase was washed with aq. sat. NaHCO$_3$ sol., brine, dried, concentrated and purified by flash chromatography (DCM/MeOH from 100:0 to 90:10) to give the title compound (20%) as a pale yellow solid. $^1$H-NMR (400 MHz, 300 K, DMSO-d$_6$) (60:40* mixture of rotamers) δ 12.44* and 12.11 (s, 1H), 8.82 and 8.77* (s, 1H), 7.95 and 7.86* (d, 1H, J=7.9 Hz), 7.80-7.78 and 7.71-7.77* (m, 2H), 7.80-7.78* and 7.71-7.77 (m, 1H), 7.62 (t, 1H, J=7.89 Hz), 7.45 (t, 1H, J=7.4 Hz), 7.29 and 7.13* (s, 1H), 6.99 (dd, 1H, J=8.8, 2.19 Hz), 5.83-5.81 and 5.67-5.66* (m, 1H), 5.78-5.35 (m, 2H), 4.41-4.37* and 4.10 and 3.59-3.56 and 2.87-2.85* (m, 2H), 4.17* and 4.15 (s, 3H), 3.77 and 3.67* (s, 3H), 3.67-3.63 and 3.51-3.47* (m, 1H), 3.34 and 3.31* (s, 3H), 2.89-0.85* and 2.71-2.68 and 1.91-1.84* and 1.60-1.53 (m 2H), 2.23-2.20 and 2.09-2.07* and 1.46-1.40* and 1.19-1.15* (m, 2H). MS (ES$^+$) m/z 595 (M+H)$^+$.

The following compounds (Table 1) were prepared according to the procedures described in Examples.

TABLE 1

Synthesized compounds

| Entry | Compound Name | Molecular Ion [M + H]$^+$ | Procedure |
|---|---|---|---|
| 1 | methyl 4-(4-(2-(5-methoxy-2-methyl-1H-indol-3-yl)acetyl)-3-(5-(naphthalen-2-yl)-1H-imidazol-2-yl)piperazin-1-yl)butanoate | 581 | Example 1 |
| 2 | 4-(4-(2-(5-methoxy-2-methyl-1H-indol-3-yl)acetyl)-3-(5-(naphthalen-2-yl)-1H-imidazol-2-yl)piperazin-1-yl)butanoic acid | NA | Example 1 |
| 3 | 4-(4-(2-(5-methoxy-2-methyl-1H-indol-3-yl)acetyl)-3-(5-(naphthalen-2-yl)-1H-imidazol-2-yl)piperazin-1-yl)butanamide | 566 | Example 1 |
| 4 | 4-(4-(2-(5-methoxy-2-methyl-1H-indol-3-yl)acetyl)-3-(5-(naphthalen-2-yl)-1H-imidazol-2-yl)piperazin-1-yl)-N-methylbutanamide | 580 | Example 1 |
| 5 | 6-(4-(2-(5-methoxy-2-methyl-1H-indol-3-yl)acetyl)-3-(5-(naphthalen-2-yl)-1H-imidazol-2-yl)piperazin-1-yl)hexan-3-one | 579 | Example 1 |
| 6 | 6-(3-(5-(naphthalen-2-yl)-1H-imidazol-2-yl)piperazin-1-yl)hexan-3-one | NA | Example 1 |
| 7 | 6-(4-(1-methylpiperidine-4-carbonyl)-3-(5-(naphthalen-2-yl)-1H-imidazol-2-yl)piperazin-1-yl)hexan-3-one | 503 | Example 1 |
| 8 | 6-(3-(5-(naphthalen-2-yl)-1H-imidazol-2-yl)-4-(thiazole-5-carbonyl)piperazin-1-yl)hexan-3-one | 489 | Example 1 |
| 9 | N,N-dimethyl-2-(2-(5-(naphthalen-2-yl)-1H-imidazol-2-yl)-4-(4-oxohexyl)piperazin-1-yl)-2-oxoacetamide | 477 | Example 1 |
| 10 | 6-(3-(5-(naphthalen-2-yl)-1H-imidazol-2-yl)-4-(naphthalen-2-ylsulfonyl)piperazin-1-yl)hexan-3-one | NA | Example 2 |
| 11 | 6-(4-ethyl-3-(5-(naphthalen-2-yl)-1H-imidazol-2-yl)piperazin-1-yl)hexan-3-one | 406 | Example 5 |
| 12 | 6-(4-acetyl-3-(5-(naphthalen-2-yl)-1H-imidazol-2-yl)piperazin-1-yl)hexan-3-one | 420 | Example 1 |
| 13 | 1-(4-(2-(5-methoxy-2-methyl-1H-indol-3-yl)acetyl)-3-(5-(naphthalen-2-yl)-1H-imidazol-2-yl)piperazin-1-yl)hexane-1,4-dione | 593 | Example 7 |
| 14 | 1-(4-acetyl-3-(5-(naphthalen-2-yl)-1H-imidazol-2-yl)piperazin-1-yl)hexane-1,4-dione | 434 | Example 7 |
| 15 | 1-(4-hexyl-2-(5-(naphthalen-2-yl)-1H-imidazol-2-yl)piperazin-1-yl)-2-(5-methoxy-2-methyl-1H-indol-3-yl)ethan-1-one | 565 | Example 1 |
| 16 | 2-(5-methoxy-2-methyl-1H-indol-3-yl)-1-(4-methyl-2-(5-(naphthalen-2-yl)-1H-imidazol-2-yl)piperazin-1-yl)ethan-1-one | 495 | Example 1 |
| 17 | 6-(4-benzoyl-3-(5-(naphthalen-2-yl)-1H-imidazol-2-yl)piperazin-1-yl)hexan-3-one | 482 | Example 1 |
| 18 | 6-(3-(5-(naphthalen-2-yl)-1H-imidazol-2-yl)-4-nicotinoylpiperazin-1-yl)hexan-3-one | 483 | Example 1 |
| 19 | 6-(3-(5-(naphthalen-2-yl)-1H-imidazol-2-yl)-4-(2-phenylacetyl)piperazin-1-yl)hexan-3-one | 496 | Example 1 |
| 20 | 6-(4-(3-(1H-pyrazol-4-yl)propanoyl)-3-(5-(naphthalen-2-yl)-1H-imidazol-2-yl)piperazin-1-yl)hexan-3-one | 500 | Example 1 |
| 21 | 6-(4-(2-(1H-indol-3-yl)acetyl)-3-(5-(naphthalen-2-yl)-1H-imidazol-2-yl)piperazin-1-yl)hexan-3-one | 535 | Example 1 |
| 22 | 6-(4-(2-(1H-pyrrolo[2,3-b]pyridin-3-yl)acetyl)-3-(5-(naphthalen-2-yl)-1H-imidazol-2-yl)piperazin-1-yl)hexan-3-one | 536 | Example 1 |
| 23 | 6-(4-(2-(1H-1,2,3-triazol-1-yl)acetyl)-3-(5-(naphthalen-2-yl)-1H-imidazol-2-yl)piperazin-1-yl)hexan-3-one | 487 | Example 1 |
| 24 | 6-(3-(5-(naphthalen-2-yl)-1H-imidazol-2-yl)-4-(phenylsulfonyl)piperazin-1-yl)hexan-3-one | 518 | Example 2 |
| 25 | 2-(5-(naphthalen-2-yl)-1H-imidazol-2-yl)-4-(4-oxohexyl)-N-phenylpiperazine-1-carboxamide | 497 | Example 3 |
| 26 | phenyl 2-(5-(naphthalen-2-yl)-1H-imidazol-2-yl)-4-(4-oxohexyl)piperazine-1-carboxylate | 498 | Example 4 |
| 27 | 6-(4-benzyl-3-(5-(naphthalen-2-yl)-1H-imidazol-2-yl)piperazin-1-yl)hexan-3-one | 468 | Example 1 |
| 28 | 1-(4-(4-hydroxyhexyl)-2-(5-(naphthalen-2-yl)-1H-imidazol-2-yl)piperazin-1-yl)-2-(5-methoxy-2-methyl-1H-indol-3-yl)ethan-1-one | 581 | Example 1 |

TABLE 1-continued

Synthesized compounds

| Entry | Compound Name | Molecular Ion [M + H]+ | Procedure |
|---|---|---|---|
| 29 | 6-(4-(2-(5-methoxy-2-methyl-1H-indol-3-yl)acetyl)-3-(5-(naphthalen-2-yl)-1,3,4-oxadiazol-2-yl)piperazin-1-yl)hexan-3-one | 581 | Example 11 |
| 30 | 6-(4-(2-(5-methoxy-2-methyl-1H-indol-3-yl)acetyl)-3-(5-phenyl-1H-imidazol-2-yl)piperazin-1-yl)hexan-3-one | 529 | Example 10 |
| 31 | 6-(4-(2-(5-methoxy-2-methyl-1H-indol-3-yl)acetyl)-3-(5-(naphthalen-2-yl)oxazol-2-yl)piperazin-1-yl)hexan-3-one | 580 | Example 10 |
| 32 | benzyl 4-(3-(2-ethyl-1,3-dioxolan-2-yl)propyl)-2-(5-(2-methoxyquinolin-3-yl)-1H-imidazol-2-yl)piperazine-1-carboxylate | 587 | Example 1 |
| 33 | benzyl 4-(3-(2-ethyl-1,3-dioxolan-2-yl)propyl)-2-(5-(2-methoxyquinolin-3-yl)oxazol-2-yl)piperazine-1-carboxylate | 588 | Example 1 |
| 34 | 6-(4-(2-(5-methoxy-2-methyl-1H-indol-3-yl)acetyl)-3-(5-(2-methoxyquinolin-3-yl)-1H-imidazol-2-yl)piperazin-1-yl)hexan-3-one | 610 | Example 1 |
| 35 | 6-(4-(2-(1H-pyrrolo[2,3-b]pyridin-3-yl)acetyl)-3-(5-(2-methoxyquinolin-3-yl)-1H-imidazol-2-yl)piperazin-1-yl)hexan-3-one | 567 | Example 1 |
| 36 | 6-(4-(2-(5-methoxy-2-methyl-1H-indol-3-yl)acetyl)-3-(5-(2-methoxyquinolin-3-yl)oxazol-2-yl)piperazin-1-yl)hexan-3-one | 611 | Example 1 |
| 37 | 6-(4-(2-(1H-pyrrolo[2,3-b]pyridin-3-yl)acetyl)-3-(5-(2-methoxyquinolin-3-yl)oxazol-2-yl)piperazin-1-yl)hexan-3-one | 568 | Example 10 |
| 38 | benzyl 4-methyl-2-(5-(naphthalen-2-yl)-1H-imidazol-2-yl)piperazine-1-carboxylate | 428 | Example 1 |
| 39 | (R)-6-(4-(2-(1H-indol-3-yl)acetyl)-3-(5-(naphthalen-2-yl)-1H-imidazol-2-yl)piperazin-1-yl)hexan-3-one | 535 | Example 1 |
| 40 | (S)-6-(4-(2-(1H-indol-3-yl)acetyl)-3-(5-(naphthalen-2-yl)-1H-imidazol-2-yl)piperazin-1-yl)hexan-3-one | 535 | Example 1 |
| 41 | tert-butyl 3-(5-(naphthalen-2-yl)-1H-imidazol-2-yl)morpholine-4-carboxylate | 380 | Example 17 |
| 42 | 3-(5-(naphthalen-2-yl)-1H-imidazol-2-yl)morpholine | 280 | Example 17 |
| 43 | 1-(3-(5-(naphthalen-2-yl)-1H-imidazol-2-yl)morpholino)-2-(1H-pyrrolo[2,3-b]pyridin-3-yl)ethan-1-one | 439 | Example 17 |
| 44 | 1-(2-(5-(naphthalen-2-yl)-1H-imidazol-2-yl)piperidin-1-yl)-2-(1H-pyrrolo[2,3-b]pyridin-3-yl)ethan-1-one | 437 | Example 17 |
| 45 | 5-(naphthalen-2-yl)-2-(pyrrolidin-2-yl)-1H-imidazole | 264 | Example 17 |
| 46 | 1-(2-(5-(naphthalen-2-yl)-1H-imidazol-2-yl)pyrrolidin-1-yl)-2-(1H-pyrrolo[2,3-b]pyridin-3-yl)ethan-1-one | 423 | Example 17 |
| 47 | 1-(4-methyl-2-(5-(1-methyl-1H-indazol-5-yl)-1H-imidazol-2-yl)piperazin-1-yl)-2-phenylethan-1-one | 416 | Example 12 |
| 48 | 1-(4-methyl-2-(5-(pyridin-3-yl)-1H-imidazol-2-yl)piperazin-1-yl)-2-phenylethan-1-one | 362 | Example 12 |
| 49 | 1-(4-methyl-2-(5-(pyrimidin-5-yl)-1H-imidazol-2-yl)piperazin-1-yl)-2-phenylethan-1-one | 363 | Example 12 |
| 50 | 1-(2-(1H-imidazol-2-yl)-4-methylpiperazin-1-yl)-2-phenylethan-1-one | 285 | Example 12 |
| 51 | 1-(4-methyl-2-(5-(1-methyl-1H-pyrazol-4-yl)-1H-imidazol-2-yl)piperazin-1-yl)-2-phenylethan-1-one | 365 | Example 12 |
| 52 | 1-(2-(5-(1H-pyrazol-1-yl)-1H-imidazol-2-yl)-4-methylpiperazin-1-yl)-2-phenylethan-1-one | 351 | Example 12 |
| 53 | 1-methyl-3-(5-(naphthalen-2-yl)-1H-imidazol-2-yl)piperazine | 293 | Example 1 |
| 54 | 1-(4-methyl-2-(5-(quinoxalin-6-yl)-1H-imidazol-2-yl)piperazin-1-yl)-2-phenylethan-1-one | 413 | Example 12 |
| 55 | (3-fluoropyridin-4-yl)(4-methyl-2-(5-(naphthalen-2-yl)-1H-imidazol-2-yl)piperazin-1-yl)methanone | 416 | Example 1 |
| 56 | 1-(4-methyl-2-(5-(naphthalen-2-yl)-1H-imidazol-2-yl)piperazin-1-yl)-2-(pyridin-2-yl)ethan-1-one | 413 | Example 1 |
| 57 | (4-methyl-2-(5-(naphthalen-2-yl)-1H-imidazol-2-yl)piperazin-1-yl)(1-methylpiperidin-3-yl)methanone | 419 | Example 1 |
| 58 | 1-(4-methyl-2-(5-(naphthalen-2-yl)-1H-imidazol-2-yl)piperazin-1-yl)-2-(pyridin-3-yl)ethan-1-one | 413 | Example 1 |
| 59 | 1-(4-methyl-2-(5-(naphthalen-2-yl)-1H-imidazol-2-yl)piperazin-1-yl)-4-(4-methylpiperazin-1-yl)butane-1,4-dione | 476 | Example 1 |
| 60 | 1-(4-methyl-2-(5-(naphthalen-2-yl)-1H-imidazol-2-yl)piperazin-1-yl)-2-(pyridin-4-yl)ethan-1-one | 413 | Example 1 |
| 61 | 2-(2-fluorophenyl)-1-(4-methyl-2-(5-(naphthalen-2-yl)-1H-imidazol-2-yl)piperazin-1-yl)ethan-1-one | 430 | Example 1 |
| 62 | 1-(4-methyl-2-(5-(naphthalen-2-yl)-1H-imidazol-2-yl)piperazin-1-yl)-3-(phenylsulfonyl)propan-1-one | 490 | Example 1 |
| 63 | (4-methyl-2-(5-(naphthalen-2-yl)-1H-imidazol-2-yl)piperazin-1-yl)(1-phenylcyclopropyl)methanone | 438 | Example 1 |
| 64 | 2-(4-methoxyphenyl)-1-(4-methyl-2-(5-(naphthalen-2-yl)-1H-imidazol-2-yl)piperazin-1-yl)ethan-1-one | 442 | Example 1 |

TABLE 1-continued

Synthesized compounds

| Entry | Compound Name | Molecular Ion [M + H]+ | Procedure |
|---|---|---|---|
| 65 | 2-cyclopropyl-1-(4-methyl-2-(5-(naphthalen-2-yl)-1H-imidazol-2-yl)piperazin-1-yl)ethan-1-one | 375 | Example 1 |
| 66 | 1-(4-methyl-2-(5-(naphthalen-2-yl)-1H-imidazol-2-yl)piperazin-1-yl)-3-morpholinopropan-1-one | 435 | Example 1 |
| 67 | 2-(benzo[d]isoxazol-3-yl)-1-(4-methyl-2-(5-(naphthalen-2-yl)-1H-imidazol-2-yl)piperazin-1-yl)ethan-1-one | 453 | Example 1 |
| 68 | 1-(4-methyl-2-(5-(naphthalen-2-yl)-1H-imidazol-2-yl)piperazin-1-yl)-2-(quinolin-3-yl)ethan-1-one | 463 | Example 1 |
| 69 | (2-fluorophenyl)(4-methyl-2-(5-(naphthalen-2-yl)-1H-imidazol-2-yl)piperazin-1-yl)methanone | 415 | Example 1 |
| 70 | (2-methoxyphenyl)(4-methyl-2-(5-(naphthalen-2-yl)-1H-imidazol-2-yl)piperazin-1-yl)methanone | 428 | Example 1 |
| 71 | (3,3-difluorocyclobutyl)(4-methyl-2-(5-(naphthalen-2-yl)-1H-imidazol-2-yl)piperazin-1-yl)methanone | 411 | Example 1 |
| 72 | 3-(1,1-dioxidothiomorpholino)-1-(4-methyl-2-(5-(naphthalen-2-yl)-1H-imidazol-2-yl)piperazin-1-yl)propan-1-one | 483 | Example 1 |
| 73 | 1-(4-methyl-2-(5-(naphthalen-2-yl)-1H-imidazol-2-yl)piperazin-1-yl)-2-(1-methylpiperidin-4-yl)ethan-1-one | 433 | Example 1 |
| 74 | 1-(4-methyl-2-(5-(naphthalen-2-yl)-1H-imidazol-2-yl)piperazin-1-yl)-2-(1H-1,2,4-triazol-1-yl)ethan-1-one | 402 | Example 1 |
| 75 | 2-(2H-indazol-2-yl)-1-(4-methyl-2-(5-(naphthalen-2-yl)-1H-imidazol-2-yl)piperazin-1-yl)ethan-1-one | 452 | Example 1 |
| 76 | 4-(4-methyl-2-(5-(naphthalen-2-yl)-1H-imidazol-2-yl)piperazine-1-carbonyl)pyrrolidin-2-one | 404 | Example 1 |
| 77 | (4-methyl-2-(5-(naphthalen-2-yl)-1H-imidazol-2-yl)piperazin-1-yl)(tetrahydro-2H-pyran-4-yl)methanone | 406 | Example 1 |
| 78 | (2,3-dihydro-1H-inden-1-yl)(4-methyl-2-(5-(naphthalen-2-yl)-1H-imidazol-2-yl)piperazin-1-yl)methanone | 438 | Example 1 |
| 79 | 1-methyl-5-(4-methyl-2-(5-(naphthalen-2-yl)-1H-imidazol-2-yl)piperazine-1-carbonyl)piperidin-2-one | 433 | Example 1 |
| 80 | 2-(1H-indazol-3-yl)-1-(4-methyl-2-(5-(naphthalen-2-yl)-1H-imidazol-2-yl)piperazin-1-yl)ethan-1-one | 452 | Example 1 |
| 81 | 1-(4-methyl-2-(5-(naphthalen-2-yl)-1H-imidazol-2-yl)piperazin-1-yl)-3-(pyrazin-2-yl)propan-1-one | 428 | Example 1 |
| 82 | (4-methyl-2-(5-(naphthalen-2-yl)-1H-imidazol-2-yl)piperazin-1-yl)(2-methyltetrahydro-2H-pyran-2-yl)methanone | 420 | Example 1 |
| 83 | (4-methyl-2-(5-(naphthalen-2-yl)-1H-imidazol-2-yl)piperazin-1-yl)(2-(pyridin-2-yl)cyclopropyl)methanone | 439 | Example 1 |
| 84 | 1-(2-(4-methyl-2-(5-(naphthalen-2-yl)-1H-imidazol-2-yl)piperazine-1-carbonyl)pyrrolidin-1-yl)ethan-1-one | 433 | Example 1 |
| 85 | (4-methyl-2-(5-(naphthalen-2-yl)-1H-imidazol-2-yl)piperazin-1-yl)(2-phenylcyclopropyl)methanone | 438 | Example 1 |
| 86 | 2-(imidazo[2,1-b]thiazol-6-yl)-1-(4-methyl-2-(5-(naphthalen-2-yl)-1H-imidazol-2-yl)piperazin-1-yl)ethan-1-one | 458 | Example 1 |
| 87 | 1-(benzylsulfonyl)-4-methyl-2-(5-(naphthalen-2-yl)-1H-imidazol-2-yl)piperazine | 448 | Example 2 |
| 88 | 4-methyl-2-(5-(naphthalen-2-yl)-1H-imidazol-2-yl)-1-((2,2,2-trifluoroethyl)sulfonyl)piperazine | 439 | Example 2 |
| 89 | 4-methyl-2-(5-(naphthalen-2-yl)-1H-imidazol-2-yl)-1-((pyridin-2-ylmethyl)sulfonyl)piperazine | 449 | Example 2 |
| 90 | 1-benzyl 4-(tert-butyl) 2-(5-(2-methoxyquinolin-3-yl)-1H-imidazol-2-yl)piperazine-1,4-dicarboxylate | 545 | Example 6 |
| 91 | 1-(4-acetyl-2-(5-(2-methoxyquinolin-3-yl)-1H-imidazol-2-yl)piperazin-1-yl)-2-phenylethan-1-one | 471 | Example 7 |
| 92 | 1-(4-methyl-2-(5-(oxazol-5-yl)-1H-imidazol-2-yl)piperazin-1-yl)-2-phenylethan-1-one | 352 | Example 12 |
| 93 | 1-(4-methyl-2-(5-(quinolin-6-yl)-1H-imidazol-2-yl)piperazin-1-yl)-2-phenylethan-1-one | 413 | Example 12 |
| 94 | 1-(2-(5-(isoquinolin-7-yl)-1H-imidazol-2-yl)-4-methylpiperazin-1-yl)-2-phenylethan-1-one | 413 | Example 12 |
| 95 | 1-(4-methyl-2-(5-(pyridin-4-yl)-1H-imidazol-2-yl)piperazin-1-yl)-2-phenylethan-1-one | 362 | Example 12 |
| 96 | 1-(2-(5-(3-(1H-pyrazol-1-yl)phenyl)-1H-imidazol-2-yl)-4-methylpiperazin-1-yl)-2-phenylethan-1-one | 428 | Example 12 |
| 97 | 1-(4-methyl-2-(5-(quinolin-5-yl)-1H-imidazol-2-yl)piperazin-1-yl)-2-phenylethan-1-one | 413 | Example 12 |
| 98 | 1-(2-(5-(2-methoxyquinolin-3-yl)-1H-imidazol-2-yl)-4-methylpiperazin-1-yl)-2-phenylethan-1-one | 443 | Example 12 |
| 99 | benzyl (R)-4-methyl-2-(5-(naphthalen-2-yl)-1H-imidazol-2-yl)piperazine-1-carboxylate | 428 | Example 1 |
| 100 | benzyl (S)-4-methyl-2-(5-(naphthalen-2-yl)-1H-imidazol-2-yl)piperazine-1-carboxylate | 428 | Example 1 |
| 101 | tert-butyl 3-(5-(2-methoxyquinolin-3-yl)-1H-imidazol-2-yl)piperazine-1-carboxylate | 410 | Example 6 |

TABLE 1-continued

Synthesized compounds

| Entry | Compound Name | Molecular Ion [M + H]+ | Procedure |
|---|---|---|---|
| 102 | 1-(4-methyl-2-(5-(naphthalen-2-yl)-1H-imidazol-2-yl)piperazin-1-yl)-2-phenylethan-1-one | 412 | Example 1 |
| 103 | 1-(2-(5-(2-methoxyquinolin-3-yl)-1H-imidazol-2-yl)piperazin-1-yl)-2-phenylethan-1-one | 429 | Example 6 |
| 104 | 1-(2-(5-(2-methoxyquinolin-3-yl)-1H-imidazol-2-yl)-4-(methylsulfonyl)piperazin-1-yl)-2-phenylethan-1-one | 507 | Example 8 |
| 105 | 1-(4-isopropyl-2-(5-(2-methoxyquinolin-3-yl)-1H-imidazol-2-yl)piperazin-1-yl)-2-phenylethan-1-one | 471 | Example 6 |
| 106 | (R)-1-methyl-3-(5-(naphthalen-2-yl)-1H-imidazol-2-yl)piperazine | 293 | Example 1 |
| 107 | 1-(4-(2,2-difluoroethyl)-2-(5-(2-methoxyquinolin-3-yl)-1H-imidazol-2-yl)piperazin-1-yl)-2-phenylethan-1-one | 493 | Example 6 |
| 108 | (S)-1-methyl-3-(5-(naphthalen-2-yl)-1H-imidazol-2-yl)piperazine | 293 | Example 1 |
| 109 | (S)-1-(4-methyl-2-(5-(naphthalen-2-yl)-1H-imidazol-2-yl)piperazin-1-yl)-2-phenylethan-1-one | 412 | Example 1 |
| 110 | 1-(4-methyl-2-(5-(naphthalen-2-yl)-1H-imidazol-2-yl)piperazin-1-yl)-2-(1H-1,2,3-triazol-1-yl)ethan-1-one | 402 | Example 1 |
| 111 | (R)-1-(4-methyl-2-(5-(naphthalen-2-yl)-1H-imidazol-2-yl)piperazin-1-yl)-2-phenylethan-1-one | 412 | Example 1 |
| 112 | 1-(4-methyl-2-(5-(naphthalen-2-yl)-1H-imidazol-2-yl)piperazin-1-yl)-2-(1H-pyrrolo[2,3-b]pyridin-3-yl)ethan-1-one | 452 | Example 1 |
| 113 | 4-benzyl 1-(tert-butyl) 2-(5-phenyl-1H-imidazol-2-yl)piperazine-1,4-dicarboxylate | 464 | Example 1 |
| 114 | tert-butyl 2-(5-phenyl-1H-imidazol-2-yl)piperazine-1-carboxylate | 329 | Example 1 |
| 115 | tert-butyl 4-methyl-2-(5-phenyl-1H-imidazol-2-yl)piperazine-1-carboxylate | 343 | Example 1 |
| 116 | 1-(4-methyl-2-(5-phenyl-1H-imidazol-2-yl)piperazin-1-yl)-2-(1H-pyrrolo[2,3-b]pyridin-3-yl)ethan-1-one | 401 | Example 1 |
| 117 | 1-(4-methyl-2-(5-phenyl-1H-imidazol-2-yl)piperazin-1-yl)-2-phenylethan-1-one | 361 | Example 1 |
| 118 | 2-methoxy-3-(2-(4-methylpiperazin-2-yl)-1H-imidazol-5-yl)quinoline | 324 | Example 6 |
| 119 | 2-(5-methoxy-2-methyl-1H-indol-3-yl)-1-(2-(5-(2-methoxyquinolin-3-yl)-1H-imidazol-2-yl)-4-methylpiperazin-1-yl)ethan-1-one | 526 | Example 6 |
| 120 | 1-(2-(5-(2-methoxyquinolin-3-yl)-1H-imidazol-2-yl)-4-methylpiperazin-1-yl)-2-(1H-pyrrolo[2,3-b]pyridin-3-yl)ethan-1-one | 483 | Example 6 |
| 121 | 2-(5-methoxy-2-methyl-1H-indol-3-yl)-1-(4-methyl-2-(5-phenyl-1H-imidazol-2-yl)piperazin-1-yl)ethan-1-one | 445 | Example 1 |
| 122 | 6-(3-(5-(2-methoxyquinolin-3-yl)-1H-imidazol-2-yl)-4-(2-phenylacetyl)piperazin-1-yl)hexan-3-one | 527 | Example 1 |
| 123 | 1-(4-(cyclopropylmethyl)-2-(5-(naphthalen-2-yl)-1H-imidazol-2-yl)piperazin-1-yl)-2-(5-methoxy-2-methyl-1H-indol-3-yl)ethan-1-one | 535 | Example 1 |
| 124 | 2-(5-methoxy-2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | 565 | Example 1 |
| 125 | 1-(4-(cyclopropylmethyl)-2-(5-(naphthalen-2-yl)-1H-imidazol-2-yl)piperazin-1-yl)-2-(4-methylthiazol-2-yl)ethan-1-one | 473 | Example 1 |
| 126 | 1-(4-benzyl-2-(5-(naphthalen-2-yl)-1H-imidazol-2-yl)piperazin-1-yl)-2-(4-methylthiazol-2-yl)ethan-1-one | 509 | Example 1 |
| 127 | 2-(4-methylthiazol-2-yl)-1-(2-(5-(naphthalen-2-yl)-1H-imidazol-2-yl)-4-phenethylpiperazin-1-yl)ethan-1-one | 523 | Example 1 |
| 128 | 2-(benzo[d]oxazol-2-yl)-1-(4-(cyclopropylmethyl)-2-(5-(naphthalen-2-yl)-1H-imidazol-2-yl)piperazin-1-yl)ethan-1-one | 493 | Example 1 |
| 129 | 2-(benzo[d]oxazol-2-yl)-1-(2-(5-(naphthalen-2-yl)-1H-imidazol-2-yl)-4-((tetrahydrofuran-3-yl)methyl)piperazin-1-yl)ethan-1-one | 523 | Example 1 |
| 130 | 5-methoxy-3-(2-(4-methyl-2-(5-(naphthalen-2-yl)-1H-imidazol-2-yl)piperazin-1-yl)-2-oxoethyl)indolin-2-one | 497 | Example 1 |
| 131 | 3-(2-(4-hexyl-2-(5-(naphthalen-2-yl)-1H-imidazol-2-yl)piperazin-1-yl)-2-oxoethyl)-5-methoxyindolin-2-one | 567 | Example 1 |
| 132 | 3-(2-(4-(cyclopropylmethyl)-2-(5-(naphthalen-2-yl)-1H-imidazol-2-yl)piperazin-1-yl)-2-oxoethyl)-5-methoxyindolin-2-one | 537 | Example 1 |
| 133 | 5-methoxy-3-(2-(2-(5-(naphthalen-2-yl)-1H-imidazol-2-yl)-4-((tetrahydrofuran-3-yl)methyl)piperazin-1-yl)-2-oxoethyl)indolin-2-one | 567 | Example 1 |
| 134 | 3-(2-(4-benzyl-2-(5-(naphthalen-2-yl)-1H-imidazol-2-yl)piperazin-1-yl)-2-oxoethyl)-5-methoxyindolin-2-one | 573 | Example 1 |

TABLE 1-continued

Synthesized compounds

| Entry | Compound Name | Molecular Ion [M + H]+ | Procedure |
|---|---|---|---|
| 135 | 5-methoxy-3-(2-(2-(5-(naphthalen-2-yl)-1H-imidazol-2-yl)-4-phenethylpiperazin-1-yl)-2-oxoethyl)indolin-2-one | 587 | Example 1 |
| 136 | 1-(4-hexyl-2-(5-(naphthalen-2-yl)-1H-imidazol-2-yl)piperazin-1-yl)-2-(1H-pyrrolo[3,2-b]pyridin-3-yl)ethan-1-one | 522 | Example 1 |
| 137 | 2-(1-methyl-1H-indol-3-yl)-1-(4-methyl-2-(5-(naphthalen-2-yl)-1H-imidazol-2-yl)piperazin-1-yl)ethan-1-one | 465 | Example 1 |
| 138 | 1-(4-hexyl-2-(5-(naphthalen-2-yl)-1H-imidazol-2-yl)piperazin-1-yl)-2-(1-methyl-1H-indol-3-yl)ethan-1-one | 535 | Example 1 |
| 139 | 1-(4-(cyclopropylmethyl)-2-(5-(naphthalen-2-yl)-1H-imidazol-2-yl)piperazin-1-yl)-2-(1-methyl-1H-indol-3-yl)ethan-1-one | 505 | Example 1 |
| 140 | 2-(1-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | 535 | Example 1 |
| 141 | 1-(4-benzyl-2-(5-(naphthalen-2-yl)-1H-imidazol-2-yl)piperazin-1-yl)-2-(1-methyl-1H-indol-3-yl)ethan-1-one | 541 | Example 1 |
| 142 | 1-(4-hexyl-2-(5-(naphthalen-2-yl)-1H-imidazol-2-yl)piperazin-1-yl)-2-(5-hydroxy-1H-indol-3-yl)ethan-1-one | 537 | Example 1 |
| 143 | 1-(4-(cyclopropylmethyl)-2-(5-(naphthalen-2-yl)-1H-imidazol-2-yl)piperazin-1-yl)-2-(5-hydroxy-1H-indol-3-yl)ethan-1-one | 507 | Example 1 |
| 144 | 2-(5-hydroxy-1H-indol-3-yl)-1-(2-(5-(naphthalen-2-yl)-1H-imidazol-2-yl)-4-((tetrahydrofuran-3-yl)methyl)piperazin-1-yl)ethan-1-one | 537 | Example 1 |
| 145 | 1-(4-benzyl-2-(5-(naphthalen-2-yl)-1H-imidazol-2-yl)piperazin-1-yl)-2-(5-hydroxy-1H-indol-3-yl)ethan-1-one | 543 | Example 1 |
| 146 | 2-(5-hydroxy-1H-indol-3-yl)-1-(2-(5-(naphthalen-2-yl)-1H-imidazol-2-yl)-4-phenethylpiperazin-1-yl)ethan-1-one | 557 | Example 1 |
| 147 | 1-(4-hexyl-2-(5-(naphthalen-2-yl)-1H-imidazol-2-yl)piperazin-1-yl)-2-(2-methyl-1H-indol-3-yl)ethan-1-one | 535 | Example 1 |
| 148 | 1-(4-(cyclopropylmethyl)-2-(5-(naphthalen-2-yl)-1H-imidazol-2-yl)piperazin-1-yl)-2-(2-methyl-1H-indol-3-yl)ethan-1-one | 505 | Example 1 |
| 149 | 2-(2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | 535 | Example 1 |
| 150 | 1-(4-benzyl-2-(5-(naphthalen-2-yl)-1H-imidazol-2-yl)piperazin-1-yl)-2-(2-methyl-1H-indol-3-yl)ethan-1-one | 541 | Example 1 |
| 151 | 2-(2-methyl-1H-indol-3-yl)-1-(2-(5-(naphthalen-2-yl)-1H-imidazol-2-yl)-4-phenethylpiperazin-1-yl)ethan-1-one | 555 | Example 1 |
| 152 | 1-(4-hexyl-2-(5-(naphthalen-2-yl)-1H-imidazol-2-yl)piperazin-1-yl)-2-(1H-indazol-3-yl)ethan-1-one | 522 | Example 1 |
| 153 | 1-(4-(cyclopropylmethyl)-2-(5-(naphthalen-2-yl)-1H-imidazol-2-yl)piperazin-1-yl)-2-(1H-indazol-3-yl)ethan-1-one | 492 | Example 1 |
| 154 | 2-(1H-indazol-3-yl)-1-(2-(5-(naphthalen-2-yl)-1H-imidazol-2-yl)-4-((tetrahydrofuran-3-yl)methyl)piperazin-1-yl)ethan-1-one | 522 | Example 1 |
| 155 | 1-(4-benzyl-2-(5-(naphthalen-2-yl)-1H-imidazol-2-yl)piperazin-1-yl)-2-(1H-indazol-3-yl)ethan-1-one | 528 | Example 1 |
| 156 | 2-(1H-indazol-3-yl)-1-(2-(5-(naphthalen-2-yl)-1H-imidazol-2-yl)-4-phenethylpiperazin-1-yl)ethan-1-one | 542 | Example 1 |
| 157 | 1-(4-(cyclopropylmethyl)-2-(5-(naphthalen-2-yl)-1H-imidazol-2-yl)piperazin-1-yl)ethan-1-one | 376 | Example 1 |
| 158 | 1-(4-benzyl-2-(5-(naphthalen-2-yl)-1H-imidazol-2-yl)piperazin-1-yl)ethan-1-one | 412 | Example 1 |
| 159 | 1-(2-(5-(naphthalen-2-yl)-1H-imidazol-2-yl)-4-phenethylpiperazin-1-yl)ethan-1-one | 426 | Example 1 |
| 160 | (4-hexyl-2-(5-(naphthalen-2-yl)-1H-imidazol-2-yl)piperazin-1-yl)(1H-imidazol-2-yl)methanone | 458 | Example 1 |
| 161 | 6-(3-(5-phenyl-1H-imidazol-2-yl)-4-(2-phenylacetyl)piperazin-1-yl)hexan-3-one | 446 | Example 1 |
| 162 | 6-(4-(2-(1H-pyrrolo[2,3-b]pyridin-3-yl)acetyl)-3-(5-phenyl-1H-imidazol-2-yl)piperazin-1-yl)hexan-3-one | 486 | Example 1 |
| 163 | (S)-3,3,3-trifluoro-2-methoxy-1-((R)-4-methyl-2-(5-(naphthalen-2-yl)-1H-imidazol-2-yl)piperazin-1-yl)-2-phenylpropan-1-one | 510 | Example 1 |
| 164 | (R)-3,3,3-trifluoro-2-methoxy-1-((R)-4-methyl-2-(5-(naphthalen-2-yl)-1H-imidazol-2-yl)piperazin-1-yl)-2-phenylpropan-1-one | 510 | Example 1 |
| 165 | (3S)-5-methoxy-3-(2-(4-methyl-2-(5-(naphthalen-2-yl)-1H-imidazol-2-yl)piperazin-1-yl)-2-oxoethyl)indolin-2-one | 497 | Example 1 |
| 166 | 4-(2-(5-methoxy-2-methyl-1H-indol-3-yl)acetyl)-1-methyl-5-(5-(naphthalen-2-yl)-1H-imidazol-2-yl)piperazin-2-one | 509 | Example 16 |
| 167 | 1-(4-methyl-2-(5-phenyl-1H-imidazol-2-yl)piperazin-1-yl)-2-(1H-1,2,3-triazol-1-yl)ethan-1-one | 352 | Example 1 |
| 168 | 6-(4-(2-(1H-1,2,3-triazol-1-yl)acetyl)-3-(5-phenyl-1H-imidazol-2-yl)piperazin-1-yl)hexan-3-one | 437 | Example 1 |
| 169 | 1-(2-(5-(2-methoxyquinolin-3-yl)-1H-imidazol-2-yl)-4-methylpiperazin-1-yl)-2-(1H-1,2,3-triazol-1-yl)ethan-1-one | 434 | Example 6 |

TABLE 1-continued

Synthesized compounds

| Entry | Compound Name | Molecular Ion [M + H]+ | Procedure |
|---|---|---|---|
| 170 | 6-(4-(2-(1H-1,2,3-triazol-1-yl)acetyl)-3-(5-(2-methoxyquinolin-3-yl)-1H-imidazol-2-yl)piperazin-1-yl)hexan-3-one | 518 | Example 6 |
| 171 | 4-benzyl 1-(tert-butyl) 2-(5-(naphthalen-2-yl)-1H-imidazol-2-yl)-1,4-diazepane-1,4-dicarboxylate | 528 | Example 1 |
| 172 | tert-butyl 4-methyl-2-(5-(naphthalen-2-yl)-1H-imidazol-2-yl)-1,4-diazepane-1-carboxylate | 408 | Example 15 |
| 173 | 2-(5-methoxy-2-methyl-1H-indol-3-yl)-1-(4-methyl-2-(5-(naphthalen-2-yl)-1H-imidazol-2-yl)-1,4-diazepan-1-yl)ethan-1-one | 509 | Example 15 |
| 174 | 2-(5-methoxy-2-methyl-1H-indol-3-yl)-1-(4-methyl-2-(1-methyl-5-(naphthalen-2-yl)-1H-imidazol-2-yl)piperazin-1-yl)ethan-1-one | 509 | Example 1 |
| 175 | 2-(5-methoxy-2-methyl-1H-indol-3-yl)-1-(4-methyl-7-(5-(naphthalen-2-yl)-1H-imidazol-2-yl)-1,4-diazepan-1-yl)ethan-1-one | 509 | Example 14 |
| 176 | 1-(4-hexyl-2-(5-(2-methoxyquinolin-3-yl)-1H-imidazol-2-yl)piperazin-1-yl)-2-(2-methyl-3a,7a-dihydro-1H-indol-3-yl)ethan-1-one | 568 | Example 6 |
| 177 | 1-(4-(cyclopropylmethyl)-2-(5-(2-methoxyquinolin-3-yl)-1H-imidazol-2-yl)piperazin-1-yl)-2-(2-methyl-3a,7a-dihydro-1H-indol-3-yl)ethan-1-one | 538 | Example 6 |
| 178 | 1-(4-benzyl-2-(5-(2-methoxyquinolin-3-yl)-1H-imidazol-2-yl)piperazin-1-yl)-2-(2-methyl-3a,7a-dihydro-1H-indol-3-yl)ethan-1-one | 574 | Example 6 |
| 179 | 1-(4-hexyl-2-(5-(2-hydroxyquinolin-3-yl)-1H-imidazol-2-yl)piperazin-1-yl)-2-(2-methyl-3a,7a-dihydro-1H-indol-3-yl)ethan-1-one | 554 | Example 6 |
| 180 | (5-(benzyloxy)-1H-indol-2-yl)(2-(5-(2-methoxyqumolin-3-yl)-1H-imidazol-2-yl)-4-((tetrahydrofuran-3-yl)methyl)piperazin-1-yl)methanone | 644 | Example 6 |
| 181 | 1-(2-(5-(2-methoxyquinolin-3-yl)-1H-imidazol-2-yl)-4-((tetrahydrofuran-3-yl)methyl)piperazin-1-yl)-2-(phenylsulfonyl)ethan-1-one | 577 | Example 6 |
| 182 | 2-methoxy-3-(2-(4-((tetrahydrofuran-3-yl)methyl)-1-((1,3,5-trimethyl-1H-pyrazol-4-yl)sulfonyl)piperazin-2-yl)-1H-imidazol-5-yl)quinoline | 567 | Example 6 |
| 183 | 2-(6-methoxybenzofuran-3-yl)-1-(2-(5-(2-methoxyquinolin-3-yl)-1H-imidazol-2-yl)-4-((tetrahydrofuran-3-yl)methyl)piperazin-1-yl)ethan-1-one | 583 | Example 6 |
| 184 | 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | 584 | Example 6 |
| 185 | 1-(2-(5-(2-methoxyquinolin-3-yl)-1H-imidazol-2-yl)-4-((tetrahydrofuran-3-yl)methyl)piperazin-1-yl)-2-(3-methylbenzo[b]thiophen-2-yl)ethan-1-one | 583 | Example 6 |
| 186 | 2-(5-methoxy-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | 582 | Example 6 |
| 187 | 7-(2-(2-(5-(2-methoxyquinolin-3-yl)-1H-imidazol-2-yl)-4-((tetrahydrofuran-3-yl)methyl)piperazin-1-yl)-2-oxoethyl)-1,3-dimethyl-3,7-dihydro-1H-purine-2,6-dione | 615 | Example 6 |
| 188 | (2-hydroxy-6-methoxyquinolin-4-yl)(2-(5-(2-methoxyquinolin-3-yl)-1H-imidazol-2-yl)-4-((tetrahydrofuran-3-yl)methyl)piperazin-1-yl)methanone | 596 | Example 6 |
| 189 | 2-(benzo[d]isoxazol-3-yl)-1-(2-(5-(2-methoxyquinolin-3-yl)-1H-imidazol-2-yl)-4-((tetrahydrofuran-3-yl)methyl)piperazin-1-yl)ethan-1-one | 554 | Example 6 |
| 190 | 1-(2-(5-(2-methoxyquinolin-3-yl)-1H-imidazol-2-yl)-4-((tetrahydrofuran-3-yl)methyl)piperazin-1-yl)-2-(2-methyl-1H-benzo[d]imidazol-1-yl)ethan-1-one | 567 | Example 6 |
| 191 | (1-benzyl-5-methyl-1H-pyrazol-3-yl)(2-(5-(2-methoxyquinolin-3-yl)-1H-imidazol-2-yl)-4-((tetrahydrofuran-3-yl)methyl)piperazin-1-yl)methanone | 593 | Example 6 |
| 192 | 2-(3,5-dimethyl-1H-1,2,4-triazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 532 | Example 6 |
| 193 | 3-(3-(2-(5-(2-methoxyquinolin-3-yl)-1H-imidazol-2-yl)-4-((tetrahydrofuran-3-yl)methyl)piperazin-1-yl)-3-oxopropyl)-4,5,6,7-tetrahydro-1H-indazol-2-ium | 572 | Example 6 |
| 194 | 1-(4-(2-(2-(5-(2-methoxyquinolin-3-yl)-1H-imidazol-2-yl)-4-((tetrahydrofuran-3-yl)methyl)piperazin-1-yl)-2-oxoethyl)phenyl)imidazolidin-2-one | 597 | Example 6 |

TABLE 1-continued

Synthesized compounds

| Entry | Compound Name | Molecular Ion [M + H]+ | Procedure |
|---|---|---|---|
| 195 | (2-(5-(2-methoxyquinolin-3-yl)-1H-imidazol-2-yl)-4-((tetrahydrofuran-3-yl)methyl)piperazin-1-yl)(5-(tetrahydrofuran-2-yl)thiophen-2-yl)methanone | 575 | Example 6 |
| 196 | (5-(4-methoxyphenyl)furan-2-yl)(2-(5-(2-methoxyquinolin-3-yl)-1H-imidazol-2-yl)-4-((tetrahydrofuran-3-yl)methyl)piperazin-1-yl)methanone | 595 | Example 6 |
| 197 | 1-(2-(5-(2-methoxyquinolin-3-yl)-1H-imidazol-2-yl)-4-((tetrahydrofuran-3-yl)methyl)piperazin-1-yl)-3-(1H-1,2,4-triazol-1-yl)propan-1-one | 518 | Example 6 |
| 198 | 1-(2-(5-(2-methoxyquinolin-3-yl)-1H-imidazol-2-yl)-4-((tetrahydrofuran-3-yl)methyl)piperazin-1-yl)-3-(5-methyl-1H-pyrazol-1-yl)propan-1-one | 531 | Example 6 |
| 199 | 6-(2-(2-(5-(2-methoxyquinolin-3-yl)-1H-imidazol-2-yl)-4-((tetrahydrofuran-3-yl)methyl)piperazin-1-yl)-2-oxoethyl)-7H-imidazo[2,1-b]thiazol-4-ium | 560 | Example 6 |
| 200 | 5-methoxy-3-(2-(2-(5-(2-methoxyquinolin-3-yl)-1H-imidazol-2-yl)-4-((tetrahydrofuran-3-yl)methyl)piperazin-1-yl)-2-oxoethyl)indolin-2-one | 598 | Example 6 |
| 201 | 1-(2-(2-(5-(2-methoxyquinolin-3-yl)-1H-imidazol-2-yl)-4-((tetrahydrofuran-3-yl)methyl)piperazin-1-yl)-2-oxoethyl)-1H-indole-5-carbonitrile | 577 | Example 6 |
| 202 | 3-(3-methoxyphenyl)-1-(2-(5-(2-methoxyquinolin-3-yl)-1H-imidazol-2-yl)-4-((tetrahydrofuran-3-yl)methyl)piperazin-1-yl)propan-1-one | 557 | Example 6 |
| 203 | 2-(5-methoxy-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | 596 | Example 6 |
| 204 | benzyl 2-(5-(pyridin-3-yl)-1H-imidazol-2-yl)-4-((tetrahydrofuran-3-yl)methyl)piperazine-1-carboxylate | 449 | Example 12 |
| 205 | benzyl 2-(1H-imidazol-2-yl)-4-((tetrahydrofuran-3-yl)methyl)piperazine-1-carboxylate | 371 | Example 12 |
| 206 | 1-(2-(5-(2-methoxyquinolin-3-yl)-1H-imidazol-2-yl)-4-((tetrahydrofuran-3-yl)methyl)piperazin-1-yl)-2-(2-methyl-1H-indol-3-yl)ethan-1-one | 566 | Example 6 |
| 207 | 3-(2-(1,4-bis((tetrahydrofuran-3-yl)methyl)piperazin-2-yl)-1H-imidazol-5-yl)-2-methoxyquinoline | 479 | Example 6 |
| 208 | tert-butyl 4-(2-(5-methoxy-2-methyl-1H-indol-3-yl)acetyl)-3-(5-(2-methoxyquinolin-3-yl)-1H-imidazol-2-yl)piperazine-1-carboxylate | 612 | Example 6 |
| 209 | 2-(5-methoxy-2-methyl-1H-indol-3-yl)-1-(2-(5-(2-methoxyquinolin-3-yl)-1H-imidazol-2-yl)piperazin-1-yl)ethan-1-one | 512 | Example 6 |
| 210 | 1-(4-(cyclopropylmethyl)-2-(5-(2-methoxyquinolin-3-yl)-1H-imidazol-2-yl)piperazin-1-yl)-2-(5-fluoro-2-methyl-1H-indol-3-yl)ethan-1-one | 554 | Example 6 |
| 211 | 1-(4-(cyclopentylmethyl)-2-(5-(2-methoxyquinolin-3-yl)-1H-imidazol-2-yl)piperazin-1-yl)-2-(5-fluoro-2-methyl-1H-indol-3-yl)ethan-1-one | 582 | Example 6 |
| 212 | 2-(5-fluoro-2-methyl-1H-indol-3-yl)-1-(2-(5-(2-methoxyquinolin-3-yl)-1H-imidazol-2-yl)-4-(thiazol-2-ylmethyl)piperazin-1-yl)ethan-1-one | 597 | Example 6 |
| 213 | 2-(5-fluoro-2-methyl-1H-indol-3-yl)-1-(4-(furan-3-ylmethyl)-2-(5-(2-methoxyquinolin-3-yl)-1H-imidazol-2-yl)piperazin-1-yl)ethan-1-one | 580 | Example 6 |
| 214 | 2-(5-fluoro-2-methyl-1H-indol-3-yl)-1-(4-isobutyl-2-(5-(2-methoxyquinolin-3-yl)-1H-imidazol-2-yl)piperazin-1-yl)ethan-1-one | 556 | Example 6 |
| 215 | 1-(4-benzyl-2-(5-(2-methoxyquinolin-3-yl)-1H-imidazol-2-yl)piperazin-1-yl)-2-(5-fluoro-2-methyl-1H-indol-3-yl)ethan-1-one | 590 | Example 6 |
| 216 | 2-(5-fluoro-2-methyl-1H-indol-3-yl)-1-(2-(5-(2-methoxyquinolin-3-yl)-1H-imidazol-2-yl)-4-(1-methylpiperidin-4-yl)piperazin-1-yl)ethan-1-one | 597 | Example 6 |
| 217 | 2-(5-fluoro-2-methyl-1H-indol-3-yl)-1-(2-(5-(2-methoxyquinolin-3-yl)-1H-imidazol-2-yl)-4-(pyridin-3-ylmethyl)piperazin-1-yl)ethan-1-one | 591 | Example 6 |
| 218 | 1-(4-cyclobutyl-2-(5-(2-methoxyquinolin-3-yl)-1H-imidazol-2-yl)piperazin-1-yl)-2-(5-fluoro-2-methyl-1H-indol-3-yl)ethan-1-one | 554 | Example 6 |
| 219 | 2-(5-fluoro-2-methyl-1H-indol-3-yl)-1-(2-(5-(2-methoxyquinolin-3-yl)-1H-imidazol-2-yl)-4-((1-methyl-1H-pyrazol-4-yl)methyl)piperazin-1-yl)ethan-1-one | 594 | Example 6 |

TABLE 1-continued

Synthesized compounds

| Entry | Compound Name | Molecular Ion [M + H]+ | Procedure |
|---|---|---|---|
| 220 | 2-(5-fluoro-2-methyl-1H-indol-3-yl)-1-(2-(5-(2-methoxyquinolin-3-yl)-1H-imidazol-2-yl)-4-(tetrahydro-2H-pyran-4-yl)piperazin-1-yl)ethan-1-one | 584 | Example 6 |
| 221 | 2-(5-fluoro-2-methyl-1H-indol-3-yl)-1-(2-(5-(2-methoxyquinolin-3-yl)-1H-imidazol-2-yl)-4-methylpiperazin-1-yl)ethan-1-one | 514 | Example 6 |
| 222 | 2-(5-fluoro-2-methyl-1H-indol-3-yl)-1-(2-(5-(2-methoxyquinolin-3-yl)-1H-imidazol-2-yl)piperazin-1-yl)ethan-1-one | 500 | Example 6 |
| 223 | 1-benzyl 4-(tert-butyl) 2-(5-(4-(1H-pyrazol-1-yl)phenyl)-1H-imidazol-2-yl)piperazine-1,4-dicarboxylate | 530 | Example 1 |
| 224 | tert-butyl 3-(5-(4-(1H-pyrazol-1-yl)phenyl)-1H-imidazol-2-yl)-4-(2-(5-fluoro-2-methyl-1H-indol-3-yl)acetyl)piperazine-1-carboxylate | 585 | Example 1 |
| 225 | 2-(5-fluoro-2-methyl-1H-indol-3-yl)-1-(2-(5-(2-hydroxyquinolin-3-yl)-1H-imidazol-2-yl)piperazin-1-yl)ethan-1-one | 486 | Example 1 |
| 226 | 1-(2-(5-(4-(1H-pyrazol-1-yl)phenyl)-1H-imidazol-2-yl)piperazin-1-yl)-2-(5-fluoro-2-methyl-1H-indol-3-yl)ethan-1-one | 485 | Example 1 |
| 227 | 1-(2-(5-(4-(1H-pyrazol-1-yl)phenyl)-1H-imidazol-2-yl)-4-((tetrahydrofuran-3-yl)methyl)piperazin-1-yl)-2-(5-fluoro-2-methyl-1H-indol-3-yl)ethan-1-one | 569 | Example 1 |
| 228 | 2-(5-fluoro-2-methyl-1H-indol-3-yl)-1-(2-(5-(2-methoxyquinolin-3-yl)-1H-imidazol-2-yl)-4-(tetrahydrofuran-3-carbonyl)piperazin-1-yl)ethan-1-one | 598 | Example 7 |
| 229 | 2-(5-fluoro-2-methyl-1H-indol-3-yl)-1-(2-(5-(2-methoxyquinolin-3-yl)-1H-imidazol-2-yl)-4-(1-methylpiperidine-4-carbonyl)piperazin-1-yl)ethan-1-one | 625 | Example 7 |
| 230 | 2-(5-fluoro-2-methyl-1H-indol-3-yl)-1-(4-(isopropylsulfonyl)-2-(5-(2-methoxyquinolin-3-yl)-1H-imidazol-2-yl)piperazin-1-yl)ethan-1-one | 606 | Example 8 |
| 231 | 4-(2-(5-fluoro-2-methyl-1H-indol-3-yl)acetyl)-3-(5-(2-methoxyquinolin-3-yl)-1H-imidazol-2-yl)-N,N-dimethylpiperazine-1-sulfonamide | 607 | Example 8 |
| 232 | 3-(5-(naphthalen-2-yl)-1H-imidazol-2-yl)thiomorpholine 1,1-dioxide | 328 | Example 17 |
| 233 | 2-(5-fluoro-2-methyl-1H-indol-3-yl)-1-(3-(5-(naphthalen-2-yl)-1H-imidazol-2-yl)-1,1-dioxidothiomorpholino)ethan-1-one | 518 | Example 17 |
| 234 | tert-buryl 3-(5-(naphthalen-2-yl)-1H-imidazol-2-yl)thiomorpholine-4-carboxylate 1,1-dioxide | 429 | Example 17 |
| 235 | 2-(5-fluoro-2-methyl-1H-indol-3-yl)-1-(4-(1-isopropyl-1H-pyrazole-4-carbonyl)-2-(5-(2-methoxyquinolin-3-yl)-1H-imidazol-2-yl)piperazin-1-yl)ethan-1-one | 636 | Example 7 |
| 236 | (3,5-dimethylisoxazol-4-yl)(2-(5-(2-methoxyquinolin-3-yl)-1H-imidazol-2-yl)-4-((tetrahydrofuran-3-yl)methyl)piperazin-1-yl)methanone | 518 | Example 6 |
| 237 | 2-(1H-benzo[d][1,2,3]triazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 554 | Example 6 |
| 238 | (2-(5-(2-methoxyquinolin-3-yl)-1H-imidazol-2-yl)-4-((tetrahydrofuran-3-yl)methyl)piperazin-1-yl)(pyrazin-2-yl)methanone | 501 | Example 6 |
| 239 | 3-(1H-imidazol-1-yl)-1-(2-(5-(2-methoxyquinolin-3-yl)-1H-imidazol-2-yl)-4-((tetrahydrofuran-3-yl)methyl)piperazin-1-yl)propan-1-one | 517 | Example 6 |
| 240 | (2-(5-(2-methoxyquinolin-3-yl)-1H-imidazol-2-yl)-4-((tetrahydrofuran-3-yl)methyl)piperazin-1-yl)(4-methyl-2-(pyrazin-2-yl)thiazol-5-yl)methanone | 598 | Example 6 |
| 241 | (3-fluoropyridin-4-yl)(2-(5-(2-methoxyquinolin-3-yl)-1H-imidazol-2-yl)-4-((tetrahydrofuran-3-yl)methyl)piperazin-1-yl)methanone | 518 | Example 6 |
| 242 | (2-(5-(2-methoxyquinolin-3-yl)-1H-imidazol-2-yl)-4-((tetrahydrofuran-3-yl)methyl)piperazin-1-yl)(5-methyl-3-phenylisoxazol-4-yl)methanone | 580 | Example 6 |
| 243 | 2-(2-(2-(5-(2-methoxyquinolin-3-yl)-1H-imidazol-2-yl)-4-((tetrahydrofuran-3-yl)methyl)piperazin-1-yl)-2-oxoethyl)isoindoline-1,3-dione | 582 | Example 6 |
| 244 | (2-(5-(2-methoxyquinolin-3-yl)-1H-imidazol-2-yl)-4-((tetrahydrofuran-3-yl)methyl)piperazin-1-yl)(quinolin-2-yl)methanone | 550 | Example 6 |
| 245 | (2-(5-(2-methoxyquinolin-3-yl)-1H-imidazol-2-yl)-4-((tetrahydrofuran-3-yl)methyl)piperazin-1-yl)(1H-pyrazol-3-yl)methanone | 489 | Example 6 |

TABLE 1-continued

Synthesized compounds

| Entry | Compound Name | Molecular Ion [M + H]+ | Procedure |
|---|---|---|---|
| 246 | (2-(5-(2-methoxyquinolin-3-yl)-1H-imidazol-2-yl)-4-((tetrahydrofuran-3-yl)methyl)piperazin-1-yl)(4-methyl-1,2,3-thiadiazol-5-yl)methanone | 521 | Example 6 |
| 247 | 5-(2-(5-(2-methoxyquinolin-3-yl)-1H-imidazol-2-yl)-4-((tetrahydrofuran-3-yl)methyl)piperazine-1-carbonyl)picolinonitrile | 525 | Example 6 |
| 248 | 1-(2-(5-(2-methoxyquinolin-3-yl)-1H-imidazol-2-yl)-4-((tetrahydrofuran-3-yl)methyl)piperazin-1-yl)-2-morpholinoethan-1-one | 522 | Example 6 |
| 249 | 3-(2-(2-(5-(2-methoxyquinolin-3-yl)-1H-imidazol-2-yl)-4-((tetrahydrofuran-3-yl)methyl)piperazin-1-yl)-2-oxoethyl)oxazolidin-2-one | 522 | Example 6 |
| 250 | 1-(2-(5-(2-methoxyquinolin-3-yl)-1H-imidazol-2-yl)-4-((tetrahydrofuran-3-yl)methyl)piperazin-1-yl)-2-(pyrazolo[1,5-a]pyrimidin-7-yl)ethan-1-one | 554 | Example 6 |
| 251 | 2-(2-(2-(5-(2-methoxyquinolin-3-yl)-1H-imidazol-2-yl)-4-((tetrahydrofuran-3-yl)methyl)piperazin-1-yl)-2-oxoethyl)-4-methylphthalazin-1(2H)-one | 595 | Example 6 |
| 252 | 1-(2-(2-(5-(2-methoxyquinolin-3-yl)-1H-imidazol-2-yl)-4-((tetrahydrofuran-3-yl)methyl)piperazin-1-yl)-2-(4-(3-methylpyrazin-2-yl)phenyl)ethan-1-one | 605 | Example 6 |
| 253 | 1-(2-(2-(5-(2-methoxyquinolin-3-yl)-1H-imidazol-2-yl)-4-((tetrahydrofuran-3-yl)methyl)piperazin-1-yl)-2-oxoethyl)quinazolin-2(1H)-one | 581 | Example 6 |
| 254 | isoquinolin-1-yl(2-(5-(2-methoxyquinolin-3-yl)-1H-imidazol-2-yl)-4-((tetrahydrofuran-3-yl)methyl)piperazin-1-yl)methanone | 550 | Example 6 |
| 255 | (2-(5-(2-methoxyquinolin-3-yl)-1H-imidazol-2-yl)-4-((tetrahydrofuran-3-yl)methyl)piperazin-1-yl)(quinolin-6-yl)methanone | 550 | Example 6 |
| 256 | 6-(2-(5-(2-methoxyquinolin-3-yl)-1H-imidazol-2-yl)-4-((tetrahydrofuran-3-yl)methyl)piperazine-1-carbonyl)pyrimidine-2,4(1H,3H)-dione | 533 | Example 6 |
| 257 | (2-(5-(2-methoxyquinolin-3-yl)-1H-imidazol-2-yl)-4-((tetrahydrofuran-3-yl)methyl)piperazin-1-yl)(pyridazin-4-yl)methanone | 501 | Example 6 |
| 258 | (2-(5-(2-methoxyquinolin-3-yl)-1H-imidazol-2-yl)-4-((tetrahydrofuran-3-yl)methyl)piperazin-1-yl)(quinolin-3-yl)methanone | 550 | Example 6 |
| 259 | (6-aminopyridin-3-yl)(2-(5-(2-methoxyquinolin-3-yl)-1H-imidazol-2-yl)-4-((tetrahydrofuran-3-yl)methyl)piperazin-1-yl)methanone | 515 | Example 6 |
| 260 | (2-(5-(2-methoxyquinolin-3-yl)-1H-imidazol-2-yl)-4-((tetrahydrofuran-3-yl)methyl)piperazin-1-yl)(quinoxalin-6-yl)methanone | 551 | Example 6 |
| 261 | 1-(2-(5-(2-methoxyquinolin-3-yl)-1H-imidazol-2-yl)-4-((tetrahydrofuran-3-yl)methyl)piperazin-1-yl)-2-(1H-pyrrolo[3,2-c]pyridin-3-yl)ethan-1-one | 553 | Example 6 |
| 262 | 2-(imidazo[1,2-a]pyridin-3-yl)-1-(2-(5-(2-methoxyquinolin-3-yl)-1H-imidazol-2-yl)-4-((tetrahydrofuran-3-yl)methyl)piperazin-1-yl)ethan-1-one | 553 | Example 6 |
| 263 | 1-(2-(5-(2-methoxyquinolin-3-yl)-1H-imidazol-2-yl)-4-((tetrahydrofuran-3-yl)methyl)piperazin-1-yl)-2-(2-phenyl-1H-imidazol-1-yl)ethan-1-one | 579 | Example 6 |
| 264 | 1-(2-(5-(2-methoxyquinolin-3-yl)-1H-imidazol-2-yl)-4-((tetrahydrofuran-3-yl)methyl)piperazin-1-yl)-2-(4-methylpiperazin-1-yl)ethan-1-one | 535 | Example 6 |
| 265 | cyclopropyl(2-(5-(2-methoxyquinolin-3-yl)-1H-imidazol-2-yl)-4-((tetrahydrofuran-3-yl)methyl)piperazin-1-yl)methanone | 463 | Example 6 |
| 266 | 2-(2H-benzo[d][1,2,3]triazol-2-yl)-1-(2-(5-(2-methoxyquinolin-3-yl)-1H-imidazol-2-yl)-4-((tetrahydrofuran-3-yl)methyl)piperazin-1-yl)ethan-1-one | 554 | Example 6 |
| 267 | 1-(2-(5-(2-methoxyquinolin-3-yl)-1H-imidazol-2-yl)-4-((tetrahydrofuran-3-yl)methyl)piperazin-1-yl)-3-(pyridin-3-yl)propan-1-one | 528 | Example 6 |
| 268 | (2-(5-(2-methoxyquinolin-3-yl)-1H-imidazol-2-yl)-4-((tetrahydrofuran-3-yl)methyl)piperazin-1-yl)(5-methylpyrazin-2-yl)methanone | 515 | Example 6 |
| 269 | (2-(5-(2-methoxyquinolin-3-yl)-1H-imidazol-2-yl)-4-((tetrahydrofuran-3-yl)methyl)piperazin-1-yl)(1-phenyl-1H-pyrazol-5-yl)methanone | 565 | Example 6 |
| 270 | 1-(2-(5-(2-methoxyquinolin-3-yl)-1H-imidazol-2-yl)-4-((tetrahydrofuran-3-yl)methyl)piperazin-1-yl)-2-(5-methyl-2-phenyloxazol-4-yl)ethan-1-one | 594 | Example 6 |

TABLE 1-continued

Synthesized compounds

| Entry | Compound Name | Molecular Ion [M + H]+ | Procedure |
|---|---|---|---|
| 271 | (1H-indazol-3-yl)(2-(5-(2-methoxyquinolin-3-yl)-1H-imidazol-2-yl)-4-((tetrahydrofuran-3-yl)methyl)piperazin-1-yl)methanone | 539 | Example 6 |
| 272 | 3-(2-(5-(2-methoxyquinolin-3-yl)-1H-imidazol-2-yl)-4-((tetrahydrofuran-3-yl)methyl)piperazine-1-carbonyl)pyridine 1-oxide | 516 | Example 6 |
| 273 | (6-hydroxypyridin-3-yl)(2-(5-(2-methoxyquinolin-3-yl)-1H-imidazol-2-yl)-4-((tetrahydrofuran-3-yl)methyl)piperazin-1-yl)methanone | 516 | Example 6 |
| 274 | (2-(5-(2-methoxyquinolin-3-yl)-1H-imidazol-2-yl)-4-((tetrahydrofuran-3-yl)methyl)piperazin-1-yl)(quinolin-4-yl)methanone | 550 | Example 6 |
| 275 | 2-methoxy-3-(2-(4-((tetrahydrofuran-3-yl)methyl)piperazin-2-yl)-1H-imidazol-5-yl)quinoline | 394 | Example 6 |
| 276 | benzyl 4-(2-(5-fluoro-2-methyl-1H-indol-3-yl)acetyl)-3-(5-(2-methoxyquinolin-3-yl)-1H-imidazol-2-yl)piperazine-1-carboxylate | 634 | Example 6 |
| 277 | benzyl 3-(5-(2-methoxyquinolin-3-yl)-1H-imidazol-2-yl)-4-(2-(2-methyl-1H-benzo[d]imidazol-1-yl)acetyl)piperazine-1-carboxylate | 617 | Example 6 |
| 278 | tert-butyl 3-(5-(2-methoxyquinolin-3-yl)-1H-imidazol-2-yl)morpholine-4-carboxylate | 411 | Example 17 |
| 279 | 2-(5-fluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 585 | Example 6 |
| 280 | 2-(6-fluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 585 | Example 6 |
| 281 | 2-(5,6-difluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 603 | Example 6 |
| 282 | 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one | 621 | Example 9 |
| 283 | 2-(2-cyclopropyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | 593 | Example 6 |
| 284 | 1-(2-(5-(2-methoxyquinolin-3-yl)-1H-imidazol-2-yl)piperazin-1-yl)-2-(2-methyl-1H-benzo[d]imidazol-1-yl)ethan-1-one | 483 | Example 6 |
| 285 | 2-(5-fluoro-2-methyl-1H-indol-3-yl)-1-(4-((2-methoxypyrimidin-5-yl)methyl)-2-(5-(2-methoxyquinolin-3-yl)-1H-imidazol-2-yl)piperazin-1-yl)ethan-1-one | 622 | Example 6 |
| 286 | tert-butyl 3-(5-(2-methoxyquinolin-3-yl)-1H-imidazol-2-yl)thiomorpholine-4-carboxylate 1,1-dioxide | 460 | Example 17 |
| 287 | 2-(5-fluoro-2-methyl-1H-indol-3-yl)-1-(2-(5-(2-methoxyquinolin-3-yl)-1H-imidazol-2-yl)-4-(pyrazin-2-ylmethyl)piperazin-1-yl)ethan-1-one | 592 | Example 6 |
| 288 | 4-((4-(2-(5-fluoro-2-methyl-1H-indol-3-yl)acetyl)-3-(5-(2-methoxyquinolin-3-yl)-1H-imidazol-2-yl)piperazin-1-yl)methyl)pyridine 1-oxide | 607 | Example 6 |
| 289 | 2-(5-fluoro-2-methyl-1H-indol-3-yl)-1-(2-(5-(2-methoxyquinolin-3-yl)-1H-imidazol-2-yl)-4-((1-methyl-1H-1,2,3-triazol-4-yl)methyl)piperazin-1-yl)ethan-1-one | 595 | Example 6 |
| 290 | 2-(5-fluoro-2-methyl-1H-indol-3-yl)-1-(2-(5-(2-methoxyquinolin-3-yl)-1H-imidazol-2-yl)-4-(oxazol-4-ylmethyl)piperazin-1-yl)ethan-1-one | 581 | Example 6 |
| 291 | 1-(4-(1,1-dioxidotetrahydro-2H-thiopyran-4-yl)-2-(5-(2-methoxyquinolin-3-yl)-1H-imidazol-2-yl)piperazin-1-yl)-2-(5-fluoro-2-methyl-1H-indol-3-yl)ethan-1-one | 632 | Example 6 |
| 292 | 3-(5-(2-methoxyquinolin-3-yl)-1H-imidazol-2-yl)thiomorpholine 1,1-dioxide | 359 | Example 17 |
| 293 | 2-(5-fluoro-2-methyl-1H-indol-3-yl)-1-(3-(5-(2-methoxyquinolin-3-yl)-1H-imidazol-2-yl)-1,1-dioxidothiomorpholino)ethan-1-one | 549 | Example 17 |
| 294 | 1-(3-(5-(2-methoxyquinolin-3-yl)-1H-imidazol-2-yl)-1,1-dioxidothiomorpholino)-2-(2-methyl-1H-benzo[d]imidazol-1-yl)ethan-1-one | 532 | Example 17 |
| 295 | 2-(2-(3-(5-(2-methoxyquinolin-3-yl)-1H-imidazol-2-yl)-1,1-dioxidothiomorpholino)-2-oxoethyl)-4-methylphthalazin-1(2H)-one | 560 | Example 17 |
| 296 | 2-(5-fluoro-2-methyl-1H-indol-3-yl)-1-(3-(5-(2-methoxyquinolin-3-yl)-1H-imidazol-2-yl)morpholino)ethan-1-one | 501 | Example 17 |

TABLE 1-continued

Synthesized compounds

| Entry | Compound Name | Molecular Ion [M + H]+ | Procedure |
|---|---|---|---|
| 297 | 1-(3-(5-(2-methoxyquinolin-3-yl)-1H-imidazol-2-yl)morpholino)-2-(2-methyl-1H-benzo[d]imidazol-1-yl)ethan-1-one | 484 | Example 17 |
| 298 | 2-(1H-benzo[d][1,2,3]triazol-1-yl)-1-(3-(5-(2-methoxyquinolin-3-yl)-1H-imidazol-2-yl)morpholino)ethan-1-one | 471 | Example 17 |
| 299 | 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one | 621 | Example 13 |
| 300 | 1-((S)-2-(5-(2-methoxyquinolin-3-yl)-1H-imidazol-2-yl)-4-(((S)-tetrahydrofuran-3-yl)methyl)piperazin-1-yl)-2-(2-(trifluoromethyl)-1H-benzo[d]imidazol-1-yl)ethan-1-one | 621 | Example 13 |
| 301 | 1-((S)-2-(5-(2-methoxyquinolin-3-yl)-1H-imidazol-2-yl)-4-(((R)-tetrahydrofuran-3-yl)methyl)piperazin-1-yl)-2-(2-(trifluoromethyl)-1H-benzo[d]imidazol-1-yl)ethan-1-one | 621 | Example 13 |
| 302 | (S)-1-(2-(5-(2-methoxyquinolin-3-yl)-1H-imidazol-2-yl)-4-((1-methyl-1H-pyrazol-4-yl)methyl)piperazin-1-yl)-2-(2-(trifluoromethyl)-1H-benzo[d]imidazol-1-yl)ethan-1-one | 631 | Example 13 |
| 303 | (S)-1-(2-(5-(2-methoxyquinolin-3-yl)-1H-imidazol-2-yl)-4-((1-methyl-1H-pyrazol-3-yl)methyl)piperazin-1-yl)-2-(2-(trifluoromethyl)-1H-benzo[d]imidazol-1-yl)ethan-1-one | 631 | Example 13 |
| 304 | (S)-1-(4-(isoxazol-3-ylmethyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 618 | Example 13 |
| 305 | (S)-1-(2-(5-(2-methoxyquinolin-3-yl)-1H-imidazol-2-yl)-4-(thiazol-4-ylmethyl)piperazin-1-yl)-2-(2-(trifluoromethyl)-1H-benzo[d]imidazol-1-yl)ethan-1-one | 634 | Example 13 |
| 306 | (S)-1-(2-(5-(2-methoxyquinolin-3-yl)-1H-imidazol-2-yl)-4-(thiazol-2-ylmethyl)piperazin-1-yl)-2-(2-(trifluoromethyl)-1H-benzo[d]imidazol-1-yl)ethan-1-one | 634 | Example 13 |
| 307 | (S)-1-(2-(5-(2-methoxyquinolin-3-yl)-1H-imidazol-2-yl)-4-(pyridin-3-ylmethyl)piperazin-1-yl)-2-(2-(trifluoromethyl)-1H-benzo[d]imidazol-1-yl)ethan-1-one | 628 | Example 13 |
| 308 | (S)-1-(2-(5-(2-methoxyquinolin-3-yl)-1H-imidazol-2-yl)-4-(pyridin-2-ylmethyl)piperazin-1-yl)-2-(2-(trifluoromethyl)-1H-benzo[d]imidazol-1-yl)ethan-1-one | 628 | Example 13 |
| 309 | (S)-1-(2-(5-(2-methoxyquinolin-3-yl)-1H-imidazol-2-yl)-4-(oxetan-3-yl)piperazin-1-yl)-2-(2-(trifluoromethyl)-1H-benzo[d]imidazol-1-yl)ethan-1-one | 593 | Example 13 |
| 310 | (S)-1-(2-(5-(2-methoxyquinolin-3-yl)-1H-imidazol-2-yl)-4-(tetrahydro-2H-pyran-4-yl)piperazin-1-yl)-2-(2-(trifluoromethyl)-1H-benzo[d]imidazol-1-yl)ethan-1-one | 621 | Example 13 |
| 311 | (S)-1-(4-benzyl-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 627 | Example 13 |
| 312 | (S)-1-(4-(1-acetylpiperidin-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 662 | Example 13 |
| 313 | (S)-1-(4-(4,4-difluorocyclohexyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 655 | Example 13 |
| 314 | (S)-1-(2-(5-(2-methoxyquinolin-3-yl)-1H-imidazol-2-yl)-4-((5-methyl-1,2,4-oxadiazol-3-yl)methyl)piperazin-1-yl)-2-(2-(trifluoromethyl)-1H-benzo[d]imidazol-1-yl)ethan-1-one | 633 | Example 13 |
| 315 | (S)-1-(4-(2-fluorobenzyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 645 | Example 13 |
| 316 | (S)-1-(2-(5-(2-methoxyquinolin-3-yl)-1H-imidazol-2-yl)-4-(oxazol-2-ylmethyl)piperazin-1-yl)-2-(2-(trifluoromethyl)-1H-benzo[d]imidazol-1-yl)ethan-1-one | 618 | Example 13 |
| 317 | (S)-1-(2-(5-(2-methoxyquinolin-3-yl)-1H-imidazol-2-yl)-4-(oxazol-4-ylmethyl)piperazin-1-yl)-2-(2-(trifluoromethyl)-1H-benzo[d]imidazol-1-yl)ethan-1-one | 618 | Example 13 |
| 318 | (S)-1-(2-(5-(2-methoxyquinolin-3-yl)-1H-imidazol-2-yl)-4-(2,2,2-trifluoroethyl)piperazin-1-yl)-2-(2-(trifluoromethyl)-1H-benzo[d]imidazol-1-yl)ethan-1-one | 619 | Example 13 |
| 319 | (S)-1-(2-(5-(2-methoxyquinolin-3-yl)-1H-imidazol-2-yl)-4-(pyrimidin-5-ylmethyl)piperazin-1-yl)-2-(2-(trifluoromethyl)-1H-benzo[d]imidazol-1-yl)ethan-1-one | 629 | Example 13 |
| 320 | (S)-1-(4-((5-fluoropyridin-3-yl)methyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 646 | Example 13 |
| 321 | (S)-1-(2-(5-(2-methoxyquinolin-3-yl)-1H-imidazol-2-yl)-4-(oxetan-3-ylmethyl)piperazin-1-yl)-2-(2-(trifluoromethyl)-1H-benzo[d]imidazol-1-yl)ethan-1-one | 607 | Example 13 |

TABLE 1-continued

Synthesized compounds

| Entry | Compound Name | Molecular Ion [M + H]+ | Procedure |
|---|---|---|---|
| 322 | (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | 669 | Example 13 |
| 323 | (S)-1-(2-(5-(2-methoxyquinolin-3-yl)-1H-imidazol-2-yl)-4-(pyrazin-2-ylmethyl)piperazin-1-yl)-2-(2-(trifluoromethyl)-1H-benzo[d]imidazol-1-yl)ethan-1-one | 629 | Example 13 |
| 324 | 2-(5-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 651 | Example 13 |
| 325 | 2-(6-methoxy-2-methyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 597 | Example 13 |
| 326 | 2-(5,6-dimethoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 681 | Example 13 |
| 327 | 2-(6-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 651 | Example 13 |
| 328 | 2-(2-(tert-butyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 609 | Example 13 |
| 329 | 2-(2-cyclobutyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 607 | Example 13 |
| 330 | 1-((2S)-2-(5-(2-methoxyquinolin-3-yl)-1H-imidazol-2-yl)-4-((tetrahydrofuran-3-yl)methyl)piperazin-1-yl)-2-(2-(2,2,2-trifluoroethyl)-1H-benzo[d]imidazol-1-yl)ethan-1-one | 635 | Example 13 |
| 331 | 1-((2S)-2-(5-(2-methoxyquinolin-3-yl)-1H-imidazol-2-yl)-4-((tetrahydrofuran-3-yl)methyl)piperazin-1-yl)-2-(2-methyl-5-(trifluoromethyl)-1H-benzo[d]imidazol-1-yl)ethan-1-one | 635 | Example 13 |
| 332 | 1-((2S)-2-(5-(2-methoxyquinolin-3-yl)-1H-imidazol-2-yl)-4-((tetrahydrofuran-3-yl)methyl)piperazin-1-yl)-2-(2-methyl-6-(trifluoromethyl)-1H-benzo[d]imidazol-1-yl)ethan-1-one | 635 | Example 13 |
| 333 | 1-((2S)-2-(5-(2-methoxyquinolin-3-yl)-1H-imidazol-2-yl)-4-((tetrahydrofuran-3-yl)methyl)piperazin-1-yl)-2-methyl-2-(2-(trifluoromethyl)-1H-benzo[d]imidazol-1-yl)propan-1-one | 649 | Example 13 |
| 334 | 2-(6-methoxy-2-methyl-1H-indol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 596 | Example 13 |
| 335 | 1-((2S)-2-(5-(2-methoxyquinolin-3-yl)-1H-imidazol-2-yl)-4-((tetrahydrofuran-3-yl)methyl)piperazin-1-yl)-2-(2-methyl-4-(trifluoromethyl)-1H-imidazol-1-yl)ethan-1-one | 585 | Example 13 |
| 336 | 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-imidazo[4,5-b]pyridin-1-yl)ethan-1-one | 622 | Example 13 |
| 337 | 2-(5-methoxybenzo[d]isoxazol-3-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 584 | Example 13 |
| 338 | 1-(2-((2S)-2-(5-(2-methoxyquinolin-3-yl)-1H-imidazol-2-yl)-4-((tetrahydrofuran-3-yl)methyl)piperazin-1-yl)-2-oxoethyl)-1H-benzo[d]imidazole-2-carboxamide | 596 | Example 13 |
| 339 | 2-(5-fluorobenzo[d]isoxazol-3-yl)-1-((2S)-2-(5-(2-methoxyquinolin-3-yl)-1H-imidazol-2-yl)-4-((tetrahydrofuran-3-yl)methyl)piperazin-1-yl)ethan-1-one | 572 | Example 13 |
| 340 | benzyl 3-(5-(2-methoxyquinolin-3-yl)-1H-imidazol-2-yl)morpholine-4-carboxylate | 445 | Example 17 |
| 341 | 2-(6-methoxy-2-methyl-1H-benzo[d]imidazol-1-yl)-1-(3-(5-(2-methoxyquinolin-3-yl)-1H-imidazol-2-yl)morpholino)ethan-1-one | 514 | Example 17 |
| 342 | 2-(6-methoxy-2-(trifluoromethyl)-1H-benzo[d]imidazol-1-yl)-1-(3-(5-(2-methoxyquinolin-3-yl)-1H-imidazol-2-yl)morpholino)ethan-1-one | 568 | Example 17 |
| 343 | 2-(6-methoxy-2-methyl-1H-indol-1-yl)-1-(3-(5-(2-methoxyquinolin-3-yl)-1H-imidazol-2-yl)morpholino)ethan-1-one | 513 | Example 17 |
| 344 | 2-(6-methoxy-2-methyl-1H-benzo[d]imidazol-1-yl)-1-(3-(5-(2-methoxyquinolin-3-yl)-1H-imidazol-2-yl)-1,1-dioxidothiomorpholino)ethan-1-one | 562 | Example 17 |
| 345 | (S)-1-(4-(1-acetylpiperidin-4-yl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | 638 | Example 13 |
| 346 | (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | 645 | Example 13 |

TABLE 1-continued

Synthesized compounds

| Entry | Compound Name | Molecular Ion [M + H]+ | Procedure |
|---|---|---|---|
| 347 | 2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one | 616 | Example 17 |
| 348 | 2-(6-methoxy-2-methyl-1H-indol-1-yl)-1-(3-(5-(2-methoxyquinolin-3-yl)-1H-imidazol-2-yl)-1,1-dioxidothiomorpholino)ethan-1-one | 561 | Example 17 |
| 349 | 2-(6-methoxy-2-methyl-1H-indol-1-yl)-1-(7-(5-(2-methoxyquinolin-3-yl)-1H-imidazol-2-yl)-4-methyl-1,4-diazepan-1-yl)ethan-1-one | 540 | Example 14 |
| 350 | 2-(6-methoxy-2-methyl-1H-benzo[d]imidazol-1-yl)-1-(7-(5-(2-methoxyquinolin-3-yl)-1H-imidazol-2-yl)-4-methyl-1,4-diazepan-1-yl)ethan-1-one | 541 | Example 14 |
| 351 | 2-(6-methoxy-2-(trifluoromethyl)-1H-benzo[d]imidazol-1-yl)-1-(7-(5-(2-methoxyquinolin-3-yl)-1H-imidazol-2-yl)-4-methyl-1,4-diazepan-1-yl)ethan-1-one | 595 | Example 14 |
| 352 | 1-((2S)-2-(5-(2-methoxyquinolin-3-yl)-1H-imidazol-2-yl)-4-((tetrahydrofuran-3-yl)methyl)piperazin-1-yl)-2-(8-methyl-9H-purin-9-yl)ethan-1-one | 569 | Example 13 |
| 353 | 1-((2S)-2-(5-(2-methoxyquinolin-3-yl)-1H-imidazol-2-yl)-4-((tetrahydrofuran-3-yl)methyl)piperazin-1-yl)-2-(8-methyl-7H-purin-7-yl)ethan-1-one | 569 | Example 13 |
| 354 | 2-(6-methoxy-2-(trifluoromethyl)-1H-benzo[d]imidazol-1-yl)-1-(2-(5-(2-methoxyquinolin-3-yl)-1H-imidazol-2-yl)piperidin-1-yl)ethan-1-one | 565 | Example 17 |
| 355 | 2-(6-methoxy-2-methyl-1H-indol-1-yl)-1-(2-(5-(2-methoxyquinolin-3-yl)-1H-imidazol-2-yl)piperidin-1-yl)ethan-1-one | 510 | Example 17 |
| 356 | 2-(6-methoxy-2-methyl-1H-benzo[d]imidazol-1-yl)-1-(2-(5-(2-methoxyquinolin-3-yl)-1H-imidazol-2-yl)piperidin-1-yl)ethan-1-one | 511 | Example 17 |
| 357 | 1-(2-(2-(5-(2-methoxyquinolin-3-yl)-1H-imidazol-2-yl)-4-((tetrahydrofuran-3-yl)methyl)piperazin-1-yl)-2-oxoethyl)-1H-benzo[d]imidazole-2-carbonitrile | 577 | Example 13 |
| 358 | (S)-2-(6-methoxy-2-methyl-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one | 609 | Example 13 |
| 359 | 1-((2S)-2-(5-(2-methoxyquinolin-3-yl)-1H-imidazol-2-yl)-4-((tetrahydrofuran-3-yl)methyl)piperazin-1-yl)-2-(2-(methylsulfonyl)-1H-benzo[d]imidazol-1-yl)ethan-1-one | 630 | Example 17 |
| 360 | 2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one | 677 | Example 21 |
| 361 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one | 663 | Example 13 |
| 362 | 2-(6-methoxy-2-(trifluoromethyl)-1H-benzo[d]imidazol-1-yl)-1-(7-(5-(2-methoxyquinolin-3-yl)-1H-imidazol-2-yl)-4-((tetrahydrofuran-3-yl)methyl)-1,4-diazepan-1-yl)ethan-1-one | 664 | Example 21 |
| 363 | 1-((2S)-2-(5-(2-methoxyquinolin-3-yl)-1H-imidazol-2-yl)-4-((tetrahydrofuran-3-yl)methyl)piperazin-1-yl)-2-(2-methyl-6-(methylsulfonyl)-1H-benzo[d]imidazol-1-yl)ethan-1-one | 644 | Example 13 |
| 364 | 2-(6-methoxy-2-methyl-1H-benzo[d]imidazol-1-yl)-1-(2-(5-(2-methoxy-6-phenylpyridin-3-yl)-1H-imidazol-2-yl)-4-(((S)-tetrahydrofuran-3-yl)methyl)piperazin-1-yl)ethan-1-one | 622 | Example 24 |
| 365 | 2-(6-methoxy-2-methyl-1H-benzo[d]imidazol-1-yl)-1-(2-(5-(2-methoxy-6-phenylpyridin-3-yl)-1H-imidazol-2-yl)-4-(((R)-tetrahydrofuran-3-yl)methyl)piperazin-1-yl)ethan-1-one | 622 | Example 24 |
| 366 | 1-(2-(5-(1H-pyrrolo[2,3-b]pyridin-5-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 555 | Example 24 |
| 367 | 2-(6-methoxy-2-methyl-1H-benzo[d]imidazol-1-yl)-1-(7-(5-(2-methoxyquinolin-3-yl)-1H-imidazol-2-yl)-4-(oxetan-3-ylmethyl)-1,4-diazepan-1-yl)ethan-1-one | 596 | Example 21 |
| 368 | 2-(6-methoxy-2-methyl-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one | 618 | Example 21 |
| 369 | 2-(6-methoxy-2-methyl-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one | 623 | Example 21 |
| 370 | 2-(6-methoxy-2-methyl-1H-benzo[d]imidazol-1-yl)-1-(7-(5-(2-methoxyquinolin-3-yl)-1H-imidazol-2-yl)-1,4-diazepan-1-yl)ethan-1-one | 526 | Example 21 |

TABLE 1-continued

Synthesized compounds

| Entry | Compound Name | Molecular Ion [M + H]+ | Procedure |
|---|---|---|---|
| 371 | tert-buryl 4-(2-(6-methoxy-2-methyl-1H-benzo[d]imidazol-1-yl)aceryl)-5-(5-(2-methoxyquinolin-3-yl)-1H-imidazol-2-yl)-1,4-diazepane-1-carboxylate | 626 | Example 21 |
| 372 | (S)-2-(6-methoxy-2-methyl-1H-benzo[d]imidazol-1-yl)-1-(2-(5-(2-methoxyquinolin-3-yl)-1H-imidazol-2-yl)-4-((5-methyl-13,4-oxadiazol-2-yl)methyl)piperazin-1-yl)ethan-1-one | 608 | Example 20B |
| 373 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one | 658 | Example 13 |
| 374 | 2-(6-methoxy-2-(trifluoromethyl)-1H-benzo[d]imidazol-1-yl)-1-(7-(5-(2-methoxyquinolin-3-yl)-1H-imidazol-2-yl)-4-(oxetan-3-ylmethyl)-1,4-diazepan-1-yl)ethan-1-one | 650 | Example 21 |
| 375 | 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 674 | Example 21 |
| 376 | 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(pyridin-2-yl)ethyl)-1,4-diazepan-1-yl)ethan-1-one | 685 | Example 22A |
| 377 | 2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one | 651 | Example 18 |
| 378 | 1-(4-(2-(1H-pyrazol-1-yl)ethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 674 | Example 22B |
| 379 | (S)-2-(6-methoxy-2-(trifluoromethyl)-1H-benzo[d]imidazol-1-yl)-1-(2-(5-(2-methoxyquinolin-3-yl)-4H-1,2,4-triazol-3-yl)-4-(thiazol-2-ylmethyl)piperazin-1-yl)ethan-1-one | 664 | Example 18 |
| 380 | (S)-2-(6-methoxy-2-methyl-1H-benzo[d]imidazol-1-yl)-1-(2-(5-(2-methoxyquinolin-3-yl)-1H-imidazol-2-yl)-4-((4-methyl-4H-1,2,4-triazol-3-yl)methyl)piperazin-1-yl)ethan-1-one | 607 | Example 20B |
| 381 | 2-(6-methoxy-2-(trifluoromethyl)-1H-benzo[d]imidazol-1-yl)-1-(7-(5-(2-methoxyquinolin-3-yl)-1H-imidazol-2-yl)-4-(pyridin-2-ylmethyl)-1,4-diazepan-1-yl)ethan-1-one | 671 | Example 21 |
| 382 | (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | 660 | Example 20A |
| 383 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(pyridin-2-yl)ethyl)piperazin-1-yl)ethan-1-one | 671 | Example 20B |
| 384 | (S)-1-(4-(2-(4H-1,2,4-triazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | 661 | Example 20B |
| 385 | 1-(2-(5-(1H-benzo[d]imidazol-5-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 555 | Example 24 |
| 386 | 1-(2-(5-(4-((dimethylamino)methyl)phenyl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 572 | Example 24 |
| 387 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(2-methylthiazol-4-yl)ethyl)piperazin-1-yl)ethan-1-one | 691 | Example 20A |
| 388 | 2-(6-methoxy-2-(trifluoromethyl)-1H-benzo[d]imidazol-1-yl)-1-((2S)-2-(5-(2-methoxyquinolin-3-yl)-1,2,4-oxadiazol-3-yl)-4-((tetrahydrofuran-3-yl)methyl)piperazin-1-yl)ethan-1-one | 652 | Example 19 |
| 389 | 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(1-methyl-1H-pyrazol-5-yl)ethyl)-1,4-diazepan-1-yl)ethan-1-one | 688 | Example 22B |
| 390 | 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(2-methylthiazol-4-yl)ethyl)-1,4-diazepan-1-yl)ethan-1-one | 705 | Example 22B |
| 391 | 1-((2S)-2-(5-(benzo[d]thiazol-6-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 572 | Example 24 |
| 392 | 1-(2-(1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 439 | Example 24 |
| 393 | tert-buryl 2-(2-((2S)-1-(2-(6-methoxy-2-methyl-1H-benzo[d]imidazol-1-yl)acetyl)-4-((tetrahydrofuran-3-yl)methyl)piperazin-2-yl)-1H-imidazol-5-yl)-1H-indole-1-carboxylate | 655 | Example 24 |
| 394 | 1-((2S)-2-(5-(1H-pyrrolo[2,3-b]pyridin-3-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 555 | Example 24 |

TABLE 1-continued

Synthesized compounds

| Entry | Compound Name | Molecular Ion [M + H]+ | Procedure |
|---|---|---|---|
| 395 | 1-((2S)-2-(5-(1-benzyl-1H-pyrazol-4-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 595 | Example 24 |
| 396 | 1-((2S)-2-(5-(1H-indol-2-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 554 | Example 24 |
| 397 | 1-((2S)-2-(5-(2-cyclopropylpyrimidin-5-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 557 | Example 24 |
| 398 | 2-(6-methoxy-2-methyl-1H-benzo[d]imidazol-1-yl)-1-((2S)-2-(5-(pyridin-2-ylethynyl)-1H-imidazol-2-yl)-4-((tetrahydrofuran-3-yl)methyl)piperazin-1-yl)ethan-1-one | 540 | Example 25A |
| 399 | 2-(6-methoxy-2-methyl-1H-benzo[d]imidazol-1-yl)-1-((2S)-2-(5-(2-methoxypyridin-3-yl)-1H-imidazol-2-yl)-4-((tetrahydrofuran-3-yl)methyl)piperazin-1-yl)ethan-1-one | 546 | Example 24 |
| 400 | 2-(6-methoxy-2-methyl-1H-benzo[d]imidazol-1-yl)-1-((2S)-2-(5-(2-methoxy-5-phenylpyridin-3-yl)-1H-imidazol-2-yl)-4-((tetrahydrofuran-3-yl)methyl)piperazin-1-yl)ethan-1-one | 622 | Example 24 |
| 401 | 2-(6-methoxy-2-(trifluoromethyl)-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one | 672 | Example 21 |
| 402 | (S)-1-(4-(2-(isoxazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | 661 | Example 20A |
| 403 | 1-((2S,4S)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 608 | Example 23 |
| 404 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one | 660 | Example 13 |
| 405 | 1-((2S,4S)-4-amino-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 580 | Example 23 |
| 406 | 2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 620 | Example 21 |
| 407 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(thiazol-2-ylmethyl)amino)piperidin-1-yl)ethan-1-one | 691 | Example 23 |
| 408 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((thiazol-2-ylmethyl)amino)piperidin-1-yl)ethan-1-one | 677 | Example 23 |
| 409 | 2-(6-methoxy-2-(trifluoromethyl)-1H-benzo[d]imidazol-1-yl)-1-(7-(5-(2-methoxyquinolin-3-yl)-1H-imidazol-2-yl)-4-((5-methyl-1,2,4-oxadiazol-3-yl)methyl)-1,4-diazepan-1-yl)ethan-1-one | 676 | Example 21 |
| 410 | 2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-4-ylmethyl)-1,4-diazepan-1-yl)ethan-1-one | 677 | Example 21 |
| 411 | 2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-4-ylmethyl)-1,4-diazepan-1-yl)ethan-1-one | 661 | Example 21 |
| 412 | 2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-2-ylmethyl)-1,4-diazepan-1-yl)ethan-1-one | 661 | Example 21 |
| 413 | 1-(4-(isoxazol-3-ylmethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 661 | Example 21 |
| 414 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((tetrahydrofuran-3-yl)amino)piperidin-1-yl)ethan-1-one | 650 | Example 23 |
| 415 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(tetrahydrofuran-3-yl)amino)piperidin-1-yl)ethan-1-one | 664 | Example 23 |
| 416 | 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-((tetrahydrofuran-3-yl)amino)piperidin-1-yl)ethan-1-one | 650 | Example 23 |
| 417 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one | 647 | Example 13 |
| 418 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-4-ylmethyl)piperazin-1-yl)ethan-1-one | 663 | Example 13 |

TABLE 1-continued

Synthesized compounds

| Entry | Compound Name | Molecular Ion [M + H]+ | Procedure |
|---|---|---|---|
| 419 | 1-((2S,4R)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 608 | Example 23 |
| 420 | 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-((thiazol-2-ylmethyl)amino)piperidin-1-yl)ethan-1-one | 677 | Example 23 |
| 421 | (R)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 674 | Example 21 |
| 422 | (S)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 674 | Example 21 |
| 423 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyrazin-2-ylmethyl)amino)piperidin-1-yl)ethan-1-one | 672 | Example 23 |
| 424 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-pyrazol-3-yl)methyl)amino)piperidin-1-yl)ethan-1-one | 674 | Example 23 |
| 425 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one | 664 | Example 23 |
| 426 | (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | 698 | Example 13 |
| 427 | 1-((2S)-2-(5-(6-(1H-pyrazol-1-yl)pyridin-3-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 582 | Example 24 |
| 428 | 1-(4-(1,1-dioxidotetrahydro-2H-thiopyran-4-yl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 712 | Example 13 |
| 429 | 1-((2S,4S)-4-((isoxazol-3-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 661 | Example 23 |
| 430 | 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((tetrahydrofuran-3-yl)methyl)amino)piperidin-1-yl)ethan-1-one | 678 | Example 23 |
| 431 | 1-((2S,4S)-4-((2-(1H-pyrazol-1-yl)ethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 674 | Example 23 |
| 432 | 1-((2S)-2-(5-(isoquinolin-3-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 566 | Example 25B |
| 433 | 1-((2S)-2-(5-benzyl-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 529 | Example 24 |
| 434 | 2-(6-methoxy-2-methyl-1H-benzo[d]imidazol-1-yl)-1-((2S)-2-(5-(quinolin-6-yl)-1H-imidazol-2-yl)-4-((tetrahydrofuran-3-yl)methyl)piperazin-1-yl)ethan-1-one | 566 | Example 24 |
| 435 | 2-(6-methoxy-2-methyl-1H-benzo[d]imidazol-1-yl)-1-((2S)-2-(5-(quinolin-3-yl)-1H-imidazol-2-yl)-4-((tetrahydrofuran-3-yl)methyl)piperazin-1-yl)ethan-1-one | 566 | Example 24 |
| 436 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(oxetan-3-ylamino)piperidin-1-yl)ethan-1-one | 636 | Example 23 |
| 437 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-1,2,4-triazol-5-yl)methyl)piperazin-1-yl)ethan-1-one | 661 | Example 20B |
| 438 | 1-((2S,4S)-4-(isopropylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 622 | Example 23 |
| 439 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyridazin-4-ylmethyl)piperazin-1-yl)ethan-1-one | 658 | Example 13 |
| 440 | 1-((2S,4S)-4-(isobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 636 | Example 23 |

TABLE 1-continued

Synthesized compounds

| Entry | Compound Name | Molecular Ion [M + H]+ | Procedure |
|---|---|---|---|
| 441 | 1-((2S,4S)-4-(cyclobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 634 | Example 23 |
| 442 | (R)-2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 620 | Example 21 |
| 443 | 1-((2S,4S)-4-(isopropyl((1-methyl-1H-pyrazol-3-yl)methyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 716 | Example 23 |
| 444 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((S)-tetrahydrofuran-3-yl)amino)piperidin-1-yl)ethan-1-one | 650 | Example 23 |
| 445 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((R)-tetrahydrofuran-3-yl)amino)piperidin-1-yl)ethan-1-one | 650 | Example 23 |
| 446 | 1-((2S,4S)-4-((2-hydroxyethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 624 | Example 23 |
| 447 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyridin-2-ylmethyl)amino)piperidin-1-yl)ethan-1-one | 671 | Example 23 |
| 448 | 2-(6-methoxy-2-(trifluoromethyl)-1H-benzo[d]imidazol-1-yl)-1-((2S)-2-(5-(2-methoxyquinolin-3-yl)-1H-imidazol-2-yl)-4-(methyl(pyrazin-2-ylmethyl)amino)piperidin-1-yl)ethan-1-one | 686 | Example 23 |
| 449 | 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((1-methyl-1H-pyrazol-3-yl)methyl)amino)piperidin-1-yl)ethan-1-one | 688 | Example 23 |
| 450 | 1-((2S,4S)-4-methoxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 595 | Example 23 |
| 451 | 1-((2S,4S)-4-methoxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one | 541 | Example 23 |
| 452 | 1-((2S)-4-hydroxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 581 | Example 23 |
| 453 | 1-((2S)-4-hydroxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one | 527 | Example 23 |
| 454 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-imidazol-5-yl)methyl)amino)piperidin-1-yl)ethan-1-one | 674 | Example 23 |
| 455 | 1-((2S,4S)-4-(ethyl(tetrahydrofuran-3-yl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 678 | Example 23 |
| 456 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one | 650 | Example 23 |
| 457 | 2-(6-methoxy-2-(trifluoromethyl)-1H-benzo[d]imidazol-1-yl)-1-((2S,4S)-4-((3-methoxycyclobutyl)amino)-2-(5-(2-methoxyquinolin-3-yl)-1H-imidazol-2-yl)piperidin-1-yl)ethan-1-one | 664 | Example 23 |
| 458 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((oxetan-3-ylmethyl)amino)piperidin-1-yl)ethan-1-one | 650 | Example 23 |
| 459 | 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(pyrrolidin-1-yl)piperidin-1-yl)ethan-1-one | 635 | Example 24A |
| 460 | (S)-2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 620 | Example 21 |
| 461 | 2-(6-methoxy-2-methyl-1H-benzo[d]imidazol-1-yl)-1-((2S)-2-(5-(4-(pyridin-2-yl)phenyl)-1H-imidazol-2-yl)-4-((tetrahydrofuran-3-yl)methyl)piperazin-1-yl)ethan-1-one | 592 | Example 25 |
| 462 | 2-(6-methoxy-2-methyl-1H-benzo[d]imidazol-1-yl)-1-((2S)-2-(5-(4-(pyridin-3-yl)phenyl)-1H-imidazol-2-yl)-4-((tetrahydrofuran-3-yl)methyl)piperazin-1-yl)ethan-1-one | 592 | Example 25 |
| 463 | 2-(6-methoxy-2-methyl-1H-benzo[d]imidazol-1-yl)-1-((2S)-2-(5-(4-(pyridin-4-yl)phenyl)-1H-imidazol-2-yl)-4-((tetrahydrofuran-3-yl)methyl)piperazin-1-yl)ethan-1-one | 592 | Example 25 |

TABLE 1-continued

Synthesized compounds

| Entry | Compound Name | Molecular Ion [M + H]+ | Procedure |
|---|---|---|---|
| 464 | 2-(6-methoxy-2-methyl-1H-benzo[d]imidazol-1-yl)-1-((2S)-2-(5-(2-methoxy-6-phenylpyridin-3-yl)-1H-imidazol-2-yl)-4-((tetrahydrofuran-3-yl)methyl)piperazin-1-yl)ethan-1-one | 622 | Example 25 |
| 465 | (S)-2-(6-methoxy-2-methyl-1H-benzo[d]imidazol-1-yl)-1-(2-(5-(2-methoxyquinolin-3-yl)-1H-imidazol-2-yl)-4-(pyridazin-4-ylmethyl)piperazin-1-yl)ethan-1-one | 604 | Example 13 |
| 466 | 2-(6-methoxy-2-methyl-1H-benzo[d]imidazol-1-yl)-1-((2S)-2-(5-(quinolin-2-yl)-1H-imidazol-2-yl)-4-((tetrahydrofuran-3-yl)methyl)piperazin-1-yl)ethan-1-one | 566 | Example 26B |
| 467 | 2-(6-methoxy-2-methyl-1H-benzo[d]imidazol-1-yl)-1-((2S)-2-(5-(pyrazin-2-ylethynyl)-1H-imidazol-2-yl)-4-((tetrahydrofuran-3-yl)methyl)piperazin-1-yl)ethan-1-one | 541 | Example 26A |
| 468 | 2-(6-methoxy-2-methyl-1H-benzo[d]imidazol-1-yl)-1-((2S)-2-(5-(pyridin-4-ylethynyl)-1H-imidazol-2-yl)-4-((tetrahydrofuran-3-yl)methyl)piperazin-1-yl)ethan-1-one | 540 | Example 26A |
| 469 | 2-(6-methoxy-2-methyl-1H-benzo[d]imidazol-1-yl)-1-((2S)-2-(5-(pyridazin-3-ylethynyl)-1H-imidazol-2-yl)-4-((tetrahydrofuran-3-yl)methyl)piperazin-1-yl)ethan-1-one | 540 | Example 26A |
| 470 | 1-((2S)-2-(5-([1,1'-biphenyl]-2-ylmethyl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 605 | Example 26B |
| 471 | 2-(6-methoxy-2-methyl-1H-benzo[d]imidazol-1-yl)-1-((2S)-2-(5-((E)-styyl)-1H-imidazol-2-yl)-4-((tetrahydrofuran-3-yl)methyl)piperazin-1-yl)ethan-1-one | 541 | Example 26C |
| 472 | 1-((2S)-4-((1,1-dioxidotetrahydrothiophen-3-yl)methyl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | 643 | Example 20C |
| 473 | 1-((2S,4S)-4-((isoxazol-4-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | 661 | Example 23 |
| 474 | 2-(6-methoxy-2-methyl-1H-benzo[d]imidazol-1-yl)-1-((2S,4S)-2-(5-(2-methoxyquinolin-3-yl)-1H-imidazol-2-yl)-4-(methyl(pyrazin-2-ylmethyl)amino)piperidin-1-yl)ethan-1-one | 632 | Example 23 |
| 475 | 2-(6-methoxy-2-methyl-1H-benzo[d]imidazol-1-yl)-1-((2S)-2-(5-(5-methylpyridin-2-yl)-1H-imidazol-2-yl)-4-((tetrahydrofuran-3-yl)methyl)piperazin-1-yl)ethan-1-one | 530 | Example 26B |
| 476 | 1-((2S)-2-(5-iodo-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | 565 | Example 25 |
| 477 | 2-(6-methoxy-2-methyl-1H-benzo[d]imidazol-1-yl)-1-((2S,4S)-2-(5-(2-methoxyquinolin-3-yl)-1H-imidazol-2-yl)-4-(((1-methyl-1H-pyrazol-3-yl)methyl)amino)piperidin-1-yl)ethan-1-one | 620 | Example 23 |
| 478 | 2-(6-methoxy-2-methyl-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one | 610 | Example 23 |
| 479 | (R)-2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one | 615 | Example 17 |
| 480 | (S)-2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one | 615 | Example 17 |
| 481 | 2-(6-methoxy-2-methyl-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one | 595 | Example 24B |
| 482 | 2-(6-methoxy-2-(trifluoromethyl)-1H-benzo[d]imidazol-1-yl)-1-((2S,5R)-2-(5-(2-methoxyquinolin-3-yl)-1H-imidazol-2-yl)-5-((tetrahydrofuran-3-yl)amino)piperidin-1-yl)ethan-1-one | 650 | Example 27 |
| 483 | 2-(6-methoxy-2-(trifluoromethyl)-1H-benzo[d]imidazol-1-yl)-1-((2S,5S)-2-(5-(2-methoxyquinolin-3-yl)-1H-imidazol-2-yl)-5-((tetrahydrofuran-3-yl)amino)piperidin-1-yl)ethan-1-one | 650 | Example 27 |
| 484 | (S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one | 660 | Example 13 |
| 485 | (S)-3,3,3-trifluoro-2-methoxy-1-((S)-7-(5-(2-methoxyquinolin-3-yl)-1H-imidazol-2-yl)-4-((1-methyl-1H-pyrazol-3-yl)methyl)-1,4-diazepan-1-yl)-2-phenylpropan-1-one | 634 | Example 21 |
| 486 | (R)-3,3,3-trifluoro-2-methoxy-1-((S)-7-(5-(2-methoxyquinolin-3-yl)-1H-imidazol-2-yl)-4-((1-methyl-1H-pyrazol-3-yl)methyl)-1,4-diazepan-1-yl)-2-phenylpropan-1-one | 634 | Example 21 |
| 487 | 2-(6-methoxy-2-methyl-1H-benzo[d]imidazol-1-yl)-1-((2S)-2-(5-(2-methoxyquinolin-3-yl)-1H-imidazol-2-yl)-4-(tetrahydrofuran-3-yl)piperazin-1-yl)ethan-1-one | 582 | Example 13 |

TABLE 1-continued

Synthesized compounds

| Entry | Compound Name | Molecular Ion [M + H]+ | Procedure |
|---|---|---|---|
| 488 | (S)-2-(6-methoxy-2-methyl-1H-benzo[d]imidazol-1-yl)-1-(2-(5-(2-methoxyquinolin-3-yl)-1H-imidazol-2-yl)-4-(tetrahydro-2H-pyran-4-yl)piperazin-1-yl)ethan-1-one | 596 | Example 13 |
| 489 | (S)-2-(6-methoxy-2-methyl-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one | 593 | Example 13 |
| 490 | (S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-1,2,3-triazol-4-yl)methyl)piperazin-1-yl)ethan-1-one | 607 | Example 13 |
| 491 | (S)-2-(6-methoxy-2-methyl-1H-benzo[d]imidazol-1-yl)-1-(2-(5-(2-methoxyquinolin-3-yl)-1H-imidazol-2-yl)-4-(oxetan-3-ylmethyl)piperazin-1-yl)ethan-1-one | 582 | Example 13 |
| 492 | 2-(6-methoxy-2-methyl-1H-indol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 619 | Example 15 |
| 493 | 2-(5-methoxy-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 619 | Example 15 |
| 494 | 2-(5-fluoro-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 607 | Example 15 |
| 495 | 1-(7-(5-(2-methoxyquinolin-3-yl)-1H-imidazol-2-yl)-4-((1-methyl-1H-pyrazol-3-yl)methyl)-1,4-diazepan-1-yl)-2-(2-(trifluoromethyl)-1H-benzo[d]imidazol-1-yl)ethan-1-one | 644 | Example 15 |
| 496 | 1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | 460 | Example 15 |
| 497 | (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | 606 | Example 20C |
| 498 | 1-(4-((1-ethyl-1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 688 | Example 21 |
| 499 | 1-(4-((1,5-dimethyl-1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 688 | Example 21 |
| 500 | 1-(4-((1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 660 | Example 21 |
| 501 | 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-4-yl)methyl)-1,4-diazepan-1-yl)ethan-1-one | 674 | Example 21 |
| 502 | 2-(6-methoxy-2-(trifluoromethyl)-1H-benzo[d]imidazol-1-yl)-1-(7-(5-(2-methoxyquinolin-3-yl)-1H-imidazol-2-yl)-4-((2-methylthiazol-5-yl)methyl)-1,4-diazepan-1-yl)ethan-1-one | 691 | Example 21 |
| 503 | 2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydrofuran-3-yl)-1,4-diazepan-1-yl)ethan-1-one | 650 | Example 21 |
| 504 | 1-(4-isopropyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 622 | Example 21 |
| 505 | 1-(4-cyclobutyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 634 | Example 21 |
| 506 | 1-(4-cyclopentyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | 648 | Example 21 |
| 507 | 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-1,2,3-triazol-4-yl)methyl)-1,4-diazepan-1-yl)ethan-1-one | 675 | Example 21 |
| 508 | (S)-2-(6-methoxy-2-methyl-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one | 604 | Example 13 |
| 509 | 1-((2S)-4-((1-acetylpyrrolidin-3-yl)methyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | 691 | Example 13 |
| 510 | (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(1-methylpiperidin-4-yl)piperazin-1-yl)ethan-1-one | 663 | Example 13 |
| 511 | 2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydro-2H-pyran-4-yl)-1,4-diazepan-1-yl)ethan-1-one | 664 | Example 21 |

TABLE 1-continued

Synthesized compounds

| Entry | Compound Name | Molecular Ion [M + H]+ | Procedure |
|---|---|---|---|
| 512 | 1-benzyl 4-(tert-butyl) 2-(5-(naphthalen-2-yl)-1H-imidazol-2-yl)piperazine-1,4-dicarboxylate | 513 | Example 1 |
| 513 | tert-butyl 2-(5-(naphthalen-2-yl)-1H-imidazol-2-yl)piperidine-1-carboxylate | 378 | Example 17 |
| 514 | 2-(5-(naphthalen-2-yl)-1H-imidazol-2-yl)piperidine | 278 | Example 17 |
| 515 | benzyl 2-(5-(naphthalen-2-yl)-1H-imidazol-2-yl)piperazine-1-carboxylate | 413 | Example 1 |
| 516 | tert-butyl 2-(5-(naphthalen-2-yl)-1H-imidazol-2-yl)pyrrolidine-1-carboxylate | 363 | Example 17 |
| 517 | 2-(5-fluoro-2-methyl-1H-indol-3-yl)-1-(2-(5-(2-hydroxyquinolin-3-yl)-1H-imidazol-2-yl)-4-((tetrahydrofuran-3-yl)methyl)piperazin-1-yl)ethan-1-one | 569 | Example 6 |

B. Biology
Growth Inhibition Assay
*Trypanosoma brucei* Cultivation

Bloodstream form of *Trypanosoma brucei*, strain Lister 427 (provided by Prof. Miguel Navarro, Instituto de Parasitologia y Biomedicina "Lopez-Neyra" Avda. Conocimiento S/N Parque Tecnologico Ciencias de la Salud—Spain; ref. Navarro M. and Cross G. A. M. *Molecular and Cellular Biology*, 1996, Vol. 16, No. 7, pp. 3615-3625) were grown in IMDM Iscove's Modified Dulbecco's Medium (SIGMA #17633) supplemented with: 3.024 g/l sodium bicarbonate, hypoxanthine 1 mM, thymidine 0.16 mM, bathocuprione sulfonic acid 0.05 mM, cysteine 1.5 mM, ß-mercaptoethanol 14 1/l and 10% foetal bovine serum (heat-inactivated at 56° C. for 30 min). Parasites were grown at 37° C. in flasks with vented caps in a 5% $CO_2$ incubator to a maximum cell density of about $2\times10^6$/ml and diluted every two-three days.

*Trypanosoma brucei* Growth Assay

The compounds of the invention were dissolved in DMSO and transferred to assay plates by acoustic droplet ejection (ATS-100, EDC Biosystems, USA) in order to obtain an appropriate concentration and to keep the concentration of DMSO below or equal to 0.25% in the final assay volume of 30 µL. 1500 parasites resuspended in 30 µL of culture medium were then transferred to each well of a 384-well plate.

After an incubation period of 24 hours at 37° C., each well is added 15 µl of CellTiter-Glo® Reagent (Promega) and incubated at room temperature. 5-10 min post incubation, the plate is read using a luminometer (ViewLux®). A known inhibitor of the growth of *T. brucei* was used as the reference positive control.

HeLa and HUVEC Cytotoxicity Assays

HeLa cells (ATCC® CCL2™) in DMEM (Dulbecco Modified Eagle's Medium) without phenol red, Thermo, 11880, USA)+10% FBS+1x PenStrep+1x Gln or HUVEC cells (ATCC® CRL1730™) in EBM-2 (Endothelial Growth Basal Medium, Lonza, CC3156)+EGM-2 SingleQuotsTM-Supplements and Growth Factors (Lonza, CC4176)+1x Penicyllin-Streptomycin (PenStrep, ThermoFisher)+1x Glutamine, are plated in a 384 well plate (Thermo, 4334-11, USA) to a density of 2000 cells per well and let recover for four hours at 37° C., 5% $CO_2$ in a humidified atmosphere. After the recovery, compounds are transferred to assay plates as per compound preparation method. Assay plates are then incubated at 37° C., 5% $CO_2$ in a humidified atmosphere for 72 hours. Cell viability is measured by the CellTiter Glo (Promega, G8080, USA) as per manufacturer instruction.

C. Pharmacology
Rat PK Studies

C57BL/6 mice were used to evaluate plasma exposure and pharmacokinetic parameters after intravenous, oral and intraperitoneal administration (5, 10, 30 mpk). In each animal an indwelling cannula was implanted in the right jugular vein for blood sampling. The surgery was performed under light anaesthesia (Ketamine-Xilazine (85 mg/kg and 2.5 mg/kg respectively i.m.) one day prior the experiment). During the kinetic study, all animals were housed individually in plastic metabolism cages, and were unrestrained throughout the experiment. Compounds (6 mg/mL) were dissolved in PEG400/$H_2O$ (50/50). After an overnight fast, the mice (15 animals per experiment) received an i.v. (via caudal vein) or an oral dose of the compound. Blood samples were collected at different times point after dosing. Plasma was separated immediately after blood sampling by centrifugation, and the plasma samples were kept frozen (−20° C.) until assayed by LC/MS/MS.

Analytical procedures: Plasma samples were extracted using Liquid Handling Robot MultiProbe Packard by protein precipitation with acetonitrile. Then the samples were centrifuged (3000 rpm×15 min at 4° C.) and the supernatant transferred and dried under nitrogen. The samples were reconstituted in water/acetonitrile 90/10 and then injected directly into an HPLC column. Sample analyses were performed using a an API 3000 or/and API 2000 or/and API 4000 Mass Spectrometer interfaced via the Turbo Ion Spray (ESI)/APCI to an LC system consisting of an HTS PAL CTC autosampler and an Agilen HP 1100 Binary Pump. The results are calculated using Analyst Software linear regression with 1/x*x weighting. The Assay Precision was calculated for the Quality Controls by Watson Lims database.

Pharmacokinetic Analysis: The plasma clearance (CLp) of the compounds were calculated (using Watson PK program) as the dose divided by the area under the plasma concentration-time curve from time zero to infinity (AUC0-∞). The apparent half-life was estimated from the slope of the terminal phase of the log plasma concentration-time data. The volume of distribution (Vdss) was determined using the following noncompartmental method:

$$Vdss=(Dose\ IV\times AUMC)/(AUC_{0-\infty})2$$

where AUMC is the total area under the first moment of the drug concentration time curve from time zero to infinity. Bioavailability was estimated as the $AUC_{0-\infty}$ ratio following oral and intravenous administration, normalized for differences in dose.

Results

All the compounds of the invention inhibited proliferation of *T. brucei* in erythrocytes following treatment at 25 μM. Most of compounds had an estimated $EC_{50}$ (amount of drug that inhibits population growth 50%) between 0.001 μM and 5.0 μM. Top compounds showed $EC_{50}$<0.1 μM. Results are reported in the following Table 2.

TABLE 2

Activity of compounds

| Compound Name | T. Brucei GI $EC_{50}$[a] |
|---|---|
| methyl 4-(4-(2-(5-methoxy-2-methyl-1H-indol-3-yl)acetyl)-3-(5-(naphthalen-2-yl)-1H-imidazol-2-yl)piperazin-1-yl)butanoate | B |
| 4-(4-(2-(5-methoxy-2-methyl-1H-indol-3-yl)acetyl)-3-(5-(naphthalen-2-yl)-1H-imidazol-2-yl)piperazin-1-yl)butanoic acid | D |
| 4-(4-(2-(5-methoxy-2-methyl-1H-indol-3-yl)acetyl)-3-(5-(naphthalen-2-yl)-1H-imidazol-2-yl)piperazin-1-yl)butanamide | B |
| 4-(4-(2-(5-methoxy-2-methyl-1H-indol-3-yl)acetyl)-3-(5-(naphthalen-2-yl)-1H-imidazol-2-yl)piperazin-1-yl)-N-methylbutanamide | B |
| 6-(4-(2-(5-methoxy-2-methyl-1H-indol-3-yl)acetyl)-3-(5-(naphthalen-2-yl)-1H-imidazol-2-yl)piperazin-1-yl)hexan-3-one | A |
| 6-(4-(1-methylpiperidine-4-carbonyl)-3-(5-(naphthalen-2-yl)-1H-imidazol-2-yl)piperazin-1-yl)hexan-3-one | D |
| 6-(3-(5-(naphthalen-2-yl)-1H-imidazol-2-yl)-4-(thiazole-5-carbonyl)piperazin-1-yl)hexan-3-one | D |
| 6-(3-(5-(naphthalen-2-yl)-1H-imidazol-2-yl)-4-(naphthalen-2-ylsulfonyl)piperazin-1-yl)hexan-3-one | D |
| 1-(4-(2-(5-methoxy-2-methyl-1H-indol-3-yl)acetyl)-3-(5-(naphthalen-2-yl)-1H-imidazol-2-yl)piperazin-1-yl)hexane-1,4-dione | B |
| 1-(4-hexyl-2-(5-(naphthalen-2-yl)-1H-imidazol-2-yl)piperazin-1-yl)-2-(5-methoxy-2-methyl-1H-indol-3-yl)ethan-1-one | A |
| 2-(5-methoxy-2-methyl-1H-indol-3-yl)-1-(4-methyl-2-(5-(naphthalen-2-yl)-1H-imidazol-2-yl)piperazin-1-yl)ethan-1-one | A |
| 6-(4-benzoyl-3-(5-(naphthalen-2-yl)-1H-imidazol-2-yl)piperazin-1-yl)hexan-3-one | D |
| 6-(3-(5-(naphthalen-2-yl)-1H-imidazol-2-yl)-4-(2-phenylacetyl)piperazin-1-yl)hexan-3-one | D |
| 6-(4-(2-(1H-indol-3-yl)acetyl)-3-(5-(naphthalen-2-yl)-1H-imidazol-2-yl)piperazin-1-yl)hexan-3-one | B |
| 6-(4-(2-(1H-pyrrolo[2,3-b]pyridin-3-yl)acetyl)-3-(5-(naphthalen-2-yl)-1H-imidazol-2-yl)piperazin-1-yl)hexan-3-one | C |
| 6-(4-(2-(1H-1,2,3-triazol-1-yl)acetyl)-3-(5-(naphthalen-2-yl)-1H-imidazol-2-yl)piperazin-1-yl)hexan-3-one | D |
| 6-(3-(5-(naphthalen-2-yl)-1H-imidazol-2-yl)-4-(phenylsulfonyl)piperazin-1-yl)hexan-3-one | D |
| 2-(5-(naphthalen-2-yl)-1H-imidazol-2-yl)-4-(4-oxohexyl)-N-phenylpiperazine-1-carboxamide | D |
| phenyl 2-(5-(naphthalen-2-yl)-1H-imidazol-2-yl)-4-(4-oxohexyl)piperazine-1-carboxylate | D |
| 6-(4-benzyl-3-(5-(naphthalen-2-yl)-1H-imidazol-2-yl)piperazin-1-yl)hexan-3-one | D |
| 1-(4-(4-hydroxyhexyl)-2-(5-(naphthalen-2-yl)-1H-imidazol-2-yl)piperazin-1-yl)-2-(5-methoxy-2-methyl-1H-indol-3-yl)ethan-1-one | A |
| 6-(4-(2-(5-methoxy-2-methyl-1H-indol-3-yl)acetyl)-3-(5-(naphthalen-2-yl)-1,3,4-oxadiazol-2-yl)piperazin-1-yl)hexan-3-one | B |
| 6-(4-(2-(5-methoxy-2-methyl-1H-indol-3-yl)acetyl)-3-(5-phenyl-1H-imidazol-2-yl)piperazin-1-yl)hexan-3-one | B |
| 6-(4-(2-(5-methoxy-2-methyl-1H-indol-3-yl)acetyl)-3-(5-(naphthalen-2-yl)oxazol-2-yl)piperazin-1-yl)hexan-3-one | D |
| 6-(4-(2-(5-methoxy-2-methyl-1H-indol-3-yl)acetyl)-3-(5-(2-methoxyquinolin-3-yl)-1H-imidazol-2-yl)piperazin-1-yl)hexan-3-one | A |
| 6-(4-(2-(1H-pyrrolo[2,3-b]pyridin-3-yl)acetyl)-3-(5-(2-methoxyquinolin-3-yl)-1H-imidazol-2-yl)piperazin-1-yl)hexan-3-one | C |
| 6-(4-(2-(5-methoxy-2-methyl-1H-indol-3-yl)acetyl)-3-(5-(2-methoxyquinolin-3-yl)oxazol-2-yl)piperazin-1-yl)hexan-3-one | D |
| (R)-6-(4-(2-(1H-indol-3-yl)acetyl)-3-(5-(naphthalen-2-yl)-1H-imidazol-2-yl)piperazin-1-yl)hexan-3-one | D |
| (S)-6-(4-(2-(1H-indol-3-yl)acetyl)-3-(5-(naphthalen-2-yl)-1H-imidazol-2-yl)piperazin-1-yl)hexan-3-one | B |
| 1-(3-(5-(naphthalen-2-yl)-1H-imidazol-2-yl)morpholino)-2-(1H-pyrrolo[2,3-b]pyridin-3-yl)ethan-1-one | D |
| 1-(2-(5-(naphthalen-2-yl)-1H-imidazol-2-yl)piperidin-1-yl)-2-(1H-pyrrolo[2,3-b]pyridin-3-yl)ethan-1-one | D |
| 1-(4-methyl-2-(5-(naphthalen-2-yl)-1H-imidazol-2-yl)piperazin-1-yl)-2-(pyridin-4-yl)ethan-1-one | D |
| 2-(2-fluorophenyl)-1-(4-methyl-2-(5-(naphthalen-2-yl)-1H-imidazol-2-yl)piperazin-1-yl)ethan-1-one | D |
| 1-(4-methyl-2-(5-(naphthalen-2-yl)-1H-imidazol-2-yl)piperazin-1-yl)-3-(phenylsulfonyl)propan-1-one | D |

TABLE 2-continued

Activity of compounds

| Compound Name | T. Brucei GI EC$_{50}$$^a$ |
|---|---|
| (4-methyl-2-(5-(naphthalen-2-yl)-1H-imidazol-2-yl)piperazin-1-yl)(1-phenylcyclopropyl)methanone | D |
| 2-(4-methoxyphenyl)-1-(4-methyl-2-(5-(naphthalen-2-yl)-1H-imidazol-2-yl)piperazin-1-yl)ethan-1-one | D |
| 2-(benzo[d]isoxazol-3-yl)-1-(4-methyl-2-(5-(naphthalen-2-yl)-1H-imidazol-2-yl)piperazin-1-yl)ethan-1-one | D |
| 1-(4-methyl-2-(5-(naphthalen-2-yl)-1H-imidazol-2-yl)piperazin-1-yl)-2-(quinolin-3-yl)ethan-1-one | D |
| (2-methoxyphenyl)(4-methyl-2-(5-(naphthalen-2-yl)-1H-imidazol-2-yl)piperazin-1-yl)methanone | D |
| 2-(2H-indazol-2-yl)-1-(4-methyl-2-(5-(naphthalen-2-yl)-1H-imidazol-2-yl)piperazin-1-yl)ethan-1-one | D |
| 1-(benzylsulfonyl)-4-methyl-2-(5-(naphthalen-2-yl)-1H-imidazol-2-yl)piperazine | D |
| 1-(4-acetyl-2-(5-(2-methoxyquinolin-3-yl)-1H-imidazol-2-yl)piperazin-1-yl)-2-phenylethan-1-one | D |
| 1-(4-methyl-2-(5-(quinolin-6-yl)-1H-imidazol-2-yl)piperazin-1-yl)-2-phenylethan-1-one | D |
| 1-(2-(5-(2-methoxyquinolin-3-yl)-1H-imidazol-2-yl)-4-methylpiperazin-1-yl)-2-phenylethan-1-one | D |
| 1-(4-methyl-2-(5-(naphthalen-2-yl)-1H-imidazol-2-yl)piperazin-1-yl)-2-phenylethan-1-one | D |
| 1-(2-(5-(2-methoxyquinolin-3-yl)-1H-imidazol-2-yl)piperazin-1-yl)-2-phenylethan-1-one | D |
| 1-(2-(5-(2-methoxyquinolin-3-yl)-1H-imidazol-2-yl)-4-(methylsulfonyl)piperazin-1-yl)-2-phenylethan-1-one | D |
| 1-(4-isopropyl-2-(5-(2-methoxyquinolin-3-yl)-1H-imidazol-2-yl)piperazin-1-yl)-2-phenylethan-1-one | D |
| 1-(4-(2,2-difluoroethyl)-2-(5-(2-methoxyquinolin-3-yl)-1H-imidazol-2-yl)piperazin-1-yl)-2-phenylethan-1-one | D |
| (S)-1-(4-methyl-2-(5-(naphthalen-2-yl)-1H-imidazol-2-yl)piperazin-1-yl)-2-phenylethan-1-one | D |
| 1-(4-methyl-2-(5-(naphthalen-2-yl)-1H-imidazol-2-yl)piperazin-1-yl)-2-(1H-pyrrolo[2,3-b]pyridin-3-yl)ethan-1-one | D |
| 2-(5-methoxy-2-methyl-1H-indol-3-yl)-1-(2-(5-(2-methoxyquinolin-3-yl)-1H-imidazol-2-yl)-4-methylpiperazin-1-yl)ethan-1-one | B |
| 1-(2-(5-(2-methoxyquinolin-3-yl)-1H-imidazol-2-yl)-4-methylpiperazin-1-yl)-2-(1H-pyrrolo[2,3-b]pyridin-3-yl)ethan-1-one | D |
| 2-(5-methoxy-2-methyl-1H-indol-3-yl)-1-(4-methyl-2-(5-phenyl-1H-imidazol-2-yl)piperazin-1-yl)ethan-1-one | D |
| 6-(3-(5-(2-methoxyquinolin-3-yl)-1H-imidazol-2-yl)-4-(2-phenylacetyl)piperazin-1-yl)hexan-3-one | D |
| 1-(4-(cyclopropylmethyl)-2-(5-(naphthalen-2-yl)-1H-imidazol-2-yl)piperazin-1-yl)-2-(5-methoxy-2-methyl-1H-indol-3-yl)ethan-1-one | A |
| 2-(5-methoxy-2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | A |
| 1-(4-(cyclopropylmethyl)-2-(5-(naphthalen-2-yl)-1H-imidazol-2-yl)piperazin-1-yl)-2-(4-methylthiazol-2-yl)ethan-1-one | D |
| 1-(4-benzyl-2-(5-(naphthalen-2-yl)-1H-imidazol-2-yl)piperazin-1-yl)-2-(4-methylthiazol-2-yl)ethan-1-one | D |
| 2-(4-methylthiazol-2-yl)-1-(2-(5-(naphthalen-2-yl)-1H-imidazol-2-yl)-4-phenethylpiperazin-1-yl)ethan-1-one | D |
| 2-(benzo[d]oxazol-2-yl)-1-(4-(cyclopropylmethyl)-2-(5-(naphthalen-2-yl)-1H-imidazol-2-yl)piperazin-1-yl)ethan-1-one | D |
| 2-(benzo[d]oxazol-2-yl)-1-(2-(5-(naphthalen-2-yl)-1H-imidazol-2-yl)-4-((tetrahydrofuran-3-yl)methyl)piperazin-1-yl)ethan-1-one | C |
| 5-methoxy-3-(2-(4-methyl-2-(5-(naphthalen-2-yl)-1H-imidazol-2-yl)piperazin-1-yl)-2-oxoethyl)indolin-2-one | D |
| 3-(2-(4-hexyl-2-(5-(naphthalen-2-yl)-1H-imidazol-2-yl)piperazin-1-yl)-2-oxoethyl)-5-methoxyindolin-2-one | D |
| 3-(2-(4-(cyclopropylmethyl)-2-(5-(naphthalen-2-yl)-1H-imidazol-2-yl)piperazin-1-yl)-2-oxoethyl)-5-methoxyindolin-2-one | D |
| 5-methoxy-3-(2-(2-(5-(naphthalen-2-yl)-1H-imidazol-2-yl)-4-((tetrahydrofuran-3-yl)methyl)piperazin-1-yl)-2-oxoethyl)indolin-2-one | D |
| 3-(2-(4-benzyl-2-(5-(naphthalen-2-yl)-1H-imidazol-2-yl)piperazin-1-yl)-2-oxoethyl)-5-methoxyindolin-2-one | C |
| 5-methoxy-3-(2-(2-(5-(naphthalen-2-yl)-1H-imidazol-2-yl)-4-phenethylpiperazin-1-yl)-2-oxoethyl)indolin-2-one | C |
| 1-(4-hexyl-2-(5-(naphthalen-2-yl)-1H-imidazol-2-yl)piperazin-1-yl)-2-(1H-pyrrolo[3,2-b]pyridin-3-yl)ethan-1-one | D |
| 2-(1-methyl-1H-indol-3-yl)-1-(4-methyl-2-(5-(naphthalen-2-yl)-1H-imidazol-2-yl)piperazin-1-yl)ethan-1-one | D |
| 1-(4-hexyl-2-(5-(naphthalen-2-yl)-1H-imidazol-2-yl)piperazin-1-yl)-2-(1-methyl-1H-indol-3-yl)ethan-1-one | D |
| 1-(4-(cyclopropylmethyl)-2-(5-(naphthalen-2-yl)-1H-imidazol-2-yl)piperazin-1-yl)-2-(1-methyl-1H-indol-3-yl)ethan-1-one | D |

TABLE 2-continued

Activity of compounds

| Compound Name | T. Brucei GI EC$_{50}$$^a$ |
|---|---|
| 2-(1-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | B |
| 1-(4-benzyl-2-(5-(naphthalen-2-yl)-1H-imidazol-2-yl)piperazin-1-yl)-2-(1-methyl-1H-indol-3-yl)ethan-1-one | D |
| 1-(4-hexyl-2-(5-(naphthalen-2-yl)-1H-imidazol-2-yl)piperazin-1-yl)-2-(5-hydroxy-1H-indol-3-yl)ethan-1-one | D |
| 1-(4-(cyclopropylmethyl)-2-(5-(naphthalen-2-yl)-1H-imidazol-2-yl)piperazin-1-yl)-2-(5-hydroxy-1H-indol-3-yl)ethan-1-one | D |
| 2-(5-hydroxy-1H-indol-3-yl)-1-(2-(5-(naphthalen-2-yl)-1H-imidazol-2-yl)-4-((tetrahydrofuran-3-yl)methyl)piperazin-1-yl)ethan-1-one | C |
| 1-(4-benzyl-2-(5-(naphthalen-2-yl)-1H-imidazol-2-yl)piperazin-1-yl)-2-(5-hydroxy-1H-indol-3-yl)ethan-1-one | D |
| 2-(5-hydroxy-1H-indol-3-yl)-1-(2-(5-(naphmalen-2-yl)-1H-imidazol-2-yl)-4-phenethylpiperazin-1-yl)ethan-1-one | D |
| 1-(4-hexyl-2-(5-(naphthalen-2-yl)-1H-imidazol-2-yl)piperazin-1-yl)-2-(2-methyl-1H-indol-3-yl)ethan-1-one | C |
| 1-(4-(cyclopropylmethyl)-2-(5-(naphthalen-2-yl)-1H-imidazol-2-yl)piperazin-1-yl)-2-(2-methyl-1H-indol-3-yl)ethan-1-one | B |
| 2-(2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | A |
| 1-(4-benzyl-2-(5-(naphthalen-2-yl)-1H-imidazol-2-yl)piperazin-1-yl)-2-(2-methyl-1H-indol-3-yl)ethan-1-one | D |
| 2-(2-methyl-1H-indol-3-yl)-1-(2-(5-(naphthalen-2-yl)-1H-imidazol-2-yl)-4-phenethylpiperazin-1-yl)ethan-1-one | C |
| 1-(4-hexyl-2-(5-(naphthalen-2-yl)-1H-imidazol-2-yl)piperazin-1-yl)-2-(1H-indazol-3-yl)ethan-1-one | D |
| 1-(4-(cyclopropylmethyl)-2-(5-(naphthalen-2-yl)-1H-imidazol-2-yl)piperazin-1-yl)-2-(1H-indazol-3-yl)ethan-1-one | D |
| 2-(1H-indazol-3-yl)-1-(2-(5-(naphthalen-2-yl)-1H-imidazol-2-yl)-4-((tetrahydrofuran-3-yl)methyl)piperazin-1-yl)ethan-1-one | D |
| 1-(4-benzyl-2-(5-(naphthalen-2-yl)-1H-imidazol-2-yl)piperazin-1-yl)-2-(1H-indazol-3-yl)ethan-1-one | D |
| 2-(1H-indazol-3-yl)-1-(2-(5-(naphthalen-2-yl)-1H-imidazol-2-yl)-4-phenethylpiperazin-1-yl)ethan-1-one | D |
| (S)-3,3,3-trifluoro-2-methoxy-1-((R)-4-methyl-2-(5-(naphthalen-2-yl)-1H-imidazol-2-yl)piperazin-1-yl)-2-phenylpropan-1-one | D |
| (R)-3,3,3-trifluoro-2-methoxy-1-((R)-4-methyl-2-(5-(naphthalen-2-yl)-1H-imidazol-2-yl)piperazin-1-yl)-2-phenylpropan-1-one | D |
| (3S)-5-methoxy-3-(2-(4-methyl-2-(5-(naphthalen-2-yl)-1H-imidazol-2-yl)piperazin-1-yl)-2-oxoethyl)indolin-2-one | D |
| 4-(2-(5-methoxy-2-methyl-1H-indol-3-yl)acetyl)-1-methyl-5-(5-(naphthalen-2-yl)-1H-imidazol-2-yl)piperazin-2-one | C |
| 2-(5-methoxy-2-methyl-1H-indol-3-yl)-1-(4-methyl-2-(5-(naphthalen-2-yl)-1H-imidazol-2-yl)-1,4-diazepan-1-yl)ethan-1-one | D |
| 2-(5-methoxy-2-methyl-1H-indol-3-yl)-1-(4-methyl-2-(1-methyl-5-(naphthalen-2-yl)-1H-imidazol-2-yl)piperazin-1-yl)ethan-1-one | D |
| 2-(5-methoxy-2-methyl-1H-indol-3-yl)-1-(4-methyl-7-(5-(naphthalen-2-yl)-1H-imidazol-2-yl)-1,4-diazepan-1-yl)ethan-1-one | B |
| 1-(4-hexyl-2-(5-(2-methoxyquinolin-3-yl)-1H-imidazol-2-yl)piperazin-1-yl)-2-(2-methyl-3a,7a-dihydro-1H-indol-3-yl)ethan-1-one | B |
| 1-(4-(cyclopropylmethyl)-2-(5-(2-methoxyquinolin-3-yl)-1H-imidazol-2-yl)piperazin-1-yl)-2-(2-methyl-3a,7a-dihydro-1H-indol-3-yl)ethan-1-one | B |
| 1-(4-benzyl-2-(5-(2-methoxyquinolin-3-yl)-1H-imidazol-2-yl)piperazin-1-yl)-2-(2-methyl-3a,7a-dihydro-1H-indol-3-yl)ethan-1-one | B |
| 1-(4-hexyl-2-(5-(2-hydroxyquinolin-3-yl)-1H-imidazol-2-yl)piperazin-1-yl)-2-(2-methyl-3a,7a-dihydro-1H-indol-3-yl)ethan-1-one | D |
| (5-(benzyloxy)-1H-indol-2-yl)(2-(5-(2-methoxyquinolin-3-yl)-1H-imidazol-2-yl)-4-((tetrahydrofuran-3-yl)methyl)piperazin-1-yl)methanone | D |
| 1-(2-(5-(2-methoxyquinolin-3-yl)-1H-imidazol-2-yl)-4-((tetrahydrofuran-3-yl)methyl)piperazin-1-yl)-2-(phenylsulfonyl)ethan-1-one | D |
| 2-(6-methoxybenzofuran-3-yl)-1-(2-(5-(2-methoxyquinolin-3-yl)-1H-imidazol-2-yl)-4-((tetrahydrofuran-3-yl)methyl)piperazin-1-yl)ethan-1-one | C |
| 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | A |
| 1-(2-(5-(2-methoxyquinolin-3-yl)-1H-imidazol-2-yl)-4-((tetrahydrofuran-3-yl)methyl)piperazin-1-yl)-2-(3-methylbenzo[b]thiophen-2-yl)ethan-1-one | B |
| 2-(5-methoxy-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | B |
| (2-hydroxy-6-methoxyquinolin-4-yl)(2-(5-(2-methoxyquinolin-3-yl)-1H-imidazol-2-yl)-4-((tetrahydrofuran-3-yl)methyl)piperazin-1-yl)methanone | D |
| 2-(benzo[d]isoxazol-3-yl)-1-(2-(5-(2-methoxyquinolin-3-yl)-1H-imidazol-2-yl)-4-((tetrahydrofuran-3-yl)methyl)piperazin-1-yl)ethan-1-one | C |
| 1-(2-(5-(2-methoxyquinolin-3-yl)-1H-imidazol-2-yl)-4-((tetrahydrofuran-3-yl)methyl)piperazin-1-yl)-2-(2-methyl-1H-benzo[d]imidazol-1-yl)ethan-1-one | B |

TABLE 2-continued

Activity of compounds

| Compound Name | T. Brucei GI EC$_{50}$$^a$ |
|---|---|
| (1-benzyl-5-methyl-1H-pyrazol-3-yl)(2-(5-(2-methoxyquinolin-3-yl)-1H-imidazol-2-yl)-4-((tetrahydrofuran-3-yl)methyl)piperazin-1-yl)methanone | D |
| 3-(3-(2-(5-(2-methoxyquinolin-3-yl)-1H-imidazol-2-yl)-4-((tetrahydrofuran-3-yl)methyl)piperazin-1-yl)-3-oxopropyl)-4,5,6,7-tetrahydro-1H-indazol-2-ium | D |
| 1-(4-(2-(2-(5-(2-methoxyquinolin-3-yl)-1H-imidazol-2-yl)-4-((tetrahydrofuran-3-yl)methyl)piperazin-1-yl)-2-oxoethyl)phenyl)imidazolidin-2-one | D |
| (2-(5-(2-methoxyquinolin-3-yl)-1H-imidazol-2-yl)-4-((tetrahydrofuran-3-yl)methyl)piperazin-1-yl)(5-(tetrahydrofuran-2-yl)thiophen-2-yl)methanone | D |
| (5-(4-methoxyphenyl)furan-2-yl)(2-(5-(2-methoxyquinolin-3-yl)-1H-imidazol-2-yl)-4-((tetrahydrofuran-3-yl)methyl)piperazin-1-yl)methanone | D |
| 6-(2-(2-(5-(2-methoxyquinolin-3-yl)-1H-imidazol-2-yl)-4-((tetrahydrofuran-3-yl)methyl)piperazin-1-yl)-2-oxoethyl)-7H-imidazo[2,1-b]thiazol-4-ium | D |
| 5-methoxy-3-(2-(2-(5-(2-methoxyquinolin-3-yl)-1H-imidazol-2-yl)-4-((tetrahydrofuran-3-yl)methyl)piperazin-1-yl)-2-oxoethyl)indolin-2-one | D |
| 1-(2-(2-(5-(2-methoxyquinolin-3-yl)-1H-imidazol-2-yl)-4-((tetrahydrofuran-3-yl)methyl)piperazin-1-yl)-2-oxoethyl)-1H-indole-5-carbonitrile | C |
| 3-(3-methoxyphenyl)-1-(2-(5-(2-methoxyquinolin-3-yl)-1H-imidazol-2-yl)-4-((tetrahydrofuran-3-yl)methyl)piperazin-1-yl)propan-1-one | D |
| 2-(5-methoxy-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | A |
| 1-(2-(5-(2-methoxyquinolin-3-yl)-1H-imidazol-2-yl)-4-((tetrahydrofuran-3-yl)methyl)piperazin-1-yl)-2-(2-methyl-1H-indol-3-yl)ethan-1-one | B |
| tert-butyl 4-(2-(5-methoxy-2-methyl-1H-indol-3-yl)acetyl)-3-(5-(2-methoxyquinolin-3-yl)-1H-imidazol-2-yl)piperazine-1-carboxylate | B |
| 2-(5-methoxy-2-methyl-1H-indol-3-yl)-1-(2-(5-(2-methoxyquinolin-3-yl)-1H-imidazol-2-yl)piperazin-1-yl)ethan-1-one | C |
| 1-(4-(cyclopropylmethyl)-2-(5-(2-methoxyquinolin-3-yl)-1H-imidazol-2-yl)piperazin-1-yl)-2-(5-fluoro-2-methyl-1H-indol-3-yl)ethan-1-one | B |
| 1-(4-(cyclopentylmethyl)-2-(5-(2-methoxyquinolin-3-yl)-1H-imidazol-2-yl)piperazin-1-yl)-2-(5-fluoro-2-methyl-1H-indol-3-yl)ethan-1-one | B |
| 2-(5-fluoro-2-methyl-1H-indol-3-yl)-1-(2-(5-(2-methoxyquinolin-3-yl)-1H-imidazol-2-yl)-4-(thiazol-2-ylmethyl)piperazin-1-yl)ethan-1-one | A |
| 2-(5-fluoro-2-methyl-1H-indol-3-yl)-1-(4-(furan-3-ylmethyl)-2-(5-(2-methoxyquinolin-3-yl)-1H-imidazol-2-yl)piperazin-1-yl)ethan-1-one | B |
| 2-(5-fluoro-2-methyl-1H-indol-3-yl)-1-(4-isobutyl-2-(5-(2-methoxyquinolin-3-yl)-1H-imidazol-2-yl)piperazin-1-yl)ethan-1-one | B |
| 1-(4-benzyl-2-(5-(2-methoxyquinolin-3-yl)-1H-imidazol-2-yl)piperazin-1-yl)-2-(5-fluoro-2-methyl-1H-indol-3-yl)ethan-1-one | B |
| 2-(5-fluoro-2-methyl-1H-indol-3-yl)-1-(2-(5-(2-methoxyquinolin-3-yl)-1H-imidazol-2-yl)-4-(1-methylpiperidin-4-yl)piperazin-1-yl)ethan-1-one | C |
| 2-(5-fluoro-2-methyl-1H-indol-3-yl)-1-(2-(5-(2-methoxyquinolin-3-yl)-1H-imidazol-2-yl)-4-(pyridin-3-ylmethyl)piperazin-1-yl)ethan-1-one | B |
| 1-(4-cyclobutyl-2-(5-(2-methoxyquinolin-3-yl)-1H-imidazol-2-yl)piperazin-1-yl)-2-(5-fluoro-2-methyl-1H-indol-3-yl)ethan-1-one | B |
| 2-(5-fluoro-2-methyl-1H-indol-3-yl)-1-(2-(5-(2-methoxyquinolin-3-yl)-1H-imidazol-2-yl)-4-((1-methyl-1H-pyrazol-4-yl)methyl)piperazin-1-yl)ethan-1-one | B |
| 2-(5-fluoro-2-methyl-1H-indol-3-yl)-1-(2-(5-(2-methoxyquinolin-3-yl)-1H-imidazol-2-yl)-4-(tetrahydro-2H-pyran-4-yl)piperazin-1-yl)ethan-1-one | B |
| 2-(5-fluoro-2-methyl-1H-indol-3-yl)-1-(2-(5-(2-methoxyquinolin-3-yl)-1H-imidazol-2-yl)-4-methylpiperazin-1-yl)ethan-1-one | B |
| 2-(5-fluoro-2-methyl-1H-indol-3-yl)-1-(2-(5-(2-methoxyquinolin-3-yl)-1H-imidazol-2-yl)piperazin-1-yl)ethan-1-one | D |
| 1-(2-(5-(4-(1H-pyrazol-1-yl)phenyl)-1H-imidazol-2-yl)-4-((tetrahydrofuran-3-yl)methyl)piperazin-1-yl)-2-(5-fluoro-2-methyl-1H-indol-3-yl)ethan-1-one | D |
| 2-(5-fluoro-2-methyl-1H-indol-3-yl)-1-(2-(5-(2-methoxyquinolin-3-yl)-1H-imidazol-2-yl)-4-(tetrahydrofuran-3-carbonyl)piperazin-1-yl)ethan-1-one | D |
| 2-(5-fluoro-2-methyl-1H-indol-3-yl)-1-(2-(5-(2-methoxyquinolin-3-yl)-1H-imidazol-2-yl)-4-(1-methylpiperidine-4-carbonyl)piperazin-1-yl)ethan-1-one | D |
| 2-(5-fluoro-2-methyl-1H-indol-3-yl)-1-(4-(isopropylsulfonyl)-2-(5-(2-methoxyquinolin-3-yl)-1H-imidazol-2-yl)piperazin-1-yl)ethan-1-one | D |
| 4-(2-(5-fluoro-2-methyl-1H-indol-3-yl)acetyl)-3-(5-(2-methoxyquinolin-3-yl)-1H-imidazol-2-yl)-N,N-dimethylpiperazine-1-sulfonamide | D |
| 2-(5-fluoro-2-methyl-1H-indol-3-yl)-1-(3-(5-(naphthalen-2-yl)-1H-imidazol-2-yl)-1,1-dioxidothiomorpholino)ethan-1-one | B |
| 2-(5-fluoro-2-methyl-1H-indol-3-yl)-1-(4-(1-isopropyl-1H-pyrazole-4-carbonyl)-2-(5-(2-methoxyquinolin-3-yl)-1H-imidazol-2-yl)piperazin-1-yl)ethan-1-one | D |
| 2-(1H-benzo[d][1,2,3]triazol-1-yl)-1-(2-(5-(2-methoxyquinolin-3-yl)-1H-imidazol-2-yl)-4-((tetrahydrofuran-3-yl)methyl)piperazin-1-yl)ethan-1-one | C |
| (2-(5-(2-methoxyquinolin-3-yl)-1H-imidazol-2-yl)-4-((tetrahydrofuran-3-yl)methyl)piperazin-1-yl)(4-methyl-2-(pyrazin-2-yl)thiazol-5-yl)methanone | D |
| (2-(5-(2-methoxyquinolin-3-yl)-1H-imidazol-2-yl)-4-((tetrahydrofuran-3-yl)methyl)piperazin-1-yl)(5-methyl-3-phenylisoxazol-4-yl)methanone | D |
| 2-(2-(5-(2-methoxyquinolin-3-yl)-1H-imidazol-2-yl)-4-((tetrahydrofuran-3-yl)methyl)piperazin-1-yl)-2-oxoethyl)isoindoline-1,3-dione | C |

TABLE 2-continued

Activity of compounds

| Compound Name | T. Brucei GI EC$_{50}$$^a$ |
|---|---|
| 2-(2-(2-(5-(2-methoxyquinolin-3-yl)-1H-imidazol-2-yl)-4-((tetrahydrofuran-3-yl)methyl)piperazin-1-yl)-2-oxoethyl)-4-methylphthalazin-1(2H)-one | C |
| 1-(2-(5-(2-methoxyquinolin-3-yl)-1H-imidazol-2-yl)-4-((tetrahydrofuran-3-yl)methyl)piperazin-1-yl)-2-(4-(3-methylpyrazin-2-yl)phenyl)ethan-1-one | D |
| 1-(2-(2-(5-(2-methoxyquinolin-3-yl)-1H-imidazol-2-yl)-4-((tetrahydrofuran-3-yl)methyl)piperazin-1-yl)-2-oxoethyl)quinazolin-2(1H)-one | D |
| isoquinolin-1-yl(2-(5-(2-methoxyquinolin-3-yl)-1H-imidazol-2-yl)-4-((tetrahydrofuran-3-yl)methyl)piperazin-1-yl)methanone | D |
| (2-(5-(2-methoxyquinolin-3-yl)-1H-imidazol-2-yl)-4-((tetrahydrofuran-3-yl)methyl)piperazin-1-yl)(quinolin-6-yl)methanone | D |
| (2-(5-(2-methoxyquinolin-3-yl)-1H-imidazol-2-yl)-4-((tetrahydrofuran-3-yl)methyl)piperazin-1-yl)(quinolin-3-yl)methanone | D |
| 1-(2-(5-(2-methoxyquinolin-3-yl)-1H-imidazol-2-yl)-4-((tetrahydrofuran-3-yl)methyl)piperazin-1-yl)-2-(1H-pyrrolo[3,2-c]pyridin-3-yl)ethan-1-one | D |
| 2-(imidazo[1,2-a]pyridin-3-yl)-1-(2-(5-(2-methoxyquinolin-3-yl)-1H-imidazol-2-yl)-4-((tetrahydrofuran-3-yl)methyl)piperazin-1-yl)ethan-1-one | D |
| 1-(2-(5-(2-methoxyquinolin-3-yl)-1H-imidazol-2-yl)-4-((tetrahydrofuran-3-yl)methyl)piperazin-1-yl)-2-(2-phenyl-1H-imidazol-1-yl)ethan-1-one | D |
| 2-(2H-benzo[d][1,2,3]triazol-2-yl)-1-(2-(5-(2-methoxyquinolin-3-yl)-1H-imidazol-2-yl)-4-((tetrahydrofuran-3-yl)methyl)piperazin-1-yl)ethan-1-one | D |
| 1-(2-(5-(2-methoxyquinolin-3-yl)-1H-imidazol-2-yl)-4-((tetrahydrofuran-3-yl)methyl)piperazin-1-yl)-2-(5-methyl-2-phenyloxazol-4-yl)ethan-1-one | D |
| (2-(5-(2-methoxyquinolin-3-yl)-1H-imidazol-2-yl)-4-((tetrahydrofuran-3-yl)methyl)piperazin-1-yl)(quinolin-4-yl)methanone | D |
| benzyl 4-(2-(5-fluoro-2-methyl-1H-indol-3-yl)acetyl)-3-(5-(2-methoxyquinolin-3-yl)-1H-imidazol-2-yl)piperazine-1-carboxylate | D |
| benzyl 3-(5-(2-methoxyquinolin-3-yl)-1H-imidazol-2-yl)-4-(2-(2-methyl-1H-benzo[d]imidazol-1-yl)acetyl)piperazine-1-carboxylate | D |
| 2-(5-fluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | B |
| 2-(6-fluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | B |
| 2-(5,6-difluoro-2-methyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | B |
| 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one | A |
| 2-(2-cyclopropyl-1H-benzo[d]imidazol-1-yl)-1-(2-(5-(2-methoxyquinolin-3-yl)-1H-imidazol-2-yl)-4-((tetrahydrofuran-3-yl)methyl)piperazin-1-yl)ethan-1-one | B |
| 1-(2-(5-(2-methoxyquinolin-3-yl)-1H-imidazol-2-yl)piperazin-1-yl)-2-(2-methyl-1H-benzo[d]imidazol-1-yl)ethan-1-one | D |
| 2-(5-fluoro-2-methyl-1H-indol-3-yl)-1-(4-((2-methoxypyrimidin-5-yl)methyl)-2-(5-(2-methoxyquinolin-3-yl)-1H-imidazol-2-yl)piperazin-1-yl)ethan-1-one | B |
| 2-(5-fluoro-2-methyl-1H-indol-3-yl)-1-(2-(5-(2-methoxyquinolin-3-yl)-1H-imidazol-2-yl)-4-(pyrazin-2-ylmethyl)piperazin-1-yl)ethan-1-one | A |
| 4-((4-(2-(5-fluoro-2-methyl-1H-indol-3-yl)acetyl)-3-(5-(2-methoxyquinolin-3-yl)-1H-imidazol-2-yl)piperazin-1-yl)methyl)pyridine 1-oxide | D |
| 2-(5-fluoro-2-methyl-1H-indol-3-yl)-1-(2-(5-(2-methoxyquinolin-3-yl)-1H-imidazol-2-yl)-4-((1-methyl-1H-1,2,3-triazol-4-yl)methyl)piperazin-1-yl)ethan-1-one | B |
| 2-(5-fluoro-2-methyl-1H-indol-3-yl)-1-(2-(5-(2-methoxyquinolin-3-yl)-1H-imidazol-2-yl)-4-(oxazol-4-ylmethyl)piperazin-1-yl)ethan-1-one | B |
| 1-(4-(1,1-dioxidotetrahydro-2H-thiopyran-4-yl)-2-(5-(2-methoxyquinolin-3-yl)-1H-imidazol-2-yl)piperazin-1-yl)-2-(5-fluoro-2-methyl-1H-indol-3-yl)ethan-1-one | B |
| 2-(5-fluoro-2-methyl-1H-indol-3-yl)-1-(3-(5-(2-methoxyquinolin-3-yl)-1H-imidazol-2-yl)-1,1-dioxidothiomorpholino)ethan-1-one | B |
| 1-(3-(5-(2-methoxyquinolin-3-yl)-1H-imidazol-2-yl)-1,1-dioxidothiomorpholino)-2-(2-methyl-1H-benzo[d]imidazol-1-yl)ethan-1-one | D |
| 2-(2-(3-(5-(2-methoxyquinolin-3-yl)-1H-imidazol-2-yl)-1,1-dioxidothiomorpholino)-2-oxoethyl)-4-methylphthalazin-1(2H)-one | D |
| 2-(5-fluoro-2-methyl-1H-indol-3-yl)-1-(3-(5-(2-methoxyquinolin-3-yl)-1H-imidazol-2-yl)morpholino)ethan-1-one | C |
| 1-(3-(5-(2-methoxyquinolin-3-yl)-1H-imidazol-2-yl)morpholino)-2-(2-methyl-1H-benzo[d]imidazol-1-yl)ethan-1-one | D |
| 2-(1H-benzo[d][1,2,3]triazol-1-yl)-1-(3-(5-(2-methoxyquinolin-3-yl)-1H-imidazol-2-yl)morpholino)ethan-1-one | D |
| 2-(2-(3-(5-(2-methoxyquinolin-3-yl)-1H-imidazol-2-yl)morpholino)-2-oxoethyl)-4-methylphthalazin-1(2H)-one | D |
| 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one | A |
| 1-((S)-2-(5-(2-methoxyquinolin-3-yl)-1H-imidazol-2-yl)-4-(((S)-tetrahydrofuran-3-yl)methyl)piperazin-1-yl)-2-(2-(trifluoromethyl)-1H-benzo[d]imidazol-1-yl)ethan-1-one | A |

TABLE 2-continued

Activity of compounds

| Compound Name | T. Brucei GI EC$_{50}$$^a$ |
|---|---|
| 1-((S)-2-(5-(2-methoxyquinolin-3-yl)-1H-imidazol-2-yl)-4-(((R)-tetrahydrofuran-3-yl)methyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-((1-methyl-1H-pyrazol-4-yl)methyl)piperazin-1-yl)-2-(2-(trifluoromethyl)-1H-benzo[d]imidazol-1-yl)ethan-1-one | B |
| (S)-1-(2-(5-(2-methoxyquinolin-3-yl)-1H-imidazol-2-yl)-4-((1-methyl-1H-pyrazol-3-yl)methyl)piperazin-1-yl)-2-(2-(trifluoromethyl)-1H-benzo[d]imidazol-1-yl)ethan-1-one | A |
| (S)-1-(4-(isoxazol-3-ylmethyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(thiazol-4-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(thiazol-2-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(pyridin-3-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(pyridin-2-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(oxetan-3-yl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(tetrahydro-2H-pyran-4-yl)piperazin-1-yl)-2-(2-(trifluoromethyl)-1H-benzo[d]imidazol-1-yl)ethan-1-one | A |
| (S)-1-(4-benzyl-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(4-(1-acetylpiperidin-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(4-(4,4-difluorocyclohexyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-((5-methyl-1,2,4-oxadiazol-3-yl)methyl)piperazin-1-yl)-2-(2-(trifluoromethyl)-1H-benzo[d]imidazol-1-yl)ethan-1-one | A |
| (S)-1-(4-(2-fluorobenzyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | B |
| (S)-1-(2-(5-(2-methoxyquinolin-3-yl)-1H-imidazol-2-yl)-4-(oxazol-2-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(oxazol-4-ylmethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(2,2,2-trifluoroethyl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(pyrimidin-5-ylmethyl)piperazin-1-yl)-2-(2-(trifluoromethyl)-1H-benzo[d]imidazol-1-yl)ethan-1-one | A |
| (S)-1-(4-((5-fluoropyridin-3-yl)methyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(oxetan-3-ylmethyl)piperazin-1-yl)-2-(2-(trifluoromethyl)-1H-benzo[d]imidazol-1-yl)ethan-1-one | A |
| (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one | A |
| (S)-1-(2-(5-(2-methoxyquinolin-3-yl)-1H-imidazol-2-yl)-4-(pyrazin-2-ylmethyl)piperazin-1-yl)-2-(2-(trifluoromethyl)-1H-benzo[d]imidazol-1-yl)ethan-1-one | A |
| 2-(5-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |
| 2-(6-methoxy-2-methyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |
| 2-(5,6-dimethoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |
| 2-(6-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |
| 2-(2-(tert-butyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |

TABLE 2-continued

Activity of compounds

| Compound Name | T. Brucei GI EC$_{50}$$^a$ |
|---|---|
| 2-(2-cyclobutyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | B |
| 1-((2S)-2-(5-(2-methoxyquinolin-3-yl)-1H-imidazol-2-yl)-4-((tetrahydrofuran-3-yl)methyl)piperazin-1-yl)-2-(2-(2,2,2-trifluoroethyl)-1H-benzo[d]imidazol-1-yl)ethan-1-one | B |
| 1-((2S)-2-(5-(2-methoxyquinolin-3-yl)-1H-imidazol-2-yl)-4-((tetrahydrofuran-3-yl)methyl)piperazin-1-yl)-2-(2-methyl-5-(trifluoromethyl)-1H-benzo[d]imidazol-1-yl)ethan-1-one | B |
| 1-((2S)-2-(5-(2-methoxyquinolin-3-yl)-1H-imidazol-2-yl)-4-((tetrahydrofuran-3-yl)methyl)piperazin-1-yl)-2-(2-methyl-6-(trifluoromethyl)-1H-benzo[d]imidazol-1-yl)ethan-1-one | A |
| 1-((2S)-2-(5-(2-methoxyquinolin-3-yl)-1H-imidazol-2-yl)-4-((tetrahydrofuran-3-yl)methyl)piperazin-1-yl)-2-methyl-2-(2-(trifluoromethyl)-1H-benzo[d]imidazol-1-yl)propan-1-one | D |
| 2-(6-methoxy-2-methyl-1H-indol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one | A |
| 1-((2S)-2-(5-(2-methoxyquinolin-3-yl)-1H-imidazol-2-yl)-4-((tetrahydrofuran-3-yl)methyl)piperazin-1-yl)-2-(2-methyl-4-(trifluoromethyl)-1H-imidazol-1-yl)ethan-1-one | D |
| 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-imidazo[4,5-b]pyridin-1-yl)ethan-1-one | D |
| 2-(5-methoxybenzo[d]isoxazol-3-yl)-1-((2S)-2-(5-(2-methoxyquinolin-3-yl)-1H-imidazol-2-yl)-4-((tetrahydrofuran-3-yl)methyl)piperazin-1-yl)ethan-1-one | B |
| 1-(2-((2S)-2-(5-(2-methoxyquinolin-3-yl)-1H-imidazol-2-yl)-4-((tetrahydrofuran-3-yl)methyl)piperazin-1-yl)-2-oxoethyl)-1H-benzo[d]imidazole-2-carboxamide | C |
| 2-(5-fluorobenzo[d]isoxazol-3-yl)-1-((2S)-2-(5-(2-methoxyquinolin-3-yl)-1H-imidazol-2-yl)-4-((tetrahydrofuran-3-yl)methyl)piperazin-1-yl)ethan-1-one | D |
| benzyl 3-(5-(2-methoxyquinolin-3-yl)-1H-imidazol-2-yl)morpholine-4-carboxylate | D |
| 2-(6-methoxy-2-methyl-1H-benzo[d]imidazol-1-yl)-1-(3-(5-(2-methoxyquinolin-3-yl)-1H-imidazol-2-yl)morpholino)ethan-1-one | D |
| 2-(6-methoxy-2-(trifluoromethyl)-1H-benzo[d]imidazol-1-yl)-1-(3-(5-(2-methoxyquinolin-3-yl)-1H-imidazol-2-yl)morpholino)ethan-1-one | B |
| 2-(6-methoxy-2-methyl-1H-indol-1-yl)-1-(3-(5-(2-methoxyquinolin-3-yl)-1H-imidazol-2-yl)morpholino)ethan-1-one | C |
| 2-(6-methoxy-2-methyl-1H-benzo[d]imidazol-1-yl)-1-(3-(5-(2-methoxyquinolin-3-yl)-1H-imidazol-2-yl)-1,1-dioxidothiomorpholino)ethan-1-one | D |
| (S)-1-(4-(1-acetylpiperidin-4-yl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | C |
| (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | C |
| 2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one | B |
| 2-(6-methoxy-2-methyl-1H-indol-1-yl)-1-(3-(5-(2-methoxyquinolin-3-yl)-1H-imidazol-2-yl)-1,1-dioxidothiomorpholino)ethan-1-one | C |
| 2-(6-methoxy-2-methyl-1H-indol-1-yl)-1-(7-(5-(2-methoxyquinolin-3-yl)-1H-imidazol-2-yl)-4-methyl-1,4-diazepan-1-yl)ethan-1-one | C |
| 2-(6-methoxy-2-methyl-1H-benzo[d]imidazol-1-yl)-1-(7-(5-(2-methoxyquinolin-3-yl)-1H-imidazol-2-yl)-4-methyl-1,4-diazepan-1-yl)ethan-1-one | D |
| 2-(6-methoxy-2-(trifluoromethyl)-1H-benzo[d]imidazol-1-yl)-1-(7-(5-(2-methoxyquinolin-3-yl)-1H-imidazol-2-yl)-4-methyl-1,4-diazepan-1-yl)ethan-1-one | C |
| 1-((2S)-2-(5-(2-methoxyquinolin-3-yl)-1H-imidazol-2-yl)-4-((tetrahydrofuran-3-yl)methyl)piperazin-1-yl)-2-(8-methyl-9H-purin-9-yl)ethan-1-one | B |
| 1-((2S)-2-(5-(2-methoxyquinolin-3-yl)-1H-imidazol-2-yl)-4-((tetrahydrofuran-3-yl)methyl)piperazin-1-yl)-2-(8-methyl-7H-purin-7-yl)ethan-1-one | D |
| 2-(6-methoxy-2-(trifluoromethyl)-1H-benzo[d]imidazol-1-yl)-1-(2-(5-(2-methoxyquinolin-3-yl)-1H-imidazol-2-yl)piperidin-1-yl)ethan-1-one | A |
| 2-(6-methoxy-2-methyl-1H-indol-1-yl)-1-(2-(5-(2-methoxyquinolin-3-yl)-1H-imidazol-2-yl)piperidin-1-yl)ethan-1-one | B |
| 2-(6-methoxy-2-methyl-1H-benzo[d]imidazol-1-yl)-1-(2-(5-(2-methoxyquinolin-3-yl)-1H-imidazol-2-yl)piperidin-1-yl)ethan-1-one | B |
| 1-(2-(2-(5-(2-methoxyquinolin-3-yl)-1H-imidazol-2-yl)-4-((tetrahydrofuran-3-yl)methyl)piperazin-1-yl)-2-oxoethyl)-1H-benzo[d]imidazole-2-carbonitrile | D |
| (S)-2-(6-methoxy-2-methyl-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one | A |
| 1-((2S)-2-(5-(2-methoxyquinolin-3-yl)-1H-imidazol-2-yl)-4-((tetrahydrofuran-3-yl)methyl)piperazin-1-yl)-2-(2-(methylsulfonyl)-1H-benzo[d]imidazol-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one | A |

TABLE 2-continued

Activity of compounds

| Compound Name | T. Brucei GI EC$_{50}$$^a$ |
|---|---|
| 2-(6-methoxy-2-(trifluoromethyl)-1H-benzo[d]imidazol-1-yl)-1-(7-(5-(2-methoxyquinolin-3-yl)-1H-imidazol-2-yl)-4-((tetrahydrofuran-3-yl)methyl)-1,4-diazepan-1-yl)ethan-1-one | A |
| 1-((2S)-2-(5-(2-methoxyquinolin-3-yl)-1H-imidazol-2-yl)-4-((tetrahydrofuran-3-yl)methyl)piperazin-1-yl)-2-(2-methyl-6-(methylsulfonyl)-1H-benzo[d]imidazol-1-yl)ethan-1-one | B |
| 2-(6-methoxy-2-methyl-1H-benzo[d]imidazol-1-yl)-1-(2-(5-(2-methoxy-6-phenylpyridin-3-yl)-1H-imidazol-2-yl)-4-(((S)-tetrahydrofuran-3-yl)methyl)piperazin-1-yl)ethan-1-one | D |
| 2-(6-methoxy-2-methyl-1H-benzo[d]imidazol-1-yl)-1-(2-(5-(2-methoxy-6-phenylpyridin-3-yl)-1H-imidazol-2-yl)-4-(((R)-tetrahydrofuran-3-yl)methyl)piperazin-1-yl)ethan-1-one | B |
| 2-(6-methoxy-2-methyl-1H-benzo[d]imidazol-1-yl)-1-(7-(5-(2-methoxyquinolin-3-yl)-1H-imidazol-2-yl)-4-(oxetan-3-ylmethyl)-1,4-diazepan-1-yl)ethan-1-one | C |
| 2-(6-methoxy-2-methyl-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one | B |
| 2-(6-methoxy-2-methyl-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one | A |
| (S)-2-(6-methoxy-2-methyl-1H-benzo[d]imidazol-1-yl)-1-(2-(5-(2-methoxyquinolin-3-yl)-1H-imidazol-2-yl)-4-((5-methyl-1,3,4-oxadiazol-2-yl)methyl)piperazin-1-yl)ethan-1-one | B |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(oxetan-3-ylmethyl)-1,4-diazepan-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(pyridin-2-yl)ethyl)-1,4-diazepan-1-yl)ethan-1-one | B |
| 2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one | A |
| 1-(4-(2-(1H-pyrazol-1-yl)ethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-4H-1,2,4-triazol-3-yl)-4-(thiazol-2-ylmethyl)piperazin-1-yl)ethan-1-one | A |
| (S)-2-(6-methoxy-2-methyl-1H-benzo[d]imidazol-1-yl)-1-(2-(5-(2-methoxyquinolin-3-yl)-1H-imidazol-2-yl)-4-((4-methyl-4H-1,2,4-triazol-3-yl)methyl)piperazin-1-yl)ethan-1-one | C |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(pyridin-2-ylmethyl)-1,4-diazepan-1-yl)ethan-1-one | A |
| (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(pyridin-2-yl)ethyl)piperazin-1-yl)ethan-1-one | A |
| (S)-1-(4-(2-(4H-1,2,4-triazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | D |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(2-methylthiazol-4-yl)ethyl)piperazin-1-yl)ethan-1-one | A |
| 2-(6-methoxy-2-(trifluoromethyl)-1H-benzo[d]imidazol-1-yl)-1-((2S)-2-(5-(2-methoxyquinolin-3-yl)-1,2,4-oxadiazol-3-yl)-4-((tetrahydrofuran-3-yl)methyl)piperazin-1-yl)ethan-1-one | D |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(1-methyl-1H-pyrazol-5-yl)ethyl)-1,4-diazepan-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(2-(2-methylthiazol-4-yl)ethyl)-1,4-diazepan-1-yl)ethan-1-one | B |
| 1-((2S)-2-(5-(benzo[d]thiazol-6-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | D |
| tert-butyl 2-(2-((2S)-1-(2-(6-methoxy-2-methyl-1H-benzo[d]imidazol-1-yl)acetyl)-4-((tetrahydrofuran-3-yl)methyl)piperazin-2-yl)-1H-imidazol-5-yl)-1H-indole-1-carboxylate | D |

TABLE 2-continued

Activity of compounds

| Compound Name | T. Brucei GI EC$_{50}$$^a$ |
|---|---|
| 1-((2S)-2-(5-(1H-indol-2-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | D |
| 2-(6-methoxy-2-methyl-1H-benzo[d]imidazol-1-yl)-1-((2S)-2-(5-(pyridin-2-ylethynyl)-1H-imidazol-2-yl)-4-((tetrahydrofuran-3-yl)methyl)piperazin-1-yl)ethan-1-one | D |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one | A |
| (S)-1-(4-(2-(isoxazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | A |
| 1-((2S,4S)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one | A |
| 1-((2S,4S)-4-amino-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | D |
| 2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(thiazol-2-ylmethyl)amino)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((thiazol-2-ylmethyl)amino)piperidin-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-((5-methyl-1,2,4-oxadiazol-3-yl)methyl)-1,4-diazepan-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-4-ylmethyl)-1,4-diazepan-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-4-ylmethyl)-1,4-diazepan-1-yl)ethan-1-one | A |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-2-ylmethyl)-1,4-diazepan-1-yl)ethan-1-one | A |
| 1-(4-(isoxazol-3-ylmethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((tetrahydrofuran-3-yl)amino)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(tetrahydrofuran-3-yl)amino)piperidin-1-yl)ethan-1-one | A |
| 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-((tetrahydrofuran-3-yl)amino)piperidin-1-yl)ethan-1-one | B |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-4-ylmethyl)piperazin-1-yl)ethan-1-one | A |
| 1-((2S,4R)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | C |
| 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-((thiazol-2-ylmethyl)amino)piperidin-1-yl)ethan-1-one | B |
| (R)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | D |
| (S)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyrazin-2-ylmethyl)amino)piperidin-1-yl)ethan-1-one | A |

TABLE 2-continued

Activity of compounds

| Compound Name | T. Brucei GI EC$_{50}$$^a$ |
|---|---|
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-pyrazol-3-yl)methyl)amino)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one | A |
| (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | A |
| 1-(4-(1,1-dioxidotetrahydro-2H-thiopyran-4-yl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | A |
| 1-((2S,4S)-4-((isoxazol-3-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(memyl((tetrahydrofuran-3-yl)methyl)amino)piperidin-1-yl)ethan-1-one | A |
| 1-((2S,4S)-4-((2-(1H-pyrazol-1-yl)ethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 1-((2S)-2-(5-(isoquinolin-3-yl)-1H-imidazol-2-yl)-4-((tetrahydrofuran-3-yl)methyl)piperazin-1-yl)-2-(6-methoxy-2-methyl-1H-benzo[d]imidazol-1-yl)ethan-1-one | B |
| 2-(6-methoxy-2-methyl-1H-benzo[d]imidazol-1-yl)-1-((2S)-2-(5-(quinolin-6-yl)-1H-imidazol-2-yl)-4-((tetrahydrofuran-3-yl)methyl)piperazin-1-yl)ethan-1-one | D |
| 2-(6-methoxy-2-methyl-1H-benzo[d]imidazol-1-yl)-1-((2S)-2-(5-(quinolin-3-yl)-1H-imidazol-2-yl)-4-((tetrahydrofuran-3-yl)methyl)piperazin-1-yl)ethan-1-one | C |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(oxetan-3-ylamino)piperidin-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-1,2,4-triazol-5-yl)methyl)piperazin-1-yl)ethan-1-one | B |
| 1-((2S,4S)-4-(isopropylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyridazin-4-ylmethyl)piperazin-1-yl)ethan-1-one | A |
| 1-((2S,4S)-4-(isobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 1-((2S,4S)-4-(cyclobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| (R)-2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 1-((2S,4S)-4-(isopropyl((1-methyl-1H-pyrazol-3-yl)methyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((S)-tetrahydrofuran-3-yl)amino)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((R)-tetrahydrofuran-3-yl)amino)piperidin-1-yl)ethan-1-one | A |
| 1-((2S,4S)-4-((2-hydroxyethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyridin-2-ylmethyl)amino)piperidin-1-yl)ethan-1-one | A |
| 2-(6-methoxy-2-(trifluoromethyl)-1H-benzo[d]imidazol-1-yl)-1-((2S)-2-(5-(2-methoxyquinolin-3-yl)-1H-imidazol-2-yl)-4-(methyl(pyrazin-2-ylmethyl)amino)piperidin-1-yl)ethan-1-one | A |
| 2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((1-methyl-1H-pyrazol-3-yl)methyl)amino)piperidin-1-yl)ethan-1-one | A |
| 1-((2S,4S)-4-methoxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 1-((2S,4S)-4-methoxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one | A |

TABLE 2-continued

Activity of compounds

| Compound Name | T. Brucei GI $EC_{50}{}^a$ |
|---|---|
| 1-((2S)-4-hydroxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 1-((2S)-4-hydroxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one | C |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-imidazol-5-yl)methyl)amino)piperidin-1-yl)ethan-1-one | A |
| 1-((2S,4S)-4-(ethyl(tetrahydrofuran-3-yl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one | A |
| 2-(6-methoxy-2-(trifluoromethyl)-1H-benzo[d]imidazol-1-yl)-1-((2S,4S)-4-((3-methoxycyclobutyl)amino)-2-(5-(2-methoxyquinolin-3-yl)-1H-imidazol-2-yl)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((oxetan-3-ylmethyl)amino)piperidin-1-yl)ethan-1-one | A |
| 2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(pyrrolidin-1-yl)piperidin-1-yl)ethan-1-one | A |
| 2-(6-methoxy-2-methyl-1H-benzo[d]imidazol-1-yl)-1-((2S)-2-(5-(2-methoxy-6-phenylpyridin-3-yl)-1H-imidazol-2-yl)-4-((tetrahydrofuran-3-yl)methyl)piperazin-1-yl)ethan-1-one | C |
| 2-(6-methoxy-2-methyl-1H-benzo[d]imidazol-1-yl)-1-((2S)-2-(5-(quinolin-2-yl)-1H-imidazol-2-yl)-4-((tetrahydrofuran-3-yl)methyl)piperazin-1-yl)ethan-1-one | D |
| 2-(6-methoxy-2-methyl-1H-benzo[d]imidazol-1-yl)-1-((2S)-2-(5-((E)-styryl)-1H-imidazol-2-yl)-4-((tetrahydrofuran-3-yl)methyl)piperazin-1-yl)ethan-1-one | D |
| 1-((2S,4S)-4-((isoxazol-4-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one | A |
| 2-(6-methoxy-2-methyl-1H-benzo[d]imidazol-1-yl)-1-((2S,4S)-2-(5-(2-methoxyquinolin-3-yl)-1H-imidazol-2-yl)-4-(methyl(pyrazin-2-ylmethyl)amino)piperidin-1-yl)ethan-1-one | B |
| 2-(6-methoxy-2-methyl-1H-benzo[d]imidazol-1-yl)-1-((2S,4S)-2-(5-(2-methoxyquinolin-3-yl)-1H-imidazol-2-yl)-4-(((1-methyl-1 H-pyrazol-3-yl)methyl)amino)piperidin-1-yl)ethan-1-one | D |
| 2-(6-methoxy-2-methyl-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one | D |
| (R)-2-(6-methoxy-2-(trifluoromethyl)-1H-benzo[d]imidazol-1-yl)-1-(3-(5-(2-methoxyquinolin-3-yl)-1H-imidazol-2-yl)-1,1-dioxidothiomorpholino)ethan-1-one | B |
| 2-(6-methoxy-2-methyl-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one | B |
| 2-(6-methoxy-2-(trifluoromethyl)-1H-benzo[d]imidazol-1-yl)-1-((2S,5R)-2-(5-(2-methoxyquinolin-3-yl)-1H-imidazol-2-yl)-5-((tetrahydrofuran-3-yl)amino)piperidin-1-yl)ethan-1-one | A |
| 2-(6-methoxy-2-(trifluoromethyl)-1H-benzo[d]imidazol-1-yl)-1-((2S,5S)-2-(5-(2-methoxyquinolin-3-yl)-1H-imidazol-2-yl)-5-((tetrahydrofuran-3-yl)amino)piperidin-1-yl)ethan-1-one | C |
| (S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one | A |
| (S)-3,3,3-trifluoro-2-methoxy-1-((S)-7-(5-(2-methoxyquinolin-3-yl)-1H-imidazol-2-yl)-4-((1-methyl-1H-pyrazol-3-yl)methyl)-1,4-diazepan-1-yl)-2-phenylpropan-1-one | D |
| (R)-3,3,3-trifluoro-2-methoxy-1-((S)-7-(5-(2-methoxyquinolin-3-yl)-1H-imidazol-2-yl)-4-((1-methyl-1H-pyrazol-3-yl)methyl)-1,4-diazepan-1-yl)-2-phenylpropan-1-one | D |
| 2-(6-methoxy-2-methyl-1H-benzo[d]imidazol-1-yl)-1-((2S)-2-(5-(2-methoxyquinolin-3-yl)-1H-imidazol-2-yl)-4-(tetrahydrofuran-3-yl)piperazin-1-yl)ethan-1-one | B |
| (S)-2-(6-methoxy-2-methyl-1H-benzo[d]imidazol-1-yl)-1-(2-(5-(2-methoxyquinolin-3-yl)-1H-imidazol-2-yl)-4-(tetrahydro-2H-pyran-4-yl)piperazin-1-yl)ethan-1-one | B |
| (S)-2-(6-methoxy-2-methyl-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one | A |
| (S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-1,2,3-triazol-4-yl)methyl)piperazin-1-yl)ethan-1-one | C |
| (S)-2-(6-methoxy-2-methyl-1H-benzo[d]imidazol-1-yl)-1-(2-(5-(2-methoxyquinolin-3-yl)-1H-imidazol-2-yl)-4-(oxetan-3-ylmethyl)piperazin-1-yl)ethan-1-one | A |
| 2-(6-methoxy-2-methyl-1H-indol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |

TABLE 2-continued

Activity of compounds

| Compound Name | T. Brucei GI EC$_{50}$$^a$ |
|---|---|
| 2-(5-methoxy-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 2-(5-fluoro-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one | A |
| 1-(7-(5-(2-methoxyquinolin-3-yl)-1H-imidazol-2-yl)-4-((1-methyl-1H-pyrazol-3-yl)methyl)-1,4-diazepan-1-yl)-2-(2-(trifluoromethyl)-1H-benzo[d]imidazol-1-yl)ethan-1-one | A |
| (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-methyl-1H-benzo[d]imidazol-1-yl)ethan-1-one | B |
| 1-(4-((1-ethyl-1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | C |
| 1-(4-((1,5-dimethyl-1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | B |
| 1-(4-((1H-pyrazol-4-yl)methyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-4-yl)methyl)-1,4-diazepan-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-((2-methylthiazol-5-yl)methyl)-1,4-diazepan-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydrofuran-3-yl)-1,4-diazepan-1-yl)ethan-1-one | A |
| 1-(4-isopropyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | B |
| 1-(4-cyclobutyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | A |
| 1-(4-cyclopentyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-1,2,3-triazol-4-yl)methyl)-1,4-diazepan-1-yl)ethan-1-one | B |
| (S)-2-(6-methoxy-2-methyl-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one | A |
| 1-((2S)-4-((1-acetylpyrrolidin-3-yl)methyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one | A |
| (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(1-methylpiperidin-4-yl)piperazin-1-yl)ethan-1-one | B |
| 2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydro-2H-pyran-4-yl)-1,4-diazepan-1-yl)ethan-1-one | A |

$^a$T. Brucei Growth Inhibition Assay; EC$_{50}$ values are expressed as: A: <0.10 µM; B: 0.10 µM-0.50 µM; C: 0.51 µM-1.00 µM; D: 1.01 µM-5.00 µM The data reported in Table 2 demonstrate that compounds of the invention are potent *Trypanosoma brucei* growth inhibitors.

Several compounds of the invention were tested for their cytotoxicity properties in human cervical cancer cells (Hela) and in normal endothelial cells. The majority of the compounds showed no or only minor cytotoxicity at the highest concentration tested (25 µM). Results are summarized in the following Table 3.

TABLE 3

Comparison between growth inhibiting activity and cytotoxicity of selected compounds

| Compound Name | T. brucei GI EC$_{50}$ (nM) | Cell Proliferation Hela IC$_{50}$ (nM) | Cell Proliferation HUVEC IC$_{50}$ (nM) |
|---|---|---|---|
| 6-(4-(2-(5-methoxy-2-methyl-1H-indol-3-yl)acetyl)-3-(5-(naphthalen-2-yl)-1H-imidazol-2-yl)piperazin-1-yl)hexan-3-one | 9.9207 | 12267 | 25000 |
| 1-(4-hexyl-2-(5-(naphthalen-2-yl)-1H-imidazol-2-yl)piperazin-1-yl)-2-(5-methoxy-2-methyl-1H-indol-3-yl)ethan-1-one | 78.681 | 25000 | 25000 |
| 2-(5-methoxy-2-methyl-1H-indol-3-yl)-1-(4-methyl-2-(5-(naphthalen-2-yl)-1H-imidazol-2-yl)piperazin-1-yl)ethan-1-one | 39.893 | 25000 | 21812 |
| 6-(4-(2-(1H-indol-3-yl)acetyl)-3-(5-(naphthalen-2-yl)-1H-imidazol-2-yl)piperazin-1-yl)hexan-3-one | 489.48 | 25000 | 9974.8 |
| 6-(4-(2-(1H-pyrrolo[2,3-b]pyridin-3-yl)acetyl)-3-(5-(naphthalen-2-yl)-1H-imidazol-2-yl)piperazin-1-yl)hexan-3-one | 545.33 | 25000 | 25000 |
| 1-(4-(4-hydroxyhexyl)-2-(5-(naphthalen-2-yl)-1H-imidazol-2-yl)piperazin-1-yl)-2-(5-methoxy-2-methyl-1H-indol-3-yl)ethan-1-one | 12.956 | 13053 | 9267.1 |
| 6-(4-(2-(5-methoxy-2-methyl-1H-indol-3-yl)acetyl)-3-(5-(naphthalen-2-yl)-1,3,4-oxadiazol-2-yl)piperazin-1-yl)hexan-3-one | 350.3 | 25000 | 25000 |
| 6-(4-(2-(5-methoxy-2-methyl-1H-indol-3-yl)acetyl)-3-(5-(2-methoxyquinolin-3-yl)-1H-imidazol-2-yl)piperazin-1-yl)hexan-3-one | 34.225 | 25000 | 21423 |
| 2-(5-methoxy-2-methyl-1H-indol-3-yl)-1-(2-(5-(2-methoxyquinolin-3-yl)-1H-imidazol-2-yl)-4-methylpiperazin-1-yl)ethan-1-one | 139.04 | 25000 | 25000 |
| 1-(4-(cyclopropylmethyl)-2-(5-(naphthalen-2-yl)-1H-imidazol-2-yl)piperazin-1-yl)-2-(5-methoxy-2-methyl-1H-indol-3-yl)ethan-1-one | 17.607 | 25000 | 8063 |
| 2-(5-methoxy-2-methyl-1H-indol-3-yl)-1-(2-(5-(naphthalen-2-yl)-1H-imidazol-2-yl)-4-((tetrahydrofuran-3-yl)methyl)piperazin-1-yl)ethan-1-one | 4.7246 | 25000 | 18666 |
| 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | 35.144 | 18662 | 9625.9 |
| 1-(2-(5-(2-methoxyquinolin-3-yl)-1H-imidazol-2-yl)-4-((tetrahydrofuran-3-yl)methyl)piperazin-1-yl)-2-(2-methyl-1H-benzo[d]imidazol-1-yl)ethan-1-one | 162.85 | 20556 | 25000 |
| 2-(5-methoxy-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one | 22.919 | 25000 | 23202 |
| 2-(5-fluoro-2-methyl-1H-indol-3-yl)-1-(2-(5-(2-methoxyquinolin-3-yl)-1H-imidazol-2-yl)-4-(thiazol-2-ylmethyl)piperazin-1-yl)ethan-1-one | 60.585 | 25000 | 8197.9 |
| 2-(5-fluoro-2-methyl-1H-indol-3-yl)-1-(2-(5-(2-methoxyquinolin-3-yl)-1H-imidazol-2-yl)-4-((1-methyl-1H-pyrazol-4-yl)methyl)piperazin-1-yl)ethan-1-one | 172.26 | 17393 | 6721.8 |
| 2-(5-fluoro-2-methyl-1H-indol-3-yl)-1-(2-(5-(2-methoxyquinolin-3-yl)-1H-imidazol-2-yl)-4-(tetrahydro-2H-pyran-4-yl)piperazin-1-yl)ethan-1-one | 116.89 | 25000 | 10555 |
| 2-(5-fluoro-2-methyl-1H-indol-3-yl)-1-(2-(5-(2-methoxyquinolin-3-yl)-1H-imidazol-2-yl)-4-methylpiperazin-1-yl)ethan-1-one | 122.05 | 18062 | 5680.7 |

TABLE 3-continued

Comparison between growth inhibiting activity and cytotoxicity of selected compounds

| Compound Name | T. brucei GI EC$_{50}$ (nM) | Cell Proliferation Hela IC$_{50}$ (nM) | Cell Proliferation HUVEC IC$_{50}$ (nM) |
|---|---|---|---|
| 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one | 29.925 | 21453 | 14075 |

In addition, the pharmacokinetic profiles of the representative compound were evaluated.

Table 4 summarized the profile of one representative compound of the invention, 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one.

TABLE 4

Summary pharmacokinetic profile for one representative compound

| Structure | 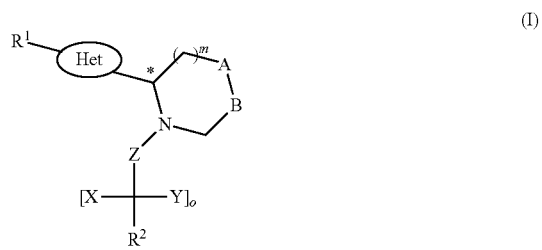 |
|---|---|
| T. brucei Growth inhibition EC$_{50}$ (nM) | 30 |
| T. brucei Growth inhibition EC$_{90}$ (nM) | 287 |
| Clearance (ml/min/kg) | 44.7 |
| AUC (μM/h) | 4.6 |
| Oral Bio-availability F % | 78 |
| i.p. max brain concentration (nM) | 190 |

As shown in Table 4, the compound achieved good oral bioavailability (78%) in mouse (10 mpk, po), after a single oral dose, and moderate clearance. Further, after intraperitoneal injection (30 mpk), the concentration in brain was 190 nM. The blood brain barrier permeability is a very important feature of the compound as the *trypanosoma* parasites enter the central nervous system (CNS), giving rise to the classic symptoms of HAT, eventually leading to coma and death.

It is demonstrated by the data reported herein that the compounds of the present invention are potent Kinetoplastida (or Kinetoplastea) inhibitors, in particular *Trypanosoma brucei* inhibitors, with EC$_{50}$ in the low micromolar to low nanomolar range. Worthy of specific note is the fact that the measured activity of the compounds is invariably several orders of magnitude higher than the cytotoxicity measured in Hela and Huvec cells. Then compounds of the invention present a high safety profile for human or veterinary use.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:
1. A compound of general formula (I):

$$\text{(I)}$$

wherein:
* indicates a stereogenic center;
A is absent, or is N—(CH$_2$)$_p$R$^3$, O, S, SO$_2$, CH—N(R$^4$)(CH$_2$)$_p$R$^5$ or CH—OR$^6$;
B is absent, or is (CH$_2$)$_n$ or CO;
Z is absent, or is CO, SO$_2$, CONR$^a$ or COO;
X and Y are each independently selected from H, C$_{1-6}$alkyl, halo-C$_{1-6}$alkyl, C$_{1-6}$alkoxy or X and Y are linked together forming a ring selected from cyclopropyl, cyclobutyl, cyclopentyl or cyclohexyl;
m and n are selected from 1 or 2, with the proviso that at least one of m and n must be equal to 1;
o and p are independently 0, 1 or 2;
Het is a 5 membered heterocycle selected from 1H-imidazole, 4H-1,2,4-triazole, 1,3,4-oxadiazole, 1,2,4-oxadiazole or oxazole;
R$^1$ is a substituent selected from naphthalen-2-yl, 2-methoxyquinolin-3-yl, pyrimidin-5-yl, 1-methyl-1H-pyrazol-4-yl, 1-methyl-1H-indazol-5-yl, oxazol-4-yl, quinoxalin-6-yl, 1H-pyrazol-1-yl, quinolin-6-yl, isoquinolin-7-yl, quinolin-5-yl, 2-methoxy-6-phenylpyridin-3-yl, 4-(1H-pyrazol-1-yl)phenyl, 1H-pyrrolo[2,3-b]pyridin-5-yl, 3H-imidazo[4,5-b]pyridin-6-yl, benzo[d]thiazol-6-yl, 1H-indol-2-yl, 1H-pyrrolo[2,3-b]pyridin-3-yl, 1-benzyl-1H-pyrazol-4-yl, 2-cyclopropylpyrimidin-5-yl, pyridin-2-ylethynyl, 2-methoxy-5-phenylpyridin-3-yl, isoquinolin-3-yl, quinolin-3-yl, 1H-benzo[d]imidazol-5-yl, 2-methoxypyridin-3-yl, 6-(1H-pyrazol-1-yl)pyridin-3-yl, 4-pyridin-2-yl-phenyl, 4-pyridin-3-yl-phenyl, 4-pyridin-4-yl-phenyl, quinolin-2-yl, pyrazin-2-yl-ethynyl, pyridin-4-yl-ethynyl, pyridazin-3-yl-ethynyl, 5-methylpyridin-2-yl, styryl; any of which being optionally further substituted with one or more groups independently chosen from cyano, halogen, hydroxy, $C_{1-6}$ alkyl, $C_{3-10}$ cycloalkyl, $C_{1-6}$ alkoxy, halo$C_{1-6}$ alkoxy, $N(R^a)_2$, $C_{1-6}$ alkyl-$N(R^a)_2$, $SO_2N(R^a)_2$;

each $R^a$ is independently selected from hydrogen, $C_{1-6}$ alkyl, $C_{6-10}$aryl, or $N(R^a)_2$ is a cyclic amine selected from pyrrolidine, pyperidine, pyperazine, N-methyl-piperazine, morpholine, thiomorpholine, azetidine;

$R^2$ is selected from H, $C_{6-10}$ aryl, $C_{6-10}$ aryl-$SO_2$, $C_{3-15}$ heterocyclyl, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, 8-13 membered unsaturated or partially saturated heterocycle containing heteroatoms independently selected from O, N and S wherein each of said ring is optionally substituted by one or more groups independently chosen from $C_{1-6}$ alkyl, $C_{1-6}$ alkoxy, halogen, cyano, hydroxyl, halo-$C_{1-6}$ alkyl, $CONH_2$, $SO_2C_{1-6}$ alkyl, $C_{3-10}$ cycloalkyl, benzyl, tetrahydrofuranyl, 2-oxoimid-azolidinyl, phenyl or 6 membered unsaturated heterocycle containing 1, 2 or 3 nitrogen atoms wherein said phenyl and 6 membered unsaturated heterocycle are optionally substituted with one or more methyl or methoxy groups;

$R^3$ is selected from H, $C_{1-6}$alkyl, $C_{1-6}$alkylsulphonyl, N,N-dimethylsulphamoyl, 4-oxo-hexanoyl, 4-oxo-hexyl, 4-hydroxyhexyl, 4-methoxy-4-oxobutyl, 4-amino-4-oxobutyl, 4-methyl-amino4oxobutyl, 3-carboxypropyl, oxetan-3-yl, tetrahydrofuran-3-yl, tetrahydro-2H-pyran-4-yl, tetrahydro-2H-thiopyran-4-yl, 1,1-dioxidotetrahydro-2H-pyran-4-yl, piperidin-4-yl, $C_{3-10}$ cyclo-alkyl, phenyl, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, tetrahydrofuran-3-carbonyl, piperidine-4-carbonyl, 1H-pyrazole-4-carbonyl, any of which substituent being optionally substituted with one or more groups selected from halogen, $C_{1-6}$alkyl, $C_{1-6}$alkoxy;

$R^4$ is H or $C_{1-6}$alkyl;

$R^5$ is selected from H, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, oxetan-3-yl, tetrahydrofuran-3-yl, tetrahydro-2H-pyran-4-yl, $C_{3-10}$ cycloalkyl, any of said rings being optionally substituted with one or more substituent selected from halogen, hydroxyl, $C_{1-6}$ alkyl, $C_{1-6}$ alkoxy;

or $R^4$ and $R^5$ are linked together forming a cyclic amine ring selected from aziridine, azetidine, pyrrolidine, piperidine, morpholine, thiomorpholine or piperazine;

$R^6$ is selected from linear or branched $C_{1-6}$ alkyl, $C_{3-10}$ cycloalkyl, phenyl-C-3 alkyl, heteroaryl-$C_{1-3}$ alkyl;

and pharmaceutically acceptable salts, tautomers, stereoisomers thereof.

2. The compound according to claim 1 having general formula (II):

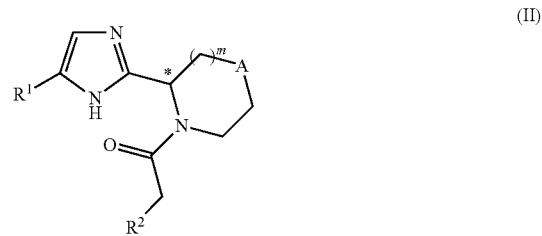

wherein A is as defined in claim 1;

m is selected from 1 or 2;

$R^1$ is a substituent selected from naphthalen-2-yl, 2-methoxyquinolin-3-yl, 1-methyl-1H-indazol-5-yl, quinoxalin-6-yl, quinolin-6-yl, isoquinolin-7-yl, quinolin-5-yl, 2-methoxy-6-phenylpyridin-3-yl, 4-(1H-pyrazol-1-yl)phenyl, 1H-pyrrolo[2,3-b]pyridin-5-yl, 3H-imidazo[4,5-b]pyridin-6-yl, benzo[d]thiazol-6-yl, 1H-indol-2-yl, 1H-pyrrolo[2,3-b]pyridin-3-yl, 2-methoxy-5-phenylpyridin-3-yl, isoquinolin-3-yl, quinolin-3-yl, 1H-benzo[d]imidazol-5-yl, 6-(1H-pyrazol-1-yl)pyridin-3-yl; any of which being optionally further substituted with one or more groups independently chosen from cyano, halogen, hydroxy, $C_{1-6}$alkyl, $C_{3-10}$cycloalkyl, $C_{1-6}$alkoxy, halo$C_{1-6}$alkoxy, $N(R^a)_2$, $C_{1-6}$ alkyl-$N(R^a)_2$, $SO_2N(R^a)_2$;

$R^2$ is 8-13 membered unsaturated or partially saturated heterocycle containing heteroatoms independently selected from O, N and S, optionally substituted by one or more groups independently chosen from $C_{1-6}$alkyl, $C_{1-6}$alkoxy, halogen, cyano, hydroxyl, halo-$C_{1-6}$ alkyl, $CONH_2$, $SO_2C_{1-6}$ alkyl, $C_{3-10}$ cycloalkyl;

and pharmaceutically acceptable salts, tautomers, stereoisomers thereof.

3. The compound according to claim 1 wherein:

A is N—$CH_2$—$R^3$;

$R^3$ is selected from H, cyclopropyl, difluoromethyl, trifluoromethyl, cyclobutyl, tetrahydrofuran-3-yl, oxetan-3-yl, phenyl, 2-fluorophenyl, thiazol-2-yl, furan-3-yl, pyridin-3-yl, pyridin-2-yl, 1-methyl-1H-pyrazol-3-yl, 1-methyl-H-pyrazol-4-yl, 2-methoxypyrimidin5-yl, pyrazyn-2-yl, 1-methyl-1H-1,2,3-triazol-4-yl, oxazol-4-yl, isoxazol-3-yl, thiazol-4-yl, 5-methyl-1,2,4-oxadiazol-3-yl, oxazol-2-yl, pyrimidin-5-yl, 5-fluoropyridin-3-yl, pyrazine-2-yl; (pyridin-2-yl)methyl; (1H-pyrazol-1-yl)methyl; (4H-1,2,4-triazol-4-yl)methyl; (2-methylthiazol-4-yl)methyl; (1-methyl-1H-pyrazol-5-yl)methyl; (isoxazol-4-yl)methyl; 5-methyl-1,2,4-oxadiazol-3-yl; oxazol-2-yl; isoxazol-3-yl;

and pharmaceutically acceptable salts, tautomers, stereoisomers thereof.

4. The compound according to claim 1 wherein:

$R^2$ is selected from 5-methoxy-2-methyl-1H-indol-3-yl, 1H-indol-3-yl, 1-methyl-1H-indol-3-yl, 1H-pyrrolo[2,3-b]pyridin-3-yl, 5-fluoro-2-methyl-1H-indol-3-yl, 3-methylbenzo[b]thiophen-2-yl, 5-methoxy-1-H-indol-3-yl, 2-methyl-1H-benzo[d]imidazol-1-yl, 5,6-difluoro-2-methyl-1H-benzo[d]imidazol-1-yl, 2-trifluoromethyl-1H-benzo[d]imidazol-1-yl, 2-cyclopropyl-1H-benzo[d]imidazol-1-yl, 5-methoxybenzo[d]isoxazol-3-yl, (6-methoxy-2-methyl-1H-benzo[d]

imidazol-1-yl, (6-methoxy-2-methyl-1H-indol-1-yl) and (6-methoxy-2-(trifluoromethyl)-1H-benzo[d]imidazol-1-yl);

and pharmaceutically acceptable salts, tautomers, stereoisomers thereof.

5. The compound according to claim 1 wherein the stereogenic center marked by * is in the S-configuration in enantiomerically resolved state and pharmaceutically acceptable salts and tautomers thereof.

6. The compound according to claim 1, wherein the stereogenic center marked by * is in the R-configuration in enantiomerically resolved state and pharmaceutically acceptable salts and tautomers thereof.

7. The compound of general formula (I) according to claim 1 selected from the following list:

- 6-(4-(2-(5-methoxy-2-methyl-1H-indol-3-yl)acetyl)-3-(5-(naphthalen-2-yl)-1H-imidazol-2-yl)piperazin-1-yl) hexan-3-one;
- 1-(4-hexyl-2-(5-(naphthalen-2-yl)-1H-imidazol-2-yl)piperazin-1-yl)-2-(5-methoxy-2-methyl-1H-indol-3-yl) ethan-1-one;
- 2-(5-methoxy-2-methyl-1H-indol-3-yl)-1-(4-methyl-2-(5-(naphthalen-2-yl)-1H-imidazol-2-yl)piperazin-1-yl) ethan-1-one;
- 1-(4-(4-hydroxyhexyl)-2-(5-(naphthalen-2-yl)-1H-imidazol-2-yl)piperazin-1-yl)-2-(5-methoxy-2-methyl-1H-indol-3-yl)ethan-1-one;
- 6-(4-(2-(5-methoxy-2-methyl-1H-indol-3-yl)acetyl)-3-(5-(2-methoxyquinolin-3-yl)-1H-imidazol-2-yl)piperazin-1-yl)hexan-3-one;
- 1-(4-(cyclopropylmethyl)-2-(5-(naphthalen-2-yl)-1H-imidazol-2-yl)piperazin-1-yl)-2-(5-methoxy-2-methyl-1H-indol-3-yl)ethan-1-one;
- 2-(5-methoxy-2-methyl-1H-indol-3-yl)-1-(2-(5-(naphthalen-2-yl)-1H-imidazol-2-yl)-4-((tetrahydrofuran-3-yl) methyl)piperazin-1-yl)ethan-1-one;
- 2-(2-methyl-1H-indol-3-yl)-1-(2-(5-(naphthalen-2-yl)-1H-imidazol-2-yl)-4-((tetrahydrofuran-3-yl)methyl) piperazin-1-yl)ethan-1-one;
- 2-(5-fluoro-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one;
- 2-(5-methoxy-2-methyl-1H-indol-3-yl)-1-(2-(5-(2-methoxyquinolin-3-yl)-1H-imidazol-2-yl)-4-((tetrahydrofuran-3-yl)methyl)piperazin-1-yl)ethan-1-one;
- 2-(5-fluoro-2-methyl-1H-indol-3-yl)-1-(2-(5-(2-methoxyquinolin-3-yl)-1H-imidazol-2-yl)-4-(thiazol-2-ylmethyl)piperazin-1-yl)ethan-1-one;
- 1-(2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one;
- 2-(5-fluoro-2-methyl-1H-indol-3-yl)-1-(2-(5-(2-methoxyquinolin-3-yl)-1H-imidazol-2-yl)-4-(pyrazin-2-ylmethyl)piperazin-1-yl)ethan-1-one;
- 1-((2S)-2-(5-(2-methoxyquinolin-3-yl)-1H-imidazol-2-yl)-4-((tetrahydrofuran-3-yl)methyl)piperazin-1-yl)-2-(2-(trifluoromethyl)-1H-benzo[d]imidazol-1-yl)ethan-1-one;
- 1-((S)-2-(5-(2-methoxyquinolin-3-yl)-1H-imidazol-2-yl)-4-(((S)-tetrahydrofuran-3-yl)methyl)piperazin-1-yl)-2-(2-(trifluoromethyl)-1H-benzo[d]imidazol-1-yl)ethan-1-one;
- 1-((S)-2-(5-(2-methoxyquinolin-3-yl)-1H-imidazol-2-yl)-4-(((R)-tetrahydrofuran-3-yl)methyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-((1-methyl-1H-pyrazol-3-yl)methyl)piperazin-1-yl)-2-(2-(trifluoromethyl)-1H-benzo[d]imidazol-1-yl) ethan-1-one;
- (S)-1-(4-(isoxazol-3-ylmethyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(thiazol-4-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(thiazol-2-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(pyridin-3-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(pyridin-2-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(oxetan-3-yl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(tetrahydro-2H-pyran-4-yl)piperazin-1-yl)-2-(2-(trifluoromethyl)-1H-benzo[d]imidazol-1-yl)ethan-1-one;
- (S)-1-(4-benzyl-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
- (S)-1-(4-(1-acetylpiperidin-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
- (S)-1-(4-(4,4-difluorocyclohexyl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-((5-methyl-1,2,4-oxadiazol-3-yl)methyl)piperazin-1-yl)-2-(2-(trifluoromethyl)-1H-benzo[d]imidazol-1-yl) ethan-1-one;
- (S)-1-(2-(5-(2-methoxyquinolin-3-yl)-1H-imidazol-2-yl)-4-(oxazol-2-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(oxazol-4-ylmethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(2,2,2-trifluoroethyl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(pyrimidin-5-ylmethyl)piperazin-1-yl)-2-(2-(trifluoromethyl)-1H-benzo[d]imidazol-1-yl)ethan-1-one;
- (S)-1-(4-((5-fluoropyridin-3-yl)methyl)-2-(5-(2-methoxyquinolin-3-yl)-1H-imidazol-2-yl)piperazin-1-yl)-2-(2-(trifluoromethyl)-1H-benzo[d]imidazol-1-yl) ethan-1-one;
- (S)-1-(2-(5-(2-methoxyquinolin-3-yl)-1H-imidazol-2-yl)-4-(oxetan-3-ylmethyl)piperazin-1-yl)-2-(2-(trifluoromethyl)-1H-benzo[d]imidazol-1-yl)ethan-1-one;
- (S)-1-(4-(1,1-dioxidotetrahydro-2H-thiopyran-4-yl)-2-(5-(2-methoxyquinolin-3-yl)-1H-imidazol-2-yl)piperazin-1-yl)-2-(2-(trifluoromethyl)-1H-benzo[d]imidazol-1-yl)ethan-1-one;
- (S)-1-(2-(5-(2-methoxyquinolin-3-yl)-1H-imidazol-2-yl)-4-(pyrazin-2-ylmethyl)piperazin-1-yl)-2-(2-(trifluoromethyl)-1H-benzo[d]imidazol-1-yl)ethan-1-one;

2-(5-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-methyl-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(5,6-dimethoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-(trifluoromethyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(2-(tert-butyl)-1H-benzo[d]imidazol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

1-((2S)-2-(5-(2-methoxyquinolin-3-yl)-1H-imidazol-2-yl)-4-((tetrahydrofuran-3-yl)methyl)piperazin-1-yl)-2-(2-methyl-6-(trifluoromethyl)-1H-benzo[d]imidazol-1-yl)ethan-1-one;

2-(6-methoxy-2-methyl-1H-indol-1-yl)-1-((2S)-2-(5-(2-methoxyquinolin-3-yl)-1H-imidazol-2-yl)-4-((tetrahydrofuran-3-yl)methyl)piperazin-1-yl)ethan-1-one;

2-(6-methoxy-2-(trifluoromethyl)-1H-benzo[d]imidazol-1-yl)-1-(2-(5-(2-methoxyquinolin-3-yl)-1H-imidazol-2-yl)piperidin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-((tetrahydrofuran-3-yl)methyl)-1,4-diazepan-1-yl)ethan-1-one;

2-(6-methoxy-2-methyl-1H-benzo[d]imidazol-1-yl)-1-(7-(5-(2-methoxyquinolin-3-yl)-1H-imidazol-2-yl)-4-(thiazol-2-ylmethyl)-1,4-diazepan-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-H-pyrazol-3-yl)methyl)-1,4-diazepan-1-yl)ethan-1-one;

2-(6-methoxy-2-(trifluoromethyl)-1H-benzo[d]imidazol-1-yl)-1-((2S)-2-(5-(2-methoxyquinolin-3-yl)-4H-1,2,4-triazol-3-yl)-4-((tetrahydrofuran-3-yl)methyl)piperazin-1-yl)ethan-1-one;

1-(4-(2-(1H-pyrazol-1-yl)ethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one;

(S)-2-(6-methoxy-2-(trifluoromethyl)-1H-benzo[d]imidazol-1-yl)-1-(2-(5-(2-methoxyquinolin-3-yl)-4H-1,2,4-triazol-3-yl)-4-(thiazol-2-ylmethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(pyridin-2-ylmethyl)-1,4-diazepan-1-yl)ethan-1-one (S)-1-(4-(2-(1H-pyrazol-1-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one (S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(pyridin-2-yl)ethyl)piperazin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(2-(2-methylthiazol-4-yl)ethyl)piperazin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(2-(1-methyl-1H-pyrazol-5-yl)ethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(pyrazin-2-ylmethyl)-1,4-diazepan-1-yl)ethan-1-one;

(S)-1-(4-(2-(isoxazol-4-yl)ethyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

1-((2S,4S)-4-(dimethylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one;

2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(thiazol-2-ylmethyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((thiazol-2-ylmethyl)amino)piperidin-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(thiazol-4-ylmethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-4-ylmethyl)-1,4-diazepan-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(oxazol-2-ylmethyl)-1,4-diazepan-1-yl)ethan-1-one;

1-(4-(isoxazol-3-ylmethyl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((tetrahydrofuran-3-yl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(methyl(tetrahydrofuran-3-yl)amino)piperidin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(thiazol-4-ylmethyl)piperazin-1-yl)ethan-1-one;

(S)-2-(6-methoxy-2-(trifluoromethyl)-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyrazin-2-ylmethyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-pyrazol-3-yl)methyl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((tetrahydrofuran-3-yl)methyl)amino)piperidin-1-yl)ethan-1-one;

(S)-1-(4-(1,1-dioxidotetrahydro-2H-thiopyran-4-yl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

1-(4-(1,1-dioxidotetrahydro-2H-thiopyran-4-yl)-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one;

1-((2S,4S)-4-((isoxazol-3-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((tetrahydrofuran-3-yl)methyl)amino)piperidin-1-yl)ethan-1-one;

1-((2S,4S)-4-((2-(1H-pyrazol-1-yl)ethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(oxetan-3-ylamino)piperidin-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-((1-methyl-1H-1,2,4-triazol-5-yl)methyl)piperazin-1-yl)ethan-1-one;

1-((2S,4S)-4-(isopropylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(S)-2-(6-methoxy-2-(trifluoromethyl)-1H-benzo[d]imidazol-1-yl)-1-(2-(5-(2-methoxyquinolin-3-yl)-1H-imidazol-2-yl)-4-(pyridazin-4-ylmethyl)piperazin-1-yl)ethan-1-one;

1-((2S,4S)-4-(isobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

1-((2S,4S)-4-(cyclobutylamino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

(R)-2-(6-methoxy-2-methyl-1H-benzo[d]imidazol-1-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

1-((2S,4S)-4-(isopropyl((1-methyl-1H-pyrazol-3-yl)methyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((S)-tetrahydrofuran-3-yl)amino)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((R)-tetrahydrofuran-3-yl)amino)piperidin-1-yl)ethan-1-one;

1-((2S,4S)-4-((2-hydroxyethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((pyridin-2-ylmethyl)amino)piperidin-1-yl)ethan-1-one;

2-(6-methoxy-2-(trifluoromethyl)-1H-benzo[d]imidazol-1-yl)-1-((2S)-2-(5-(2-methoxyquinolin-3-yl)-1H-imidazol-2-yl)-4-(methyl(pyrazin-2-ylmethyl)amino)piperidin-1-yl)ethan-1-one;

2-(6-methoxy-2-(trifluoromethyl)-1H-benzo[d]imidazol-1-yl)-1-((2S,4R)-2-(5-(2-methoxyquinolin-3-yl)-1H-imidazol-2-yl)-4-(methyl((1-methyl-1H-pyrazol-3-yl)methyl)amino)piperidin-1-yl)ethan-1-one;

1-((2S,4S)-4-methoxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

1-((2S,4S)-4-methoxy-2-(5-(2-methoxyquinolin-3-yl)-1H-imidazol-2-yl)piperidin-1-yl)-2-(6-methoxy-2-methyl-1H-benzo[d]imidazol-1-yl)ethan-1-one;

1-((2S)-4-hydroxy-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(((1-methyl-1H-imidazol-5-yl)methyl)amino)piperidin-1-yl)ethan-1-one;

1-((2S,4S)-4-(ethyl(tetrahydrofuran-3-yl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-morpholinopiperidin-1-yl)ethan-1-one;

2-(6-methoxy-2-(trifluoromethyl)-1H-benzo[d]imidazol-1-yl)-1-((2S,4S)-4-((3-methoxycyclobutyl)amino)-2-(5-(2-methoxyquinolin-3-yl)-1H-imidazol-2-yl)piperidin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-((oxetan-3-ylmethyl)amino)piperidin-1-yl)ethan-1-one;

2-(5-methoxy-2-methyl-1H-indol-3-yl)-1-(2-(5-(2-methoxyquinolin-3-yl)-1H-imidazol-2-yl)-4-methylpiperazin-1-yl)ethan-1-one;

1-(2-(5-(2-methoxyquinolin-3-yl)-1H-imidazol-2-yl)-4-((tetrahydrofuran-3-yl)methyl)piperazin-1-yl)-2-(2-methyl-1H-benzo[d]imidazol-1-yl)ethan-1-one;

2-(5-fluoro-2-methyl-1H-indol-3-yl)-1-(2-(5-(2-methoxyquinolin-3-yl)-1H-imidazol-2-yl)-4-((1-methyl-1H-pyrazol-4-yl)methyl)piperazin-1-yl)ethan-1-one;

2-(5-fluoro-2-methyl-1H-indol-3-yl)-1-(2-(5-(2-methoxyquinolin-3-yl)-1H-imidazol-2-yl)-4-(tetrahydro-2H-pyran-4-yl)piperazin-1-yl)ethan-1-one;

2-(5-fluoro-2-methyl-1H-indol-3-yl)-1-(2-(5-(2-methoxyquinolin-3-yl)-1H-imidazol-2-yl)-4-methylpiperazin-1-yl)ethan-1-one;

2-(6-methoxy-2-(trifluoromethyl)-1H-benzo[d]imidazol-1-yl)-1-((2S,4S)-2-(5-(2-methoxyquinolin-3-yl)-1H-imidazol-2-yl)-4-(pyrrolidin-1-yl)piperidin-1-yl)ethan-1-one;

1-((2S,4S)-4-((isoxazol-4-ylmethyl)amino)-2-(5-(2-methoxyquinolin-3-yl)-1H-imidazol-2-yl)piperidin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-((2S,5R)-2-(5-(2-methoxyquinolin-3-yl)-1H-imidazol-2-yl)-5-((tetrahydrofuran-3-yl)amino)piperidin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-((1-methyl-1H-pyrazol-3-yl)methyl)piperazin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(oxazol-4-ylmethyl)piperazin-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(oxetan-3-ylmethyl)piperazin-1-yl)ethan-1-one;

2-(6-methoxy-2-methyl-1H-indol-1-yl)-1-(7-(5-(2-methoxyquinolin-3-yl)-1H-imidazol-2-yl)-4-((1-methyl-H-pyrazol-3-yl)methyl)-1,4-diazepan-1-yl)ethan-1-one;

2-(5-methoxy-2-methyl-1H-indol-3-yl)-1-(7-(5-(2-methoxyquinolin-3-yl)-1H-imidazol-2-yl)-4-((1-methyl-1H-pyrazol-3-yl)methyl)-1,4-diazepan-1-yl)ethan-1-one;

2-(5-fluoro-2-methyl-1H-indol-3-yl)-1-(7-(5-(2-methoxyquinolin-3-yl)-1H-imidazol-2-yl)-4-((1-methyl-H-pyrazol-3-yl)methyl)-1,4-diazepan-1-yl)ethan-1-one;

1-(7-(5-(2-methoxyquinolin-3-yl)-1H-imidazol-2-yl)-4-((1-methyl-1H-pyrazol-3-yl)methyl)-1,4-diazepan-1-yl)-2-(2-(trifluoromethyl)-1H-benzo[d]imidazol-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydrofuran-3-yl)-1,4-diazepan-1-yl)ethan-1-one;

1-(4-cyclobutyl-7-(5-(2-methoxyquinolin-3-yl)-1H-imidazol-2-yl)-1,4-diazepan-1-yl)-2-(6-methoxy-2-(trifluoromethyl)-1H-benzo[d]imidazol-1-yl)ethan-1-one;

(S)-2-(6-methoxy-2-methyl-1H-benzo[d]imidazol-1-yl)-1-(2-(5-(2-methoxyquinolin-3-yl)-1H-imidazol-2-yl)-4-(pyrazin-2-ylmethyl)piperazin-1-yl)ethan-1-one;

1-((2S)-4-((1-acetylpyrrolidin-3-yl)methyl)-2-(5-(2-methoxyquinolin-3-yl)-1H-imidazol-2-yl)piperazin-1-yl)-2-(6-methoxy-2-(trifluoromethyl)-1H-benzo[d]imidazol-1-yl)ethan-1-one;

2-(6-methoxy-2-(trifluoromethyl)-1H-benzo[d]imidazol-1-yl)-1-(7-(5-(2-methoxyquinolin-3-yl)-1H-imidazol-2-yl)-4-(tetrahydro-2H-pyran-4-yl)-1,4-diazepan-1-yl)ethan-1-one and pharmaceutically acceptable salts, tautomers, stereoisomers thereof.

8. A method for the treatment or prevention of a kinetoplastid infection, comprising administering an effective amount of a compound of claim 1 to a patient in need thereof.

9. The method according to claim 8 wherein the kinetoplastid infection is a *Trypanosoma* infection or a *Leishmania* infection.

10. The method according to claim 9, wherein the *Trypanosoma* infection is a *Trypanosoma brucei* infection.

11. A pharmaceutical composition comprising an effective amount of one or more compounds according to claim 1, alone or in combination with at least one further active compound, and at least one pharmaceutically acceptable excipient.

12. The pharmaceutical composition according to claim 11, wherein the further active compound is selected from the group consisting of: agents useful for treating or preventing parasitic diseases, anti-inflammatory agents, anti-pain agents and antipyretic agents.

13. The pharmaceutical composition according to claim 12 wherein the further active compound is selected from the group consisting of: cloroquine, proguanil, mefloquine, quinine, pyrimethamine-sulphadoxine, doxocycline, berberine, halofantrine, primaquine, atovaquone, pyrimethamine-dapsone, artemisinin, meglumine antimonite, sodium stibogluconate, amphotericin B, praziquantel, oxamniquine, Suramin, pentamidine, and melarsoprol, Eflornithine, Nifurtimox.

14. The pharmaceutical composition according to claim 12 wherein the parasitic disease is selected from the group consisting of malaria, toxoplasmosis, trypanosomiasis, Chagas disease, leishmaniasis, schistosomiasis, amebiasis, giardiasis, clonorchiasis, fasciolopsiasis, lymphatic filariasis, onchocerciasis, thricomoniasis and cestodiasis.

\* \* \* \* \*